US011371024B2

(12) United States Patent
Collins et al.

(10) Patent No.: US 11,371,024 B2
(45) Date of Patent: Jun. 28, 2022

(54) ATTENUATION OF HUMAN RESPIRATORY SYNCYTIAL VIRUS BY GENOME SCALE CODON-PAIR DEOPTIMIZATION

(71) Applicants: The USA, as represented by the Secretary, Dept. of Health and Human Services, Bethesda, MD (US); The Research Foundation for the State University of New York, Albany, NY (US)

(72) Inventors: Peter L. Collins, Silver Spring, MD (US); Cyril Le Nouën, Bethesda, MD (US); Linda G. Brock, Bethesda, MD (US); Ursula J. Buchholz, Silver Spring, MD (US); Joshua Marc DiNapoli, Lexington, MA (US); Steffen Mueller, Kings Point, NY (US); Eckard Wimmer, E. Setauket, NY (US)

(73) Assignees: THE UNITED STATES OF AMERICA, AS REPRESENTED BY THE SECRETARY, DEPT. OF HEALTH AND HUMAN SERVICES, Bethesda, MD (US); THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

(21) Appl. No.: 15/924,012

(22) Filed: Mar. 16, 2018

(65) Prior Publication Data

US 2018/0208906 A1 Jul. 26, 2018

Related U.S. Application Data

(62) Division of application No. 14/766,620, filed as application No. PCT/US2014/015274 on Feb. 7, 2014, now Pat. No. 9,957,486.

(60) Provisional application No. 61/762,768, filed on Feb. 8, 2013, provisional application No. 61/794,155, filed on Mar. 15, 2013.

(51) Int. Cl.

| | |
|---|---|
| ***C12N 7/00*** | (2006.01) |
| ***A61K 39/155*** | (2006.01) |
| ***C07K 14/005*** | (2006.01) |
| *A61K 39/00* | (2006.01) |

(52) U.S. Cl.

CPC .............. *C12N 7/00* (2013.01); *A61K 39/155* (2013.01); *C07K 14/005* (2013.01); *A61K 2039/5254* (2013.01); *A61K 2039/53* (2013.01); *A61K 2039/55* (2013.01); *C12N 2760/00021* (2013.01); *C12N 2760/00034* (2013.01); *C12N 2760/00062* (2013.01); *C12N 2760/18522* (2013.01); *C12N 2760/18534* (2013.01); *C12N 2760/18561* (2013.01); *C12N 2760/18562* (2013.01)

(58) Field of Classification Search

None

See application file for complete search history.

(56) References Cited

U.S. PATENT DOCUMENTS

| | | | | |
|---|---|---|---|---|
| 9,476,032 | B2 * | 10/2016 | Wimmer ................. | A61P 31/12 |
| 9,957,486 | B2 | 5/2018 | Collins et al. | |
| 2008/0118530 | A1 * | 5/2008 | Kew .................. | A61K 39/0258 424/207.1 |
| 2012/0264217 | A1 | 10/2012 | Moore et al. | |

FOREIGN PATENT DOCUMENTS

| | | |
|---|---|---|
| EP | 1690940 | 8/2006 |
| WO | WO 98/02530 | 1/1998 |
| WO | WO 98/53078 | 11/1998 |
| WO | WO 02/42326 | 5/2002 |
| WO | WO 2006/042156 | 4/2006 |
| WO | WO 2006/085987 | 8/2006 |
| WO | WO 2008/121992 | 10/2008 |
| WO | WO 2010/053883 | 5/2010 |
| WO | WO 2018/057950 | 3/2018 |

OTHER PUBLICATIONS

Johnson et al. (PNAS. 1987; 84: 5625-5629.*

Lee et al. (Journal of Virology. Dec. 2012; 86 (24): 13810-13811).*

Nouen et al. (PNAS. Sep. 2014; 111 (36): 13169-13174).*

Nouen et al. (PNAS. Jan. 2017; 114 (3): E386-E395).*

Le Nouen et al. (Journal of Virology. Jan. 2020; 94 (2): e01296-19).*

Mueller et al. (Vaccine. 2020; 38: 2943-2948).*

Ruckwardt et al. (Immunity. Sep. 2019; 51: 429-442).*

Official Action for Australia Patent Application No. 2014214763, dated Feb. 19, 2019 3 pages.

Official Action for European Patent Application No. 14706207.9, dated Jan. 4, 2019 4 pages.

Abil et al. "Synthetic biology for therapeutic applications," Molecular Pharmaceutics, 2015, vol. 12, No. 2, pp. 322-331.

(Continued)

*Primary Examiner* — Shanon A. Foley

(74) *Attorney, Agent, or Firm* — McBee Moore & Vanik IP, LLC

(57) ABSTRACT

Described herein are RSV polynucleotide sequences that make use of multiple codons that are containing silent nucleotide substitutions engineered in multiple locations in the genome, wherein the substitutions introduce a numerous synonymous codons into the genome. Due to the large number of defects involved, the attenuated viruses disclosed herein provide a means of producing attenuated, live vaccines against RSV.

17 Claims, 38 Drawing Sheets

Specification includes a Sequence Listing.

(56) References Cited

OTHER PUBLICATIONS

Belshe et al. "Experimental respiratory syncytial virus infection of four species of primates," Journal of Medical Virology, 1977, vol. 1, pp. 157-162 (Abstract Only).
Blondot et al. "Structure and functional analysis of the RNA- and viral phosphoprotein-binding domain of respiratory syncytial virus M2-1 protein," PLoS Pathog, 2012, vol. 8, No. 5, e1002734.
Broadbent et al. "Evaluation of the attenuation, immunogenicity, and efficacy of a live virus vaccine generated by codon-pair bias de-optimization of the 2009 pandemic H1N1 influenza virus, in ferrets," Vaccine, Jan. 2016, vol. 34, No. 4, pp. 563-570.
Brooks et al. "CHARMM: the biomolecular simulation program," Journal of Computational Chemistry, 2009, vol. 30, No. 10, pp. 1545-1614 (Abstract Only).
Buchholz et al. "Generation of bovine respiratory syncytial virus (BRSV) from cDNA: BRSV NS2 is not essential for virus replication in tissue culture, and the human RSV leader region acts as a functional BRSV genome promoter," J. Virol., 1999, vol. 73, No. 1, pp. 251-259.
Bukreyev et al. "Granulocyte-macrophage colony-stimulating factor expressed by recombinant respiratory syncytial virus attenuates viral replication and increases the level of pulmonary antigen-presenting cells," J. Virol. 2001, vol. 75, pp. 12128-12140.
Bukreyev et al. "Recombinant respiratory syncytial virus from which the entire SH gene has been deleted grows efficiently in cell culture and exhibits site-specific attenuation in the respiratory tract of the mouse.," J. Virol., 1997, vol. 71, No. 12, pp. 8973-8982.
Bull et al. "Slow fitness recovery in a codon-modified viral genome," Mol. Biol. Evol., 2012, vol. 29, No. 10, pp. 2997-3004.
Bull "Evolutionary reversion of live viral vaccines: Can genetic engineering subdue it?" Virus Evolutions, 2015, vol. 1, No. 1, vev005.
Burns et al. "Modulation of poliovirus replicative fitness in HeLa cells by deoptimization of synonymous codon usage in the capsid region," J. Virol., 2006, vol. 80, No. 7, pp. 3259-3272.
Chapman eta l. Initial genome sequencing and analysis of multiple myeloma, Nature, 2011, vol. 471, No. 7339, pp. 467-472.
Cheng et al. "Development of live-attenuated arenavirus vaccines based on codon deoptimization," J. Virol, 2015, vol. 89, No. 7, pp. 3523-3533.
Cheng et al. "Effective amplification of long targets from cloned inserts and human genomic DNA," Proc. Natl. Acad. Sci. USA, 1994, vol. 91, No. 12, pp. 5695-5699.
Chirkova et al. "Respiratory Syncytial Virus G Protein CX3C Motif Impairs Human Airway Epithelial and Immune Cell Responses," J. Virol., 2013, vol. 87, No. 24, pp. 13466-13479.
Collins et al. "Viral and Host Factors in Human Respiratory Syncytial Virus Pathogenesis," Journal of Virology, 2008, vol. 82, No. 5, pp. 2040-2055.
Collins et al. "Progress in understanding and controlling respiratory syncytial virus: Still crazy after all these years" Virus Research, 2011, vol. 162, No. 1-2, pp. 80-99.
Collins et al. "Respiratory Syncytial Virus: Virology, Reverse Genetics, and Pathogenesis of Disease," Current Topics in Microbiology and Immunology, 2013, vol. 372, pp. 3-38.
Collins et al. "Production of infectious human respiratory syncytial virus from cloned cDNA confirms an essential role for the transcription elongation factor from the 5' proximal open reading frame of the M2 mRNA in gene expression and provides a capability for vaccine development," Proc. Natl. Acad. Sci. USA, 1995, vol. 92, pp. 11563-11567.
Collins et al. "Nucleotide Sequences for the Gene Junctions of Human Respiratory Syncytial Virus Reveal Distinctive Features of Intergenic Structure and Gene Order," Proc. Natl. Acad. Sci. USA, 1986, vol. 83, No. 13, pp. 4594-4598.
Collins et al. "Gene overlap and site-specific attenuation of transcription of the viral polymerase Lgene of human respiratory syncytial virus," Proc. Natl. Acad. Sci. USA, 1987, vol. 84, No. 15, pp. 5134-5138.
Collins et al. "Rational Design of Live-Attenuated Recombinant Vaccine Virus for Human Respiratory Syncytial Virus by Reverse Genetics," Advances in Virus Research, 1999, vol. 54, pp. 423-451.
Connors et al. "A Cold-Passaged, Attenuated Strain of Human Respiratory Syncytial Virus Contains Mutations in the F and L Genes," Virology, 1995, vol. 208, No. 2, pp. 478-484.
Crowe et al. "A comparison in chimpanzees of the immunogenicity and efficacy of live attenuated respiratory syncytial virus (RSV) temperature-sensitive mutant vaccines and vaccinia virus recombinants that express the surface glycoproteins of RSV," Vaccine, 1993, vol. 11, No. 14, pp. 1395-1404 (Abstract Only).
Diaz-San et al. "Synonymous deoptimization of the foot-and-mouth disease virus causes attenuation in vivo while inducing a strong neutralizing antibody response," J. Virol., 2016, vol. 90, No. 3, pp. 1298-1310.
Durbin et al. "Recovery of Infectious Human Parainfluenza Virus Type 3 from cDNA," Virology, 1997, vol. 235, No. 2, pp. 323-332.
Fearns et al. "Role of the M2-1 transcription antitermination protein of respiratory syncytial virus in sequential transcription," J. Virol., 1999, vol. 73, No. 7, pp. 5852-5864.
Firestone et al. "Nucleotide Sequence Analysis of the Respiratory Syncytial Virus Subgroup A Cold-Passaged (cp) Temperature Sensitive (ts) cpts-248/404 Live Attenuated Virus Vaccine Candidate," Virology, 1996, vol. 225, No. 2, pp. 419-422.
Friedewald et al. "Low-Temperature-Grown RS Virus in Adult Volunteers," J. Amer. Med. Assoc., 1968, vol. 204, pp. 690-694 (Abstract Only).
Gaunt et al. "Elevation of CpG frequencies in influenza A genome attenuates pathogenicity but enhances host response to infection," Elife 5, Feb. 2016, e12735, 19 pages.
Gharpure et al. "Temperature-sensitive Mutants of Respiratory Syncytial Virus," J. Virol., 1969, vol. 3, No. 4, pp. 414-421.
Hanley "The double-edged sword: How evolution can make or break a live-attenuated virus vaccine," Evolution (N Y), 2011, vol. 4, No. 4, pp. 635-643.
Hoffman et al. "An infectious clone of human parainfluenza virus type 3," J. Virol., 1997, vol. 71, No. 6, pp. 4272-4277.
Humphrey et al. "VMD: visual molecular dynamics," Journal of Molecular Graphics, 1996, vol. 14, No. 1, pp. 33-38, 27-38 (Abstract Only).
Juhasz et al. "The two amino acid substitutions in the L protein of cpts530/1009, a live-attenuated respiratory syncytial virus candidate vaccine, are independent temperature-sensitive and attenuation mutations," Vaccine, 1999, vol. 17, No. 11-12, pp. 1416-1424.
Karron et al. "Respiratory syncytial virus (RSV) SH and G proteins are not essential for viral replication in vitro: Clinical evaluation and molecular characterization of a cold-passaged, attenuated RSV subgroup B mutant," Proc. Natl. Acad. Sci. USA, 1997, vol. 94, pp. 13961-13966.
Karron et al. "A gene deletion that up-regulates viral gene expression yields an attenuated RSV vaccine with improved antibody responses in children," Science Transl. Med., 2015, vol. 7, No. 312, pp. 312ra175.
Kato et al. "The paramyxovirus, Sendai virus, V protein encodes a luxury function required for viral pathogenesis," The EMBO. Journal, 1997, vol. 16, pp. 578-587.
Kunec et al. "Codon Pair Bias Is a Direct Consequence of Dinucleotide Bias," Cell reports, Jan. 2016, vol. 14, No. 1, pp. 55-67.
Lauring et al. "Rationalizing the development of live attenuated virus vaccines," Nature Biotechnology, 2010, vol. 28, No. 6, pp. 573-579.
Liang eta l. "Enhanced Neutralizing Antibody Response Induced by Respiratory Syncytial Virus Pre-fusion F Protein Expressed by a Vaccine Candidate," J. Virol., 2015, vol. 89, pp. 9499-9510.
Luongo et al. "Increased Genetic and Phenotypic Stability of a Promising Live-Attenuated Respiratory Syncytial Virus Vaccine Candidate by Reverse Genetics," J. Virol., 2012, vol. 86, No. 19, pp. 10792-10804.
Luongo eta l. "Respiratory Syncytial Virus Modified by Deletions of the NS2 Gene and Amino Acid S1313 of the L Polymerase Protein Is a Temperature-Sensitive, Live-Attenuated Vaccine Candidate That Is Phenotypically Stable at Physiological Temperature," J. Virol., 2013, vol. 87, No. 4, pp. 1985-1996.

(56) References Cited

OTHER PUBLICATIONS

Martinez et al. "Synonymous Virus Genome Recoding as a Tool to Impact Viral Fitness," Trends in Microbiology, Feb. 2016, vol. 24, No. 2, pp. 134-147 (Abstract Only).
Mason et al. "Interaction between human respiratory syncytial virus (RSV) M2-1 and P proteins is required for reconstitution of M2-1-dependent RSV minigenome activity," J. Virol., 2003, vol. 77, No. 19, pp. 10670-10676.
Mclellan et al. "Structure of RSV Fusion Glycoprotein Trimer Bound to a Prefusion-Specific Neutralizing Antibody," Science, 2013, vol. 340, No. 6136, pp. 1113-1117.
Mclellan et al."Structure-Based Design of a Fusion Glycoprotein Vaccine for Respiratory Syncytial Virus," Science, 2013, vol. 342, No. 6158, pp. 592-598.
Meng et al. "Refining the balance of attenuation and immunogenicity of respiratory syncytial virus by targeted codon deoptimization of virulence genes," Mbio., 2014, vol. 5, No. 5, pp. e01704-01714.
Mink et al. "Nucleotide sequences of the 3' leader and 5' trailer regions of human respiratory syncytial virus genomic RNA," Virology, 1991, vol. 185, No. 2, pp. 615-624 (Abstract Only).
Ni et al. "Computer-aided codon-pairs deoptimization of the major envelope GP5 gene attenuates porcine reproductive and respiratory syndrome virus," Virology, 2014, vol. 450-451, pp. 132-139.
Nielsen "Molecular signatures of natural selection," Annu. Rev. Genet., 2005, vol. 39, pp. 197-218 (Abstract Only).
Nogales et al. "Influenza A virus attenuation by codon deoptimization of the NS gene for vaccine development," J. Virol., 2014, vol. 88, No. 18, pp. 10525-10540.
Nougairdede et al. "Random codon re-encoding induces stable reduction of replicative fitness of Chikungunya virus in primate and mosquito cells," PLoS Pathog., 2013, vol. 9, No. 2, e1003172.
Phillips et al. "Scalable molecular dynamics with NAMD," Journal of Computational Chemistry, 2005, vol. 26, No. 16, pp. 1781-1802.
Rothberg et al. "An integrated semiconductor device enabling non-optical genome sequencing," Nature, 2011, vol. 475, No. 7356, pp. 348-352.
Samal et al. "RNA replication by a respiratory syncytial virus RNA analog does not obey the rule of six and retains a nonviral trinucleotide extension at the leader end," J. Virol., 1996, vol. 70, pp. 5075-5082.
Shen et al. "Large-scale recoding of an arbovirus genome to rebalance its insect versus mammalian preference," Proc. Natl. Acad. Sci. USA, 2015, vol. 112, No. 15, pp. 4749-4754.
Teng et al. "Recombinant Respiratory Syncytial Virus That Does Not Express the NS1 or M2-2 Protein Is Highly Attenuated and Immunogenic in Chimpanzees," J. Virol. 2000, vol. 74, No. 19, pp. 9317-9321.
Tanner et al. "Crystal structure of the essential transcription antiterminator M2-1 protein of human respiratory syncytial virus and implications of its phosphorylation," Proc. Natl. Acad. Sci. USA, 2014, vol. 111, No. 4, pp. 1580-1585.
Tran et al. "The respiratory syncytial virus M2-1 protein forms tetramers and interacts with RNA and P in a competitive manner," J. Virol, 2009, vol. 83, No. 13, pp. 6363-6374.
Vabret et al. "Large-scale nucleotide optimization of simian immunodeficiency virus reduces its capacity to stimulate type I interferon in vitro," J. Virol., 2014, vol. 88, No. 8, pp. 4161-4172.
White et al. "Human body temperature and new approaches to constructing temperature-sensitive bacterial vaccines," Cellular and Molecular Life Sciences: CMLS, Sep. 2011, vol. 68, No. 18, pp. 3019-3031.
Whitehead et al. "Recombinant Respiratory Syncytial Virus (RSV) Bearing a Set of Mutations from Cold-Passaged RSV Is Attenuated in Chimpanzees," J. Virol., 1998, vol. 72, No. 5, pp. 4467-4471.
Whitehead et al. "Addition of a Missense Mutation Present in the L Gene of Respiratory Syncytial Virus (RSV) cpts530/1030 to RSV Vaccine Candidate cpts248/404 Increases Its Attenuation and Temperature Sensitivity," J. Virol., 1999, vol. 73, No. 2, pp. 871-877.
Whitehead et al. "A Single Nucleotide Substitution in the Transcription Start Signal of the M2 Gene of Respiratory Syncytial Virus Vaccine Candidatecpts248/404 Is the Major Determinant of the Temperature-Sensitive and Attenuation Phenotypes," Virology, 1998, vol. 247, No. 2, pp. 232-239.
Whitehead et al. "Recombinant Respiratory Syncytial Virus Bearing a Deletion of either the NS2 or SH Gene Is Attenuated in Chimpanzees," J. Virol. 1999, vol. 73, No. 4, pp. 3438-3442.
Wright et al. "The absence of enhanced disease with wild type respiratory syncytial virus infection occurring after receipt of live, attenuated, respiratory syncytial virus vaccines," Vaccine, 2007, vol. 25, No. 42, pp. 7372-7378.
Wyatt et al. "Replication-Deficient Vaccinia Virus Encoding Bacteriophage T7 RNA Polymerase for Transient Gene Expression in Mammalian Cells," Virology, 1995, vol. 210, No. 1, pp. 202-205.
Yang et al. "Deliberate reduction of hemagglutinin and neuraminidase expression of influenza virus leads to a n ultraprotective live vaccine in mice," Proc. Natl. Acad. Sci. USA, 2013, vol. 110, No. 23, pp. 9481-9486.
Sequence alignment of 8387 to 14884 of SEQ ID No. 5 with geneseq database access No. AAV18276 by Udem et al in WO9813501 on Apr. 2, 1998, 13 pages.
Sequence alignment of 8387 to 14884 of SEQ ID No. 5 with geneseq database access No. AAT63430 by Collins et al. in WO 97/12032.
Coleman et al. "Virus Attenuation by Genome-Scale Changes in Codon Pair Bias," Science, Jun. 2008, vol. 320, pp. 1784-1787.
Atkinson et al. "The influence of CpG and UpA dinucleotide frequencies on RNA virus replication and characterization of the innate cellular pathways underlying virus attenuation and enhanced replication," Nucleic Acids Research, 2014, vol. 42, No. 7, pp. 4527-4545.
Buchholz et al., "Chimeric bovine respiratory syncytial virus with glycoprotein gene substitutions from human respiratory syncytial virus /HRSV): effects on host range and evaluation as a live-attenuated vaccine", Journal of Virology, Feb. 2000, vol. 74, No. 3, pp. 1187-1199.
Johnson et al. "The G glycoprotein of human respiratory syncytial viruses of subgroups A and B: Extensive sequence divergence between antigenically related proteins," PNAS, Aug. 1987, vol. 84, pp. 5625-5629.
Lee et al. "Complete Genome Sequence of Human Respiratory Syncytial Virus Genotype A with a 72-Nucleotide Duplication in the Attachment Protein G Gene," Journal of Virology, Dec. 2012, vol. 86, No. 24, pp. 13810-13811.
Le Nouen et al. "Attenuation of human respiratory syncytial virus by genome-scale codon-pair deoptimization," PNAS, Sep. 2014, vol. 111, No. 36, pp. 13169-13174.
Mueller et al. "Reduction of the Rate of Poliovirus Protein Synthesis through Large-Scale Codon Deoptimization Causes Attenuation of Viral Virulence by Lowering Specific Infectivity," Journal of Virology, Oct. 2006, vol. 80, No. 19, pp. 9687-9696.
Mueller et al. "Live attenuated influenza virus vaccines by computer-aided rational design," Nature Biotechnology, Jul. 2010, vol. 28, No. 7, pp. 723-727.
Nouen et al. "Attenuation of human respiratory syncytial virus by genome-scale codon-pair deoptimization," PNAS, Sep. 2014, vol. 111, No. 36, pp. 13169-13174.
Nouen et al. "Genetic stability of genome-scale deoptimized RNA virus vaccine candidates under selective pressure," PNAS, Jan. 2017, vol. 114, No. 3, pp. E386-E395.
Stec et al. "Sequence analysis of the polymerase L gene of human respiratory syncytial virus and predicted phylogeny of nonsegmented negative-strand viruses." Virology, Jul. 1991, vol. 183, No. 1, pp. 273-287 (Abstract Only).
Tulloch et al. "RNA virus attenuation by codon pair deoptimisation is an artefact of increases in CpG/UpA dinucleotide frequencies," eLife, Dec. 2014, 3, e04531,15 pages.
Yunus et al. "Sequence analysis of a functional polymerase (L) gene of bovine respiratory syncytial virus: determination of minimal trans-acting requirements for RNA replication," Journal of General Virology, Sep. 1998, vol. 79, pp. 2231-2238.
International Search Report and Written Opinion for International (PCT) Patent Application No. PCT/US2014/015274, dated Feb. 7, 2014 19 pages.

(56) References Cited

OTHER PUBLICATIONS

International Preliminary Report on Patentability for International (PCT) Patent Application No. PCT/US2014/015274, dated Aug. 11, 2015 10 pages.
Official Action for European Patent Application No. 14706207.9, dated May 22, 2017 10 pages.
Official Action for U.S. Appl. No. 14/766,620, dated Jul. 20, 2016 11 pages Restriction Requirement.
Official Action for U.S. Appl. No. 14/766,620, dated Oct. 28, 2016 15 pages.
Official Action for U.S. Appl. No. 14/766,620, dated Jun. 1, 2017 11 pages.
Official Acton for U.S. Appl. No. 14/766,620, dated Nov. 8, 2017 13 pages.
Notice of Allowance for U.S. Appl. No. 14/766,620, dated Dec. 27, 2017 9 pages.
Official Action for European Patent Application No. 14706207.9, dated Feb. 9, 2018 5 pages.
Coleman et al. "Designed Reduction of *Streptococcus pneumoniae* Pathogenicity via Synthetic Changes in Virulence Factor Codon-pair Bias," The Journal of Infectious Diseases, May 2011, vol. 203, No. 9, pp. 1264-1273.
Official Action for Canada Patent Application No. 2,900,713, dated Dec. 10, 2019 4 pages.
Official Action for Australia Patent Application No. 2014214763, dated Dec. 17, 2019 2 pages.
Notice of Acceptance for Australia Patent Application No. 2014214763, dated Feb. 18, 2020 3 pages.
Second Examiner's Report of Canadian Application No. 2,900,713 dated Dec. 9, 2020.
Yunus et al., "Bovine respiratory syncytial virus A51908, partial sequence—AF295544", GenBank, XP055361188, Dec. 2, 2001.
Afonso, Claudio L. et al., "Taxonomy of the order Mononegavirales: update 2016", Archives of Virology, 2016, pp. 2351-2360, vol. 161.
Pandya, Mansi C. et al., "A Contemporary View of Respiratory Syncytial Virus (RSV) Biology and Strain-Specific Differences", Pathogens, May 21, 2019, pp. 1-15, vol. 8, No. 2.
Tan, Lydia et al., "Genetic Variability among Complete Human Respiratory Syncytial Virus Subgroup A Genomes: Bridging Molecular Evolutionary Dynamics and Epidemiology", PLOS ONE, Dec. 2012, vol. 7, No. 12.
Whitehead, S.S. et al., "Replacement of the F and G Proteins of Respiratory Syncytial Virus (RSV) Subgroup A with Those of Subgroup B Generates Chimeric Live Attenuated RSV Subgroup B Vaccine Candidates", Journal of Virology, Dec. 1999, pp. 9773-9780, vol. 73, No. 12.
Collins, Peter L. and Ruth A. Karron, "Respiratory Syncytial Virus and Metapneumovirus", Fields Virology, Sixth Edition, Chapter 38, 2013, pp. 1086-1123.
Mink, Michael A., et al. "Nucleotide sequences of the 3' leader and 5' trailer regions of human respiratory syncytial virus genomic RNA" Virology, (1991), vol. 185, No. 2, 615-624.
Stec, David S., et al. "Sequence analysis of the polymerase L gene of human respiratory syncytial virus and predicted phylogeny of nonsegmented negative-strand viruses." Virology, (1991), vol. 183, No. 1, 273-287.
Bessaud, Maël, et al. "Development of a Taqman RT-PCR assay for the detection and quantification of negatively stranded RNA of human enteroviruses: evidence for false-priming and improvement by tagged RT-PCR." Journal of Virological Methods, (2008), vol. 153, No. 2, 182-189.
Belshe, Robert B., et al. "Experimental respiratory syncytial virus infection of four species of primates." Journal of Medical Virology, (1977), vol. 1, No. 3, 157-162.
Genbank, "Human respiratory syncytial virus nonstructural protein 1, nonstructural protein 2, nucleocapsid protein, phosphoprotein, matrix protein, small hydrophobic protein, glycoprotein, fusion glycoprotein, 22K/M2 protein and L protein mRNA, complete cds." Human orthopneumovirus (HRSV), accession version M74568.1, (1993), Accessed Jan. 7, 2022, https://www.ncbi.nlm.nih.gov/nuccore/M74568.1: 6 pages.
Friedewald, William T., et al. "Low-temperature-grown RS virus in adult volunteers." JAMA, (1968), vol. 204, No. 8, 690-694.
Karron, Ruth A., et al. "Identification of a recombinant live attenuated respiratory syncytial virus vaccine candidate that is highly attenuated in infants." The Journal of Infectious Diseases, (2005), vol. 191, No. 7, 1093-1104.
Wright, P. F., et al. "Genetic studies of respiratory syneytial virus temperature-sensitive mutants." Archiv für die gesamte Virusforschung, (1973), vol. 41, No. 3, 238-247.

* cited by examiner

Alignment RSV-WT with Min sequences

```
1     ACGGGAAAAAATGCGTACAACAAACTTGCATAAACCAAAAAAATGGGGCAAATAAGAATT   60   RSV_WT
1     ACGGGAAAAAATGCGTACAACAAACTTGCATAAACCAAAAAAATGGGGCAAATAAGAATT   60   MinA
1     ACGGGAAAAAATGCGTACAACAAACTTGCATAAACCAAAAAAATGGGGCAAATAAGAATT   60   MinB
1     ACGGGAAAAAATGCGTACAACAAACTTGCATAAACCAAAAAAATGGGGCAAATAAGAATT   60   MinL
1     ACGGGAAAAAATGCGTACAACAAACTTGCATAAACCAAAAAAATGGGGCAAATAAGAATT   60   MinFLC
      ************************************************************

61    TGATAAGTACCACTTAAATTTAACTCCCTTGGTTAGAGATGGGCAGCAATTCATTGAGTA   120  RSV_WT
61    TGATAAGTACCACTTAAATTTAACTCCCTTGGTTAGAGATGGGCAGCAATTCATTGAGTA   120  MinA
61    TGATAAGTACCACTTAAATTTAACTCCCTTGGTTAGAGATGGGCAGCAATTCATTGAGTA   120  MinB
61    TGATAAGTACCACTTAAATTTAACTCCCTTGGTTAGAGATGGGCAGCAATTCATTGAGTA   120  MinL
61    TGATAAGTACCACTTAAATTTAACTCCCTTGGTTAGAGATGGGCAGCAATTCATTGAGTA   120  MinFLC
      ************************************************************

121   TGATAAAAGTTAGATTACAAAATTTGTTTGACAATGATGAAGTAGCATTGTTAAAAATAA   180  RSV_WT
121   TGATAAAAGTCAGATTGCAAAATCTATTCGATAATGACGAAGTGGCACTATTAAAAATTA   180  MinA
121   TGATAAAAGTTAGATTACAAAATTTGTTTGACAATGATGAAGTAGCATTGTTAAAAATAA   180  MinB
121   TGATAAAAGTTAGATTACAAAATTTGTTTGACAATGATGAAGTAGCATTGTTAAAAATAA   180  MinL
121   TGATAAAAGTCAGATTGCAAAATCTATTCGATAATGACGAAGTGGCACTATTAAAAATTA   180  MinFLC
      ********** *****.****** *.** ** ***** *****.*** *.********:*

181   CATGCTATACTGATAAATTAATACATTTAACTAATGCTTTGGCTAAGGCAGTGATACATA   240  RSV_WT
181   CATGTTATACCGATAAATTGATACATCTAACTAATGCATTAGCTAAAGCTGTAATACATA   240  MinA
181   CATGCTATACTGATAAATTAATACATTTAACTAATGCTTTGGCTAAGGCAGTGATACATA   240  MinB
181   CATGCTATACTGATAAATTAATACATTTAACTAATGCTTTGGCTAAGGCAGTGATACATA   240  MinL
181   CATGTTATACCGATAAATTGATACATCTAACTAATGCATTAGCTAAAGCTGTAATACATA   240  MinFLC
      **** ***** ********.****** **********:**.*****.**:**.*******

241   CAATCAAATTGAATGGCATTGTGTTTGTGCATGTTATTACAAGTAGTGATATTTGCCCTA   300  RSV_WT
241   CAATTAAACTTAATGGAATAGTGTTTGTACATGTAATTACATCTAGTGATATATGCCCTA   300  MinA
241   CAATCAAATTGAATGGCATTGTGTTTGTGCATGTTATTACAAGTAGTGATATTTGCCCTA   300  MinB
241   CAATCAAATTGAATGGCATTGTGTTTGTGCATGTTATTACAAGTAGTGATATTTGCCCTA   300  MinL
241   CAATTAAACTTAATGGAATAGTGTTTGTACATGTAATTACATCTAGTGATATATGCCCTA   300  MinFLC
      **** *** * *****.**:********.*****:******: *********:*******

301   ATAATAATATTGTAGTAAAATCCAATTTCACAACAATGCCAGTACTACAAAATGGAGGTT   360  RSV_WT
301   ATAATAATATCGTAGTCAAGTCTAATTTTACAACAATGCCAGTGTTACAAAATGGCGGAT   360  MinA
301   ATAATAATATTGTAGTAAAATCCAATTTCACAACAATGCCAGTACTACAAAATGGAGGTT   360  MinB
301   ATAATAATATTGTAGTAAAATCCAATTTCACAACAATGCCAGTACTACAAAATGGAGGTT   360  MinL
301   ATAATAATATCGTAGTCAAGTCTAATTTTACAACAATGCCAGTGTTACAAAATGGCGGAT   360  MinFLC
      ********** *****.**.** ***** **************. **********.**:*

361   ATATATGGGAAATGATGGAATTAACACATTGCTCTCAACCTAATGGTCTACTAGATGACA   420  RSV_WT
361   ATATTTGGGAAATGATGGAATTGACACATTGCTCACAACCTAATGGTCTATTAGACGATA   420  MinA
361   ATATATGGGAAATGATGGAATTAACACATTGCTCTCAACCTAATGGTCTACTAGATGACA   420  MinB
361   ATATATGGGAAATGATGGAATTAACACATTGCTCTCAACCTAATGGTCTACTAGATGACA   420  MinL
361   ATATTTGGGAAATGATGGAATTGACACATTGCTCACAACCTAATGGTCTATTAGACGATA   420  MinFLC
      ****:*****************.***********:*************** **** ** *

421   ATTGTGAAATTAAATTCTCCAAAAAACTAAGTGATTCAACAATGACCAATTATATGAATC   480  RSV_WT
421   ATTGCGAAATTAAATTTAGTAAGAAATTATCCGATAGTACAATGACTAATTATATGAATC   480  MinA
421   ATTGTGAAATTAAATTCTCCAAAAAACTAAGTGATTCAACAATGACCAATTATATGAATC   480  MinB
421   ATTGTGAAATTAAATTCTCCAAAAAACTAAGTGATTCAACAATGACCAATTATATGAATC   480  MinL
421   ATTGCGAAATTAAATTTAGTAAGAAATTATCCGATAGTACAATGACTAATTATATGAATC   480  MinFLC
      **** *********** :  **.*** **:  ***: :******** *************

481   AATTATCTGAATTACTTGGATTTGATCTTAATCCATAAATTATAATTAATATCAACTAGC   540  RSV_WT
481   AATTATCCGAATTGTTAGGTTTCGATCTTAATCCATAAATTATAATTAATATCAACTAGC   540  MinA
481   AATTATCTGAATTACTTGGATTTGATCTTAATCCATAAATTATAATTAATATCAACTAGC   540  MinB
481   AATTATCTGAATTACTTGGATTTGATCTTAATCCATAAATTATAATTAATATCAACTAGC   540  MinL
481   AATTATCCGAATTGTTAGGTTTCGATCTTAATCCATAAATTATAATTAATATCAACTAGC   540  MinFLC
      ******* *****. *:**:** *************************************
```

Figure 7

```
541  AAATCAATGTCACTAACACCATTAGTTAATATAAAACTTAACAGAAGACAAAAATGGGGC  600  RSV_WT
541  AAATCAATGTCACTAACACCATTAGTTAATATAAAACTTAACAGAAGACAAAAATGGGGC  600  MinA
541  AAATCAATGTCACTAACACCATTAGTTAATATAAAACTTAACAGAAGACAAAAATGGGGC  600  MinB
541  AAATCAATGTCACTAACACCATTAGTTAATATAAAACTTAACAGAAGACAAAAATGGGGC  600  MinL
541  AAATCAATGTCACTAACACCATTAGTTAATATAAAACTTAACAGAAGACAAAAATGGGGC  600  MinFLC
     ************************************************************

601  AAATAAATCAATTCAGCCAACCCAACCATGGACACAACCCACAATGATAATACACCACAA  660  RSV_WT
601  AAATAAATCAATTCAGCCAACCCAACCATGGACACAACCCACAATGATAATACACCACAA  660  MinA
601  AAATAAATCAATTCAGCCAACCCAACCATGGACACAACCCACAATGATAATACACCACAA  660  MinB
601  AAATAAATCAATTCAGCCAACCCAACCATGGACACAACCCACAATGATAATACACCACAA  660  MinL
601  AAATAAATCAATTCAGCCAACCCAACCATGGACACAACCCACAATGATAATACACCACAA  660  MinFLC
     ************************************************************

661  AGACTGATGATCACAGACATGAGACCGTTGTCACTTGAGACCATAATAACATCACTAACC  720  RSV_WT
661  AGACTGATGATTACCGATATGAGACCGTTGTCACTTGAGACAATTATAACTAGCCTAACT  720  MinA
661  AGACTGATGATCACAGACATGAGACCGTTGTCACTTGAGACCATAATAACATCACTAACC  720  MinB
661  AGACTGATGATCACAGACATGAGACCGTTGTCACTTGAGACCATAATAACATCACTAACC  720  MinL
661  AGACTGATGATTACCGATATGAGACCGTTGTCACTTGAGACAATTATAACTAGCCTAACT  720  MinFLC
     *********** **.** ***********************.**:*****:: .*****

721  AGAGACATCATAACACACAAATTTATATACTTGATAAATCATGAATGCATAGTGAGAAAA  780  RSV_WT
721  AGAGATATAATAACACATAAATTTATATATCTGATTAATCACGAATGCATCGTGAGGAAA  780  MinA
721  AGAGACATCATAACACACAAATTTATATACTTGATAAATCATGAATGCATAGTGAGAAAA  780  MinB
721  AGAGACATCATAACACACAAATTTATATACTTGATAAATCATGAATGCATAGTGAGAAAA  780  MinL
721  AGAGATATAATAACACATAAATTTATATATCTGATTAATCACGAATGCATCGTGAGGAAA  780  MinFLC
     ***** **.******** ***********  ****:***** ********.*****.***

781  CTTGATGAAAGACAGGCCACATTTACATTCCTGGTCAACTATGAAATGAAACTATTACAC  840  RSV_WT
781  TTGGACGAAAGACAGGCCACATTTACATTCTTAGTCAATTACGAAATGAAACTATTGCAT  840  MinA
781  CTTGATGAAAGACAGGCCACATTTACATTCCTGGTCAACTATGAAATGAAACTATTACAC  840  MinB
781  CTTGATGAAAGACAGGCCACATTTACATTCCTGGTCAACTATGAAATGAAACTATTACAC  840  MinL
781  TTGGACGAAAGACAGGCCACATTTACATTCTTAGTCAATTACGAAATGAAACTATTGCAT  840  MinFLC
      * ** ************************ *.***** ** **************.**

841  AAAGTAGGAAGCACTAAATATAAAAAATATACTGAATACAACACAAAATATGGCACTTTC  900  RSV_WT
841  AAGGTAGGCTCAACTAAGTATAAGAAATATACCGAATATAACACTAAATACGGAACATTC  900  MinA
841  AAAGTAGGAAGCACTAAATATAAAAAATATACTGAATACAACACAAAATATGGCACTTTC  900  MinB
841  AAAGTAGGAAGCACTAAATATAAAAAATATACTGAATACAACACAAAATATGGCACTTTC  900  MinL
841  AAGGTAGGCTCAACTAAGTATAAGAAATATACCGAATATAACACTAAATACGGAACATTC  900  MinFLC
     **.*****.: .*****.*****.******** ***** *****:***** **.**:***

901  CCTATGCCAATATTCATCAATCATGATGGGTTCTTAGAATGCATTGGCATTAAGCCTACA  960  RSV_WT
901  CCAATGCCTATATTCATAAATCACGACGGGTTTCTCGAATGCATAGGCATAAAACCTACA  960  MinA
901  CCTATGCCAATATTCATCAATCATGATGGGTTCTTAGAATGCATTGGCATTAAGCCTACA  960  MinB
901  CCTATGCCAATATTCATCAATCATGATGGGTTCTTAGAATGCATTGGCATTAAGCCTACA  960  MinL
901  CCAATGCCTATATTCATAAATCACGACGGGTTTCTCGAATGCATAGGCATAAAACCTACA  960  MinFLC
     **:*****:********.***** ** *****  *.********:*****:**.******

961  AAGCATACTCCCATAATATACAAGTATGATCTCAATCCATAAATTTCAACACAATATTCA 1020  RSV_WT
961  AAACATACACCCATAATCTATAAATACGATCTTAACCCATAAATTTCAACACAATATTCA 1020  MinA
961  AAGCATACTCCCATAATATACAAGTATGATCTCAATCCATAAATTTCAACACAATATTCA 1020  MinB
961  AAGCATACTCCCATAATATACAAGTATGATCTCAATCCATAAATTTCAACACAATATTCA 1020  MinL
961  AAACATACACCCATAATCTATAAATACGATCTTAACCCATAAATTTCAACACAATATTCA 1020  MinFLC
     **.*****:********.** **.** ***** ** ************************

1021 CACAATCTAAAACAACAACTCTATGCATAACTATACTCCATAGTCCAGATGGAGCCTGAA 1080  RSV_WT
1021 CACAATCTAAAACAACAACTCTATGCATAACTATACTCCATAGTCCAGATGGAGCCTGAA 1080  MinA
1021 CACAATCTAAAACAACAACTCTATGCATAACTATACTCCATAGTCCAGATGGAGCCTGAA 1080  MinB
1021 CACAATCTAAAACAACAACTCTATGCATAACTATACTCCATAGTCCAGATGGAGCCTGAA 1080  MinL
1021 CACAATCTAAAACAACAACTCTATGCATAACTATACTCCATAGTCCAGATGGAGCCTGAA 1080  MinFLC
     ************************************************************

1081 AATTATAGTAATTTAAAACTTAAGGAGAGATATAAGATAGAAGATGGGGCAAATACAACC 1140  RSV_WT
1081 AATTATAGTAATTTAAAACTTAAGGAGAGATATAAGATAGAAGATGGGGCAAATACAACC 1140  MinA
1081 AATTATAGTAATTTAAAACTTAAGGAGAGATATAAGATAGAAGATGGGGCAAATACAACC 1140  MinB
1081 AATTATAGTAATTTAAAACTTAAGGAGAGATATAAGATAGAAGATGGGGCAAATACAACC 1140  MinL
1081 AATTATAGTAATTTAAAACTTAAGGAGAGATATAAGATAGAAGATGGGGCAAATACAACC 1140  MinFLC
     ************************************************************
```

Figure 7 cont.

```
1141 ATGGCTCTTAGCAAAGTCAAGTTGAATGATACACTCAACAAAGATCAACTTCTGTCATCC 1200  RSV_WT
1141 ATGGCTCTTAGCAAAGTCAAGTTGAATGATACATTGAATAAAGATCAATTACTATCTAGC 1200  MinA
1141 ATGGCTCTTAGCAAAGTCAAGTTGAATGATACACTCAACAAAGATCAACTTCTGTCATCC 1200  MinB
1141 ATGGCTCTTAGCAAAGTCAAGTTGAATGATACACTCAACAAAGATCAACTTCTGTCATCC 1200  MinL
1141 ATGGCTCTTAGCAAAGTCAAGTTGAATGATACATTGAATAAAGATCAATTACTATCTAGC 1200  MinFLC
     ********************************* * ** ********* *:**.**:: *

1201 AGCAAATACACCATCCAACGGAGCACAGGAGATAGTATTGATACTCCTAATTATGATGTG 1260  RSV_WT
1201 TCGAAATATACTATCCAACGGTCTACAGGCGATTCAATAGATACACCTAATTACGATGTG 1260  MinA
1201 AGCAAATACACCATCCAACGGAGCACAGGAGATAGTATTGATACTCCTAATTATGATGTG 1260  MinB
1201 AGCAAATACACCATCCAACGGAGCACAGGAGATAGTATTGATACTCCTAATTATGATGTG 1260  MinL
1201 TCGAAATATACTATCCAACGGTCTACAGGCGATTCAATAGATACACCTAATTACGATGTG 1260  MinFLC
     :  ***** ** *********:  *****.***: :**:*****:******** ******

1261 CAGAAACACATCAATAAGTTATGTGGCATGTTATTAATCACAGAAGATGCTAATCATAAA 1320  RSV_WT
1261 CAAAAACATATTAATAAATTGTGTGGTATGTTATTGATTACCGAAGACGCAAATCATAAA 1320  MinA
1261 CAGAAACACATCAATAAGTTATGTGGCATGTTATTAATCACAGAAGATGCTAATCATAAA 1320  MinB
1261 CAGAAACACATCAATAAGTTATGTGGCATGTTATTAATCACAGAAGATGCTAATCATAAA 1320  MinL
1261 CAAAAACATATTAATAAATTGTGTGGTATGTTATTGATTACCGAAGACGCAAATCATAAA 1320  MinFLC
     **.***** ** *****.**.***** ********.** **.***** **:*********

1321 TTCACTGGGTTAATAGGTATGTTATATGCGATGTCTAGGTTAGGAAGAGAAGACACCATA 1380  RSV_WT
1321 TTTACAGGGTTAATCGGTATGTTATACGCTATGTCTAGATTAGGTAGGGAAGATACAATT 1380  MinA
1321 TTCACTGGGTTAATAGGTATGTTATATGCGATGTCTAGGTTAGGAAGAGAAGACACCATA 1380  MinB
1321 TTCACTGGGTTAATAGGTATGTTATATGCGATGTCTAGGTTAGGAAGAGAAGACACCATA 1380  MinL
1321 TTTACAGGGTTAATCGGTATGTTATACGCTATGTCTAGATTAGGTAGGGAAGATACAATT 1380  MinFLC
     ** **:********.*********** ** ********.*****:**.***** **.**:

1381 AAAATACTCAGAGATGCGGGATATCATGTAAAAGCAAATGGAGTAGATGTAACAACACAT 1440  RSV_WT
1381 AAAATACTTAGAGACGCAGGATATCACGTTAAAGCTAACGGAGTAGACGTAACTACACAT 1440  MinA
1381 AAAATACTCAGAGATGCGGGATATCATGTAAAAGCAAATGGAGTAGATGTAACAACACAT 1440  MinB
1381 AAAATACTCAGAGATGCGGGATATCATGTAAAAGCAAATGGAGTAGATGTAACAACACAT 1440  MinL
1381 AAAATACTTAGAGACGCAGGATATCACGTTAAAGCTAACGGAGTAGACGTAACTACACAT 1440  MinFLC
     ******** ***** **.******** **:*****:** ******** *****:******

1441 CGTCAAGACATTAATGGAAAAGAAATGAAATTTGAAGTGTTAACATTGGCAAGCTTAACA 1500  RSV_WT
1441 AGACAGGATATTAACGGTAAGGAAATGAAATTCGAAGTGTTAACACTCGCTAGCTTAACT 1500  MinA
1441 CGTCAAGACATTAATGGAAAAGAAATGAAATTTGAAGTGTTAACATTGGCAAGCTTAACA 1500  MinB
1441 CGTCAAGACATTAATGGAAAAGAAATGAAATTTGAAGTGTTAACATTGGCAAGCTTAACA 1500  MinL
1441 AGACAGGATATTAACGGTAAGGAAATGAAATTCGAAGTGTTAACACTCGCTAGCTTAACT 1500  MinFLC
     .*:**.** ***** **:**.*********** ************ * **:********:

1501 ACTGAAATTCAAATCAACATTGAGATAGAATCTAGAAAATCCTACAAAAAAATGCTAAAA 1560  RSV_WT
1501 ACCGAAATACAAATTAATATCGAAATCGAATCACGTAAATCTTATAAGAAAATGCTTAAA 1560  MinA
1501 ACTGAAATTCAAATCAACATTGAGATAGAATCTAGAAAATCCTACAAAAAAATGCTAAAA 1560  MinB
1501 ACTGAAATTCAAATCAACATTGAGATAGAATCTAGAAAATCCTACAAAAAAATGCTAAAA 1560  MinL
1501 ACCGAAATACAAATTAATATCGAAATCGAATCACGTAAATCTTATAAGAAAATGCTTAAA 1560  MinFLC
     ** *****:***** ** ** **.**.*****:.*:***** ** **.********:***

1561 GAAATGGGAGAGGTAGCTCCAGAATACAGGCATGACTCTCCTGATTGTGGGATGATAATA 1620  RSV_WT
1561 GAAATGGGCGAAGTCGCACCCGAATATAGACACGATAGTCCCGATTGTGGTATGATTATA 1620  MinA
1561 GAAATGGGAGAGGTAGCTCCAGAATACAGGCATGACTCTCCTGATTGTGGGATGATAATA 1620  MinB
1561 GAAATGGGAGAGGTAGCTCCAGAATACAGGCATGACTCTCCTGATTGTGGGATGATAATA 1620  MinL
1561 GAAATGGGCGAAGTCGCACCCGAATATAGACACGATAGTCCCGATTGTGGTATGATTATA 1620  MinFLC
     ********.**.**.**:**.***** **.** ** : *** ******** *****:***

1621 TTATGTATAGCAGCATTAGTAATAACTAAATTAGCAGCAGGGGACAGATCTGGTCTTACA 1680  RSV_WT
1621 CTATGTATAGCCGCATTAGTGATAACTAAGTTGGCCGCAGGCGATAGATCCGGATTAACC 1680  MinA
1621 TTATGTATAGCAGCATTAGTAATAACTAAATTAGCAGCAGGGGACAGATCTGGTCTTACA 1680  MinB
1621 TTATGTATAGCAGCATTAGTAATAACTAAATTAGCAGCAGGGGACAGATCTGGTCTTACA 1680  MinL
1621 CTATGTATAGCCGCATTAGTGATAACTAAGTTGGCCGCAGGCGATAGATCCGGATTAACC 1680  MinFLC
      **********.********.********.**.**.***** ** ***** **: *:**.

1681 GCCGTGATTAGGAGAGCTAATAATGTCCTAAAAAATGAAATGAAACGTTACAAAGGCTTA 1740  RSV_WT
1681 GCAGTGATACGTAGAGCGAATAACGTACTTAAAAACGAAATGAAACGGTATAAGGGTCTA 1740  MinA
1681 GCCGTGATTAGGAGAGCTAATAATGTCCTAAAAAATGAAATGAAACGTTACAAAGGCTTA 1740  MinB
1681 GCCGTGATTAGGAGAGCTAATAATGTCCTAAAAAATGAAATGAAACGTTACAAAGGCTTA 1740  MinL
1681 GCAGTGATACGTAGAGCGAATAACGTACTTAAAAACGAAATGAAACGGTATAAGGGTCTA 1740  MinFLC
     **.*****:.* ***** ***** **.**:***** *********** ** **.**  **
```

Figure 7 cont.

```
1741 CTACCCAAGGACATAGCCAACAGCTTCTATGAAGTGTTTGAAAAACATCCCCACTTTATA 1800  RSV_WT
1741 TTACCAAAAGATATAGCGAATAGTTTTTACGAAGTATTCGAAAAACATCCACATTTTATA 1800  MinA
1741 CTACCCAAGGACATAGCCAACAGCTTCTATGAAGTGTTTGAAAAACATCCCCACTTTATA 1800  MinB
1741 CTACCCAAGGACATAGCCAACAGCTTCTATGAAGTGTTTGAAAAACATCCCCACTTTATA 1800  MinL
1741 TTACCAAAAGATATAGCGAATAGTTTTTACGAAGTATTCGAAAAACATCCACATTTTATA 1800  MinFLC
      ****.**.** ***** ** ** ** ** *****.** ***********.** ******

1801 GATGTTTTTGTTCATTTTGGTATAGCACAATCTTCTACCAGAGGTGGCAGTAGAGTTGAA 1860  RSV_WT
1801 GACGTTTTTGTGCATTTCGGAATCGCACAATCTAGTACTAGAGGAGGATCTAGGGTTGAG 1860  MinA
1801 GATGTTTTTGTTCATTTTGGTATAGCACAATCTTCTACCAGAGGTGGCAGTAGAGTTGAA 1860  MinB
1801 GATGTTTTTGTTCATTTTGGTATAGCACAATCTTCTACCAGAGGTGGCAGTAGAGTTGAA 1860  MinL
1801 GACGTTTTTGTGCATTTCGGAATCGCACAATCTAGTACTAGAGGAGGATCTAGGGTTGAG 1860  MinFLC
     ** ******** ***** **:**.*********: *** *****:**.: ***.*****.

1861 GGGATTTTTGCAGGATTGTTTATGAATGCCTATGGTGCAGGGCAAGTGATGTTACGGTGG 1920  RSV_WT
1861 GGTATATTCGCAGGATTGTTTATGAACGCATACGGAGCAGGTCAAGTCATGCTTAGATGG 1920  MinA
1861 GGGATTTTTGCAGGATTGTTTATGAATGCCTATGGTGCAGGGCAAGTGATGTTACGGTGG 1920  MinB
1861 GGGATTTTTGCAGGATTGTTTATGAATGCCTATGGTGCAGGGCAAGTGATGTTACGGTGG 1920  MinL
1861 GGTATATTCGCAGGATTGTTTATGAACGCATACGGAGCAGGTCAAGTCATGCTTAGATGG 1920  MinFLC
     ** **:** ***************** **.** **:***** ***** *** *:.*.***

1921 GGAGTCTTAGCAAAATCGGTTAAAAATATTATGTTAGGACATGCTAGTGTGCAAGCAGAA 1980  RSV_WT
1921 GGAGTACTCGCAAAATCCGTTAAAAATATTATGTTAGGACACGCTAGCGTACAAGCCGAA 1980  MinA
1921 GGAGTCTTAGCAAAATCGGTTAAAAATATTATGTTAGGACATGCTAGTGTGCAAGCAGAA 1980  MinB
1921 GGAGTCTTAGCAAAATCGGTTAAAAATATTATGTTAGGACATGCTAGTGTGCAAGCAGAA 1980  MinL
1921 GGAGTACTCGCAAAATCCGTTAAAAATATTATGTTAGGACACGCTAGCGTACAAGCCGAA 1980  MinFLC
     *****. *.******** *********************** ***** **.*****.***

1981 ATGGAACAAGTTGTTGAGGTTTATGAATATGCCCAAAAATTGGGTGGTGAAGCAGGATTC 2040  RSV_WT
1981 ATGGAACAAGTCGTTGAGGTATACGAATACGCACAAAAATTAGGTGGAGAAGCAGGATTT 2040  MinA
1981 ATGGAACAAGTTGTTGAGGTTTATGAATATGCCCAAAAATTGGGTGGTGAAGCAGGATTC 2040  MinB
1981 ATGGAACAAGTTGTTGAGGTTTATGAATATGCCCAAAAATTGGGTGGTGAAGCAGGATTC 2040  MinL
1981 ATGGAACAAGTCGTTGAGGTATACGAATACGCACAAAAATTAGGTGGAGAAGCAGGATTT 2040  MinFLC
     *********** ********:** ***** **.********.*****:***********

2041 TACCATATATTGAACAACCCAAAAGCATCATTATTATCTTTGACTCAATTTCCTCACTTC 2100  RSV_WT
2041 TATCATATACTGAATAATCCTAAAGCTAGTCTATTAAGCTTAACACAATTTCCACATTTT 2100  MinA
2041 TACCATATATTGAACAACCCAAAAGCATCATTATTATCTTTGACTCAATTTCCTCACTTC 2100  MinB
2041 TACCATATATTGAACAACCCAAAAGCATCATTATTATCTTTGACTCAATTTCCTCACTTC 2100  MinL
2041 TATCATATACTGAATAATCCTAAAGCTAGTCTATTAAGCTTAACACAATTTCCACATTTT 2100  MinFLC
     ** ****** **** ** **:*****:: : *****:  **.**:********:** **

2101 TCCAGTGTAGTATTAGGCAATGCTGCTGGCCTAGGCATAATGGGAGAGTACAGAGGTACA 2160  RSV_WT
2101 TCTAGCGTAGTGTTAGGTAACGCAGCTGGCCTAGGCATAATGGGCGAATATAGGGGTACA 2160  MinA
2101 TCCAGTGTAGTATTAGGCAATGCTGCTGGCCTAGGCATAATGGGAGAGTACAGAGGTACA 2160  MinB
2101 TCCAGTGTAGTATTAGGCAATGCTGCTGGCCTAGGCATAATGGGAGAGTACAGAGGTACA 2160  MinL
2101 TCTAGCGTAGTGTTAGGTAACGCAGCTGGCCTAGGCATAATGGGCGAATATAGGGGTACA 2160  MinFLC
     ** ** *****.***** ** **:********************.**.** **.******

2161 CCGAGGAATCAAGATCTATATGATGCAGCAAAGGCATATGCTGAACAACTCAAAGAAAAT 2220  RSV_WT
2161 CCTAGAAATCAGGATCTATATGACGCAGCTAAAGCATACGCTGAACAATTGAAAGAGAAT 2220  MinA
2161 CCGAGGAATCAAGATCTATATGATGCAGCAAAGGCATATGCTGAACAACTCAAAGAAAAT 2220  MinB
2161 CCGAGGAATCAAGATCTATATGATGCAGCAAAGGCATATGCTGAACAACTCAAAGAAAAT 2220  MinL
2161 CCTAGAAATCAGGATCTATATGACGCAGCTAAAGCATACGCTGAACAATTGAAAGAGAAT 2220  MinFLC
     ** **.*****.*********** *****:**.***** ********* * *****.***

2221 GGTGTGATTAACTACAGTGTACTAGACTTGACAGCAGAAGAACTAGAGGCTATCAAACAT 2280  RSV_WT
2221 GGAGTGATAAATTATTCCGTACTCGATCTAACAGCCGAAGAGTTGGAGGCAATTAAACAT 2280  MinA
2221 GGTGTGATTAACTACAGTGTACTAGACTTGACAGCAGAAGAACTAGAGGCTATCAAACAT 2280  MinB
2221 GGTGTGATTAACTACAGTGTACTAGACTTGACAGCAGAAGAACTAGAGGCTATCAAACAT 2280  MinL
2221 GGAGTGATAAATTATTCCGTACTCGATCTAACAGCCGAAGAGTTGGAGGCAATTAAACAT 2280  MinFLC
     **:*****:** ** :  *****.**  *.*****.*****. *.*****:** ******

2281 CAGCTTAATCCAAAAGATAATGATGTAGAGCTTTGAGTTAATAAAAAATGGGGCAAATAA 2340  RSV_WT
2281 CAATTGAATCCGAAAGATAATGACGTTGAGTTGTGAGTTAATAAAAAATGGGGCAAATAA 2340  MinA
2281 CAGCTTAATCCAAAAGATAATGATGTAGAGCTTTGAGTTAATAAAAAATGGGGCAAATAA 2340  MinB
2281 CAGCTTAATCCAAAAGATAATGATGTAGAGCTTTGAGTTAATAAAAAATGGGGCAAATAA 2340  MinL
2281 CAATTGAATCCGAAAGATAATGACGTTGAGTTGTGAGTTAATAAAAAATGGGGCAAATAA 2340  MinFLC
     **. * *****.*********** **:*** * ***************************
```

Figure 7 cont.

```
2341 ATCATCATGGAAAAGTTTGCTCCTGAATTCCATGGAGAAGATGCAAACAACAGGGCTACT 2400  RSV_WT
2341 ATCATCATGGAAAAGTTTGCTCCTGAATTCCATGGAGAAGACGCAAATAATAGGGCAACA 2400  MinA
2341 ATCATCATGGAAAAGTTTGCTCCTGAATTCCATGGAGAAGATGCAAACAACAGGGCTACT 2400  MinB
2341 ATCATCATGGAAAAGTTTGCTCCTGAATTCCATGGAGAAGATGCAAACAACAGGGCTACT 2400  MinL
2341 ATCATCATGGAAAAGTTTGCTCCTGAATTCCATGGAGAAGACGCAAATAATAGGGCAACA 2400  MinFLC
     ***************************************** ***** ** *****.**.

2401 AAATTCCTAGAATCAATAAAGGGCAAATTCACATCACCCAAAGATCCCAAGAAAAAAGAT 2460  RSV_WT
2401 AAATTCTTAGAGTCAATCAAGGGTAAGTTTACAAGTCCAAAAGATCCAAAGAAGAAAGAT 2460  MinA
2401 AAATTCCTAGAATCAATAAAGGGCAAATTCACATCACCCAAAGATCCCAAGAAAAAAGAT 2460  MinB
2401 AAATTCCTAGAATCAATAAAGGGCAAATTCACATCACCCAAAGATCCCAAGAAAAAAGAT 2460  MinL
2401 AAATTCTTAGAGTCAATCAAGGGTAAGTTTACAAGTCCAAAAGATCCAAAGAAGAAAGAT 2460  MinFLC
     ****** ****.*****.***** **.** ***: :**.********.*****.******

2461 AGTATCATATCTGTCAACTCAATAGATATAGAAGTAACCAAAGAAAGCCCTATAACATCA 2520  RSV_WT
2461 AGTATAATAAGCGTAAACTCAATTGATATCGAGGTGACAAAGGAATCACCTATAACATCT 2520  MinA
2461 AGTATCATATCTGTCAACTCAATAGATATAGAAGTAACCAAAGAAAGCCCTATAACATCA 2520  MinB
2461 AGTATCATATCTGTCAACTCAATAGATATAGAAGTAACCAAAGAAAGCCCTATAACATCA 2520  MinL
2461 AGTATAATAAGCGTAAACTCAATTGATATCGAGGTGACAAAGGAATCACCTATAACATCT 2520  MinFLC
     *****.***:  **.********:*****.**.**.**.**.***: .***********:

2521 AATTCAACTATTATCAACCCAACAAATGAGACAGATGATACTGCAGGGAACAAGCCCAAT 2580  RSV_WT
2521 AATAGTACAATAATAAATCCCACTAACGAAACAGACGATACCGCAGGCAATAAACCTAAT 2580  MinA
2521 AATTCAACTATTATCAACCCAACAAATGAGACAGATGATACTGCAGGGAACAAGCCCAAT 2580  MinB
2521 AATTCAACTATTATCAACCCAACAAATGAGACAGATGATACTGCAGGGAACAAGCCCAAT 2580  MinL
2521 AATAGTACAATAATAAATCCCACTAACGAAACAGACGATACCGCAGGCAATAAACCTAAT 2580  MinFLC
     ***: :**:**:**.** **.**:** **.***** ***** ***** ** **.** ***

2581 TATCAAAGAAAACCTCTAGTAAGTTTCAAAGAAGACCCTACACCAAGTGATAATCCCTTT 2640  RSV_WT
2581 TATCAACGGAAACCCTTAGTGTCATTCAAAGAAGATCCAACACCTAGTGATAATCCCTTT 2640  MinA
2581 TATCAAAGAAAACCTCTAGTAAGTTTCAAAGAAGACCCTACACCAAGTGATAATCCCTTT 2640  MinB
2581 TATCAAAGAAAACCTCTAGTAAGTTTCAAAGAAGACCCTACACCAAGTGATAATCCCTTT 2640  MinL
2581 TATCAACGGAAACCCTTAGTGTCATTCAAAGAAGATCCAACACCTAGTGATAATCCCTTT 2640  MinFLC
     ******.*.*****  ****.: :*********** **:*****:***************

2641 TCTAAACTATACAAAGAAACCATAGAAACATTTGATAACAATGAAGAAGAATCCAGCTAT 2700  RSV_WT
2641 AGTAAATTGTATAAGGAAACAATCGAAACATTCGATAATAACGAAGAAGAATCATCATAC 2700  MinA
2641 TCTAAACTATACAAAGAAACCATAGAAACATTTGATAACAATGAAGAAGAATCCAGCTAT 2700  MinB
2641 TCTAAACTATACAAAGAAACCATAGAAACATTTGATAACAATGAAGAAGAATCCAGCTAT 2700  MinL
2641 AGTAAATTGTATAAGGAAACAATCGAAACATTCGATAATAACGAAGAAGAATCATCATAC 2700  MinFLC
     : **** *.** **.*****.**.******** ***** ** ***********.:  .**

2701 TCATACGAAGAAATAAATGATCAGACAAACGATAATATAACAGCAAGATTAGATAGGATT 2760  RSV_WT
2701 TCATACGAAGAGATAAACGATCAGACTAACGATAATATAACCGCTAGACTAGATAGAATA 2760  MinA
2701 TCATACGAAGAAATAAATGATCAGACAAACGATAATATAACAGCAAGATTAGATAGGATT 2760  MinB
2701 TCATACGAAGAAATAAATGATCAGACAAACGATAATATAACAGCAAGATTAGATAGGATT 2760  MinL
2701 TCATACGAAGAGATAAACGATCAGACTAACGATAATATAACCGCTAGACTAGATAGAATA 2760  MinFLC
     ***********.***** ********:**************.**:*** *******.**:

2761 GATGAAAAAATTAAGTGAAATACTAGGAATGCTTCACACATTAGTAGTGGCAAGTGCAGGA 2820  RSV_WT
2761 GACGAAAAACTATCTGAAATACTAGGTATGTTACACACACTAGTAGTCGCATCTGCCGGA 2820  MinA
2761 GATGAAAAAATTAAGTGAAATACTAGGAATGCTTCACACATTAGTAGTGGCAAGTGCAGGA 2820  MinB
2761 GATGAAAAAATTAAGTGAAATACTAGGAATGCTTCACACATTAGTAGTGGCAAGTGCAGGA 2820  MinL
2761 GACGAAAAACTATCTGAAATACTAGGTATGTTACACACACTAGTAGTCGCATCTGCCGGA 2820  MinFLC
     ** ****** **: ************:*** *:****** ******* ***: ***.***

2821 CCTACATCTGCTCGGGATGGTATAAGAGATGCCATGGTTGGTTTAAGAGAAGAAATGATA 2880  RSV_WT
2821 CCTACAAGTGCTAGAGATGGGATAAGGGATGCAATGGTAGGGTTAAGGGAAGAAATGATA 2880  MinA
2821 CCTACATCTGCTCGGGATGGTATAAGAGATGCCATGGTTGGTTTAAGAGAAGAAATGATA 2880  MinB
2821 CCTACATCTGCTCGGGATGGTATAAGAGATGCCATGGTTGGTTTAAGAGAAGAAATGATA 2880  MinL
2821 CCTACAAGTGCTAGAGATGGGATAAGGGATGCAATGGTAGGGTTAAGGGAAGAAATGATA 2880  MinFLC
     ******: ****.*.***** *****.*****.*****.**:** *****.************

2881 GAAAAAATCAGAACTGAAGCATTAATGACCAATGACAGATTAGAAGCTATGGCAAGACTC 2940  RSV_WT
2881 GAGAAAATTAGAACCGAAGCATTAATGACTAACGATAGACTCGAAGCAATGGCTAGACTT 2940  MinA
2881 GAAAAAATCAGAACTGAAGCATTAATGACCAATGACAGATTAGAAGCTATGGCAAGACTC 2940  MinB
2881 GAAAAAATCAGAACTGAAGCATTAATGACCAATGACAGATTAGAAGCTATGGCAAGACTC 2940  MinL
2881 GAGAAAATTAGAACCGAAGCATTAATGACTAACGATAGACTCGAAGCAATGGCTAGACTT 2940  MinFLC
     **.***** ***** ************** ** ** *** *.*****:*****:*****
```

Figure 7 cont.

```
2941 AGGAATGAGGAAAGTGAAAAGATGGCAAAAGACACATCAGATGAAGTGTCTCTCAATCCA 3000  RSV_WT
2941 AGAAACGAAGAATCCGAAAAGATGGCAAAAGATACATCTGACGAAGTGTCACTTAATCCT 3000  MinA
2941 AGGAATGAGGAAAGTGAAAAGATGGCAAAAGACACATCAGATGAAGTGTCTCTCAATCCA 3000  MinB
2941 AGGAATGAGGAAAGTGAAAAGATGGCAAAAGACACATCAGATGAAGTGTCTCTCAATCCA 3000  MinL
2941 AGAAACGAAGAATCCGAAAAGATGGCAAAAGATACATCTGACGAAGTGTCACTTAATCCT 3000  MinFLC
     **.** **.***:  ***************** *****:** ********:** *****:

3001 ACATCAGAGAAATTGAACAACCTATTGGAAGGGAATGATAGTGACAATGATCTATCACTT 3060  RSV_WT
3001 ACTAGCGAAAAATTGAATAATCTATTAGAGGGAAACGATAGTGATAACGATCTATCACTC 3060  MinA
3001 ACATCAGAGAAATTGAACAACCTATTGGAAGGGAATGATAGTGACAATGATCTATCACTT 3060  MinB
3001 ACATCAGAGAAATTGAACAACCTATTGGAAGGGAATGATAGTGACAATGATCTATCACTT 3060  MinL
3001 ACTAGCGAAAAATTGAATAATCTATTAGAGGGAAACGATAGTGATAACGATCTATCACTC 3060  MinFLC
     **:: .**.******** ** *****.**.**.** ******** ** ***********

3061 GAAGATTTCTGATTAGTTACCAATCTTCACATCAACACACAATACCAACAGAAGACCAAC 3120  RSV_WT
3061 GAAGATTTCTGATTAGTTACCAATCTTCACATCAACACACAATACCAACAGAAGACCAAC 3120  MinA
3061 GAAGATTTCTGATTAGTTACCAATCTTCACATCAACACACAATACCAACAGAAGACCAAC 3120  MinB
3061 GAAGATTTCTGATTAGTTACCAATCTTCACATCAACACACAATACCAACAGAAGACCAAC 3120  MinL
3061 GAAGATTTCTGATTAGTTACCAATCTTCACATCAACACACAATACCAACAGAAGACCAAC 3120  MinFLC
     ************************************************************

3121 AAACTAACCAACCCAATCATCCAACCAAACATCCATCCGCCAATCAGCCAAACAGCCAAC 3180  RSV_WT
3121 AAACTAACCAACCCAATCATCCAACCAAACATCCATCCGCCAATCAGCCAAACAGCCAAC 3180  MinA
3121 AAACTAACCAACCCAATCATCCAACCAAACATCCATCCGCCAATCAGCCAAACAGCCAAC 3180  MinB
3121 AAACTAACCAACCCAATCATCCAACCAAACATCCATCCGCCAATCAGCCAAACAGCCAAC 3180  MinL
3121 AAACTAACCAACCCAATCATCCAACCAAACATCCATCCGCCAATCAGCCAAACAGCCAAC 3180  MinFLC
     ************************************************************

3181 AAAACAACCAGCCAATCCAAAACTAACCACCCGGAAAAAATCTATAATATAGTTACAAAA 3240  RSV_WT
3181 AAAACAACCAGCCAATCCAAAACTAACCACCCGGAAAAAATCTATAATATAGTTACAAAA 3240  MinA
3181 AAAACAACCAGCCAATCCAAAACTAACCACCCGGAAAAAATCTATAATATAGTTACAAAA 3240  MinB
3181 AAAACAACCAGCCAATCCAAAACTAACCACCCGGAAAAAATCTATAATATAGTTACAAAA 3240  MinL
3181 AAAACAACCAGCCAATCCAAAACTAACCACCCGGAAAAAATCTATAATATAGTTACAAAA 3240  MinFLC
     ************************************************************

3241 AAAGGAAAGGGTGGGGCAAATATGGAAACATACGTGAACAAGCTTCACGAAGGCTCCACA 3300  RSV_WT
3241 AAAGGAAAGGGTGGGGCAAATATGGAAACATACGTGAACAAGCTTCACGAAGGATCAACA 3300  MinA
3241 AAAGGAAAGGGTGGGGCAAATATGGAAACATACGTGAACAAGCTTCACGAAGGCTCCACA 3300  MinB
3241 AAAGGAAAGGGTGGGGCAAATATGGAAACATACGTGAACAAGCTTCACGAAGGCTCCACA 3300  MinL
3241 AAAGGAAAGGGTGGGGCAAATATGGAAACATACGTGAACAAGCTTCACGAAGGATCAACA 3300  MinFLC
     *****************************************************.**.***

3301 TACACAGCTGCTGTTCAATACAATGTCTTAGAAAAAGACGATGACCCTGCATCACTTACA 3360  RSV_WT
3301 TATACAGCTGCAGTCCAATATAACGTACTCGAAAAAGACGACGATCCCGCTAGCCTAACA 3360  MinA
3301 TACACAGCTGCTGTTCAATACAATGTCTTAGAAAAAGACGATGACCCTGCATCACTTACA 3360  MinB
3301 TACACAGCTGCTGTTCAATACAATGTCTTAGAAAAAGACGATGACCCTGCATCACTTACA 3360  MinL
3301 TATACAGCTGCAGTCCAATATAACGTACTCGAAAAAGACGACGATCCCGCTAGCCTAACA 3360  MinFLC
     ** ********:** ***** ** **. *.*********** ** ** **:: .**:***

3361 ATATGGGTGCCCATGTTCCAATCATCTATGCCAGCAGATTTACTTATAAAAGAACTAGCT 3420  RSV_WT
3361 ATATGGGTCCCAATGTTTCAATCTAGTATGCCCGCTGATCTATTAATCAAAGAACTAGCT 3420  MinA
3361 ATATGGGTGCCCATGTTCCAATCATCTATGCCAGCAGATTTACTTATAAAAGAACTAGCT 3420  MinB
3361 ATATGGGTGCCCATGTTCCAATCATCTATGCCAGCAGATTTACTTATAAAAGAACTAGCT 3420  MinL
3361 ATATGGGTCCCAATGTTTCAATCTAGTATGCCCGCTGATCTATTAATCAAAGAACTAGCT 3420  MinFLC
     ******** **.***** *****:: ******.**:*** ** *:**.************

3421 AATGTCAACATACTAGTGAAACAAATATCCACACCCAAGGGACCTTCACTAAGAGTCATG 3480  RSV_WT
3421 AACGTTAACATACTAGTCAAACAAATTAGTACACCTAAGGGACCCTCACTTAGAGTGATG 3480  MinA
3421 AATGTCAACATACTAGTGAAACAAATATCCACACCCAAGGGACCTTCACTAAGAGTCATG 3480  MinB
3421 AATGTCAACATACTAGTGAAACAAATATCCACACCCAAGGGACCTTCACTAAGAGTCATG 3480  MinL
3421 AACGTTAACATACTAGTCAAACAAATTAGTACACCTAAGGGACCCTCACTTAGAGTGATG 3480  MinFLC
     ** ** *********** ********::  ***** ******** *****:***** ***

3481 ATAAACTCAAGAAGTGCAGTGCTAGCACAAATGCCCAGCAAATTTACCATATGCGCTAAT 3540  RSV_WT
3481 ATTAATAGTAGATCCGCAGTCCTAGCACAAATGCCTAGTAAGTTTACAATATGTGCTAAC 3540  MinA
3481 ATAAACTCAAGAAGTGCAGTGCTAGCACAAATGCCCAGCAAATTTACCATATGCGCTAAT 3540  MinB
3481 ATAAACTCAAGAAGTGCAGTGCTAGCACAAATGCCCAGCAAATTTACCATATGCGCTAAT 3540  MinL
3481 ATTAATAGTAGATCCGCAGTCCTAGCACAAATGCCTAGTAAGTTTACAATATGTGCTAAC 3540  MinFLC
     **:** : :***:  ***** *************** ** **.*****.***** *****
```

Figure 7 cont.

```
3541 GTGTCCTTGGATGAAAGAAGCAAACTAGCATATGATGTAACCACACCCTGTGAAATCAAG 3600  RSV_WT
3541 GTAAGCTTAGACGAACGATCAAAACTAGCATACGATGTGACAACACCATGCGAAATCAAA 3600  MinA
3541 GTGTCCTTGGATGAAAGAAGCAAACTAGCATATGATGTAACCACACCCTGTGAAATCAAG 3600  MinB
3541 GTGTCCTTGGATGAAAGAAGCAAACTAGCATATGATGTAACCACACCCTGTGAAATCAAG 3600  MinL
3541 GTAAGCTTAGACGAACGATCAAAACTAGCATACGATGTGACAACACCATGCGAAATCAAA 3600  MinFLC
     **.: ***.** ***.**: .*********** *****.**.*****.** ********.

3601 GCATGTAGTCTAACATGCCTAAAATCAAAAAATATGTTGACTACAGTTAAAGATCTCACT 3660  RSV_WT
3601 GCATGTTCATTGACATGTCTTAAATCAAAGAATATGCTAACAACAGTCAAAGATCTAACA 3660  MinA
3601 GCATGTAGTCTAACATGCCTAAAATCAAAAAATATGTTGACTACAGTTAAAGATCTCACT 3660  MinB
3601 GCATGTAGTCTAACATGCCTAAAATCAAAAAATATGTTGACTACAGTTAAAGATCTCACT 3660  MinL
3601 GCATGTTCATTGACATGTCTTAAATCAAAGAATATGCTAACAACAGTCAAAGATCTAACA 3660  MinFLC
     ******: : *.***** **:********.****** *.**:***** ********.**:

3661 ATGAAGACACTCAACCCTACACATGATATTATTGCTTTATGTGAATTTGAAAACATAGTA 3720  RSV_WT
3661 ATGAAAACACTTAATCCCACACACGATATAATCGCACTATGCGAATTCGAAAATATAGTG 3720  MinA
3661 ATGAAGACACTCAACCCTACACATGATATTATTGCTTTATGTGAATTTGAAAACATAGTA 3720  MinB
3661 ATGAAGACACTCAACCCTACACATGATATTATTGCTTTATGTGAATTTGAAAACATAGTA 3720  MinL
3661 ATGAAAACACTTAATCCCACACACGATATAATCGCACTATGCGAATTCGAAAATATAGTG 3720  MinFLC
     *****.***** ** ** ***** *****:** **: **** ***** ***** *****.

3721 ACATCAAAAAAAGTCATAATACCAACATACCTAAGATCCATCAGTGTCAGAAATAAAGAT 3780  RSV_WT
3721 ACTAGTAAGAAAGTGATAATCCCTACATACCTTAGATCAATATCCGTTAGAAATAAGGAT 3780  MinA
3721 ACATCAAAAAAAGTCATAATACCAACATACCTAAGATCCATCAGTGTCAGAAATAAAGAT 3780  MinB
3721 ACATCAAAAAAAGTCATAATACCAACATACCTAAGATCCATCAGTGTCAGAAATAAAGAT 3780  MinL
3721 ACTAGTAAGAAAGTGATAATCCCTACATACCTTAGATCAATATCCGTTAGAAATAAGGAT 3780  MinFLC
     **:: :**.***** *****.**:********:*****.**.:  ** ********.***

3781 CTGAACACACTTGAAAATATAACAACCACTGAATTCAAAAATGCTATCACAAATGCAAAA 3840  RSV_WT
3781 CTGAATACACTCGAAAATATAACAACAACCGAATTCAAAAACGCTATAACTAACGCTAAG 3840  MinA
3781 CTGAACACACTTGAAAATATAACAACCACTGAATTCAAAAATGCTATCACAAATGCAAAA 3840  MinB
3781 CTGAACACACTTGAAAATATAACAACCACTGAATTCAAAAATGCTATCACAAATGCAAAA 3840  MinL
3781 CTGAATACACTCGAAAATATAACAACAACCGAATTCAAAAACGCTATAACTAACGCTAAG 3840  MinFLC
     ***** ***** **************.** *********** *****.**:** **:**.

3841 ATCATCCCTTACTCAGGATTACTATTAGTCATCACAGTGACTGACAACAAAGGAGCATTC 3900  RSV_WT
3841 ATAATCCCTTACTCCGGACTATTGTTAGTGATAACCGTAACCGATAATAAGGGAGCATTC 3900  MinA
3841 ATCATCCCTTACTCAGGATTACTATTAGTCATCACAGTGACTGACAACAAAGGAGCATTC 3900  MinB
3841 ATCATCCCTTACTCAGGATTACTATTAGTCATCACAGTGACTGACAACAAAGGAGCATTC 3900  MinL
3841 ATAATCCCTTACTCCGGACTATTGTTAGTGATAACCGTAACCGATAATAAGGGAGCATTC 3900  MinFLC
     **.***********.*** ** *.***** **.**.**.** ** ** **.*********

3901 AAATACATAAAGCCACAAAGTCAATTCATAGTAGATCTTGGAGCTTACCTAGAAAAAGAA 3960  RSV_WT
3901 AAATACATAAAACCCCAATCCCAATTTATAGTCGATTTAGGCGCATACTTAGAAAAAGAA 3960  MinA
3901 AAATACATAAAGCCACAAAGTCAATTCATAGTAGATCTTGGAGCTTACCTAGAAAAAGAA 3960  MinB
3901 AAATACATAAAGCCACAAAGTCAATTCATAGTAGATCTTGGAGCTTACCTAGAAAAAGAA 3960  MinL
3901 AAATACATAAAACCCCAATCCCAATTTATAGTCGATTTAGGCGCATACTTAGAAAAAGAA 3960  MinFLC
     ***********.**.***:  ***** *****.*** *:**.**:*** ***********

3961 AGTATATATTATGTTACCACAAATTGGAAGCACACAGCTACACGATTTGCAATCAAACCC 4020  RSV_WT
3961 TCAATCTATTACGTTACAACTAATTGGAAACATACCGCTACTAGATTCGCAATCAAACCT 4020  MinA
3961 AGTATATATTATGTTACCACAAATTGGAAGCACACAGCTACACGATTTGCAATCAAACCC 4020  MinB
3961 AGTATATATTATGTTACCACAAATTGGAAGCACACAGCTACACGATTTGCAATCAAACCC 4020  MinL
3961 TCAATCTATTACGTTACAACTAATTGGAAACATACCGCTACTAGATTCGCAATCAAACCT 4020  MinFLC
     : :**.***** *****.**:********.** **.*****:.**** ***********

4021 ATGGAAGATTAACCTTTTTCCTCTACATCAGTGTGTTAATTCATACAAACTTTCTACCTA 4080  RSV_WT
4021 ATGGAAGATTAACCTTTTTCCTCTACATCAGTGTGTTAATTCATACAAACTTTCTACCTA 4080  MinA
4021 ATGGAAGATTAACCTTTTTCCTCTACATCAGTGTGTTAATTCATACAAACTTTCTACCTA 4080  MinB
4021 ATGGAAGATTAACCTTTTTCCTCTACATCAGTGTGTTAATTCATACAAACTTTCTACCTA 4080  MinL
4021 ATGGAAGATTAACCTTTTTCCTCTACATCAGTGTGTTAATTCATACAAACTTTCTACCTA 4080  MinFLC
     ************************************************************

4081 CATTCTTCACTTCACCATCACAATCACAAACACTCTGTGGTTCAACCAATCAAACAAAAC 4140  RSV_WT
4081 CATTCTTCACTTCACCATCACAATCACAAACACTCTGTGGTTCAACCAATCAAACAAAAC 4140  MinA
4081 CATTCTTCACTTCACCATCACAATCACAAACACTCTGTGGTTCAACCAATCAAACAAAAC 4140  MinB
4081 CATTCTTCACTTCACCATCACAATCACAAACACTCTGTGGTTCAACCAATCAAACAAAAC 4140  MinL
4081 CATTCTTCACTTCACCATCACAATCACAAACACTCTGTGGTTCAACCAATCAAACAAAAC 4140  MinFLC
     ************************************************************
```

Figure 7 cont.

```
4141 TTATCTGAAGTCCCAGATCATCCCAAGTCATTGTTTATCAGATCTAGTACTCAAATAAGT 4200  RSV_WT
4141 TTATCTGAAGTCCCAGATCATCCCAAGTCATTGTTTATCAGATCTAGTACTCAAATAAGT 4200  MinA
4141 TTATCTGAAGTCCCAGATCATCCCAAGTCATTGTTTATCAGATCTAGTACTCAAATAAGT 4200  MinB
4141 TTATCTGAAGTCCCAGATCATCCCAAGTCATTGTTTATCAGATCTAGTACTCAAATAAGT 4200  MinL
4141 TTATCTGAAGTCCCAGATCATCCCAAGTCATTGTTTATCAGATCTAGTACTCAAATAAGT 4200  MinFLC
     ************************************************************

4201 TAATAAAAAATATACACATGGGGCAAATAATCATTGGAGGAAATCCAACTAATCACAATA 4260  RSV_WT
4201 TAATAAAAAATATACACATGGGGCAAATAATCATTGGAGGAAATCCAACTAATCACAATA 4260  MinA
4201 TAATAAAAAATATACACATGGGGCAAATAATCATTGGAGGAAATCCAACTAATCACAATA 4260  MinB
4201 TAATAAAAAATATACACATGGGGCAAATAATCATTGGAGGAAATCCAACTAATCACAATA 4260  MinL
4201 TAATAAAAAATATACACATGGGGCAAATAATCATTGGAGGAAATCCAACTAATCACAATA 4260  MinFLC
     ************************************************************

4261 TCTGTTAACATAGACAAGTCCACACACCATACAGAATCAACCAATGGAAAATACATCCAT 4320  RSV_WT
4261 TCTGTTAACATAGACAAGTCCACACACCATACAGAATCAACCAATGGAAAATACATCCAT 4320  MinA
4261 TCTGTTAACATAGACAAGTCCACACACCATACAGAATCAACCAATGGAAAATACATCCAT 4320  MinB
4261 TCTGTTAACATAGACAAGTCCACACACCATACAGAATCAACCAATGGAAAATACATCCAT 4320  MinL
4261 TCTGTTAACATAGACAAGTCCACACACCATACAGAATCAACCAATGGAAAATACATCCAT 4320  MinFLC
     ************************************************************

4321 AACAATAGAATTCTCAAGCAAATTCTGGCCTTACTTTACACTAATACACATGATCACAAC 4380  RSV_WT
4321 AACAATAGAATTCTCTAGCAAATTTTGGCCTTACTTTACACTAATACACATGATAACTAC 4380  MinA
4321 AACAATAGAATTCTCAAGCAAATTCTGGCCTTACTTTACACTAATACACATGATCACAAC 4380  MinB
4321 AACAATAGAATTCTCAAGCAAATTCTGGCCTTACTTTACACTAATACACATGATCACAAC 4380  MinL
4321 AACAATAGAATTCTCTAGCAAATTTTGGCCTTACTTTACACTAATACACATGATAACTAC 4380  MinFLC
     ***************:******** *****************************.**:**

4381 AATAATCTCTTTGCTAATCATAATCTCCATCATGATTGCAATACTAAACAAACTTTGTGA 4440  RSV_WT
4381 AATCATATCCCTATTAATCATAATCTCAATTATGATCGCAATCCTTAACAAACTATGTGA 4440  MinA
4381 AATAATCTCTTTGCTAATCATAATCTCCATCATGATTGCAATACTAAACAAACTTTGTGA 4440  MinB
4381 AATAATCTCTTTGCTAATCATAATCTCCATCATGATTGCAATACTAAACAAACTTTGTGA 4440  MinL
4381 AATCATATCCCTATTAATCATAATCTCAATTATGATCGCAATCCTTAACAAACTATGTGA 4440  MinFLC
     ***.**.**  *. *************.** ***** *****.**:********:*****

4441 ATATAACGTATTCCATAACAAAACCTTTGAGTTACCAAGAGCTCGAGTTAATACTTGATA 4500  RSV_WT
4441 GTATAACGTATTCCATAACAAAACATTCGAATTGCCAAGAGCTCGAGTGAATACCTGATA 4500  MinA
4441 ATATAACGTATTCCATAACAAAACCTTTGAGTTACCAAGAGCTCGAGTTAATACTTGATA 4500  MinB
4441 ATATAACGTATTCCATAACAAAACCTTTGAGTTACCAAGAGCTCGAGTTAATACTTGATA 4500  MinL
4441 GTATAACGTATTCCATAACAAAACATTCGAATTGCCAAGAGCTCGAGTGAATACCTGATA 4500  MinFLC
     .***********************.** **.**.************** ***** *****

4501 AAGTAGTTAATTAAAAATAGTCATAACAATGAACTAGGATATCAAGACTAACAATAACAT 4560  RSV_WT
4501 AAGTAGTTAATTAAAAATAGTCATAACAATGAACTAGGATATCAAGACTAACAATAACAT 4560  MinA
4501 AAGTAGTTAATTAAAAATAGTCATAACAATGAACTAGGATATCAAGACTAACAATAACAT 4560  MinB
4501 AAGTAGTTAATTAAAAATAGTCATAACAATGAACTAGGATATCAAGACTAACAATAACAT 4560  MinL
4501 AAGTAGTTAATTAAAAATAGTCATAACAATGAACTAGGATATCAAGACTAACAATAACAT 4560  MinFLC
     ************************************************************

4561 TGGGGCAAATGCAAACATGTCCAAAAACAAGGACCAACGCACCGCTAAGACATTAGAAAG 4620  RSV_WT
4561 TGGGGCAAATGCAAACATGTCCAAAAACAAGGACCAACGCACCGCTAAGACATTAGAAAG 4620  MinA
4561 TGGGGCAAATGCAAACATGTCCAAAAACAAGGACCAACGCACCGCTAAAACACTCGAAAG 4620  MinB
4561 TGGGGCAAATGCAAACATGTCCAAAAACAAGGACCAACGCACCGCTAAGACATTAGAAAG 4620  MinL
4561 TGGGGCAAATGCAAACATGTCCAAAAACAAGGACCAACGCACCGCTAAAACACTCGAAAG 4620  MinFLC
     ***********************************************.*** *.*****

4621 GACCTGGGACACTCTCAATCATTTATTATTCATATCATCGTGCTTATATAAGTTAAATCT 4680  RSV_WT
4621 GACCTGGGACACTCTCAATCATTTATTATTCATATCATCGTGCTTATATAAGTTAAATCT 4680  MinA
4621 GACATGGGATACCCTTAATCACCTATTATTCATAAGCTCATGCTTATATAAATTGAACCT 4680  MinB
4621 GACCTGGGACACTCTCAATCATTTATTATTCATATCATCGTGCTTATATAAGTTAAATCT 4680  MinL
4621 GACATGGGATACCCTTAATCACCTATTATTCATAAGCTCATGCTTATATAAATTGAACCT 4680  MinFLC
     ***.***** ** ** *****  ***********: .**.***********.**.** **

4681 TAAATCTGTAGCACAAATCACATTATCCATTCTGGCAATGATAATCTCAACTTCACTTAT 4740  RSV_WT
4681 TAAATCTGTAGCACAAATCACATTATCCATTCTGGCAATGATAATCTCAACTTCACTTAT 4740  MinA
4681 TAAATCCGTCGCACAGATAACCCTATCAATACTCGCAATGATAATCTCAACAAGCTTAAT 4740  MinB
4681 TAAATCTGTAGCACAAATCACATTATCCATTCTGGCAATGATAATCTCAACTTCACTTAT 4740  MinL
4681 TAAATCCGTCGCACAGATAACCCTATCAATACTCGCAATGATAATCTCAACAAGCTTAAT 4740  MinFLC
     ****** **.*****.**.**. ****.**:** *****************:: . *:**
```

Figure 7 cont.

```
4741 AATTGCAGCCATCATATTCATAGCCTCGGCAAACCACAAAGTCACACCAACAACTGCAAT 4800  MinA
4741 CATAGCCGCAATAATCTTTATCGCTAGCGCTAACCATAAGGTAACCCCAACAACCGCAAT 4800  MinB
4741 AATTGCAGCCATCATATTCATAGCCTCGGCAAACCACAAAGTCACACCAACAACTGCAAT 4800  MinL
4741 CATAGCCGCAATAATCTTTATCGCTAGCGCTAACCATAAGGTAACCCCAACAACCGCAAT 4800  MinFLC
     .**:**.**.**.**.**.** **.** :  **:***** **.**.**.******** *****

4801 CATACAAGATGCAACAAGCCAGATCAAGAACACAACCCCAACATACCTCACCCAGAATCC 4860  RSV_WT
4801 CATACAAGATGCAACAAGCCAGATCAAGAACACAACCCCAACATACCTCACCCAGAATCC 4860  MinA
4801 TATACAGGACGCAACATCCCAAATCAAAAACACAACCCCAACATACTTAACCCAAAACCC 4860  MinB
4801 CATACAAGATGCAACAAGCCAGATCAAGAACACAACCCCAACATACCTCACCCAGAATCC 4860  MinL
4801 TATACAGGACGCAACATCCCAAATCAAAAACACAACCCCAACATACTTAACCCAAAACCC 4860  MinFLC
      *****.** ******: ***.*****.****************** *.*****.** **

4861 TCAGCTTGGAATCAGTCCCTCTAATCCGTCTGAAATTACATCACAAATCACCACCATACT 4920  RSV_WT
4861 TCAGCTTGGAATCAGTCCCTCTAATCCGTCTGAAATTACATCACAAATCACCACCATACT 4920  MinA
4861 ACAACTCGGAATCTCACCCTCTAACCCATCCGAAATTACCTCACAGATTACAACGATACT 4920  MinB
4861 TCAGCTTGGAATCAGTCCCTCTAATCCGTCTGAAATTACATCACAAATCACCACCATACT 4920  MinL
4861 ACAACTCGGAATCTCACCCTCTAACCCATCCGAAATTACCTCACAGATTACAACGATACT 4920  MinFLC
     :**.** ******: :******** **.** ********.*****.** **.** *****

4921 AGCTTCAACAACACCAGGAGTCAAGTCAACCCTGCAATCCACAACAGTCAAGACCAAAAA 4980  RSV_WT
4921 AGCTTCAACAACACCAGGAGTCAAGTCAACCCTGCAATCCACAACAGTCAAGACCAAAAA 4980  MinA
4921 CGCAAGTACAACCCCCCGGAGTCAAATCGACACTCCAATCGACAACCGTAAAGACTAAGAA 4980  MinB
4921 AGCTTCAACAACACCAGGAGTCAAGTCAACCCTGCAATCCACAACAGTCAAGACCAAAAA 4980  MinL
4921 CGCAAGTACAACCCCCCGGAGTCAAATCGACACTCCAATCGACAACCGTAAAGACTAAGAA 4980  MinFLC
     .**:: :*****.**.********.**.**.** ***** *****.**.***** **.**

4981 CACAACAACAACTCAAACACAACCCAGCAAGCCCACCACAAAACAACGCCAAAACAAACC 5040  RSV_WT
4981 CACAACAACAACTCAAACACAACCCAGCAAGCCCACCACAAAACAACGCCAAAACAAACC 5040  MinA
4981 TACAACAACAACCCAAACCCAACCTAGTAAGCCTACAACTAAGCAACGCCAAAACAAACC 5040  MinB
4981 CACAACAACAACTCAAACACAACCCAGCAAGCCCACCACAAAACAACGCCAAAACAAACC 5040  MinL
4981 TACAACAACAACCCAAACCCAACCTAGTAAGCCTACAACTAAGCAACGCCAAAACAAACC 5040  MinFLC
      *********** *****.***** ** ***** **.**:**.*****************

5041 ACCAAGCAAACCCAATAATGATTTTCACTTTGAAGTGTTCAACTTTGTACCCTGCAGCAT 5100  RSV_WT
5041 ACCAAGCAAACCCAATAATGATTTTCACTTTGAAGTGTTCAACTTTGTACCCTGCAGCAT 5100  MinA
5041 TCCCTCTAAACCGAATAACGATTTTCACTTCGAAGTGTTCAATTTCGTACCATGCTCAAT 5100  MinB
5041 ACCAAGCAAACCCAATAATGATTTTCACTTTGAAGTGTTCAACTTTGTACCCTGCAGCAT 5100  MinL
5041 TCCCTCTAAACCGAATAACGATTTTCACTTCGAAGTGTTCAATTTCGTACCATGCTCAAT 5100  MinFLC
     :**.:  ***** ***** *********** *********** ** *****.***: .**

5101 ATGCAGCAACAATCCAACCTGCTGGGCTATCTGCAAAAGAATACCAAACAAAAAACCAGG 5160  RSV_WT
5101 ATGCAGCAACAATCCAACCTGCTGGGCTATCTGCAAAAGAATACCAAACAAAAAACCAGG 5160  MinA
5101 TTGCTCTAATAACCCAACATGCTGGGCCATATGCAAACGCATCCCAAACAAGAAACCCGG 5160  MinB
5101 ATGCAGCAACAATCCAACCTGCTGGGCTATCTGCAAAAGAATACCAAACAAAAAACCAGG 5160  MinL
5101 TTGCTCTAATAACCCAACATGCTGGGCCATATGCAAACGCATCCCAAACAAGAAACCCGG 5160  MinFLC
     :***:  ** ** *****.******** **.******.*.**.********.*****.**

5161 AAAGAAAACCACTACCAAGCCCACAAAAAAAACCAACCCTCAAGACAACCAAAAAAGATCC 5220  RSV_WT
5161 AAAGAAAACCACTACCAAGCCCACAAAAAAAACCAACCCTCAAGACAACCAAAAAAGATCC 5220  MinA
5161 AAAGAAAACAACCACTAAGCCAACAAAGAAACCAACCCTTAAGACAACCAAGAAAGATCC 5220  MinB
5161 AAAGAAAACCACTACCAAGCCCACAAAAAAAACCAACCCTCAAGACAACCAAAAAAGATCC 5220  MinL
5161 AAAGAAAACAACCACTAAGCCAACAAAGAAACCAACCCTTAAGACAACCAAGAAAGATCC 5220  MinFLC
     *********.** ** *****.*****.*********** ***********.********

5221 CAAACCTCAAACCACTAAATCAAAGGAAGTACCCACCACCAAGCCCACAGAAGAGCCAAC 5280  RSV_WT
5221 CAAACCTCAAACCACTAAATCAAAGGAAGTACCCACCACCAAGCCCACAGAAGAGCCAAC 5280  MinA
5221 AAAACCCCAAACAACTAAGTCTAAAGAGGTCCCAACAACTAAGCCAACCGAAGAGCCAAC 5280  MinB
5221 CAAACCTCAAACCACTAAATCAAAGGAAGTACCCACCACCAAGCCCACAGAAGAGCCAAC 5280  MinL
5221 AAAACCCCAAACAACTAAGTCTAAAGAGGTCCCAACAACTAAGCCAACCGAAGAGCCAAC 5280  MinFLC
     .***** *****.*****.**:**.**.**.**.**.** *****.**.***********

5281 CATCAACACCACCAAAACAAACATCATAACTACACTACTCACCTCCAACACCACAGGAAA 5340  RSV_WT
5281 CATCAACACCACCAAAACAAACATCATAACTACACTACTCACCTCCAACACCACAGGAAA 5340  MinA
5281 AATCAATACAACTAAGACTAATATAATCACAACCTTACTGACATCTAACACAACCGGAAA 5340  MinB
5281 CATCAACACCACCAAAACAAACATCATAACTACACTACTCACCTCCAACACCACAGGAAA 5340  MinL
5281 AATCAATACAACTAAGACTAATATAATCACAACCTTACTGACATCTAACACAACCGGAAA 5340  MinFLC
     .***** **.** **.**:** **.**.**:**. **** **.** *****.**.*****
```

Figure 7 cont.

```
5341 TCCAGAACTCACAAGTCAAATGGAAACCTTCCACTCAACTTCCTCCGAAGGCAATCCAAG 5400  RSV_WT
5341 TCCAGAACTCACAAGTCAAATGGAAACCTTCCACTCAACTTCCTCCGAAGGCAATCCAAG 5400  MinA
5341 TCCCGAACTGACATCCCAAATGGAAACCTTTCACTCAACCTCTAGCGAAGGCAATCCCTC 5400  MinB
5341 TCCAGAACTCACAAGTCAAATGGAAACCTTCCACTCAACTTCCTCCGAAGGCAATCCAAG 5400  MinL
5341 TCCCGAACTGACATCCCAAATGGAAACCTTTCACTCAACCTCTAGCGAAGGCAATCCCTC 5400  MinFLC
     ***.***** ***:  ************** ******** ** : ************.:

5401 CCCTTCTCAAGTCTCTACAACATCCGAGTACCCATCACAACCTTCATCTCCACCCAACAC 5460  RSV_WT
5401 CCCTTCTCAAGTCTCTACAACATCCGAGTACCCATCACAACCTTCATCTCCACCCAACAC 5460  MinA
5401 ACCATCCCAAGTCTCAACCACTAGCGAATACCCATCCCAACCTAGCTCACCTCCCAATAC 5460  MinB
5401 CCCTTCTCAAGTCTCTACAACATCCGAGTACCCATCACAACCTTCATCTCCACCCAACAC 5460  MinL
5401 ACCATCCCAAGTCTCAACCACTAGCGAATACCCATCCCAACCTAGCTCACCTCCCAATAC 5460  MinFLC
     .**:** ********:**.**:: ***.********.******: .**:**:***** **

5461 ACCACGCCAGTAGTTACTTAAAAACATATTATCACAAAAGGCCTTGACCAACTTAAACAG 5520  RSV_WT
5461 ACCACGCCAGTAGTTACTTAAAAACATATTATCACAAAAGGCCTTGACCAACTTAAACAG 5520  MinA
5461 CCCTAGACAGTAGTTACTTAAAAACATATTATCACAAAAGGCCTTGACCAACTTAAACAG 5520  MinB
5461 ACCACGCCAGTAGTTACTTAAAAACATATTATCACAAAAGGCCTTGACCAACTTAAACAG 5520  MinL
5461 CCCTAGACAGTAGTTACTTAAAAACATATTATCACAAAAGGCCTTGACCAACTTAAACAG 5520  MinFLC
     .**:.*.****************************************************

5521 AATCAAAATAAACTCTGGGGCAAATAACAATGGAGTTGCTAATCCTCAAAGCAAATGCAA 5580  RSV_WT
5521 AATCAAAATAAACTCTGGGGCAAATAACAATGGAGTTGCTAATCCTCAAAGCAAATGCAA 5580  MinA
5521 AATCAAAATAAACTCTGGGGCAAATAACAATGGAGTTGCTAATCCTCAAAGCAAATGCAA 5580  MinB
5521 AATCAAAATAAACTCTGGGGCAAATAACAATGGAGTTGCTAATCCTCAAAGCAAATGCAA 5580  MinL
5521 AATCAAAATAAACTCTGGGGCAAATAACAATGGAGTTGCTAATCCTCAAAGCAAATGCAA 5580  MinFLC
     ************************************************************

5581 TTACCACAATCCTCACTGCAGTCACATTTTGTTTTGCTTCTGGTCAAAACATCACTGAAG 5640  RSV_WT
5581 TTACCACAATCCTCACTGCAGTCACATTTTGTTTTGCTTCTGGTCAAAACATCACTGAAG 5640  MinA
5581 TCACAACAATACTAACAGCCGTTACATTTTGTTTCGCTAGCGGACAAAACATAACCGAAG 5640  MinB
5581 TTACCACAATCCTCACTGCAGTCACATTTTGTTTTGCTTCTGGTCAAAACATCACTGAAG 5640  MinL
5581 TCACAACAATACTAACAGCCGTTACATTTTGTTTCGCTAGCGGACAAAACATAACCGAAG 5640  MinFLC
     * **.*****.**.**:**.** *********** ***:  **:********.** ****

5641 AATTTTATCAATCAACATGCAGTGCAGTTAGCAAAGGCTATCTTAGTGCTCTGAGAACTG 5700  RSV_WT
5641 AATTTTATCAATCAACATGCAGTGCAGTTAGCAAAGGCTATCTTAGTGCTCTGAGAACTG 5700  MinA
5641 AGTTTTATCAATCTACATGTTCCGCCGTAAGTAAGGGGTATCTATCCGCACTTAGAACCG 5700  MinB
5641 AATTTTATCAATCAACATGCAGTGCAGTTAGCAAAGGCTATCTTAGTGCTCTGAGAACTG 5700  MinL
5641 AGTTTTATCAATCTACATGTTCCGCCGTAAGTAAGGGGTATCTATCCGCACTTAGAACCG 5700  MinFLC
     *.***********:***** :  **.**:** **.** *****::  **:** ***** *

5701 GTTGGTATACCAGTGTTATAACTATAGAATTAAGTAATATCAAGAAAAATAAGTGTAATG 5760  RSV_WT
5701 GTTGGTATACCAGTGTTATAACTATAGAATTAAGTAATATCAAGAAAAATAAGTGTAATG 5760  MinA
5701 GATGGTATACTAGCGTAATAACAATCGAACTATCTAATATAAAGAAGAATAAGTGTAACG 5760  MinB
5701 GTTGGTATACCAGTGTTATAACTATAGAATTAAGTAATATCAAGAAAAATAAGTGTAATG 5760  MinL
5701 GATGGTATACTAGCGTAATAACAATCGAACTATCTAATATAAAGAAGAATAAGTGTAACG 5760  MinFLC
     *:******** ** **:*****:**.*** **: ******.*****.*********** *

5761 GAACAGATGCTAAGGTAAAATTGATAAAACAAGAATTAGATAAATATAAAAATGCTGTAA 5820  RSV_WT
5761 GAACAGATGCTAAGGTAAAATTGATAAAACAAGAATTAGATAAATATAAAAATGCTGTAA 5820  MinA
5761 GTACAGACGCTAAGGTTAAATTGATTAAACAGGAACTCGATAAGTATAAAAACGCCGTAA 5820  MinB
5761 GAACAGATGCTAAGGTAAAATTGATAAAACAAGAATTAGATAAATATAAAAATGCTGTAA 5820  MinL
5761 GTACAGACGCTAAGGTTAAATTGATTAAACAGGAACTCGATAAGTATAAAAACGCCGTAA 5820  MinFLC
     *:***** ********:********:*****.*** *.*****.******** ** ****

5821 CAGAATTGCAGTTGCTCATGCAAAGCACACAAGCAACAAACAATCGAGCCAGAAGAGAAC 5880  RSV_WT
5821 CAGAATTGCAGTTGCTCATGCAAAGCACACAAGCAACAAACAATCGAGCCAGAAGAGAAC 5880  MinA
5821 CCGAATTGCAATTGTTAATGCAATCTACACAAGCTACTAATAATAGGGCTAGACGTGAAT 5880  MinB
5821 CAGAATTGCAGTTGCTCATGCAAAGCACACAAGCAACAAACAATCGAGCCAGAAGAGAAC 5880  MinL
5821 CCGAATTGCAATTGTTAATGCAATCTACACAAGCTACTAATAATAGGGCTAGACGTGAAT 5880  MinFLC
     *.********.*** *.******:  ********:**:** ***.*.** ***.*:***

5881 TACCAAGGTTTATGAATTATACACTCAACAATGCCAAAAAAACCAATGTAACATTAAGCA 5940  RSV_WT
5881 TACCAAGGTTTATGAATTATACACTCAACAATGCCAAAAAAACCAATGTAACATTAAGCA 5940  MinA
5881 TGCCTAGATTTATGAATTATACACTTAATAACGCTAAGAAAACTAACGTTACACTATCTA 5940  MinB
5881 TACCAAGGTTTATGAATTATACACTCAACAATGCCAAAAAAACCAATGTAACATTAAGCA 5940  MinL
5881 TGCCTAGATTTATGAATTATACACTTAATAACGCTAAGAAAACTAACGTTACACTATCTA 5940  MinFLC
     *.**:**.**************** ** ** ** **.***** ** **:*** **:  *
```

Figure 7 cont.

```
5941 AGAAAAGGAAAAGAAGATTTCTTGGTTTTTTGTTAGGTGTTGGATCTGCAATCGCCAGTG 6000  RSV_WT
5941 AGAAAAGGAAAAGAAGATTTCTTGGTTTTTTGTTAGGTGTTGGATCTGCAATCGCCAGTG 6000  MinA
5941 AGAAACGAAAACGTAGATTCTTAGGGTTTTTACTCGGAGTCGGTTCCGCAATCGCTAGCG 6000  MinB
5941 AGAAAAGGAAAAGAAGATTTCTTGGTTTTTTGTTAGGTGTTGGATCTGCAATCGCCAGTG 6000  MinL
5941 AGAAACGAAAACGTAGATTCTTAGGGTTTTTACTCGGAGTCGGTTCCGCAATCGCTAGCG 6000  MinFLC
     *****.*.***.*:*****  *:** *****. *.**:** **:** ******** **

6001 GCGTTGCTGTATCTAAGGTCCTGCACCTAGAAGGGGAAGTGAACAAGATCAAAAGTGCTC 6060  RSV_WT
6001 GCGTTGCTGTATCTAAGGTCCTGCACCTAGAAGGGGAAGTGAACAAGATCAAAAGTGCTC 6060  MinA
6001 GAGTCGCCGTAAGTAAAGTGTTACACCTCGAAGGCGAAGTGAATAAGATAAAATCCGCAC 6060  MinB
6001 GCGTTGCTGTATCTAAGGTCCTGCACCTAGAAGGGGAAGTGAACAAGATCAAAAGTGCTC 6060  MinL
6001 GAGTCGCCGTAAGTAAAGTGTTACACCTCGAAGGCGAAGTGAATAAGATAAAATCCGCAC 6060  MinFLC
     *.** ** ***: ***.**  *.*****.***** ******** *****.***:  **:*

6061 TACTATCCACAAACAAGGCTGTAGTCAGCTTATCAAATGGAGTTAGTGTTTTAACCAGCA 6120  RSV_WT
6061 TACTATCCACAAACAAGGCTGTAGTCAGCTTATCAAATGGAGTTAGTGTTTTAACCAGCA 6120  MinA
6061 TATTATCAACTAATAAGGCAGTCGTTAGCCTATCTAACGGAGTCAGCGTATTGACATCTA 6120  MinB
6061 TACTATCCACAAACAAGGCTGTAGTCAGCTTATCAAATGGAGTTAGTGTTTTAACCAGCA 6120  MinL
6061 TATTATCAACTAATAAGGCAGTCGTTAGCCTATCTAACGGAGTCAGCGTATTGACATCTA 6120  MinFLC
     ** ****.**:** *****:**.** *** ****:** ***** ** **:**.**.:  *

6121 AAGTGTTAGACCTCAAAAACTATATAGATAAACAATTGTTACCTATTGTGAACAAGCAAA 6180  RSV_WT
6121 AAGTGTTAGACCTCAAAAACTATATAGATAAACAATTGTTACCTATTGTGAACAAGCAAA 6180  MinA
6121 AAGTGTTAGACTTAAAGAATTATATAGATAAGCAATTGTTACCAATCGTTAATAAACAAT 6180  MinB
6121 AAGTGTTAGACCTCAAAAACTATATAGATAAACAATTGTTACCTATTGTGAACAAGCAAA 6180  MinL
6121 AAGTGTTAGACTTAAAGAATTATATAGATAAGCAATTGTTACCAATCGTTAATAAACAAT 6180  MinFLC
     *********** *.**.** ***********.***********:** ** ** **.***:

6181 GCTGCAGCATATCAAATATAGAAACTGTGATAGAGTTCCAACAAAAGAACAACAGACTAC 6240  RSV_WT
6181 GCTGCAGCATATCAAATATAGAAACTGTGATAGAGTTCCAACAAAAGAACAACAGACTAC 6240  MinA
6181 CATGTTCAATATCCAATATCGAAACCGTAATCGAATTTCAACAGAAGAATAATAGATTAC 6240  MinB
6181 GCTGCAGCATATCAAATATAGAAACTGTGATAGAGTTCCAACAAAAGAACAACAGACTAC 6240  MinL
6181 CATGTTCAATATCCAATATCGAAACCGTAATCGAATTTCAACAGAAGAATAATAGATTAC 6240  MinFLC
      .** : .*****.*****.***** **.**.**.** *****.***** ** *** ***

6241 TAGAGATTACCAGGGAATTTAGTGTTAATGCAGGCGTAACTACACCTGTAAGCACTTACA 6300  RSV_WT
6241 TAGAGATTACCAGGGAATTTAGTGTTAATGCAGGCGTAACTACACCTGTAAGCACTTACA 6300  MinA
6241 TCGAAATTACTAGAGAATTTAGCGTAAACGCTGGCGTAACAACACCCGTAAGTACATATA 6300  MinB
6241 TAGAGATTACCAGGGAATTTAGTGTTAATGCAGGCGTAACTACACCTGTAAGCACTTACA 6300  MinL
6241 TCGAAATTACTAGAGAATTTAGCGTAAACGCTGGCGTAACAACACCCGTAAGTACATATA 6300  MinFLC
     *.**.***** **.******** **:** **:********:***** ***** **:** *

6301 TGTTAACTAATAGTGAATTATTGTCATTAATCAATGATATGCCTATAACAAATGATCAGA 6360  RSV_WT
6301 TGTTAACTAATAGTGAATTATTGTCATTAATCAATGATATGCCTATAACAAATGATCAGA 6360  MinA
6301 TGTTAACTAATTCCGAACTGTTAAGCTTAATTAACGATATGCCAATTACTAACGATCAGA 6360  MinB
6301 TGTTAACTAATAGTGAATTATTGTCATTAATCAATGATATGCCTATAACAAATGATCAGA 6360  MinL
6301 TGTTAACTAATTCCGAACTGTTAAGCTTAATTAACGATATGCCAATTACTAACGATCAGA 6360  MinFLC
     ***********:  *** *.**.: .***** ** ********:**:**:** *******

6361 AAAAGTTAATGTCCAACAATGTTCAAATAGTTAGACAGCAAAGTTACTCTATCATGTCCA 6420  RSV_WT
6361 AAAAGTTAATGTCCAACAATGTTCAAATAGTTAGACAGCAAAGTTACTCTATCATGTCCA 6420  MinA
6361 AGAAATTGATGTCTAATAACGTACAAATCGTTAGACAGCAATCATATTCAATTATGTCAA 6420  MinB
6361 AAAAGTTAATGTCCAACAATGTTCAAATAGTTAGACAGCAAAGTTACTCTATCATGTCCA 6420  MinL
6361 AGAAATTGATGTCTAATAACGTACAAATCGTTAGACAGCAATCATATTCAATTATGTCAA 6420  MinFLC
     *.**.**.***** ** ** **:*****.************: :** **:** *****.*

6421 TAATAAAAGAGGAAGTCTTAGCATATGTAGTACAATTACCACTATATGGTGTTATAGATA 6480  RSV_WT
6421 TAATAAAAGAGGAAGTCTTAGCATATGTAGTACAATTACCACTATATGGTGTTATAGATA 6480  MinA
6421 TTATAAAAGAAGAGGTACTCGCATACGTAGTGCAATTACCCCTATATGGCGTAATAGATA 6480  MinB
6421 TAATAAAAGAGGAAGTCTTAGCATATGTAGTACAATTACCACTATATGGTGTTATAGATA 6480  MinL
6421 TTATAAAAGAAGAGGTACTCGCATACGTAGTGCAATTACCCCTATATGGCGTAATAGATA 6480  MinFLC
     *:*******.**.**. *.***** *****.********.******** **:*******

6481 CACCCTGTTGGAAACTACACACATCCCCTCTATGTACAACCAACACAAAAGAAGGGTCCA 6540  RSV_WT
6481 CACCCTGTTGGAAACTACACACATCCCCTCTATGTACAACCAACACAAAAGAAGGGTCCA 6540  MinA
6481 CACCATGTTGGAAATTGCATACAAGTCCACTATGTACAACTAATACAAAAGAGGGATCTA 6540  MinB
6481 CACCCTGTTGGAAACTACACACATCCCCTCTATGTACAACCAACACAAAAGAAGGGTCCA 6540  MinL
6481 CACCATGTTGGAAATTGCATACAAGTCCACTATGTACAACTAATACAAAAGAGGGATCTA 6540  MinFLC
     ****.********* *.** ***:  **:*********** ** ********.**.** *
```

Figure 7 cont.

```
6541 ACATCTGTTTAACAAGAACTGACAGAGGATGGTACTGTGACAATGCAGGATCAGTATCTT 6600  RSV_WT
6541 ACATCTGTTTAACAAGAACTGACAGAGGATGGTACTGTGACAATGCAGGATCAGTATCTT 6600  MinA
6541 ATATATGCTTAACTAGAACCGATAGGGGGTGGTATTGCGATAACGCAGGTAGCGTAAGTT 6600  MinB
6541 ACATCTGTTTAACAAGAACTGACAGAGGATGGTACTGTGACAATGCAGGATCAGTATCTT 6600  MinL
6541 ATATATGCTTAACTAGAACCGATAGGGGGTGGTATTGCGATAACGCAGGTAGCGTAAGTT 6600  MinFLC
     * **.** *****:***** ** **.**.***** ** ** ** *****:: .***: **

6601 TCTTCCCACAAGCTGAAACATGTAAAGTTCAATCAAATCGAGTATTTTGTGACACAATGA 6660  RSV_WT
6601 TCTTCCCACAAGCTGAAACATGTAAAGTTCAATCAAATCGAGTATTTTGTGACACAATGA 6660  MinA
6601 TCTTTCCACAAGCCGAAACATGTAAAGTGCAATCTAATAGAGTGTTTTGCGATACAATGA 6660  MinB
6601 TCTTCCCACAAGCTGAAACATGTAAAGTTCAATCAAATCGAGTATTTTGTGACACAATGA 6660  MinL
6601 TCTTTCCACAAGCCGAAACATGTAAAGTGCAATCTAATAGAGTGTTTTGCGATACAATGA 6660  MinFLC
     **** ******** ************** *****:***.****.***** ** *******

6661 ACAGTTTAACATTACCAAGTGAAGTAAATCTCTGCAATGTTGACATATTCAACCCCAAAT 6720  RSV_WT
6661 ACAGTTTAACATTACCAAGTGAAGTAAATCTCTGCAATGTTGACATATTCAACCCCAAAT 6720  MinA
6661 ATAGCTTAACACTACCTAGCGAAGTCAATCTATGTAACGTCGATATATTCAATCCTAAAT 6720  MinB
6661 ACAGTTTAACATTACCAAGTGAAGTAAATCTCTGCAATGTTGACATATTCAACCCCAAAT 6720  MinL
6661 ATAGCTTAACACTACCTAGCGAAGTCAATCTATGTAACGTCGATATATTCAATCCTAAAT 6720  MinFLC
     * ** ****** ****:** *****.*****.** ** ** ** ******** ** ****

6721 ATGATTGTAAAATTATGACTTCAAAAACAGATGTAAGCAGCTCCGTTATCACATCTCTAG 6780  RSV_WT
6721 ATGATTGTAAAATTATGACTTCAAAAACAGATGTAAGCAGCTCCGTTATCACATCTCTAG 6780  MinA
6721 ATGATTGCAAAATTATGACTAGTAAGACTGACGTAAGTAGTAGCGTAATTACTAGTCTCG 6780  MinB
6721 ATGATTGTAAAATTATGACTTCAAAAACAGATGTAAGCAGCTCCGTTATCACATCTCTAG 6780  MinL
6721 ATGATTGCAAAATTATGACTAGTAAGACTGACGTAAGTAGTAGCGTAATTACTAGTCTCG 6780  MinFLC
     ******* ************: :**.**:** ***** ** : ***:** **:: ***.*

6781 GAGCCATTGTGTCATGCTATGGCAAAACTAAATGTACAGCATCCAATAAAAATCGTGGAA 6840  RSV_WT
6781 GAGCCATTGTGTCATGCTATGGCAAAACTAAATGTACAGCATCCAATAAAAATCGTGGAA 6840  MinA
6781 GTGCAATAGTGTCATGTTATGGTAAGACTAAGTGTACCGCTAGCAATAAGAATAGGGGGA 6840  MinB
6781 GAGCCATTGTGTCATGCTATGGCAAAACTAAATGTACAGCATCCAATAAAAATCGTGGAA 6840  MinL
6781 GTGCAATAGTGTCATGTTATGGTAAGACTAAGTGTACCGCTAGCAATAAGAATAGGGGGA 6840  MinFLC
     *:**.**:******** ***** **.*****.*****.**:: ******.***.* **.*

6841 TCATAAAGACATTTTCTAACGGGTGCGATTATGTATCAAATAAAGGGGTGGACACTGTGT 6900  RSV_WT
6841 TCATAAAGACATTTTCTAACGGGTGCGATTATGTATCAAATAAAGGGGTGGACACTGTGT 6900  MinA
6841 TAATAAAAACATTTAGTAACGGTTGCGATTACGTTAGTAATAAGGGAGTCGATACCGTAA 6900  MinB
6841 TCATAAAGACATTTTCTAACGGGTGCGATTATGTATCAAATAAAGGGGTGGACACTGTGT 6900  MinL
6841 TAATAAAAACATTTAGTAACGGTTGCGATTACGTTAGTAATAAGGGAGTCGATACCGTAA 6900  MinFLC
     *.*****.******: ****** ******** **:: :*****.**.** ** ** **.:

6901 CTGTAGGTAACACATTATATTATGTAAATAAGCAAGAAGGTAAAAGTCTCTATGTAAAAG 6960  RSV_WT
6901 CTGTAGGTAACACATTATATTATGTAAATAAGCAAGAAGGTAAAAGTCTCTATGTAAAAG 6960  MinA
6901 GCGTAGGTAATACACTATATTATGTTAATAAACAGGAAGGTAAGTCATTATACGTTAAAG 6960  MinB
6901 CTGTAGGTAACACATTATATTATGTAAATAAGCAAGAAGGTAAAAGTCTCTATGTAAAAG 6960  MinL
6901 GCGTAGGTAATACACTATATTATGTTAATAAACAGGAAGGTAAGTCATTATACGTTAAAG 6960  MinFLC
       ******** *** **********:*****.**.********.: : *.** **:****

6961 GTGAACCAATAATAAATTTCTATGACCCATTAGTATTCCCCTCTGATGAATTTGATGCAT 7020  RSV_WT
6961 GTGAACCAATAATAAATTTCTATGACCCATTAGTATTCCCCTCTGATGAATTTGATGCAT 7020  MinA
6961 GCGAACCTATAATTAATTTTTACGATCCATTAGTGTTTCCATCCGACGAATTCGACGCTA 7020  MinB
6961 GTGAACCAATAATAAATTTCTATGACCCATTAGTATTCCCCTCTGATGAATTTGATGCAT 7020  MinL
6961 GCGAACCTATAATTAATTTTTACGATCCATTAGTGTTTCCATCCGACGAATTCGACGCTA 7020  MinFLC
     * *****:*****:***** ** ** ********.** **.** ** ***** ** **::

7021 CAATATCTCAAGTCAACGAGAAGATTAACCAGAGCCTAGCATTTATTCGTAAATCCGATG 7080  RSV_WT
7021 CAATATCTCAAGTCAACGAGAAGATTAACCAGAGCCTAGCATTTATTCGTAAATCCGATG 7080  MinA
7021 GTATAAGTCAGGTAAACGAAAAGATTAACCAATCACTCGCATTCATACGAAAATCCGACG 7080  MinB
7021 CAATATCTCAAGTCAACGAGAAGATTAACCAGAGCCTAGCATTTATTCGTAAATCCGATG 7080  MinL
7021 GTATAAGTCAGGTAAACGAAAAGATTAACCAATCACTCGCATTCATACGAAAATCCGACG 7080  MinFLC
      :***: ***.**.*****.***********.: .**.***** **:**:******** *

7081 AATTATTACATAATGTAAATGCTGGTAAATCCACCACAAATATCATGATAACTACTATAA 7140  RSV_WT
7081 AATTATTACATAATGTAAATGCTGGTAAATCCACCACAAATATCATGATAACTACTATAA 7140  MinA
7081 AACTGTTACACAACGTTAACGCAGGTAAGAGTACAACTAACATAATGATAACAACAATTA 7140  MinB
7081 AATTATTACATAATGTAAATGCTGGTAAATCCACCACAAATATCATGATAACTACTATAA 7140  MinL
7081 AACTGTTACACAACGTTAACGCAGGTAAGAGTACAACTAACATAATGATAACAACAATTA 7140  MinFLC
     ** *.***** ** **:** **:*****.:  **.**:** **.********:**:**:*
```

Figure 7 cont.

```
7141 TTATAGTGATTATAGTAATATTGTTATCATTAATTGCTGTTGGACTGCTCTTATACTGTA 7200  RSV_WT
7141 TTATAGTGATTATAGTAATATTGTTATCATTAATTGCTGTTGGACTGCTCTTATACTGTA 7200  MinA
7141 TAATCGTTATAATCGTTATACTGTTAAGCTTAATCGCAGTCGGATTACTGTTATATTGTA 7200  MinB
7141 TTATAGTGATTATAGTAATATTGTTATCATTAATTGCTGTTGGACTGCTCTTATACTGTA 7200  MinL
7141 TAATCGTTATAATCGTTATACTGTTAAGCTTAATCGCAGTCGGATTACTGTTATATTGTA 7200  MinFLC
     *:**.** **:**.**:*** *****: .***** **:** *** *.** ***** ****

7201 AGGCCAGAAGCACACCAGTCACACTAAGCAAAGATCAACTGAGTGGTATAAATAATATTG 7260  RSV_WT
7201 AGGCCAGAAGCACACCAGTCACACTAAGCAAAGATCAACTGAGTGGTATAAATAATATTG 7260  MinA
7201 AAGCTAGATCAACACCCGTAACACTATCTAAAGACCAATTATCCGGTATAAATAATATCG 7260  MinB
7201 AGGCCAGAAGCACACCAGTCACACTAAGCAAAGATCAACTGAGTGGTATAAATAATATTG 7260  MinL
7201 AAGCTAGATCAACACCCGTAACACTATCTAAAGACCAATTATCCGGTATAAATAATATCG 7260  MinFLC
     *.** ***: .*****.**.******:  ***** *** *.:  ************** *

7261 CATTTAGTAACTAAATAAAAATAGCACCTAATCATGTTCTTACAATGGTTTACTATCTGC 7320  RSV_WT
7261 CATTTAGTAACTAAATAAAAATAGCACCTAATCATGTTCTTACAATGGTTTACTATCTGC 7320  MinA
7261 CATTCTCAAACTAAATAAAAATAGCACCTAATCATGTTCTTACAATGGTTTACTATCTGC 7320  MinB
7261 CATTTAGTAACTAAATAAAAATAGCACCTAATCATGTTCTTACAATGGTTTACTATCTGC 7320  MinL
7261 CATTCTCAAACTAAATAAAAATAGCACCTAATCATGTTCTTACAATGGTTTACTATCTGC 7320  MinFLC
     **** : :****************************************************

7321 TCATAGACAACCCATCTGTCATTGGATTTTCTTAAAATCTGAACTTCATCGAAACTCTCA 7380  RSV_WT
7321 TCATAGACAACCCATCTGTCATTGGATTTTCTTAAAATCTGAACTTCATCGAAACTCTCA 7380  MinA
7321 TCATAGACAACCCATCTGTCATTGGATTTTCTTAAAATCTGAACTTCATCGAAACTCTCA 7380  MinB
7321 TCATAGACAACCCATCTGTCATTGGATTTTCTTAAAATCTGAACTTCATCGAAACTCTCA 7380  MinL
7321 TCATAGACAACCCATCTGTCATTGGATTTTCTTAAAATCTGAACTTCATCGAAACTCTCA 7380  MinFLC
     ************************************************************

7381 TCTATAAACCATCTCACTTACACTATTTAAGTAGATTCCTAGTTTATAGTTATATAAAAC 7440  RSV_WT
7381 TCTATAAACCATCTCACTTACACTATTTAAGTAGATTCCTAGTTTATAGTTATATAAAAC 7440  MinA
7381 TCTATAAACCATCTCACTTACACTATTTAAGTAGATTCCTAGTTTATAGTTATATAAAAC 7440  MinB
7381 TCTATAAACCATCTCACTTACACTATTTAAGTAGATTCCTAGTTTATAGTTATATAAAAC 7440  MinL
7381 TCTATAAACCATCTCACTTACACTATTTAAGTAGATTCCTAGTTTATAGTTATATAAAAC 7440  MinFLC
     ************************************************************

7441 ACAATTGCATGCCAGATTAACTTACCATCTGTAAAAATGAAAACTGGGGCAAATATGTCA 7500  RSV_WT
7441 ACAATTGCATGCCAGATTAACTTACCATCTGTAAAAATGAAAACTGGGGCAAATATGTCA 7500  MinA
7441 ACAATTGCATGCCAGATTAACTTACCATCTGTAAAAATGAAAACTGGGGCAAATATGTCA 7500  MinB
7441 ACAATTGCATGCCAGATTAACTTACCATCTGTAAAAATGAAAACTGGGGCAAATATGTCA 7500  MinL
7441 ACAATTGCATGCCAGATTAACTTACCATCTGTAAAAATGAAAACTGGGGCAAATATGTCA 7500  MinFLC
     ************************************************************

7501 CGAAGGAATCCTTGCAAATTTGAAATTCGAGGTCATTGCTTAAATGGTAAGAGGTGTCAT 7560  RSV_WT
7501 CGAAGGAATCCTTGCAAATTTGAAATTCGAGGTCATTGCTTAAATGGTAAGAGGTGTCAT 7560  MinA
7501 CGAAGGAATCCTTGCAAATTTGAAATTCGAGGTCATTGCTTAAATGGTAAGAGGTGTCAT 7560  MinB
7501 CGAAGGAATCCTTGCAAATTTGAAATTCGAGGTCATTGCTTAAATGGTAAGAGGTGTCAT 7560  MinL
7501 CGAAGGAATCCTTGCAAATTTGAAATTCGAGGTCATTGCTTAAATGGTAAGAGGTGTCAT 7560  MinFLC
     ************************************************************

7561 TTTAGTCATAATTATTTTGAATGGCCACCCCATGCACTGCTTGTAAGACAAAACTTTATG 7620  RSV_WT
7561 TTTAGTCATAATTATTTTGAATGGCCACCCCATGCACTGCTTGTAAGACAAAACTTTATG 7620  MinA
7561 TTTAGTCATAATTATTTTGAATGGCCACCCCATGCACTGCTTGTAAGACAAAACTTTATG 7620  MinB
7561 TTTAGTCATAATTATTTTGAATGGCCACCCCATGCACTGCTTGTAAGACAAAACTTTATG 7620  MinL
7561 TTTAGTCATAATTATTTTGAATGGCCACCCCATGCACTGCTTGTAAGACAAAACTTTATG 7620  MinFLC
     ************************************************************

7621 TTAAACAGAATACTTAAGTCTATGGATAAAAGTATAGATACCTTATCAGAAATAAGTGGA 7680  RSV_WT
7621 TTAAACAGAATACTTAAGTCTATGGATAAAAGTATAGATACCTTATCAGAAATAAGTGGA 7680  MinA
7621 TTAAACAGAATACTTAAGTCTATGGATAAAAGTATAGATACCTTATCAGAAATAAGTGGA 7680  MinB
7621 TTAAACAGAATACTTAAGTCTATGGATAAAAGTATAGATACCTTATCAGAAATAAGTGGA 7680  MinL
7621 TTAAACAGAATACTTAAGTCTATGGATAAAAGTATAGATACCTTATCAGAAATAAGTGGA 7680  MinFLC
     ************************************************************

7681 GCTGCAGAGTTGGACAGAACAGAAGAGTATGCTCTTGGTGTAGTTGGAGTGCTAGAGAGT 7740  RSV_WT
7681 GCTGCAGAGTTGGACAGAACAGAAGAGTATGCTCTTGGTGTAGTTGGAGTGCTAGAGAGT 7740  MinA
7681 GCTGCAGAGTTGGACAGAACAGAAGAGTATGCTCTTGGTGTAGTTGGAGTGCTAGAGAGT 7740  MinB
7681 GCTGCAGAGTTGGACAGAACAGAAGAGTATGCTCTTGGTGTAGTTGGAGTGCTAGAGAGT 7740  MinL
7681 GCTGCAGAGTTGGACAGAACAGAAGAGTATGCTCTTGGTGTAGTTGGAGTGCTAGAGAGT 7740  MinFLC
     ************************************************************
```

Figure 7 cont.

```
7741 TATATAGGATCAATAAACAATATAACTAAACAATCAGCATGTGTTGCCATGAGCAAACTC 7800  RSV_WT
7741 TATATAGGATCAATAAACAATATAACTAAACAATCAGCATGTGTTGCCATGAGCAAACTC 7800  MinA
7741 TATATAGGATCAATAAACAATATAACTAAACAATCAGCATGTGTTGCCATGAGCAAACTC 7800  MinB
7741 TATATAGGATCAATAAACAATATAACTAAACAATCAGCATGTGTTGCCATGAGCAAACTC 7800  MinL
7741 TATATAGGATCAATAAACAATATAACTAAACAATCAGCATGTGTTGCCATGAGCAAACTC 7800  MinFLC
     ************************************************************

7801 CTCACTGAACTCAATAGTGATGATATCAAAAAGCTGAGGGACAATGAAGAGCTAAATTCA 7860  RSV_WT
7801 CTCACTGAACTCAATAGTGATGATATCAAAAAGCTGAGGGACAATGAAGAGCTAAATTCA 7860  MinA
7801 CTCACTGAACTCAATAGTGATGATATCAAAAAGCTGAGGGACAATGAAGAGCTAAATTCA 7860  MinB
7801 CTCACTGAACTCAATAGTGATGATATCAAAAAGCTGAGGGACAATGAAGAGCTAAATTCA 7860  MinL
7801 CTCACTGAACTCAATAGTGATGATATCAAAAAGCTGAGGGACAATGAAGAGCTAAATTCA 7860  MinFLC
     ************************************************************

7861 CCCAAGATAAGAGTGTACAATACTGTCATATCATATATTGAAAGCAACAGGAAAAACAAT 7920  RSV_WT
7861 CCCAAGATAAGAGTGTACAATACTGTCATATCATATATTGAAAGCAACAGGAAAAACAAT 7920  MinA
7861 CCCAAGATAAGAGTGTACAATACTGTCATATCATATATTGAAAGCAACAGGAAAAACAAT 7920  MinB
7861 CCCAAGATAAGAGTGTACAATACTGTCATATCATATATTGAAAGCAACAGGAAAAACAAT 7920  MinL
7861 CCCAAGATAAGAGTGTACAATACTGTCATATCATATATTGAAAGCAACAGGAAAAACAAT 7920  MinFLC
     ************************************************************

7921 AAACAAACTATCCATCTGTTAAAAAGATTGCCAGCAGACGTATTGAAGAAAACCATCAAA 7980  RSV_WT
7921 AAACAAACTATCCATCTGTTAAAAAGATTGCCAGCAGACGTATTGAAGAAAACCATCAAA 7980  MinA
7921 AAACAAACTATCCATCTGTTAAAAAGATTGCCAGCAGACGTATTGAAGAAAACCATCAAA 7980  MinB
7921 AAACAAACTATCCATCTGTTAAAAAGATTGCCAGCAGACGTATTGAAGAAAACCATCAAA 7980  MinL
7921 AAACAAACTATCCATCTGTTAAAAAGATTGCCAGCAGACGTATTGAAGAAAACCATCAAA 7980  MinFLC
     ************************************************************

7981 AACACATTGGATATCCATAAGAGCATAACCATCAACAACCCAAAAGAATCAACTGTTAGT 8040  RSV_WT
7981 AACACATTGGATATCCATAAGAGCATAACCATCAACAACCCAAAAGAATCAACTGTTAGT 8040  MinA
7981 AACACATTGGATATCCATAAGAGCATAACCATCAACAACCCAAAAGAATCAACTGTTAGT 8040  MinB
7981 AACACATTGGATATCCATAAGAGCATAACCATCAACAACCCAAAAGAATCAACTGTTAGT 8040  MinL
7981 AACACATTGGATATCCATAAGAGCATAACCATCAACAACCCAAAAGAATCAACTGTTAGT 8040  MinFLC
     ************************************************************

8041 GATACAAATGACCATGCCAAAAATAATGATACTACCTGACAAATATCCTTGTAGTATAAC 8100  RSV_WT
8041 GATACAAATGACCATGCCAAAAATAATGATACTACCTGACAAATATCCTTGTAGTATAAC 8100  MinA
8041 GATACAAATGACCATGCCAAAAATAATGATACTACCTGACAAATATCCTTGTAGTATAAC 8100  MinB
8041 GATACAAATGACCATGCCAAAAATAATGATACTACCTGACAAATATCCTTGTAGTATAAC 8100  MinL
8041 GATACAAATGACCATGCCAAAAATAATGATACTACCTGACAAATATCCTTGTAGTATAAC 8100  MinFLC
     ************************************************************

8101 TTCCATACTAATAACAAGTAGATGTAGAGTTACTATGTATAATCAAAAGAACACACTATA 8160  RSV_WT
8101 TTCCATACTAATAACAAGTAGATGTAGAGTTACTATGTATAATCAAAAGAACACACTATA 8160  MinA
8101 TTCCATACTAATAACAAGTAGATGTAGAGTTACTATGTATAATCAAAAGAACACACTATA 8160  MinB
8101 TTCCATACTAATAACAAGTAGATGTAGAGTTACTATGTATAATCAAAAGAACACACTATA 8160  MinL
8101 TTCCATACTAATAACAAGTAGATGTAGAGTTACTATGTATAATCAAAAGAACACACTATA 8160  MinFLC
     ************************************************************

8161 TTTCAATCAAAACAACCCAAATAACCATATGTACTCACCGAATCAAACATTCAATGAAAT 8220  RSV_WT
8161 TTTCAATCAAAACAACCCAAATAACCATATGTACTCACCGAATCAAACATTCAATGAAAT 8220  MinA
8161 TTTCAATCAAAACAACCCAAATAACCATATGTACTCACCGAATCAAACATTCAATGAAAT 8220  MinB
8161 TTTCAATCAAAACAACCCAAATAACCATATGTACTCACCGAATCAAACATTCAATGAAAT 8220  MinL
8161 TTTCAATCAAAACAACCCAAATAACCATATGTACTCACCGAATCAAACATTCAATGAAAT 8220  MinFLC
     ************************************************************

8221 CCATTGGACCTCTCAAGAATTGATTGACACAATTCAAAATTTTCTACAACATCTAGGTAT 8280  RSV_WT
8221 CCATTGGACCTCTCAAGAATTGATTGACACAATTCAAAATTTTCTACAACATCTAGGTAT 8280  MinA
8221 CCATTGGACCTCTCAAGAATTGATTGACACAATTCAAAATTTTCTACAACATCTAGGTAT 8280  MinB
8221 CCATTGGACCTCTCAAGAATTGATTGACACAATTCAAAATTTTCTACAACATCTAGGTAT 8280  MinL
8221 CCATTGGACCTCTCAAGAATTGATTGACACAATTCAAAATTTTCTACAACATCTAGGTAT 8280  MinFLC
     ************************************************************

8281 TATTGAGGATATATATACAATATATATATTAGTGTCATAACACTCAATTCTAACACTCAC 8340  RSV_WT
8281 TATTGAGGATATATATACAATATATATATTAGTGTCATAACACTCAATTCTAACACTCAC 8340  MinA
8281 TATTGAGGATATATATACAATATATATATTAGTGTCATAACACTCAATTCTAACACTCAC 8340  MinB
8281 TATTGAGGATATATATACAATATATATATTAGTGTCATAACACTCAATTCTAACACTCAC 8340  MinL
8281 TATTGAGGATATATATACAATATATATATTAGTGTCATAACACTCAATTCTAACACTCAC 8340  MinFLC
     ************************************************************
```

Figure 7 cont.

```
8341 CACATCGTTACATTATTAATTCAAACAATTCAAGTTGTGGGACAAAATGGATCCCATTAT 8400  RSV_WT
8341 CACATCGTTACATTATTAATTCAAACAATTCAAGTTGTGGGACAAAATGGATCCCATTAT 8400  MinA
8341 CACATCGTTACATTATTAATTCAAACAATTCAAGTTGTGGGACAAAATGGATCCCATTAT 8400  MinB
8341 CACATCGTTACATTATTAATTCAAACAATTCAAGTTGTGGGACAAAATGGATCCCATTAT 8400  MinL
8341 CACATCGTTACATTATTAATTCAAACAATTCAAGTTGTGGGACAAAATGGATCCCATTAT 8400  MinFLC
     ************************************************************

8401 TAATGGAAATTCTGCTAATGTTTATCTAACCGATAGTTATTTAAAAGGTGTTATCTCTTT 8460  RSV_WT
8401 TAATGGAAATTCTGCTAATGTTTATCTAACCGATAGTTATTTAAAAGGTGTTATCTCTTT 8460  MinA
8401 TAATGGAAATTCTGCTAATGTTTATCTAACCGATAGTTATTTAAAAGGTGTTATCTCTTT 8460  MinB
8401 TAATGGAAATTCTGCTAACGTATACTTAACCGATAGTTATTTAAAAGGCGTAATCAGTTT 8460  MinL
8401 TAATGGAAATTCTGCTAACGTATACTTAACCGATAGTTATTTAAAAGGCGTAATCAGTTT 8460  MinFLC
     ****************** **:**  ********************** **:***: ***

8461 CTCAGAGTGTAATGCTTTAGGAAGTTACATATTCAATGGTCCTTATCTCAAAAATGATTA 8520  RSV_WT
8461 CTCAGAGTGTAATGCTTTAGGAAGTTACATATTCAATGGTCCTTATCTCAAAAATGATTA 8520  MinA
8461 CTCAGAGTGTAATGCTTTAGGAAGTTACATATTCAATGGTCCTTATCTCAAAAATGATTA 8520  MinB
8461 TAGCGAATGTAACGCATTAGGGTCATATATCTTTAACGGTCCATATCTTAAAAACGATTA 8520  MinL
8461 TAGCGAATGTAACGCATTAGGGTCATATATCTTTAACGGTCCATATCTTAAAAACGATTA 8520  MinFLC
      : .**.***** **:*****.: :** **.** ** *****:***** ***** *****

8521 TACCAACTTAATTAGTAGACAAAATCCATTAATAGAACACATGAATCTAAAGAAACTAAA 8580  RSV_WT
8521 TACCAACTTAATTAGTAGACAAAATCCATTAATAGAACACATGAATCTAAAGAAACTAAA 8580  MinA
8521 TACCAACTTAATTAGTAGACAAAATCCATTAATAGAACACATGAATCTAAAGAAACTAAA 8580  MinB
8521 TACTAATCTAATCAGTAGACAGAATCCGTTAATCGAACATATGAATCTTAAGAAACTGAA 8580  MinL
8521 TACTAATCTAATCAGTAGACAGAATCCGTTAATCGAACATATGAATCTTAAGAAACTGAA 8580  MinFLC
     *** **  **** ********.*****.*****.***** ********:********.**

8581 TATAACACAGTCCTTAATATCTAAGTATCATAAAGGTGAAATAAAATTAGAAGAACCTAC 8640  RSV_WT
8581 TATAACACAGTCCTTAATATCTAAGTATCATAAAGGTGAAATAAAATTAGAAGAACCTAC 8640  MinA
8581 TATAACACAGTCCTTAATATCTAAGTATCATAAAGGTGAAATAAAATTAGAAGAACCTAC 8640  MinB
8581 TATCACACAATCTTTGATCAGTAAGTATCATAAAGGCGAAATCAAACTCGAAGAACCTAC 8640  MinL
8581 TATCACACAATCTTTGATCAGTAAGTATCATAAAGGCGAAATCAAACTCGAAGAACCTAC 8640  MinFLC
     ***.*****.** **.**.: *************** *****.*** *.***********

8641 TTATTTTCAGTCATTACTTATGACATACAAGAGTATGACCTCGTCAGAACAGATTGCTAC 8700  RSV_WT
8641 TTATTTTCAGTCATTACTTATGACATACAAGAGTATGACCTCGTCAGAACAGATTGCTAC 8700  MinA
8641 TTATTTTCAGTCATTACTTATGACATACAAGAGTATGACCTCGTCAGAACAGATTGCTAC 8700  MinB
8641 ATATTTTCAATCACTATTAATGACATATAAGTCTATGACATCTAGCGAACAGATCGCTAC 8700  MinL
8641 ATATTTTCAATCACTATTAATGACATATAAGTCTATGACATCTAGCGAACAGATCGCTAC 8700  MinFLC
     :********.*** ** *:******** ***: ******.** : .******** *****

8701 CACTAATTTACTTAAAAAGATAATAAGAAGAGCTATAGAAATAAGTGATGTCAAAGTCTA 8760  RSV_WT
8701 CACTAATTTACTTAAAAAGATAATAAGAAGAGCTATAGAAATAAGTGATGTCAAAGTCTA 8760  MinA
8701 CACTAATTTACTTAAAAAGATAATAAGAAGAGCTATAGAAATAAGTGATGTCAAAGTCTA 8760  MinB
8701 TACTAATCTGTTGAAGAAAATTATTAGACGAGCTATAGAGATATCTGACGTTAAGGTATA 8760  MinL
8701 TACTAATCTGTTGAAGAAAATTATTAGACGAGCTATAGAGATATCTGACGTTAAGGTATA 8760  MinFLC
      ****** *. * **.**.**:**:***.**********.***: *** ** **.**.**

8761 TGCTATATTGAATAAACTAGGGCTTAAAGAAAAGGACAAGATTAAATCCAACAATGGACA 8820  RSV_WT
8761 TGCTATATTGAATAAACTAGGGCTTAAAGAAAAGGACAAGATTAAATCCAACAATGGACA 8820  MinA
8761 TGCTATATTGAATAAACTAGGGCTTAAAGAAAAGGACAAGATTAAATCCAACAATGGACA 8820  MinB
8761 CGCTATACTGAATAAATTGGGGTTAAAAGAGAAAGATAAGATAAAATCTAATAACGGTCA 8820  MinL
8761 CGCTATACTGAATAAATTGGGGTTAAAAGAGAAAGATAAGATAAAATCTAATAACGGTCA 8820  MinFLC
      ****** ******** *.*** *:*****.**.** *****:***** ** ** **:**

8821 AGATGAAGACAACTCAGTTATTACGACCATAATCAAAGATGATATACTTTCAGCTGTTAA 8880  RSV_WT
8821 AGATGAAGACAACTCAGTTATTACGACCATAATCAAAGATGATATACTTTCAGCTGTTAA 8880  MinA
8821 AGATGAAGACAACTCAGTTATTACGACCATAATCAAAGATGATATACTTTCAGCTGTTAA 8880  MinB
8821 AGACGAAGATAATAGTGTAATTACTACAATTATTAAAGACGATATACTATCCGCAGTGAA 8880  MinL
8821 AGACGAAGATAATAGTGTAATTACTACAATTATTAAAGACGATATACTATCCGCAGTGAA 8880  MinFLC
     *** ***** ** : :**:***** **.**:** ***** ********:**.**:** **

8881 AGATAATCAATCTCATCTTAAAGCAGACAAAAATCACTCTACAAAACAAAAAGACACAAT 8940  RSV_WT
8881 AGATAATCAATCTCATCTTAAAGCAGACAAAAATCACTCTACAAAACAAAAAGACACAAT 8940  MinA
8881 AGATAATCAATCTCATCTTAAAGCAGACAAAAATCACTCTACAAAACAAAAAGACACAAT 8940  MinB
8881 GGATAATCAATCACATCTTAAAGCCGATAAAAATCATAGTACTAAACAAAAAGATACAAT 8940  MinL
8881 GGATAATCAATCACATCTTAAAGCCGATAAAAATCATAGTACTAAACAAAAAGATACAAT 8940  MinFLC
     .***********:***********.** ******** : ***:*********** *****
```

Figure 7 cont.

```
8941 CAAAACAACACTCTTGAAGAAATTGATGTGTTCAATGCAACATCCTCCATCATGGTTAAT 9000  RSV_WT
8941 CAAAACAACACTCTTGAAGAAATTGATGTGTTCAATGCAACATCCTCCATCATGGTTAAT 9000  MinA
8941 CAAAACAACACTCTTGAAGAAATTGATGTGTTCAATGCAACATCCTCCATCATGGTTAAT 9000  MinB
8941 TAAAACTACATTGTTAAAGAAATTGATGTGTTCTATGCAACATCCACCTAGTTGGTTAAT 9000  MinL
8941 TAAAACTACATTGTTAAAGAAATTGATGTGTTCTATGCAACATCCACCTAGTTGGTTAAT 9000  MinFLC
      *****:*** * **.*****************:***********:**:: :********

9001 ACATTGGTTTAACTTATACACAAAATTAAACAACATATTAACACAGTATCGATCAAATGA 9060  RSV_WT
9001 ACATTGGTTTAACTTATACACAAAATTAAACAACATATTAACACAGTATCGATCAAATGA 9060  MinA
9001 ACATTGGTTTAACTTATACACAAAATTAAACAACATATTAACACAGTATCGATCAAATGA 9060  MinB
9001 ACATTGGTTTAACTTATACACTAAGTTGAACAATATACTTACACAATATCGATCAAACGA 9060  MinL
9001 ACATTGGTTTAACTTATACACTAAGTTGAACAATATACTTACACAATATCGATCAAACGA 9060  MinFLC
     *********************:**.**.***** *** *:*****.*********** **

9061 GGTAAAAAACCATGGGTTTACATTGATAGATAATCAAACTCTTAGTGGATTTCAATTTAT 9120  RSV_WT
9061 GGTAAAAAACCATGGGTTTACATTGATAGATAATCAAACTCTTAGTGGATTTCAATTTAT 9120  MinA
9061 GGTAAAAAACCATGGGTTTACATTGATAGATAATCAAACTCTTAGTGGATTTCAATTTAT 9120  MinB
9061 AGTGAAAAATCACGGTTTTACATTGATAGATAATCAAACATTAAGCGGATTTCAATTCAT 9120  MinL
9061 AGTGAAAAATCACGGTTTTACATTGATAGATAATCAAACATTAAGCGGATTTCAATTCAT 9120  MinFLC
     .**.***** ** ** ***********************: *:** *********** **

9121 TTTGAACCAATATGGTTGTATAGTTTATCATAAGGAACTCAAAAGAATTACTGTGACAAC 9180  RSV_WT
9121 TTTGAACCAATATGGTTGTATAGTTTATCATAAGGAACTCAAAAGAATTACTGTGACAAC 9180  MinA
9121 TTTGAACCAATATGGTTGTATAGTTTATCATAAGGAACTCAAAAGAATTACTGTGACAAC 9180  MinB
9121 ACTTAACCAATACGGATGTATAGTGTATCATAAAGAATTGAAACGTATAACCGTTACAAC 9180  MinL
9121 ACTTAACCAATACGGATGTATAGTGTATCATAAAGAATTGAAACGTATAACCGTTACAAC 9180  MinFLC
     : * ******** **:******** ********.*** * ***.*:**:** ** *****

9181 CTATAATCAATTCTTGACATGGAAAGATATTAGCCTTAGTAGATTAAATGTTTGTTTAAT 9240  RSV_WT
9181 CTATAATCAATTCTTGACATGGAAAGATATTAGCCTTAGTAGATTAAATGTTTGTTTAAT 9240  MinA
9181 CTATAATCAATTCTTGACATGGAAAGATATTAGCCTTAGTAGATTAAATGTTTGTTTAAT 9240  MinB
9181 ATATAATCAATTCTTAACATGGAAAGATATAAGTCTATCTAGATTGAACGTATGCTTAAT 9240  MinL
9181 ATATAATCAATTCTTAACATGGAAAGATATAAGTCTATCTAGATTGAACGTATGCTTAAT 9240  MinFLC
     .**************.**************:** **:: ******.** **:** *****

9241 TACATGGATTAGTAACTGCTTGAACACATTAAATAAAAGCTTAGGCTTAAGATGCGGATT 9300  RSV_WT
9241 TACATGGATTAGTAACTGCTTGAACACATTAAATAAAAGCTTAGGCTTAAGATGCGGATT 9300  MinA
9241 TACATGGATTAGTAACTGCTTGAACACATTAAATAAAAGCTTAGGCTTAAGATGCGGATT 9300  MinB
9241 TACATGGATTTCGAATTGTCTTAATACACTTAATAAATCATTAGGGTTAAGATGCGGATT 9300  MinL
9241 TACATGGATTTCGAATTGTCTTAATACACTTAATAAATCATTAGGGTTAAGATGCGGATT 9300  MinFLC
     **********:  ** **  * ** *** *:******: .***** **************

9301 CAATAATGTTATCTTGACACAACTATTCCTTTATGGAGATTGTATACTAAAGCTATTTCA 9360  RSV_WT
9301 CAATAATGTTATCTTGACACAACTATTCCTTTATGGAGATTGTATACTAAAGCTATTTCA 9360  MinA
9301 CAATAATGTTATCTTGACACAACTATTCCTTTATGGAGATTGTATACTAAAGCTATTTCA 9360  MinB
9301 TAATAACGTTATACTTACACAATTGTTCTTATACGGAGATTGTATACTTAAGTTGTTCCA 9360  MinL
9301 TAATAACGTTATACTTACACAATTGTTCTTATACGGAGATTGTATACTTAAGTTGTTCCA 9360  MinFLC
      ***** *****. * ****** *:*** *:** **************:*** *.** **

9361 CAATGAGGGGTTCTACATAATAAAAGAGGTAGAGGGATTTATTATGTCTCTAATTTTAAA 9420  RSV_WT
9361 CAATGAGGGGTTCTACATAATAAAAGAGGTAGAGGGATTTATTATGTCTCTAATTTTAAA 9420  MinA
9361 CAATGAGGGGTTCTACATAATAAAAGAGGTAGAGGGATTTATTATGTCTCTAATTTTAAA 9420  MinB
9361 TAACGAAGGGTTTTATATAATAAAAGAGGTTGAGGGATTTATAATGTCATTGATACTGAA 9420  MinL
9361 TAACGAAGGGTTTTATATAATAAAAGAGGTTGAGGGATTTATAATGTCATTGATACTGAA 9420  MinFLC
      ** **.***** ** **************:***********:*****: *.**: *.**

9421 TATAACAGAAGAAGATCAATTCAGAAAACGATTTTATAATAGTATGCTCAACAACATCAC 9480  RSV_WT
9421 TATAACAGAAGAAGATCAATTCAGAAAACGATTTTATAATAGTATGCTCAACAACATCAC 9480  MinA
9421 TATAACAGAAGAAGATCAATTCAGAAAACGATTTTATAATAGTATGCTCAACAACATCAC 9480  MinB
9421 TATTACCGAAGAGGATCAATTTAGAAAAAGATTCTATAATAGTATGTTAAACAATATAAC 9480  MinL
9421 TATTACCGAAGAGGATCAATTTAGAAAAAGATTCTATAATAGTATGTTAAACAATATAAC 9480  MinFLC
     ***:**.*****.******** ******.**** ************ *.***** **.**

9481 AGATGCTGCTAATAAAGCTCAGAAAAATCTGCTATCAAGAGTATGTCATACATTATTAGA 9540  RSV_WT
9481 AGATGCTGCTAATAAAGCTCAGAAAAATCTGCTATCAAGAGTATGTCATACATTATTAGA 9540  MinA
9481 AGATGCTGCTAATAAAGCTCAGAAAAATCTGCTATCAAGAGTATGTCATACATTATTAGA 9540  MinB
9481 TGACGCAGCTAATAAAGCGCAGAAGAATCTGTTATCTAGAGTATGTCATACATTGTTAGA 9540  MinL
9481 TGACGCAGCTAATAAAGCGCAGAAGAATCTGTTATCTAGAGTATGTCATACATTGTTAGA 9540  MinFLC
     :** **:*********** *****.****** ****:*****************.*****
```

Figure 7 cont.

```
9541 TAAGACAGTGTCCGATAATATAATAAATGGCAGATGGATAATTCTATTAAGTAAGTTCCT 9600  RSV_WT
9541 TAAGACAGTGTCCGATAATATAATAAATGGCAGATGGATAATTCTATTAAGTAAGTTCCT 9600  MinA
9541 TAAGACAGTGTCCGATAATATAATAAATGGCAGATGGATAATTCTATTAAGTAAGTTCCT 9600  MinB
9541 CAAAACAGTGAGCGATAATATTATAAACGGTAGATGGATTATACTGTTATCTAAATTCTT 9600  MinL
9541 CAAAACAGTGAGCGATAATATTATAAACGGTAGATGGATTATACTGTTATCTAAATTCTT 9600  MinFLC
      **.******: *********:***** ** ********:**:**.***: ***.*** *

9601 TAAATTAATTAAGCTTGCAGGTGACAATAACCTTAACAATCTGAGTGAACTATATTTTTT 9660  RSV_WT
9601 TAAATTAATTAAGCTTGCAGGTGACAATAACCTTAACAATCTGAGTGAACTATATTTTTT 9660  MinA
9601 TAAATTAATTAAGCTTGCAGGTGACAATAACCTTAACAATCTGAGTGAACTATATTTTTT 9660  MinB
9601 AAAATTGATTAAGTTGGCAGGTGACAATAACCTTAATAACTTAAGCGAATTGTATTTCTT 9660  MinL
9601 AAAATTGATTAAGTTGGCAGGTGACAATAACCTTAATAACTTAAGCGAATTGTATTTCTT 9660  MinFLC
     :*****.****** * ******************** **  *.** *** *.***** **

9661 GTTCAGAATATTTGGACACCCAATGGTAGATGAAAGACAAGCCATGGATGCTGTTAAAAT 9720  RSV_WT
9661 GTTCAGAATATTTGGACACCCAATGGTAGATGAAAGACAAGCCATGGATGCTGTTAAAAT 9720  MinA
9661 GTTCAGAATATTTGGACACCCAATGGTAGATGAAAGACAAGCCATGGATGCTGTTAAAAT 9720  MinB
9661 ATTCAGAATATTCGGACATCCTATGGTTGACGAACGACAAGCTATGGACGCAGTGAAGAT 9720  MinL
9661 ATTCAGAATATTCGGACATCCTATGGTTGACGAACGACAAGCTATGGACGCAGTGAAGAT 9720  MinFLC
     .*********** ***** **:*****:** ***.******* ***** **:** **.**

9721 TAATTGCAATGAGACCAAATTTTACTTGTTAAGCAGTCTGAGTATGTTAAGAGGTGCCTT 9780  RSV_WT
9721 TAATTGCAATGAGACCAAATTTTACTTGTTAAGCAGTCTGAGTATGTTAAGAGGTGCCTT 9780  MinA
9721 TAATTGCAATGAGACCAAATTTTACTTGTTAAGCAGTCTGAGTATGTTAAGAGGTGCCTT 9780  MinB
9721 TAATTGTAACGAAACTAAATTCTATCTATTATCTAGTCTATCTATGCTTAGAGGCGCATT 9780  MinL
9721 TAATTGTAACGAAACTAAATTCTATCTATTATCTAGTCTATCTATGCTTAGAGGCGCATT 9780  MinFLC
     ****** ** **.** ***** **  *.***:  *****.: **** *:***** **.**

9781 TATATATAGAATTATAAAAGGGTTTGTAAATAATTACAACAGATGGCCTACTTTAAGAAA 9840  RSV_WT
9781 TATATATAGAATTATAAAAGGGTTTGTAAATAATTACAACAGATGGCCTACTTTAAGAAA 9840  MinA
9781 TATATATAGAATTATAAAAGGGTTTGTAAATAATTACAACAGATGGCCTACTTTAAGAAA 9840  MinB
9781 CATATATAGAATTATAAAAGGGTTCGTTAATAATTATAATAGATGGCCTACACTTAGAAA 9840  MinL
9781 CATATATAGAATTATAAAAGGGTTCGTTAATAATTATAATAGATGGCCTACACTTAGAAA 9840  MinFLC
      *********************** **:******** ** ***********: *:*****

9841 TGCTATTGTTTTACCCTTAAGATGGTTAACTTACTATAAACTAAACACTTATCCTTCTTT 9900  RSV_WT
9841 TGCTATTGTTTTACCCTTAAGATGGTTAACTTACTATAAACTAAACACTTATCCTTCTTT 9900  MinA
9841 TGCTATTGTTTTACCCTTAAGATGGTTAACTTACTATAAACTAAACACTTATCCTTCTTT 9900  MinB
9841 CGCTATAGTGTTACCACTTAGATGGTTAACATATTATAAATTGAATACATATCCTAGTTT 9900  MinL
9841 CGCTATAGTGTTACCACTTAGATGGTTAACATATTATAAATTGAATACATATCCTAGTTT 9900  MinFLC
      *****:** *****. *:***********:** ****** *.** **:******: ***

9901 GTTGGAACTTACAGAAAGAGATTTGATTGTGTTATCAGGACTACGTTTCTATCGTGAGTT 9960  RSV_WT
9901 GTTGGAACTTACAGAAAGAGATTTGATTGTGTTATCAGGACTACGTTTCTATCGTGAGTT 9960  MinA
9901 GTTGGAACTTACAGAAAGAGATTTGATTGTGTTATCAGGACTACGTTTCTATCGTGAGTT 9960  MinB
9901 ACTCGAATTAACCGAACGCGATCTGATAGTGTTAAGCGGACTTAGATTCTATAGAGAGTT 9960  MinL
9901 ACTCGAATTAACCGAACGCGATCTGATAGTGTTAAGCGGACTTAGATTCTATAGAGAGTT 9960  MinFLC
     . * *** *:**.***.*.*** ****:******: .*****:.*:******.*:*****

9961 TCGGTTGCCTAAAAAAGTGGATCTTGAAATGATTATAAATGATAAAGCTATATCACCTCC 10020  RSV_WT
9961 TCGGTTGCCTAAAAAAGTGGATCTTGAAATGATTATAAATGATAAAGCTATATCACCTCC 10020  MinA
9961 TCGGTTGCCTAAAAAAGTGGATCTTGAAATGATTATAAATGATAAAGCTATATCACCTCC 10020  MinB
9961 TAGATTGCCTAAGAAAGTCGATCTCGAAATGATAATTAACGATAAGGCAATTAGTCCACC 10020  MinL
9961 TAGATTGCCTAAGAAAGTCGATCTCGAAATGATAATTAACGATAAGGCAATTAGTCCACC 10020  MinFLC
     *.*.********.***** ***** ********:**:** *****.**:**:: :**:**

10021 TAAAAATTTGATATGGACTAGTTTCCCTAGAAATTACATGCCATCACACATACAAAACTA 10080  RSV_WT
10021 TAAAAATTTGATATGGACTAGTTTCCCTAGAAATTACATGCCATCACACATACAAAACTA 10080  MinA
10021 TAAAAATTTGATATGGACTAGTTTCCCTAGAAATTACATGCCATCACACATACAAAACTA 10080  MinB
10021 TAAAAACTTAATATGGACAAGCTTCCCTAGAAATTATATGCCTAGTCATATACAAAATTA 10080  MinL
10021 TAAAAACTTAATATGGACAAGCTTCCCTAGAAATTATATGCCTAGTCATATACAAAATTA 10080  MinFLC
      ****** **.********:** ************** *****:: :** ******** **

10081 TATAGAACATGAAAAATTAAAATTTTCCGAGAGTGATAAATCAAGAAGAGTATTAGAGTA 10140  RSV_WT
10081 TATAGAACATGAAAAATTAAAATTTTCCGAGAGTGATAAATCAAGAAGAGTATTAGAGTA 10140  MinA
10081 TATAGAACATGAAAAATTAAAATTTTCCGAGAGTGATAAATCAAGAAGAGTATTAGAGTA 10140  MinB
10081 TATCGAACACGAAAAATTGAAATTTAGCGAATCCGATAAGTCTAGAAGAGTGTTAGAGTA 10140  MinL
10081 TATCGAACACGAAAAATTGAAATTTAGCGAATCCGATAAGTCTAGAAGAGTGTTAGAGTA 10140  MinFLC
      ***.***** ********.******: ***.:  *****.**:********.********
```

Figure 7 cont.

```
10141 TTATTTAAGAGATAACAAATTCAATGAATGTGATTTATACAACTGTGTAGTTAATCAAAG 10200  RSV_WT
10141 TTATTTAAGAGATAACAAATTCAATGAATGTGATTTATACAACTGTGTAGTTAATCAAAG 10200  MinA
10141 TTATTTAAGAGATAACAAATTCAATGAATGTGATTTATACAACTGTGTAGTTAATCAAAG 10200  MinB
10141 TTACTTACGCGATAATAAATTTAACGAATGCGATCTATATAATTGCGTAGTGAACCAATC 10200  MinL
10141 TTACTTACGCGATAATAAATTTAACGAATGCGATCTATATAATTGCGTAGTGAACCAATC 10200  MinFLC
      *** ***.*.***** ***** ** ***** *** **** ** ** ***** ** ***:

10201 TTATCTCAACAACCCTAATCATGTGGTATCATTGACAGGCAAAGAAAGAGAACTCAGTGT 10260  RSV_WT
10201 TTATCTCAACAACCCTAATCATGTGGTATCATTGACAGGCAAAGAAAGAGAACTCAGTGT 10260  MinA
10201 TTATCTCAACAACCCTAATCATGTGGTATCATTGACAGGCAAAGAAAGAGAACTCAGTGT 10260  MinB
10201 ATATCTTAATAATCCTAATCACGTAGTGAGTCTTACAGGTAAGGAAAGAGAGTTGAGCGT 10260  MinL
10201 ATATCTTAATAATCCTAATCACGTAGTGAGTCTTACAGGTAAGGAAAGAGAGTTGAGCGT 10260  MinFLC
      :***** ** ** ******** **.**.: : * ***** **.********. * ** **

10261 AGGTAGAATGTTTGCAATGCAACCGGGAATGTTCAGACAGGTTCAAATATTGGCAGAGAA 10320  RSV_WT
10261 AGGTAGAATGTTTGCAATGCAACCGGGAATGTTCAGACAGGTTCAAATATTGGCAGAGAA 10320  MinA
10261 AGGTAGAATGTTTGCAATGCAACCGGGAATGTTCAGACAGGTTCAAATATTGGCAGAGAA 10320  MinB
10261 AGGTAGAATGTTCGCTATGCAACCCGGTATGTTTAGACAAGTGCAAATACTCGCAGAAAA 10320  MinL
10261 AGGTAGAATGTTCGCTATGCAACCCGGTATGTTTAGACAAGTGCAAATACTCGCAGAAAA 10320  MinFLC
      ************ **:******** **:***** *****.** ****** * *****.**

10321 AATGATAGCTGAAAACATTTTACAATTCTTTCCTGAAAGTCTTACAAGATATGGTGATCT 10380  RSV_WT
10321 AATGATAGCTGAAAACATTTTACAATTCTTTCCTGAAAGTCTTACAAGATATGGTGATCT 10380  MinA
10321 AATGATAGCTGAAAACATTTTACAATTCTTTCCTGAAAGTCTTACAAGATATGGTGATCT 10380  MinB
10321 GATGATAGCCGAAAATATACTGCAATTCTTTCCCGAATCATTGACTAGATACGGAGATTT 10380  MinL
10321 GATGATAGCCGAAAATATACTGCAATTCTTTCCCGAATCATTGACTAGATACGGAGATTT 10380  MinFLC
      .******** ***** **: *.*********** ***: : * **:****** **:*** *

10381 AGAACTACAAAAAATATTAGAACTGAAAGCAGGAATAAGTAACAAATCAAATCGCTACAA 10440  RSV_WT
10381 AGAACTACAAAAAATATTAGAACTGAAAGCAGGAATAAGTAACAAATCAAATCGCTACAA 10440  MinA
10381 AGAACTACAAAAAATATTAGAACTGAAAGCAGGAATAAGTAACAAATCAAATCGCTACAA 10440  MinB
10381 AGAATTGCAAAAGATACTCGAATTGAAAGCAGGTATATCTAATAAGTCTAATAGATATAA 10440  MinL
10381 AGAATTGCAAAAGATACTCGAATTGAAAGCAGGTATATCTAATAAGTCTAATAGATATAA 10440  MinFLC
      **** *.*****.*** *.*** *********:***: *** **.**:***.*.** **

10441 TGATAATTACAACAATTACATTAGTAAGTGCTCTATCATCACAGATCTCAGCAAATTCAA 10500  RSV_WT
10441 TGATAATTACAACAATTACATTAGTAAGTGCTCTATCATCACAGATCTCAGCAAATTCAA 10500  MinA
10441 TGATAATTACAACAATTACATTAGTAAGTGCTCTATCATCACAGATCTCAGCAAATTCAA 10500  MinB
10441 CGATAATTATAATAATTATATATCTAAGTGTAGTATTATTACCGATCTATCTAAATTCAA 10500  MinL
10441 CGATAATTATAATAATTATATATCTAAGTGTAGTATTATTACCGATCTATCTAAATTCAA 10500  MinFLC
       ******** ** ***** **:: ****** : *** ** **.*****.:  ********

10501 TCAAGCATTTCGATATGAAACGTCATGTATTTGTAGTGATGTGCTGGATGAACTGCATGG 10560  RSV_WT
10501 TCAAGCATTTCGATATGAAACGTCATGTATTTGTAGTGATGTGCTGGATGAACTGCATGG 10560  MinA
10501 TCAAGCATTTCGATATGAAACGTCATGTATTTGTAGTGATGTGCTGGATGAACTGCATGG 10560  MinB
10501 TCAGGCATTTAGATACGAAACTAGTTGTATATGCTCAGACGTATTAGACGAATTACACGG 10560  MinL
10501 TCAGGCATTTAGATACGAAACTAGTTGTATATGCTCAGACGTATTAGACGAATTACACGG 10560  MinFLC
      ***.******.**** ***** : :*****:** : :** **. *.** *** *.** **

10561 TGTACAATCTCTATTTTCCTGGTTACATTTAACTATTCCTCATGTCACAATAATATGCAC 10620  RSV_WT
10561 TGTACAATCTCTATTTTCCTGGTTACATTTAACTATTCCTCATGTCACAATAATATGCAC 10620  MinA
10561 TGTACAATCTCTATTTTCCTGGTTACATTTAACTATTCCTCATGTCACAATAATATGCAC 10620  MinB
10561 AGTGCAATCTTTGTTTAGTTGGTTACATTTAACTATACCTCACGTTACAATTATATGTAC 10620  MinL
10561 AGTGCAATCTTTGTTTAGTTGGTTACATTTAACTATACCTCACGTTACAATTATATGTAC 10620  MinFLC
      :**.****** *.***:  ****************:**** ** ***** :***** **

10621 ATATAGGCATGCACCCCCCTATATAGGAGATCATATTGTAGATCTTAACAATGTAGATGA 10680  RSV_WT
10621 ATATAGGCATGCACCCCCCTATATAGGAGATCATATTGTAGATCTTAACAATGTAGATGA 10680  MinA
10621 ATATAGGCATGCACCCCCCTATATAGGAGATCATATTGTAGATCTTAACAATGTAGATGA 10680  MinB
10621 ATATAGACACGCACCACCATATATAGGCGATCATATAGTCGATCTGAATAACGTAGACGA 10680  MinL
10621 ATATAGACACGCACCACCATATATAGGCGATCATATAGTCGATCTGAATAACGTAGACGA 10680  MinFLC
      ******.** *****.**.********:*******:** ***** **.** ***** **

10681 ACAAAGTGGATTATATAGATATCACATGGGTGGCATCGAAGGGTGGTGTCAAAAACTATG 10740  RSV_WT
10681 ACAAAGTGGATTATATAGATATCACATGGGTGGCATCGAAGGGTGGTGTCAAAAACTATG 10740  MinA
10681 ACAAAGTGGATTATATAGATATCACATGGGTGGCATCGAAGGGTGGTGTCAAAAACTATG 10740  MinB
10681 ACAATCCGGATTGTATAGATATCACATGGGTGGCATAGAGGGATGGTGTCAAAAATTGTG 10740  MinL
10681 ACAATCCGGATTGTATAGATATCACATGGGTGGCATAGAGGGATGGTGTCAAAAATTGTG 10740  MinFLC
      ****:  *****.********************.**.**.************ *.**
```

Figure 7 cont.

```
10741 GACCATAGAAGCTATATCACTATTGGATCTAATATCTCTCAAAGGGAAATTCTCAATTAC 10800    RSV_WT
10741 GACCATAGAAGCTATATCACTATTGGATCTAATATCTCTCAAAGGGAAATTCTCAATTAC 10800    MinA
10741 GACCATAGAAGCTATATCACTATTGGATCTAATATCTCTCAAAGGGAAATTCTCAATTAC 10800    MinB
10741 GACTATAGAGGCAATTAGTCTGTTAGATCTAATTAGTCTTAAGGGTAAGTTTTCGATTAC 10800    MinL
10741 GACTATAGAGGCAATTAGTCTGTTAGATCTAATTAGTCTTAAGGGTAAGTTTTCGATTAC 10800    MinFLC
      *** ***** **:**:: :**.**.*********:: *** **.** **.** **.*****

10801 TGCTTTAATTAATGGTGACAATCAATCAATAGATATAAGCAAACCAATCAGACTCATGGA 10860    RSV_WT
10801 TGCTTTAATTAATGGTGACAATCAATCAATAGATATAAGCAAACCAATCAGACTCATGGA 10860    MinA
10801 TGCTTTAATTAATGGTGACAATCAATCAATAGATATAAGCAAACCAATCAGACTCATGGA 10860    MinB
10801 CGCATTGATTAACGGTGATAATCAATCAATTGATATATCTAAACCGATACGGTTAATGGA 10860    MinL
10801 CGCATTGATTAACGGTGATAATCAATCAATTGATATATCTAAACCGATACGGTTAATGGA 10860    MinFLC
      **:**.***** ***** ************:******:  *****.**..*. *.*****

10861 AGGTCAAACTCATGCTCAAGCAGATTATTTGCTAGCATTAAATAGCCTTAAATTACTGTA 10920    RSV_WT
10861 AGGTCAAACTCATGCTCAAGCAGATTATTTGCTAGCATTAAATAGCCTTAAATTACTGTA 10920    MinA
10861 AGGTCAAACTCATGCTCAAGCAGATTATTTGCTAGCATTAAATAGCCTTAAATTACTGTA 10920    MinB
10861 GGGACAAACACACGCTCAAGCCGATTACTTACTCGCACTTAATTCACTTAAACTGTTATA 10920    MinL
10861 GGGACAAACACACGCTCAAGCCGATTACTTACTCGCACTTAATTCACTTAAACTGTTATA 10920    MinFLC
      .**:*****:** ********.***** **.** **.*** *:***: .****** *. *.**

10921 TAAAGAGTATGCAGGCATAGGCCACAAATTAAAAGGAACTGAGACTTATATATCACGAGA 10980    RSV_WT
10921 TAAAGAGTATGCAGGCATAGGCCACAAATTAAAAGGAACTGAGACTTATATATCACGAGA 10980    MinA
10921 TAAAGAGTATGCAGGCATAGGCCACAAATTAAAAGGAACTGAGACTTATATATCACGAGA 10980    MinB
10921 CAAAGAGTACGCAGGTATAGGGCATAAACTTAAGGGTACAGAGACATATATAAGTAGGGA 10980    MinL
10921 CAAAGAGTACGCAGGTATAGGGCATAAACTTAAGGGTACAGAGACATATATAAGTAGGGA 10980    MinFLC
      ******** ***** ***** ** *** *:**.**:**:***** :.*.**

10981 TATGCAATTTATGAGTAAAACAATTCAACATAACGGTGTATATTACCCAGCTAGTATAAA 11040    RSV_WT
10981 TATGCAATTTATGAGTAAAACAATTCAACATAACGGTGTATATTACCCAGCTAGTATAAA 11040    MinA
10981 TATGCAATTTATGAGTAAAACAATTCAACATAACGGTGTATATTACCCAGCTAGTATAAA 11040    MinB
10981 TATGCAATTTATGAGTAAGACTATACAACATAACGGAGTGTATTATCCCGCTAGTATAAA 11040    MinL
10981 TATGCAATTTATGAGTAAGACTATACAACATAACGGAGTGTATTATCCCGCTAGTATAAA 11040    MinFLC
      ******************.**:**:***********:** ***** **.**********

11041 GAAAGTCCTAAGAGTGGGACCGTGGATAAACACTATACTTGATGATTTCAAAGTGAGTCT 11100    RSV_WT
11041 GAAAGTCCTAAGAGTGGGACCGTGGATAAACACTATACTTGATGATTTCAAAGTGAGTCT 11100    MinA
11041 GAAAGTCCTAAGAGTGGGACCGTGGATAAACACTATACTTGATGATTTCAAAGTGAGTCT 11100    MinB
11041 GAAAGTGCTTAGAGTCGGACCTTGGATTAATACTATATTAGACGATTTTAAGGTTAGTCT 11100    MinL
11041 GAAAGTGCTTAGAGTCGGACCTTGGATTAATACTATATTAGACGATTTTAAGGTTAGTCT 11100    MinFLC
      ****** **:***** ***** *****:** ****** *:** ***** **.** *****

11101 AGAATCTATAGGTAGTTTGACACAAGAATTAGAATATAGAGGTGAAAGTCTATTATGCAG 11160    RSV_WT
11101 AGAATCTATAGGTAGTTTGACACAAGAATTAGAATATAGAGGTGAAAGTCTATTATGCAG 11160    MinA
11101 AGAATCTATAGGTAGTTTGACACAAGAATTAGAATATAGAGGTGAAAGTCTATTATGCAG 11160    MinB
11101 CGAATCAATCGGATCATTGACACAAGAGTTGGAGTATAGAGGCGAATCTCTATTATGCTC 11160    MinL
11101 CGAATCAATCGGATCATTGACACAAGAGTTGGAGTATAGAGGCGAATCTCTATTATGCTC 11160    MinFLC
      .*****:**.**:: :***********.**.**.******** ***:  **********:

11161 TTTAATATTTAGAAATGTATGGTTATATAATCAGATTGCTCTACAATTAAAAAATCATGC 11220    RSV_WT
11161 TTTAATATTTAGAAATGTATGGTTATATAATCAGATTGCTCTACAATTAAAAAATCATGC 11220    MinA
11161 TTTAATATTTAGAAATGTATGGTTATATAATCAGATTGCTCTACAATTAAAAAATCATGC 11220    MinB
11161 ATTGATTTTTAGAAACGTATGGTTATACAATCAGATTGCATTGCAATTGAAAAATCACGC 11220    MinL
11161 ATTGATTTTTAGAAACGTATGGTTATACAATCAGATTGCATTGCAATTGAAAAATCACGC 11220    MinFLC
      :**.**:******** *********** ***********:  *.*****.*******.**

11221 ATTATGTAACAATAAACTATATTTGGACATATTAAAGGTTCTGAAACACTTAAAAACCTT 11280    RSV_WT
11221 ATTATGTAACAATAAACTATATTTGGACATATTAAAGGTTCTGAAACACTTAAAAACCTT 11280    MinA
11221 ATTATGTAACAATAAACTATATTTGGACATATTAAAGGTTCTGAAACACTTAAAAACCTT 11280    MinB
11221 ACTATGTAATAATAAGTTGTACTTAGACATACTTAAAGTGTTAAAACATCTTAAAACATT 11280    MinL
11221 ACTATGTAATAATAAGTTGTACTTAGACATACTTAAAGTGTTAAAACATCTTAAAACATT 11280    MinFLC
      * ******* *****. *.** **.***** *:**.**  .*****  *:*****.**

11281 TTTTAATCTTGATAATATTGATACAGCATTAACATTGTATATGAATTTACCCATGTTATT 11340    RSV_WT
11281 TTTTAATCTTGATAATATTGATACAGCATTAACATTGTATATGAATTTACCCATGTTATT 11340    MinA
11281 TTTTAATCTTGATAATATTGATACAGCATTAACATTGTATATGAATTTACCCATGTTATT 11340    MinB
11281 CTTTAATCTCGATAATATAGATACCGCATTAACATTGTATATGAATCTACCTATGTTATT 11340    MinL
11281 CTTTAATCTCGATAATATAGATACCGCATTAACATTGTATATGAATCTACCTATGTTATT 11340    MinFLC
      ******* *********.*******.************** **** ********
```

Figure 7 cont.

```
11341 TGGTGGTGGTGATCCCAACTTGTTATATCGAAGTTTCTATAGAAGAACTCCTGACTTCCT 11400  RSV_WT
11341 TGGTGGTGGTGATCCCAACTTGTTATATCGAAGTTTCTATAGAAGAACTCCTGACTTCCT 11400  MinA
11341 TGGTGGTGGTGATCCCAACTTGTTATATCGAAGTTTCTATAGAAGAACTCCTGACTTCCT 11400  MinB
11341 CGGAGGGGGAGATCCTAATCTATTGTATAGATCATTCTATAGACGTACACCTGATTTCTT 11400  MinL
11341 CGGAGGGGGAGATCCTAATCTATTGTATAGATCATTCTATAGACGTACACCTGATTTCTT 11400  MinFLC
       **:** **:***** **  *.**.***.**: :*********.*:**:***** *** *

11401 CACAGAGGCTATAGTTCACTCTGTGTTCATACTTAGTTATTATACAAACCATGACTTAAA 11460  RSV_WT
11401 CACAGAGGCTATAGTTCACTCTGTGTTCATACTTAGTTATTATACAAACCATGACTTAAA 11460  MinA
11401 CACAGAGGCTATAGTTCACTCTGTGTTCATACTTAGTTATTATACAAACCATGACTTAAA 11460  MinB
11401 AACCGAAGCTATAGTGCATAGCGTATTCATACTATCATATTATACTAATCACGATCTTAA 11460  MinL
11401 AACCGAAGCTATAGTGCATAGCGTATTCATACTATCATATTATACTAATCACGATCTTAA 11460  MinFLC
      .**.**.******** ** :  **.********:: :********:** ** **  *:**

11461 AGATAAACTTCAAGATCTGTCAGATGATAGATTGAATAAGTTCTTAACATGCATAATCAC 11520  RSV_WT
11461 AGATAAACTTCAAGATCTGTCAGATGATAGATTGAATAAGTTCTTAACATGCATAATCAC 11520  MinA
11461 AGATAAACTTCAAGATCTGTCAGATGATAGATTGAATAAGTTCTTAACATGCATAATCAC 11520  MinB
11461 AGATAAGTTGCAGGATCTATCTGACGATAGATTGAATAAATTCTTAACATGTATTATAAC 11520  MinL
11461 AGATAAGTTGCAGGATCTATCTGACGATAGATTGAATAAATTCTTAACATGTATTATAAC 11520  MinFLC
      ******. * **.*****.**:** **************.*********** **:**.**

11521 GTTTGACAAAAACCCTAATGCTGAATTCGTAACATTGATGAGAGATCCTCAAGCTTTAGG 11580  RSV_WT
11521 GTTTGACAAAAACCCTAATGCTGAATTCGTAACATTGATGAGAGATCCTCAAGCTTTAGG 11580  MinA
11521 GTTTGACAAAAACCCTAATGCTGAATTCGTAACATTGATGAGAGATCCTCAAGCTTTAGG 11580  MinB
11521 ATTCGATAAAAATCCTAACGCTGAATTCGTTACACTTATGAGAGATCCACAAGCATTAGG 11580  MinL
11521 ATTCGATAAAAATCCTAACGCTGAATTCGTTACACTTATGAGAGATCCACAAGCATTAGG 11580  MinFLC
      .** ** ***** ***** ***********:*** * ***********:*****:*****

11581 GTCTGAGAGACAAGCTAAAATTACTAGCGAAATCAATAGACTGGCAGTTACAGAGGTTTT 11640  RSV_WT
11581 GTCTGAGAGACAAGCTAAAATTACTAGCGAAATCAATAGACTGGCAGTTACAGAGGTTTT 11640  MinA
11581 GTCTGAGAGACAAGCTAAAATTACTAGCGAAATCAATAGACTGGCAGTTACAGAGGTTTT 11640  MinB
11581 TTCAGAGAGACAGGCTAAAATTACTAGCGAAATTAATAGATTAGCCGTTACCGAAGTGTT 11640  MinL
11581 TTCAGAGAGACAGGCTAAAATTACTAGCGAAATTAATAGATTAGCCGTTACCGAAGTGTT 11640  MinFLC
       **:********.******************** ****** *.**.*****.**.** **

11641 GAGTACAGCTCCAAACAAAATATTCTCCAAAAGTGCACAACATTATACTACTACAGAGAT 11700  RSV_WT
11641 GAGTACAGCTCCAAACAAAATATTCTCCAAAAGTGCACAACATTATACTACTACAGAGAT 11700  MinA
11641 GAGTACAGCTCCAAACAAAATATTCTCCAAAAGTGCACAACATTATACTACTACAGAGAT 11700  MinB
11641 AAGTACCGCACCTAATAAGATATTCTCTAAATCCGCTCAACATTATACAACAACCGAAAT 11700  MinL
11641 AAGTACCGCACCTAATAAGATATTCTCTAAATCCGCTCAACATTATACAACAACCGAAAT 11700  MinFLC
      .*****.**:**:** **.******** ***:  **:***********:**:**.**.**

11701 AGATCTAAATGATATTATGCAAAATATAGAACCTACATATCCTCATGGGCTAAGAGTTGT 11760  RSV_WT
11701 AGATCTAAATGATATTATGCAAAATATAGAACCTACATATCCTCATGGGCTAAGAGTTGT 11760  MinA
11701 AGATCTAAATGATATTATGCAAAATATAGAACCTACATATCCTCATGGGCTAAGAGTTGT 11760  MinB
11701 AGATCTTAACGATATTATGCAAAATATCGAACCTACATATCCTCACGGATTACGCGTAGT 11760  MinL
11701 AGATCTTAACGATATTATGCAAAATATCGAACCTACATATCCTCACGGATTACGCGTAGT 11760  MinFLC
      ******:** *****************.***************** **. **.*.**:**

11761 TTATGAAAGTTTACCCTTTTATAAAGCAGAGAAAATAGTAAATCTTATATCAGGTACAAA 11820  RSV_WT
11761 TTATGAAAGTTTACCCTTTTATAAAGCAGAGAAAATAGTAAATCTTATATCAGGTACAAA 11820  MinA
11761 TTATGAAAGTTTACCCTTTTATAAAGCAGAGAAAATAGTAAATCTTATATCAGGTACAAA 11820  MinB
11761 TTACGAATCATTACCATTCTATAAAGCCGAAAAGATCGTTAACTTAATTAGCGGTACAAA 11820  MinL
11761 TTACGAATCATTACCATTCTATAAAGCCGAAAAGATCGTTAACTTAATTAGCGGTACAAA 11820  MinFLC
      *** ***: :*****.** ********.**.**.**.**:**  *:**:: .********

11821 ATCTATAACTAACATACTGGAAAAAACTTCTGCCATAGACTTAACAGATATTGATAGAGC 11880  RSV_WT
11821 ATCTATAACTAACATACTGGAAAAAACTTCTGCCATAGACTTAACAGATATTGATAGAGC 11880  MinA
11821 ATCTATAACTAACATACTGGAAAAAACTTCTGCCATAGACTTAACAGATATTGATAGAGC 11880  MinB
11821 ATCAATTACTAATATACTCGAAAAGACTAGCGCAATTGATTTAACCGATATAGATAGAGC 11880  MinL
11821 ATCAATTACTAATATACTCGAAAAGACTAGCGCAATTGATTTAACCGATATAGATAGAGC 11880  MinFLC
      ***:**:***** ***** *****.***:  **.**:** *****.*****:********

11881 CACTGAGATGATGAGGAAAAACATAACTTTGCTTATAAGGATACTTCCATTGGATTGTAA 11940  RSV_WT
11881 CACTGAGATGATGAGGAAAAACATAACTTTGCTTATAAGGATACTTCCATTGGATTGTAA 11940  MinA
11881 CACTGAGATGATGAGGAAAAACATAACTTTGCTTATAAGGATACTTCCATTGGATTGTAA 11940  MinB
11881 TACCGAAATGATGCGTAAAAATATAACATTACTGATACGTATACTACCATTAGATTGTAA 11940  MinL
11881 TACCGAAATGATGCGTAAAAATATAACATTACTGATACGTATACTACCATTAGATTGTAA 11940  MinFLC
       ** **.******.* ***** *****:**.** ***.* *****:*****.********
```

Figure 7 cont.

```
11941 CAGAGATAAAAGAGAGATATTGAGTATGGAAAACCTAAGTATTACTGAATTAAGCAAATA 12000  RSV_WT
11941 CAGAGATAAAAGAGAGATATTGAGTATGGAAAACCTAAGTATTACTGAATTAAGCAAATA 12000  MinA
11941 CAGAGATAAAAGAGAGATATTGAGTATGGAAAACCTAAGTATTACTGAATTAAGCAAATA 12000  MinB
11941 TAGGGATAAAAGAGAGATACTATCTATGGAGAATCTATCAATTACAGAATTGTCAAAATA 12000  MinL
11941 TAGGGATAAAAGAGAGATACTATCTATGGAGAATCTATCAATTACAGAATTGTCAAAATA 12000  MinFLC
       **.*************** *.: ******.** ***: :*****:*****.: .*****

12001 TGTTAGGGAAAGATCTTGGTCTTTATCCAATATAGTTGGTGTTACATCACCCAGTATCAT 12060  RSV_WT
12001 TGTTAGGGAAAGATCTTGGTCTTTATCCAATATAGTTGGTGTTACATCACCCAGTATCAT 12060  MinA
12001 TGTTAGGGAAAGATCTTGGTCTTTATCCAATATAGTTGGTGTTACATCACCCAGTATCAT 12060  MinB
12001 CGTTAGGGAACGATCATGGTCACTATCTAATATCGTAGGCGTAACTAGTCCTAGTATTAT 12060  MinL
12001 CGTTAGGGAACGATCATGGTCACTATCTAATATCGTAGGCGTAACTAGTCCTAGTATTAT 12060  MinFLC
       *********.****:*****: **** *****.**:** **:**:: :** ***** **

12061 GTATACAATGGACATCAAATATACTACAAGCACTATATCTAGTGGCATAATTATAGAGAA 12120  RSV_WT
12061 GTATACAATGGACATCAAATATACTACAAGCACTATATCTAGTGGCATAATTATAGAGAA 12120  MinA
12061 GTATACAATGGACATCAAATATACTACAAGCACTATATCTAGTGGCATAATTATAGAGAA 12120  MinB
12061 GTATACTATGGATATTAAGTATACAACTAGTACAATTAGTAGCGGTATAATAATCGAAAA 12120  MinL
12061 GTATACTATGGATATTAAGTATACAACTAGTACAATTAGTAGCGGTATAATAATCGAAAA 12120  MinFLC
      ******:***** ** **.*****:**:** **:**:: *** ** *****:**.**.**

12121 ATATAATGTTAACAGTTTAACACGTGGTGAGAGAGGACCCACTAAACCATGGGTTGGTTC 12180  RSV_WT
12121 ATATAATGTTAACAGTTTAACACGTGGTGAGAGAGGACCCACTAAACCATGGGTTGGTTC 12180  MinA
12121 ATATAATGTTAACAGTTTAACACGTGGTGAGAGAGGACCCACTAAACCATGGGTTGGTTC 12180  MinB
12121 ATATAACGTTAATAGTCTAACACGTGGTGAAAGGGGACCTACAAAACCTTGGGTCGGATC 12180  MinL
12121 ATATAACGTTAATAGTCTAACACGTGGTGAAAGGGGACCTACAAAACCTTGGGTCGGATC 12180  MinFLC
      ****** ***** *** *************.**.***** **:*****:***** **:**

12181 ATCTACACAAGAGAAAAAAACAATGCCAGTTTATAATAGACAAGTCTTAACCAAAAAACA 12240  RSV_WT
12181 ATCTACACAAGAGAAAAAAACAATGCCAGTTTATAATAGACAAGTCTTAACCAAAAAACA 12240  MinA
12181 ATCTACACAAGAGAAAAAAACAATGCCAGTTTATAATAGACAAGTCTTAACCAAAAAACA 12240  MinB
12181 TAGTACACAAGAGAAGAAAACTATGCCCGTATATAATAGACAGGTATTGACTAAGAAACA 12240  MinL
12181 TAGTACACAAGAGAAGAAAACTATGCCCGTATATAATAGACAGGTATTGACTAAGAAACA 12240  MinFLC
      :: ************.*****:*****.**:***********.**.**.** **.*****

12241 GAGAGATCAAATAGATCTATTAGCAAAATTGGATTGGGTGTATGCATCTATAGATAACAA 12300  RSV_WT
12241 GAGAGATCAAATAGATCTATTAGCAAAATTGGATTGGGTGTATGCATCTATAGATAACAA 12300  MinA
12241 GAGAGATCAAATAGATCTATTAGCAAAATTGGATTGGGTGTATGCATCTATAGATAACAA 12300  MinB
12241 ACGAGATCAAATAGATCTATTAGCTAAACTCGATTGGGTATACGCTAGTATAGATAATAA 12300  MinL
12241 ACGAGATCAAATAGATCTATTAGCTAAACTCGATTGGGTATACGCTAGTATAGATAATAA 12300  MinFLC
      ..**********************:*** * ********.** **:: ********* **

12301 GGATGAATTCATGGAAGAACTCAGCATAGGAACCCTTGGGTTAACATATGAAAAGGCCAA 12360  RSV_WT
12301 GGATGAATTCATGGAAGAACTCAGCATAGGAACCCTTGGGTTAACATATGAAAAGGCCAA 12360  MinA
12301 GGATGAATTCATGGAAGAACTCAGCATAGGAACCCTTGGGTTAACATATGAAAAGGCCAA 12360  MinB
12301 AGACGAATTTATGGAAGAGTTGTCAATCGGTACATTAGGGTTAACATACGAAAAAGCTAA 12360  MinL
12301 AGACGAATTTATGGAAGAGTTGTCAATCGGTACATTAGGGTTAACATACGAAAAAGCTAA 12360  MinFLC
      .** ***** ********. * : .**.**:**. *:*********** *****.** **

12361 GAAATTATTTCCACAATATTTAAGTGTCAATTATTTGCATCGCCTTACAGTCAGTAGTAG 12420  RSV_WT
12361 GAAATTATTTCCACAATATTTAAGTGTCAATTATTTGCATCGCCTTACAGTCAGTAGTAG 12420  MinA
12361 GAAATTATTTCCACAATATTTAAGTGTCAATTATTTGCATCGCCTTACAGTCAGTAGTAG 12420  MinB
12361 GAAATTGTTCCCACAATATCTATCAGTGAATTATCTACATAGATTGACAGTGAGTAGTAG 12420  MinL
12361 GAAATTGTTCCCACAATATCTATCAGTGAATTATCTACATAGATTGACAGTGAGTAGTAG 12420  MinFLC
      ******.** ********* **: :** ****** *.***.*. * ***** ********

12421 ACCATGTGAATTCCCTGCATCAATACCAGCTTATAGAACAACAAATTATCACTTTGACAC 12480  RSV_WT
12421 ACCATGTGAATTCCCTGCATCAATACCAGCTTATAGAACAACAAATTATCACTTTGACAC 12480  MinA
12421 ACCATGTGAATTCCCTGCATCAATACCAGCTTATAGAACAACAAATTATCACTTTGACAC 12480  MinB
12421 ACCATGCGAATTTCCCGCTAGTATACCCGCATATAGAACTACTAATTATCATTTCGATAC 12480  MinL
12421 ACCATGCGAATTTCCCGCTAGTATACCCGCATATAGAACTACTAATTATCATTTCGATAC 12480  MinFLC
      ****** ***** ** **:: :*****.**:********:**:******** ** ** **

12481 TAGCCCTATTAATCGCATATTAACAGAAAAGTATGGTGATGAAGATATTGACATAGTATT 12540  RSV_WT
12481 TAGCCCTATTAATCGCATATTAACAGAAAAGTATGGTGATGAAGATATTGACATAGTATT 12540  MinA
12481 TAGCCCTATTAATCGCATATTAACAGAAAAGTATGGTGATGAAGATATTGACATAGTATT 12540  MinB
12481 TAGTCCAATTAATAGAATATTAACCGAAAAATACGGAGACGAAGATATAGATATCGTATT 12540  MinL
12481 TAGTCCAATTAATAGAATATTAACCGAAAAATACGGAGACGAAGATATAGATATCGTATT 12540  MinFLC
      *** **:******.*.********.*****.** **:** ********:** **.*****
```

Figure 7 cont.

```
12541 CCAAAACTGTATAAGCTTTGGCCTTAGTTTAATGTCAGTAGTAGAACAATTTACTAATGT 12600  RSV_WT
12541 CCAAAACTGTATAAGCTTTGGCCTTAGTTTAATGTCAGTAGTAGAACAATTTACTAATGT 12600  MinA
12541 CCAAAACTGTATAAGCTTTGGCCTTAGTTTAATGTCAGTAGTAGAACAATTTACTAATGT 12600  MinB
12541 CCAAAATTGTATTAGTTTCGGATTGAGTCTTATGTCCGTAGTCGAACAATTTACTAACGT 12600  MinL
12541 CCAAAATTGTATTAGTTTCGGATTGAGTCTTATGTCCGTAGTCGAACAATTTACTAACGT 12600  MinFLC
      ****** *****:** ** **. * *** *:*****.*****.************** **

12601 ATGTCCTAACAGAATTATTCTCATACCTAAGCTTAATGAGATACATTTGATGAAACCTCC 12660  RSV_WT
12601 ATGTCCTAACAGAATTATTCTCATACCTAAGCTTAATGAGATACATTTGATGAAACCTCC 12660  MinA
12601 ATGTCCTAACAGAATTATTCTCATACCTAAGCTTAATGAGATACATTTGATGAAACCTCC 12660  MinB
12601 ATGTCCTAATAGGATTATACTGATACCTAAATTGAACGAAATACATCTTATGAAACCTCC 12660  MinL
12601 ATGTCCTAATAGGATTATACTGATACCTAAATTGAACGAAATACATCTTATGAAACCTCC 12660  MinFLC
      ********* **.*****:** ********. * ** **.****** * ***********

12661 CATATTCACAGGTGATGTTGATATTCACAAGTTAAAACAAGTGATACAAAAACAGCATAT 12720  RSV_WT
12661 CATATTCACAGGTGATGTTGATATTCACAAGTTAAAACAAGTGATACAAAAACAGCATAT 12720  MinA
12661 CATATTCACAGGTGATGTTGATATTCACAAGTTAAAACAAGTGATACAAAAACAGCATAT 12720  MinB
12661 TATTTTTACAGGCGATGTCGATATACACAAATTGAAACAGGTTATACAAAAACAACATAT 12720  MinL
12661 TATTTTTACAGGCGATGTCGATATACACAAATTGAAACAGGTTATACAAAAACAACATAT 12720  MinFLC
       **:** ***** ***** *****:*****.**.*****.** ***********.*****

12721 GTTTTTACCAGACAAAATAAGTTTGACTCAATATGTGGAATTATTCTTAAGTAATAAAAC 12780  RSV_WT
12721 GTTTTTACCAGACAAAATAAGTTTGACTCAATATGTGGAATTATTCTTAAGTAATAAAAC 12780  MinA
12721 GTTTTTACCAGACAAAATAAGTTTGACTCAATATGTGGAATTATTCTTAAGTAATAAAAC 12780  MinB
12721 GTTCTTACCCGATAAGATATCGTTAACGCAATACGTTGAGTTGTTCTTATCAAATAAAAC 12780  MinL
12721 GTTCTTACCCGATAAGATATCGTTAACGCAATACGTTGAGTTGTTCTTATCAAATAAAAC 12780  MinFLC
      *** *****.** **.***:  **.** ***** ** **.**.******: :********

12781 ACTCAAATCTGGATCTCATGTTAATTCTAATTTAATATTGGCACATAAAATATCTGACTA 12840  RSV_WT
12781 ACTCAAATCTGGATCTCATGTTAATTCTAATTTAATATTGGCACATAAAATATCTGACTA 12840  MinA
12781 ACTCAAATCTGGATCTCATGTTAATTCTAATTTAATATTGGCACATAAAATATCTGACTA 12840  MinB
12781 ACTTAAATCAGGTAGTCACGTTAATAGTAATCTGATACTCGCACATAAAATTAGCGATTA 12840  MinL
12781 ACTTAAATCAGGTAGTCACGTTAATAGTAATCTGATACTCGCACATAAAATTAGCGATTA 12840  MinFLC
      *** *****:**:: *** ******: **** *.*** * ***********::  ** **

12841 TTTTCATAATACTTACATTTTAAGTACTAATTTAGCTGGACATTGGATTCTGATTATACA 12900  RSV_WT
12841 TTTTCATAATACTTACATTTTAAGTACTAATTTAGCTGGACATTGGATTCTGATTATACA 12900  MinA
12841 TTTTCATAATACTTACATTTTAAGTACTAATTTAGCTGGACATTGGATTCTGATTATACA 12900  MinB
12841 CTTTCATAATACATATATATTGAGTACTAACTTAGCCGGACATTGGATACTGATTATACA 12900  MinL
12841 CTTTCATAATACATATATATTGAGTACTAACTTAGCCGGACATTGGATACTGATTATACA 12900  MinFLC
       ***********:** **:**.******** ***** ***********:***********

12901 ACTTATGAAAGATTCTAAAGGTATTTTTGAAAAAGATTGGGGAGAGGGATATATAACTGA 12960  RSV_WT
12901 ACTTATGAAAGATTCTAAAGGTATTTTTGAAAAAGATTGGGGAGAGGGATATATAACTGA 12960  MinA
12901 ACTTATGAAAGATTCTAAAGGTATTTTTGAAAAAGATTGGGGAGAGGGATATATAACTGA 12960  MinB
12901 ATTGATGAAAGATAGTAAGGGTATATTCGAAAAAGATTGGGGTGAGGGATATATAACCGA 12960  MinL
12901 ATTGATGAAAGATAGTAAGGGTATATTCGAAAAAGATTGGGGTGAGGGATATATAACCGA 12960  MinFLC
      * * *********: ***.*****:** **************:************** **

12961 TCATATGTTTATTAATTTGAAAGTTTTCTTCAATGCTTATAAGACCTATCTCTTGTGTTT 13020  RSV_WT
12961 TCATATGTTTATTAATTTGAAAGTTTTCTTCAATGCTTATAAGACCTATCTCTTGTGTTT 13020  MinA
12961 TCATATGTTTATTAATTTGAAAGTTTTCTTCAATGCTTATAAGACCTATCTCTTGTGTTT 13020  MinB
12961 TCATATGTTTATAAACCTTAAGGTCTTCTTTAACGCATATAAAACTTATCTATTATGTTT 13020  MinL
12961 TCATATGTTTATAAACCTTAAGGTCTTCTTTAACGCATATAAAACTTATCTATTATGTTT 13020  MinFLC
      ************:**  * **.** ***** ** **:*****.** *****.**.*****

13021 TCATAAAGGTTATGGCAAAGCAAAGCTGGAGTGTGATATGAACACTTCAGATCTTCTATG 13080  RSV_WT
13021 TCATAAAGGTTATGGCAAAGCAAAGCTGGAGTGTGATATGAACACTTCAGATCTTCTATG 13080  MinA
13021 TCATAAAGGTTATGGCAAAGCAAAGCTGGAGTGTGATATGAACACTTCAGATCTTCTATG 13080  MinB
13021 TCATAAGGGATACGGTAAGGCTAAACTCGAATGCGATATGAATACATCCGATCTATTATG 13080  MinL
13021 TCATAAGGGATACGGTAAGGCTAAACTCGAATGCGATATGAATACATCCGATCTATTATG 13080  MinFLC
      ******.**:** ** **.**:**.** **.** ******** **:**.*****: ****

13081 TGTATTGGAATTAATAGACAGTAGTTATTGGAAGTCTATGTCTAAGGTATTTTTAGAACA 13140  RSV_WT
13081 TGTATTGGAATTAATAGACAGTAGTTATTGGAAGTCTATGTCTAAGGTATTTTTAGAACA 13140  MinA
13081 TGTATTGGAATTAATAGACAGTAGTTATTGGAAGTCTATGTCTAAGGTATTTTTAGAACA 13140  MinB
13081 CGTACTCGAATTAATTGATAGTAGCTATTGGAAATCTATGAGTAAGGTATTCTTAGAGCA 13140  MinL
13081 CGTACTCGAATTAATTGATAGTAGCTATTGGAAATCTATGAGTAAGGTATTCTTAGAGCA 13140  MinFLC
       *** * ********:** ***** ********.******: ********* *****.**
```

Figure 7 cont.

```
13141 AAAAGTTATCAAATACATTCTTAGCCAAGATGCAAGTTTACATAGAGTAAAAGGATGTCA 13200  RSV_WT
13141 AAAAGTTATCAAATACATTCTTAGCCAAGATGCAAGTTTACATAGAGTAAAAGGATGTCA 13200  MinA
13141 AAAAGTTATCAAATACATTCTTAGCCAAGATGCAAGTTTACATAGAGTAAAAGGATGTCA 13200  MinB
13141 AAAGGTGATCAAGTATATACTATCTCAAGACGCTAGTTTGCATAGGGTTAAGGGATGTCA 13200  MinL
13141 AAAGGTGATCAAGTATATACTATCTCAAGACGCTAGTTTGCATAGGGTTAAGGGATGTCA 13200  MinFLC
      ***.** *****.** **:**::  ***** **:*****.*****.**:**.********

13201 TAGCTTCAAATTATGGTTTCTTAAACGTCTTAATGTAGCAGAATTCACAGTTTGCCCTTG 13260  RSV_WT
13201 TAGCTTCAAATTATGGTTTCTTAAACGTCTTAATGTAGCAGAATTCACAGTTTGCCCTTG 13260  MinA
13201 TAGCTTCAAATTATGGTTTCTTAAACGTCTTAATGTAGCAGAATTCACAGTTTGCCCTTG 13260  MinB
13201 TAGTTTTAAATTATGGTTTCTTAAAAGATTGAACGTAGCCGAATTTACAGTATGTCCTTG 13260  MinL
13201 TAGTTTTAAATTATGGTTTCTTAAAAGATTGAACGTAGCCGAATTTACAGTATGTCCTTG 13260  MinFLC
      *** ** *****************.*: * ** *****.***** *****:** *****

13261 GGTTGTTAACATAGATTATCATCCAACACATATGAAAGCAATATTAACTTATATAGATCT 13320  RSV_WT
13261 GGTTGTTAACATAGATTATCATCCAACACATATGAAAGCAATATTAACTTATATAGATCT 13320  MinA
13261 GGTTGTTAACATAGATTATCATCCAACACATATGAAAGCAATATTAACTTATATAGATCT 13320  MinB
13261 GGTCGTTAACATAGATTATCATCCTACACATATGAAAGCTATACTTACATATATAGATCT 13320  MinL
13261 GGTCGTTAACATAGATTATCATCCTACACATATGAAAGCTATACTTACATATATAGATCT 13320  MinFLC
      *** *******************:**************:*** *:**:***********

13321 TGTTAGAATGGGATTGATAAATATAGATAGAATACACATTAAAAATAAACACAAATTCAA 13380  RSV_WT
13321 TGTTAGAATGGGATTGATAAATATAGATAGAATACACATTAAAAATAAACACAAATTCAA 13380  MinA
13321 TGTTAGAATGGGATTGATAAATATAGATAGAATACACATTAAAAATAAACACAAATTCAA 13380  MinB
13321 AGTGAGAATGGGATTGATTAACATAGATAGAATACATATAAAGAATAAACATAAATTTAA 13380  MinL
13321 AGTGAGAATGGGATTGATTAACATAGATAGAATACATATAAAGAATAAACATAAATTTAA 13380  MinFLC
      :** **************:** ************** **:**.******** ***** **

13381 TGATGAATTTTATACTTCTAATCTCTTCTACATTAATTATAACTTCTCAGATAATACTCA 13440  RSV_WT
13381 TGATGAATTTTATACTTCTAATCTCTTCTACATTAATTATAACTTCTCAGATAATACTCA 13440  MinA
13381 TGATGAATTTTATACTTCTAATCTCTTCTACATTAATTATAACTTCTCAGATAATACTCA 13440  MinB
13381 CGACGAATTCTATACTAGTAATCTATTCTATATAAATTATAATTTTTCCGATAATACACA 13440  MinL
13381 CGACGAATTCTATACTAGTAATCTATTCTATATAAATTATAATTTTTCCGATAATACACA 13440  MinFLC
       ** ***** ******: ******.***** **:******** ** **.********:**

13441 TCTATTAACTAAACATATAAGGATTGCTAATTCTGAATTAGAAAATAATTACAACAAATT 13500  RSV_WT
13441 TCTATTAACTAAACATATAAGGATTGCTAATTCTGAATTAGAAAATAATTACAACAAATT 13500  MinA
13441 TCTATTAACTAAACATATAAGGATTGCTAATTCTGAATTAGAAAATAATTACAACAAATT 13500  MinB
13441 TCTATTAACTAAACATATACGTATAGCTAATAGCGAACTCGAAAATAATTATAATAAATT 13500  MinL
13441 TCTATTAACTAAACATATACGTATAGCTAATAGCGAACTCGAAAATAATTATAATAAATT 13500  MinFLC
      ******************.* **:******:  *** *.*********** ** *****

13501 ATATCATCCTACACCAGAAACCCTAGAGAATATACTAGCCAATCCGATTAAAAGTAATGA 13560  RSV_WT
13501 ATATCATCCTACACCAGAAACCCTAGAGAATATACTAGCCAATCCGATTAAAAGTAATGA 13560  MinA
13501 ATATCATCCTACACCAGAAACCCTAGAGAATATACTAGCCAATCCGATTAAAAGTAATGA 13560  MinB
13501 GTATCATCCTACACCCGAAACATTAGAGAATATACTCGCTAATCCGATTAAATCTAACGA 13560  MinL
13501 GTATCATCCTACACCCGAAACATTAGAGAATATACTCGCTAATCCGATTAAATCTAACGA 13560  MinFLC
      .**************.*****. *************.** ************: *** **

13561 CAAAAAGACACTGAATGACTATTGTATAGGTAAAAATGTTGACTCAATAATGTTACCATT 13620  RSV_WT
13561 CAAAAAGACACTGAATGACTATTGTATAGGTAAAAATGTTGACTCAATAATGTTACCATT 13620  MinA
13561 CAAAAAGACACTGAATGACTATTGTATAGGTAAAAATGTTGACTCAATAATGTTACCATT 13620  MinB
13561 TAAGAAAACACTTAACGATTATTGTATAGGTAAAAACGTTGATTCAATTATGTTACCATT 13620  MinL
13561 TAAGAAAACACTTAACGATTATTGTATAGGTAAAAACGTTGATTCAATTATGTTACCATT 13620  MinFLC
       **.**.***** ** ** ***************** ***** *****:***********

13621 GTTATCTAATAAGAAGCTTATTAAATCGTCTGCAATGATTAGAACCAATTACAGCAAACA 13680  RSV_WT
13621 GTTATCTAATAAGAAGCTTATTAAATCGTCTGCAATGATTAGAACCAATTACAGCAAACA 13680  MinA
13621 GTTATCTAATAAGAAGCTTATTAAATCGTCTGCAATGATTAGAACCAATTACAGCAAACA 13680  MinB
13621 ACTATCAAATAAGAAATTGATTAAATCTAGCGCTATGATTAGAACTAATTATAGTAAACA 13680  MinL
13621 ACTATCAAATAAGAAATTGATTAAATCTAGCGCTATGATTAGAACTAATTATAGTAAACA 13680  MinFLC
      . ****:********. * ******** :  **:*********** ***** ** *****

13681 AGATTTGTATAATTTATTCCCTATGGTTGTGATTGATAGAATTATAGATCATTCAGGCAA 13740  RSV_WT
13681 AGATTTGTATAATTTATTCCCTATGGTTGTGATTGATAGAATTATAGATCATTCAGGCAA 13740  MinA
13681 AGATTTGTATAATTTATTCCCTATGGTTGTGATTGATAGAATTATAGATCATTCAGGCAA 13740  MinB
13681 GGATCTATATAACTTATTCCCTATGGTCGTAATTGATAGAATTATAGATCATTCCGGTAA 13740  MinL
13681 GGATCTATATAACTTATTCCCTATGGTCGTAATTGATAGAATTATAGATCATTCCGGTAA 13740  MinFLC
      .*** *.***** ************* **.**********************.** **
```

Figure 7 cont.

```
13741 TACAGCCAAATCCAACCAACTTTACACTACTACTTCCCACCAAATATCCTTAGTGCACAA 13800  RSV_WT
13741 TACAGCCAAATCCAACCAACTTTACACTACTACTTCCCACCAAATATCCTTAGTGCACAA 13800  MinA
13741 TACAGCCAAATCCAACCAACTTTACACTACTACTTCCCACCAAATATCCTTAGTGCACAA 13800  MinB
13741 TACCGCTAAATCTAATCAATTGTATACAACTACTAGTCATCAAATATCATTAGTGCATAA 13800  MinL
13741 TACCGCTAAATCTAATCAATTGTATACAACTACTAGTCATCAAATATCATTAGTGCATAA 13800  MinFLC
      ***.** ***** ** *** * ** **:******:  ** ********.******** **

13801 TAGCACATCACTTTACTGCATGCTTCCTTGGCATCATATTAATAGATTCAATTTTGTATT 13860  RSV_WT
13801 TAGCACATCACTTTACTGCATGCTTCCTTGGCATCATATTAATAGATTCAATTTTGTATT 13860  MinA
13801 TAGCACATCACTTTACTGCATGCTTCCTTGGCATCATATTAATAGATTCAATTTTGTATT 13860  MinB
13801 TAGTACTAGTCTATATTGTATGTTACCATGGCATCATATTAATAGATTCAATTTCGTTTT 13860  MinL
13801 TAGTACTAGTCTATATTGTATGTTACCATGGCATCATATTAATAGATTCAATTTCGTTTT 13860  MinFLC
      *** **:: :**:** ** *** *:**:************************** **:**

13861 TAGTTCTACAGGTTGTAAAATTAGTATAGAGTATATTTTAAAAGATCTTAAAATTAAAGA 13920  RSV_WT
13861 TAGTTCTACAGGTTGTAAAATTAGTATAGAGTATATTTTAAAAGATCTTAAAATTAAAGA 13920  MinA
13861 TAGTTCTACAGGTTGTAAAATTAGTATAGAGTATATTTTAAAAGATCTTAAAATTAAAGA 13920  MinB
13861 TAGTAGTACAGGGTGTAAAATTAGTATAGAGTATATACTTAAAGATCTTAAAATTAAAGA 13920  MinL
13861 TAGTAGTACAGGGTGTAAAATTAGTATAGAGTATATACTTAAAGATCTTAAAATTAAAGA 13920  MinFLC
      ****: ****** ***********************: *:********************

13921 TCCCAATTGTATAGCATTCATAGGTGAAGGAGCAGGGAATTTATTATTGCGTACAGTAGT 13980  RSV_WT
13921 TCCCAATTGTATAGCATTCATAGGTGAAGGAGCAGGGAATTTATTATTGCGTACAGTAGT 13980  MinA
13921 TCCCAATTGTATAGCATTCATAGGTGAAGGAGCAGGGAATTTATTATTGCGTACAGTAGT 13980  MinB
13921 TCCTAATTGTATTGCATTCATAGGCGAAGGCGCAGGTAATCTGTTACTTAGAACAGTAGT 13980  MinL
13921 TCCTAATTGTATTGCATTCATAGGCGAAGGCGCAGGTAATCTGTTACTTAGAACAGTAGT 13980  MinFLC
      *** ********:*********** *****.***** *** *.*** * .*:********

13981 GGAACTTCATCCTGACATAAGATATATTTACAGAAGTCTGAAAGATTGCAATGATCATAG 14040  RSV_WT
13981 GGAACTTCATCCTGACATAAGATATATTTACAGAAGTCTGAAAGATTGCAATGATCATAG 14040  MinA
13981 GGAACTTCATCCTGACATAAGATATATTTACAGAAGTCTGAAAGATTGCAATGATCATAG 14040  MinB
13981 CGAATTGCATCCCGATATTAGATATATATATAGATCACTTAAAGATTGTAACGATCATAG 14040  MinL
13981 CGAATTGCATCCCGATATTAGATATATATATAGATCACTTAAAGATTGTAACGATCATAG 14040  MinFLC
       *** * ***** ** **:********:** ***: :** ******** ** ********

14041 TTTACCTATTGAGTTTTTAAGGCTGTACAATGGACATATCAACATTGATTATGGTGAAAA 14100  RSV_WT
14041 TTTACCTATTGAGTTTTTAAGGCTGTACAATGGACATATCAACATTGATTATGGTGAAAA 14100  MinA
14041 TTTACCTATTGAGTTTTTAAGGCTGTACAATGGACATATCAACATTGATTATGGTGAAAA 14100  MinB
14041 TCTACCAATCGAATTCCTTAGATTGTATAACGGTCATATAAACATAGATTACGGCGAAAA 14100  MinL
14041 TCTACCAATCGAATTCCTTAGATTGTATAACGGTCATATAAACATAGATTACGGCGAAAA 14100  MinFLC
      * ****:** **.**  *:**. **** ** **:*****.*****:***** ** *****

14101 TTTGACCATTCCTGCTACAGATGCAACCAACAACATTCATTGGTCTTATTTACATATAAA 14160  RSV_WT
14101 TTTGACCATTCCTGCTACAGATGCAACCAACAACATTCATTGGTCTTATTTACATATAAA 14160  MinA
14101 TTTGACCATTCCTGCTACAGATGCAACCAACAACATTCATTGGTCTTATTTACATATAAA 14160  MinB
14101 CTTAACGATACCCGCTACTGACGCTACTAATAATATACATTGGTCATACTTACATATTAA 14160  MinL
14101 CTTAACGATACCCGCTACTGACGCTACTAATAATATACATTGGTCATACTTACATATTAA 14160  MinFLC
       **.** **:** *****:** **:** ** ** **:********:** ********:**

14161 GTTTGCTGAACCTATCAGTCTTTTTGTCTGTGATGCCGAATTGTCTGTAACAGTCAACTG 14220  RSV_WT
14161 GTTTGCTGAACCTATCAGTCTTTTTGTCTGTGATGCCGAATTGTCTGTAACAGTCAACTG 14220  MinA
14161 GTTTGCTGAACCTATCAGTCTTTTTGTCTGTGATGCCGAATTGTCTGTAACAGTCAACTG 14220  MinB
14161 ATTCGCAGAACCTATAAGTCTATTCGTATGCGACGCAGAATTATCCGTTACAGTGAATTG 14220  MinL
14161 ATTCGCAGAACCTATAAGTCTATTCGTATGCGACGCAGAATTATCCGTTACAGTGAATTG 14220  MinFLC
      .** **:********.*****:** **.** ** **.*****.** **:***** ** **

14221 GAGTAAAATTATAATAGAATGGAGCAAGCATGTAAGAAAGTGCAAGTACTGTTCCTCAGT 14280  RSV_WT
14221 GAGTAAAATTATAATAGAATGGAGCAAGCATGTAAGAAAGTGCAAGTACTGTTCCTCAGT 14280  MinA
14221 GAGTAAAATTATAATAGAATGGAGCAAGCATGTAAGAAAGTGCAAGTACTGTTCCTCAGT 14280  MinB
14221 GTCTAAAATTATTATCGAATGGTCTAAACACGTTAGAAAATGCAAATATTGTTCTAGCGT 14280  MinL
14221 GTCTAAAATTATTATCGAATGGTCTAAACACGTTAGAAAATGCAAATATTGTTCTAGCGT 14280  MinFLC
      *: *********:**.******:  **.** **:*****.*****.** ***** : .**

14281 TAATAAATGTATGTTAATAGTAAAATATCATGCTCAAGATGATATTGATTTCAAATTAGA 14340  RSV_WT
14281 TAATAAATGTATGTTAATAGTAAAATATCATGCTCAAGATGATATTGATTTCAAATTAGA 14340  MinA
14281 TAATAAATGTATGTTAATAGTAAAATATCATGCTCAAGATGATATTGATTTCAAATTAGA 14340  MinB
14281 TAATAAGTGTATGTTAATCGTTAAGTATCACGCTCAAGACGATATAGATTTTAAATTAGA 14340  MinL
14281 TAATAAGTGTATGTTAATCGTTAAGTATCACGCTCAAGACGATATAGATTTTAAATTAGA 14340  MinFLC
      ******.***********.**:**.***** ******** *****:***** ********
```

Figure 7 cont.

```
14341 CAATATAACTATATTAAAAACTTATGTATGCTTAGGCAGTAAGTTAAAGGGATCGGAGGT 14400  RSV_WT
14341 CAATATAACTATATTAAAAACTTATGTATGCTTAGGCAGTAAGTTAAAGGGATCGGAGGT 14400  MinA
14341 CAATATAACTATATTAAAAACTTATGTATGCTTAGGCAGTAAGTTAAAGGGATCGGAGGT 14400  MinB
14341 TAATATAACTATACTTAAAACATACGTATGCTTAGGTAGTAAGCTTAAGGGTAGCGAAGT 14400  MinL
14341 TAATATAACTATACTTAAAACATACGTATGCTTAGGTAGTAAGCTTAAGGGTAGCGAAGT 14400  MinFLC
       ************ *:*****:** *********** ****** *:*****::  **.**

14401 TTACTTAGTCCTTACAATAGGTCCTGCGAATATATTCCCAGTATTTAATGTAGTACAAAA 14460  RSV_WT
14401 TTACTTAGTCCTTACAATAGGTCCTGCGAATATATTCCCAGTATTTAATGTAGTACAAAA 14460  MinA
14401 TTACTTAGTCCTTACAATAGGTCCTGCGAATATATTCCCAGTATTTAATGTAGTACAAAA 14460  MinB
14401 ATACTTAGTGTTAACGATAGGTCCAGCTAATATTTTTCCCGTTTTTAACGTAGTGCAAAA 14460  MinL
14401 ATACTTAGTGTTAACGATAGGTCCAGCTAATATTTTTCCCGTTTTTAACGTAGTGCAAAA 14460  MinFLC
      :********  *:**.********:** *****:** **.**:***** *****.*****

14461 TGCTAAATTGATACTATCAAGAACCAAAAATTTCATCATGCCTAAGAAAGCTGATAAAGA 14520  RSV_WT
14461 TGCTAAATTGATACTATCAAGAACCAAAAATTTCATCATGCCTAAGAAAGCTGATAAAGA 14520  MinA
14461 TGCTAAATTGATACTATCAAGAACCAAAAATTTCATCATGCCTAAGAAAGCTGATAAAGA 14520  MinB
14461 CGCTAAATTGATTCTATCTAGAACTAAAAATTTTATAATGCCTAAGAAAGCTGATAAAGA 14520  MinL
14461 CGCTAAATTGATTCTATCTAGAACTAAAAATTTTATAATGCCTAAGAAAGCTGATAAAGA 14520  MinFLC
       ***********:*****:***** ******** **.**********************

14521 GTCTATTGATGCAAATATTAAAAGTTTGATACCCTTTCTTTGTTACCCTATAACAAAAAA 14580  RSV_WT
14521 GTCTATTGATGCAAATATTAAAAGTTTGATACCCTTTCTTTGTTACCCTATAACAAAAAA 14580  MinA
14521 GTCTATTGATGCAAATATTAAAAGTTTGATACCCTTTCTTTGTTACCCTATAACAAAAAA 14580  MinB
14521 GTCAATTGACGCTAATATAAAATCATTGATACCATTCTTATGTTATCCTATAACTAAGAA 14580  MinL
14521 GTCAATTGACGCTAATATAAAATCATTGATACCATTCTTATGTTATCCTATAACTAAGAA 14580  MinFLC
      ***:***** **:*****:***: :********.**  *:***** ********:**.**

14581 AGGAATTAATACTGCATTGTCAAAACTAAAGAGTGTTGTTAGTGGAGATATACTATCATA 14640  RSV_WT
14581 AGGAATTAATACTGCATTGTCAAAACTAAAGAGTGTTGTTAGTGGAGATATACTATCATA 14640  MinA
14581 AGGAATTAATACTGCATTGTCAAAACTAAAGAGTGTTGTTAGTGGAGATATACTATCATA 14640  MinB
14581 AGGGATTAATACCGCACTATCTAAACTTAAATCCGTAGTGAGCGGAGATATACTATCTTA 14640  MinL
14581 AGGGATTAATACCGCACTATCTAAACTTAAATCCGTAGTGAGCGGAGATATACTATCTTA 14640  MinFLC
      ***.******** *** *.**:*****:**.:   **:** ** **************:**

14641 TTCTATAGCTGGACGTAATGAAGTTTTCAGCAATAAACTTATAAATCATAAGCATATGAA 14700  RSV_WT
14641 TTCTATAGCTGGACGTAATGAAGTTTTCAGCAATAAACTTATAAATCATAAGCATATGAA 14700  MinA
14641 TTCTATAGCTGGACGTAATGAAGTTTTCAGCAATAAACTTATAAATCATAAGCATATGAA 14700  MinB
14641 TAGTATAGCCGGTAGAAACGAAGTTTTTAGTAATAAATTGATTAATCATAAACATATGAA 14700  MinL
14641 TAGTATAGCCGGTAGAAACGAAGTTTTTAGTAATAAATTGATTAATCATAAACATATGAA 14700  MinFLC
      *: ****** **:.*:** ******** ** ****** * **:********.********

14701 CATCTTAAAATGGTTCAATCATGTTTTAAATTTCAGATCAACAGAACTAAACTATAACCA 14760  RSV_WT
14701 CATCTTAAAATGGTTCAATCATGTTTTAAATTTCAGATCAACAGAACTAAACTATAACCA 14760  MinA
14701 CATCTTAAAATGGTTCAATCATGTTTTAAATTTCAGATCAACAGAACTAAACTATAACCA 14760  MinB
14701 TATACTTAAATGGTTTAATCACGTACTTAATTTTAGATCAACCGAATTGAATTATAATCA 14760  MinL
14701 TATACTTAAATGGTTTAATCACGTACTTAATTTTAGATCAACCGAATTGAATTATAATCA 14760  MinFLC
       **. *:******** ***** **: *:***** ********.*** *.** ***** **

14761 TTTATATATGGTAGAATCTACATATCCTTACCTAAGTGAATTGTTAAACAGCTTGACAAC 14820  RSV_WT
14761 TTTATATATGGTAGAATCTACATATCCTTACCTAAGTGAATTGTTAAACAGCTTGACAAC 14820  MinA
14761 TTTATATATGGTAGAATCTACATATCCTTACCTAAGTGAATTGTTAAACAGCTTGACAAC 14820  MinB
14761 TCTATATATGGTCGAATCTACATATCCATACTTATCCGAACTGTTAAACTCATTGACTAC 14820  MinL
14761 TCTATATATGGTCGAATCTACATATCCATACTTATCCGAACTGTTAAACTCATTGACTAC 14820  MinFLC
      * **********.***************:*** **:   *** ********:  .*****:**

14821 CAATGAACTTAAAAAACTGATTAAAATCACAGGTAGTCTGTTATACAACTTTCATAATGA 14880  RSV_WT
14821 CAATGAACTTAAAAAACTGATTAAAATCACAGGTAGTCTGTTATACAACTTTCATAATGA 14880  MinA
14821 CAATGAACTTAAAAAACTGATTAAAATCACAGGTAGTCTGTTATACAACTTTCATAATGA 14880  MinB
14821 TAACGAATTGAAGAAATTGATTAAAATTACAGGTAGTCTGTTATACAATTTTCATAACGA 14880  MinL
14821 TAACGAATTGAAGAAATTGATTAAAATTACAGGTAGTCTGTTATACAATTTTCATAACGA 14880  MinFLC
       ** *** * **.*** ********** ******************** ******** **

14881 ATAATGAATAAAGATCTTATAATAAAAATTCCCATAGCTATACACTAACACTGTATTCAA 14940  RSV_WT
14881 ATAATGAATAAAGATCTTATAATAAAAATTCCCATAGCTATACACTAACACTGTATTCAA 14940  MinA
14881 ATAATGAATAAAGATCTTATAATAAAAATTCCCATAGCTATACACTAACACTGTATTCAA 14940  MinB
14881 ATAATGAATAAAGATCTTATAATAAAAATTCCCATAGCTATACACTAACACTGTATTCAA 14940  MinL
14881 ATAATGAATAAAGATCTTATAATAAAAATTCCCATAGCTATACACTAACACTGTATTCAA 14940  MinFLC
      ************************************************************
```

Figure 7 cont.

```
14941 TTATAGTTATTAAAAATTAAAAATCATATAATTTTTTAAATAACTTTTAGTGAACTAATC 15000  RSV_WT
14941 TTATAGTTATTAAAAATTAAAAATCATATAATTTTTTAAATAACTTTTAGTGAACTAATC 15000  MinA
14941 TTATAGTTATTAAAAATTAAAAATCATATAATTTTTTAAATAACTTTTAGTGAACTAATC 15000  MinB
14941 TTATAGTTATTAAAAATTAAAAATCATATAATTTTTTAAATAACTTTTAGTGAACTAATC 15000  MinL
14941 TTATAGTTATTAAAAATTAAAAATCATATAATTTTTTAAATAACTTTTAGTGAACTAATC 15000  MinFLC
      ************************************************************

15001 CTAAAGTTATCATTTTAATCTTGGAGGAATAAATTTAAACCCTAATCTAATTGGTTTATA 15060  RSV_WT
15001 CTAAAGTTATCATTTTAATCTTGGAGGAATAAATTTAAACCCTAATCTAATTGGTTTATA 15060  MinA
15001 CTAAAGTTATCATTTTAATCTTGGAGGAATAAATTTAAACCCTAATCTAATTGGTTTATA 15060  MinB
15001 CTAAAGTTATCATTTTAATCTTGGAGGAATAAATTTAAACCCTAATCTAATTGGTTTATA 15060  MinL
15001 CTAAAGTTATCATTTTAATCTTGGAGGAATAAATTTAAACCCTAATCTAATTGGTTTATA 15060  MinFLC
      ************************************************************

15061 TGTGTATTAACTAAATTACGAGATATTAGTTTTTGACACTTTTTTTCTCGT 15111  RSV_WT
15061 TGTGTATTAACTAAATTACGAGATATTAGTTTTTGACACTTTTTTTCTCGT 15111  MinA
15061 TGTGTATTAACTAAATTACGAGATATTAGTTTTTGACACTTTTTTTCTCGT 15111  MinB
15061 TGTGTATTAACTAAATTACGAGATATTAGTTTTTGACACTTTTTTTCTCGT 15111  MinL
15061 TGTGTATTAACTAAATTACGAGATATTAGTTTTTGACACTTTTTTTCTCGT 15111  MinFLC
      ***************************************************
```

Figure 7 cont.

SEQUENCE LISTING

<160> NUMBER OF SEQ ID NOS: 5

<210> SEQ ID NO 1
<211> LENGTH: 15111
<212> TYPE: DNA
<213> ORGANISM: Human respiratory syncytial virus

<400> SEQUENCE: 1

```
acgggaaaaa atgcgtacaa caaacttgca taaaccaaaa aaatggggca aataagaatt     60
tgataagtac cacttaaatt taactccctt ggttagagat gggcagcaat tcattgagta    120
tgataaaagt tagattacaa aatttgtttg acaatgatga agtagcattg ttaaaaataa    180
catgctatac tgataaatta atacatttaa ctaatgcttt ggctaaggca gtgatacata    240
caatcaaatt gaatggcatt gtgtttgtgc atgttattac aagtagtgat atttgcccta    300
ataataatat tgtagtaaaa tccaatttca caacaatgcc agtactacaa aatggaggtt    360
atatatggga aatgatggaa ttaacacatt gctctcaacc taatggtcta ctagatgaca    420
attgtgaaat taaattctcc aaaaaactaa gtgattcaac aatgaccaat tatatgaatc    480
aattatctga attacttgga tttgatctta atccataaat tataattaat atcaactagc    540
aaatcaatgt cactaacacc attagttaat ataaaactta acagaagaca aaaatggggc    600
aaataaatca attcagccaa cccaaccatg gacacaaccc acaatgataa tacaccacaa    660
agactgatga tcacagacat gagaccgttg tcacttgaga ccataataac atcactaacc    720
agagacatca taacacacaa atttatatac ttgataaatc atgaatgcat agtgagaaaa    780
cttgatgaaa gacaggccac atttacattc ctggtcaact atgaaatgaa actattacac    840
aaagtaggaa gcactaaata taaaaaatat actgaataca acacaaaata tggcactttc    900
cctatgccaa tattcatcaa tcatgatggg ttcttagaat gcattggcat taagcctaca    960
aagcatactc ccataatata caagtatgat ctcaatccat aaatttcaac acaatattca   1020
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acactcaaca aagatcaact tctgtcatcc   1200
agcaaataca ccatccaacg gagcacagga gatagtattg atactcctaa ttatgatgtg   1260
cagaaacaca tcaataagtt atgtggcatg ttattaatca cagaagatgc taatcataaa   1320
ttcactgggt taataggtat gttatatgcg atgtctaggt taggaagaga agacaccata   1380
aaaatactca gagatgcggg atatcatgta aaagcaaatg gagtagatgt aacaacacat   1440
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgtttttg ttcattttgg tatagcacaa tcttctacca gaggtggcag tagagttgaa   1860
gggatttttg caggattgtt tatgaatgcc tatggtgcag ggcaagtgat gttacggtgg   1920
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
```

-continued

```
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aacctttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg gggcaaataa tcattggagg aaatccaact aatcacaata   4260
tctgttaaca tagacaagtc cacacaccat acagaatcaa ccaatggaaa atacatccat   4320
aacaatagaa ttctcaagca aattctggcc ttactttaca ctaatacaca tgatcacaac   4380
aataatctct ttgctaatca taatctccat catgattgca atactaaaca aactttgtga   4440
```

-continued

```
atataacgta ttccataaca aaacctttga gttaccaaga gctcgagtta atacttgata   4500
aagtagttaa ttaaaaatag tcataacaat gaactaggat atcaagacta acaataacat   4560
tggggcaaat gcaaacatgt ccaaaaacaa ggaccaacgc accgctaaga cattagaaag   4620
gacctgggac actctcaatc atttattatt catatcatcg tgcttatata agttaaatct   4680
taaatctgta gcacaaatca cattatccat tctggcaatg ataatctcaa cttcacttat   4740
aattgcagcc atcatattca tagcctcggc aaaccacaaa gtcacaccaa caactgcaat   4800
catacaagat gcaacaagcc agatcaagaa cacaacccca acatacctca cccagaatcc   4860
tcagcttgga atcagtccct ctaatccgtc tgaaattaca tcacaaatca ccaccatact   4920
agcttcaaca acaccaggag tcaagtcaac cctgcaatcc acaacagtca agaccaaaaa   4980
cacaacaaca actcaaacac aacccagcaa gcccaccaca aaacaacgcc aaaacaaacc   5040
accaagcaaa cccaataatg attttcactt tgaagtgttc aactttgtac cctgcagcat   5100
atgcagcaac aatccaacct gctgggctat ctgcaaaaga ataccaaaca aaaaaccagg   5160
aaagaaaacc actaccaagc ccacaaaaaa accaaccctc aagacaacca aaaaagatcc   5220
caaacctcaa accactaaat caaaggaagt acccaccacc aagcccacag aagagccaac   5280
catcaacacc accaaaacaa acatcataac tacactactc acctccaaca ccacaggaaa   5340
tccagaactc acaagtcaaa tggaaacctt ccactcaact tcctccgaag gcaatccaag   5400
cccttctcaa gtctctacaa catccgagta cccatcacaa ccttcatctc cacccaacac   5460
accacgccag tagttactta aaaacatatt atcacaaaag gccttgacca acttaaacag   5520
aatcaaaata aactctgggg caaataacaa tggagttgct aatcctcaaa gcaaatgcaa   5580
ttaccacaat cctcactgca gtcacatttt gttttgcttc tggtcaaaac atcactgaag   5640
aattttatca atcaacatgc agtgcagtta gcaaaggcta tcttagtgct ctgagaactg   5700
gttggtatac cagtgttata actatagaat taagtaatat caagaaaaat aagtgtaatg   5760
gaacagatgc taaggtaaaa ttgataaaac aagaattaga taaatataaa aatgctgtaa   5820
cagaattgca gttgctcatg caaagcacac aagcaacaaa caatcgagcc agaagagaac   5880
taccaaggtt tatgaattat acactcaaca atgccaaaaa aaccaatgta acattaagca   5940
agaaaaggaa aagaagattt cttggttttt tgttaggtgt tggatctgca atcgccagtg   6000
gcgttgctgt atctaaggtc ctgcacctag aaggggaagt gaacaagatc aaaagtgctc   6060
tactatccac aaacaaggct gtagtcagct tatcaaatgg agttagtgtt ttaaccagca   6120
aagtgttaga cctcaaaaac tatatagata aacaattgtt acctattgtg aacaagcaaa   6180
gctgcagcat atcaaatata gaaactgtga tagagttcca acaaaagaac aacagactac   6240
tagagattac cagggaattt agtgttaatg caggcgtaac tacacctgta agcacttaca   6300
tgttaactaa tagtgaatta ttgtcattaa tcaatgatat gcctataaca aatgatcaga   6360
aaaagttaat gtccaacaat gttcaaatag ttagacagca aagttactct atcatgtcca   6420
taataaaaga ggaagtctta gcatatgtag tacaattacc actatatggt gttatagata   6480
caccctgttg gaaactacac acatcccctc tatgtacaac caacacaaaa gaagggtcca   6540
acatctgttt aacaagaact gacagaggat ggtactgtga caatgcagga tcagtatctt   6600
tcttcccaca agctgaaaca tgtaaagttc aatcaaatcg agtattttgt gacacaatga   6660
acagtttaac attaccaagt gaagtaaatc tctgcaatgt tgacatattc aaccccaaat   6720
atgattgtaa aattatgact tcaaaaacag atgtaagcag ctccgttatc acatctctag   6780
gagccattgt gtcatgctat ggcaaaacta aatgtacagc atccaataaa aatcgtggaa   6840
```

-continued

```
tcataaagac attttctaac gggtgcgatt atgtatcaaa taaaggggtg gacactgtgt   6900
ctgtaggtaa cacattatat tatgtaaata agcaagaagg taaaagtctc tatgtaaaag   6960
gtgaaccaat aataaatttc tatgacccat tagtattccc ctctgatgaa tttgatgcat   7020
caatatctca agtcaacgag aagattaacc agagcctagc atttattcgt aaatccgatg   7080
aattattaca taatgtaaat gctggtaaat ccaccacaaa tatcatgata actactataa   7140
ttatagtgat tatagtaata ttgttatcat taattgctgt tggactgctc ttatactgta   7200
aggccagaag cacaccagtc acactaagca aagatcaact gagtggtata aataatattg   7260
catttagtaa ctaaataaaa atagcaccta atcatgttct tacaatggtt tactatctgc   7320
tcatagacaa cccatctgtc attggatttt cttaaaatct gaacttcatc gaaactctca   7380
tctataaacc atctcactta cactatttaa gtagattcct agtttatagt tatataaaac   7440
acaattgcat gccagattaa cttaccatct gtaaaaatga aaactggggc aaatatgtca   7500
cgaaggaatc cttgcaaatt tgaaattcga ggtcattgct taaatggtaa gaggtgtcat   7560
tttagtcata attattttga atggccaccc catgcactgc ttgtaagaca aaactttatg   7620
ttaaacagaa tacttaagtc tatggataaa agtatagata ccttatcaga aataagtgga   7680
gctgcagagt tggacagaac agaagagtat gctcttggtg tagttggagt gctagagagt   7740
tatataggat caataaacaa tataactaaa caatcagcat gtgttgccat gagcaaactc   7800
ctcactgaac tcaatagtga tgatatcaaa aagctgaggg acaatgaaga gctaaattca   7860
cccaagataa gagtgtacaa tactgtcata tcatatattg aaagcaacag gaaaaacaat   7920
aaacaaacta tccatctgtt aaaaagattg ccagcagacg tattgaagaa aaccatcaaa   7980
aacacattgg atatccataa gagcataacc atcaacaacc caaaagaatc aactgttagt   8040
gatacaaatg accatgccaa aaataatgat actacctgac aaatatcctt gtagtataac   8100
ttccatacta ataacaagta gatgtagagt tactatgtat aatcaaaaga acacactata   8160
tttcaatcaa aacaacccaa ataaccatat gtactcaccg aatcaaacat tcaatgaaat   8220
ccattggacc tctcaagaat tgattgacac aattcaaaat tttctacaac atctaggtat   8280
tattgaggat atatatacaa tatatatatt agtgtcataa cactcaattc taacactcac   8340
cacatcgtta cattattaat tcaaacaatt caagttgtgg gacaaaatgg atcccattat   8400
taatggaaat tctgctaatg tttatctaac cgatagttat ttaaaaggtg ttatctcttt   8460
ctcagagtgt aatgctttag gaagttacat attcaatggt ccttatctca aaaatgatta   8520
taccaactta attagtagac aaaatccatt aatagaacac atgaatctaa agaaactaaa   8580
tataacacag tccttaatat ctaagtatca taaaggtgaa ataaaattag aagaacctac   8640
ttattttcag tcattactta tgacatacaa gagtatgacc tcgtcagaac agattgctac   8700
cactaattta cttaaaaaga taataagaag agctatagaa ataagtgatg tcaaagtcta   8760
tgctatattg aataaactag ggcttaaaga aaaggacaag attaaatcca acaatggaca   8820
agatgaagac aactcagtta ttacgaccat aatcaaagat gatatacttt cagctgttaa   8880
agataatcaa tctcatctta aagcagacaa aaatcactct acaaaacaaa aagacacaat   8940
caaaacaaca ctcttgaaga aattgatgtg ttcaatgcaa catcctccat catggttaat   9000
acattggttt aacttataca caaaattaaa caacatatta acacagtatc gatcaaatga   9060
ggtaaaaaac catgggttta cattgataga taatcaaact cttagtggat ttcaatttat   9120
tttgaaccaa tatggttgta tagtttatca taaggaactc aaaagaatta ctgtgacaac   9180
```

-continued

```
ctataatcaa ttcttgacat ggaaagatat tagccttagt agattaaatg tttgtttaat   9240
tacatggatt agtaactgct tgaacacatt aaataaaagc ttaggcttaa gatgcggatt   9300
caataatgtt atcttgacac aactattcct ttatggagat tgtatactaa agctatttca   9360
caatgagggg ttctacataa taaaagaggt agagggattt attatgtctc taattttaaa   9420
tataacagaa gaagatcaat tcagaaaacg attttataat agtatgctca acaacatcac   9480
agatgctgct aataaagctc agaaaaatct gctatcaaga gtatgtcata cattattaga   9540
taagacagtg tccgataata taataaatgg cagatggata attctattaa gtaagttcct   9600
taaattaatt aagcttgcag gtgacaataa ccttaacaat ctgagtgaac tatatttttt   9660
gttcagaata tttggacacc caatggtaga tgaaagacaa gccatggatg ctgttaaaat   9720
taattgcaat gagaccaaat tttacttgtt aagcagtctg agtatgttaa gaggtgcctt   9780
tatatataga attataaaag ggtttgtaaa taattacaac agatggccta ctttaagaaa   9840
tgctattgtt ttacccttaa gatggttaac ttactataaa ctaaacactt atccttcttt   9900
gttggaactt acagaaagag atttgattgt gttatcagga ctacgtttct atcgtgagtt   9960
tcggttgcct aaaaaagtgg atcttgaaat gattataaat gataaagcta tatcacctcc  10020
taaaaatttg atatggacta gtttccctag aaattacatg ccatcacaca tacaaaacta  10080
tatagaacat gaaaaattaa aattttccga gagtgataaa tcaagaagag tattagagta  10140
ttatttaaga gataacaaat tcaatgaatg tgatttatac aactgtgtag ttaatcaaag  10200
ttatctcaac aaccctaatc atgtggtatc attgacaggc aaagaaagag aactcagtgt  10260
aggtagaatg tttgcaatgc aaccgggaat gttcagacag gttcaaatat tggcagagaa  10320
aatgatagct gaaaacattt tacaattctt tcctgaaagt cttacaagat atggtgatct  10380
agaactacaa aaaatattag aactgaaagc aggaataagt aacaaatcaa atcgctacaa  10440
tgataattac aacaattaca ttagtaagtg ctctatcatc acagatctca gcaaattcaa  10500
tcaagcattt cgatatgaaa cgtcatgtat ttgtagtgat gtgctggatg aactgcatgg  10560
tgtacaatct ctattttcct ggttacattt aactattcct catgtcacaa taatatgcac  10620
atataggcat gcaccccccct atataggaga tcatattgta gatcttaaca atgtagatga  10680
acaaagtgga ttatatagat atcacatggg tggcatcgaa gggtggtgtc aaaaactatg  10740
gaccatagaa gctatatcac tattggatct aatatctctc aaagggaaat tctcaattac  10800
tgctttaatt aatggtgaca atcaatcaat agatataagc aaaccaatca gactcatgga  10860
aggtcaaact catgctcaag cagattattt gctagcatta aatagcctta aattactgta  10920
taaagagtat gcaggcatag gccacaaatt aaaaggaact gagacttata tatcacgaga  10980
tatgcaattt atgagtaaaa caattcaaca taacggtgta tattacccag ctagtataaa  11040
gaaagtccta agagtgggac cgtggataaa cactatactt gatgatttca aagtgagtct  11100
agaatctata ggtagtttga cacaagaatt agaatataga ggtgaaagtc tattatgcag  11160
tttaatattt agaaatgtat ggttatataa tcagattgct ctacaattaa aaaatcatgc  11220
attatgtaac aataaactat atttggacat attaaaggtt ctgaaacact taaaaacctt  11280
ttttaatctt gataatattg atacagcatt aacattgtat atgaatttac ccatgttatt  11340
tggtggtggt gatcccaact tgttatatcg aagtttctat agaagaactc ctgacttcct  11400
cacagaggct atagttcact ctgtgttcat acttagttat tatacaaacc atgacttaaa  11460
agataaactt caagatctgt cagatgatag attgaataag ttcttaacat gcataatcac  11520
gtttgacaaa aaccctaatg ctgaattcgt aacattgatg agagatcctc aagctttagg  11580
```

gtctgagaga caagctaaaa ttactagcga aatcaataga ctggcagtta cagaggtttt 11640
gagtacagct ccaaacaaaa tattctccaa aagtgcacaa cattatacta ctacagagat 11700
agatctaaat gatattatgc aaaatataga acctacatat cctcatgggc taagagttgt 11760
ttatgaaagt ttacccttttt ataaagcaga gaaaatagta aatcttatat caggtacaaa 11820
atctataact aacatactgg aaaaaacttc tgccatagac ttaacagata ttgatagagc 11880
cactgagatg atgaggaaaa acataacttt gcttataagg atacttccat tggattgtaa 11940
cagagataaa agagagatat tgagtatgga aaacctaagt attactgaat taagcaaata 12000
tgttagggaa agatcttggt ctttatccaa tatagttggt gttacatcac ccagtatcat 12060
gtatacaatg gacatcaaat atactacaag cactatatct agtggcataa ttatagagaa 12120
atataatgtt aacagtttaa cacgtggtga gagaggaccc actaaaccat gggttggttc 12180
atctacacaa gagaaaaaaa caatgccagt ttataataga caagtcttaa ccaaaaaaca 12240
gagagatcaa atagatctat tagcaaaatt ggattgggtg tatgcatcta tagataacaa 12300
ggatgaattc atggaagaac tcagcatagg aacccttggg ttaacatatg aaaaggccaa 12360
gaaattattt ccacaatatt taagtgtcaa ttatttgcat cgccttacag tcagtagtag 12420
accatgtgaa ttccctgcat caataccagc ttatagaaca acaaattatc actttgacac 12480
tagccctatt aatcgcatat taacagaaaa gtatggtgat gaagatattg acatagtatt 12540
ccaaaactgt ataagctttg gccttagttt aatgtcagta gtagaacaat ttactaatgt 12600
atgtcctaac agaattattc tcatacctaa gcttaatgag atacatttga tgaaacctcc 12660
catattcaca ggtgatgttg atattcacaa gttaaaacaa gtgatacaaa aacagcatat 12720
gtttttacca gacaaaataa gtttgactca atatgtggaa ttattcttaa gtaataaaac 12780
actcaaatct ggatctcatg ttaattctaa tttaatattg gcacataaaa tatctgacta 12840
ttttcataat acttacattt taagtactaa tttagctgga cattggattc tgattataca 12900
acttatgaaa gattctaaag gtatttttga aaaagattgg ggagagggat atataactga 12960
tcatatgttt attaatttga aagttttctt caatgcttat aagacctatc tcttgtgttt 13020
tcataaaggt tatggcaaag caaagctgga gtgtgatatg aacacttcag atcttctatg 13080
tgtattggaa ttaatagaca gtagttattg gaagtctatg tctaaggtat ttttagaaca 13140
aaaagttatc aaatacattc ttagccaaga tgcaagttta catagagtaa aaggatgtca 13200
tagcttcaaa ttatggtttc ttaaacgtct taatgtagca gaattcacag tttgcccttg 13260
ggttgttaac atagattatc atccaacaca tatgaaagca atattaactt atatagatct 13320
tgttagaatg ggattgataa atatagatag aatacacatt aaaaataaac acaaattcaa 13380
tgatgaattt tatacttcta atctcttcta cattaattat aacttctcag ataatactca 13440
tctattaact aaacatataa ggattgctaa ttctgaatta gaaaataatt acaacaaatt 13500
atatcatcct acaccagaaa ccctagagaa tatactagcc aatccgatta aaagtaatga 13560
caaaaagaca ctgaatgact attgtatagg taaaaatgtt gactcaataa tgttaccatt 13620
gttatctaat aagaagctta ttaaatcgtc tgcaatgatt agaaccaatt acagcaaaca 13680
agatttgtat aatttattcc ctatggttgt gattgataga attatagatc attcaggcaa 13740
tacagccaaa tccaaccaac tttacactac tacttcccac caaatatcct tagtgcacaa 13800
tagcacatca ctttactgca tgcttccttg gcatcatatt aatagattca attttgtatt 13860
tagttctaca ggttgtaaaa ttagtataga gtatatttta aaagatctta aaattaaaga 13920

-continued

```
tcccaattgt atagcattca taggtgaagg agcagggaat ttattattgc gtacagtagt  13980

ggaacttcat cctgacataa gatatattta cagaagtctg aaagattgca atgatcatag  14040

tttacctatt gagtttttaa ggctgtacaa tggacatatc aacattgatt atggtgaaaa  14100

tttgaccatt cctgctacag atgcaaccaa caacattcat tggtcttatt tacatataaa  14160

gtttgctgaa cctatcagtc tttttgtctg tgatgccgaa ttgtctgtaa cagtcaactg  14220

gagtaaaatt ataatagaat ggagcaagca tgtaagaaag tgcaagtact gttcctcagt  14280

taataaatgt atgttaatag taaaatatca tgctcaagat gatattgatt tcaaattaga  14340

caatataact atattaaaaa cttatgtatg cttaggcagt aagttaaagg gatcggaggt  14400

ttacttagtc cttacaatag gtcctgcgaa tatattccca gtatttaatg tagtacaaaa  14460

tgctaaattg atactatcaa gaaccaaaaa tttcatcatg cctaagaaag ctgataaaga  14520

gtctattgat gcaaatatta aaagtttgat accctttctt tgttacccta taacaaaaaa  14580

aggaattaat actgcattgt caaaactaaa gagtgttgtt agtggagata tactatcata  14640

ttctatagct ggacgtaatg aagttttcag caataaactt ataaatcata agcatatgaa  14700

catcttaaaa tggttcaatc atgttttaaa tttcagatca acagaactaa actataacca  14760

tttatatatg gtagaatcta catatcctta cctaagtgaa ttgttaaaca gcttgacaac  14820

caatgaactt aaaaaactga ttaaaatcac aggtagtctg ttatacaact ttcataatga  14880

ataatgaata aagatcttat aataaaaatt cccatagcta tacactaaca ctgtattcaa  14940

ttatagttat taaaaattaa aaatcatata attttttaaa taacttttag tgaactaatc  15000

ctaaagttat cattttaatc ttggaggaat aaatttaaac cctaatctaa ttggtttata  15060

tgtgtattaa ctaaattacg agatattagt tttgacact tttttctcg t            15111
```

<210> SEQ ID NO 2
<211> LENGTH: 15111
<212> TYPE: DNA
<213> ORGANISM: Human respiratory syncytial virus

<400> SEQUENCE: 2

```
acgggaaaaa atgcgtacaa caaacttgca taaaccaaaa aaatggggca aataagaatt     60

tgataagtac cacttaaatt taactccctt ggttagagat gggcagcaat tcattgagta    120

tgataaaagt cagattgcaa aatctattcg ataatgacga agtggcacta ttaaaaatta    180

catgttatac cgataaattg atacatctaa ctaatgcatt agctaaagct gtaatacata    240

caattaaact taatggaata gtgtttgtac atgtaattac atctagtgat atatgcccta    300

ataataatat cgtagtcaag tctaatttta caacaatgcc agtgttacaa aatggcggat    360

atatttggga aatgatggaa ttgacacatt gctcacaacc taatggtcta ttagacgata    420

attgcgaaat taaatttagt aagaaattat ccgatagtac aatgactaat tatatgaatc    480

aattatccga attgttaggt ttcgatctta atccataaat tataattaat atcaactagc    540

aaatcaatgt cactaacacc attagttaat ataaaactta acagaagaca aaaatggggc    600

aaataaatca attcagccaa cccaaccatg gacacaaccc acaatgataa tacaccacaa    660

agactgatga ttaccgatat gagaccgttg tcacttgaga caattataac tagcctaact    720

agagatataa taacacataa atttatatat ctgattaatc acgaatgcat cgtgaggaaa    780

ttggacgaaa gacaggccac atttacattc ttagtcaatt acgaaatgaa actattgcat    840

aaggtaggct caactaagta taagaaatat accgaatata acactaaata cggaacattc    900

ccaatgccta tattcataaa tcacgacggg tttctcgaat gcataggcat aaaacctaca    960
```

-continued

```
aaacatacac ccataatcta taaatacgat cttaacccat aaatttcaac acaatattca   1020
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acattgaata aagatcaatt actatctagc   1200
tcgaaatata ctatccaacg gtctacaggc gattcaatag atacacctaa ttacgatgtg   1260
caaaaacata ttaataaatt gtgtggtatg ttattgatta ccgaagacgc aaatcataaa   1320
tttacagggt taatcggtat gttatacgct atgtctagat taggtaggga agatacaatt   1380
aaaatactta gagacgcagg atatcacgtt aaagctaacg gagtagacgt aactacacat   1440
agacaggata ttaacggtaa ggaaatgaaa ttcgaagtgt taacactcgc tagcttaact   1500
accgaaatac aaattaatat cgaaatcgaa tcacgtaaat cttataagaa aatgcttaaa   1560
gaaatgggcg aagtcgcacc cgaatataga cacgatagtc ccgattgtgg tatgattata   1620
ctatgtatag ccgcattagt gataactaag ttggccgcag gcgatagatc cggattaacc   1680
gcagtgatac gtagagcgaa taacgtactt aaaaacgaaa tgaaacggta taagggtcta   1740
ttaccaaaag atatagcgaa tagtttttac gaagtattcg aaaaacatcc acattttata   1800
gacgtttttg tgcatttcgg aatcgcacaa tctagtacta gaggaggatc tagggttgag   1860
ggtatattcg caggattgtt tatgaacgca tacggagcag gtcaagtcat gcttagatgg   1920
ggagtactcg caaaatccgt taaaaatatt atgttaggac acgctagcgt acaagccgaa   1980
atggaacaag tcgttgaggt atacgaatac gcacaaaaat taggtggaga agcaggattt   2040
tatcatatac tgaataatcc taaagctagt ctattaagct taacacaatt tccacatttt   2100
tctagcgtag tgttaggtaa cgcagctggc ctaggcataa tgggcgaata taggggtaca   2160
cctagaaatc aggatctata tgacgcagct aaagcatacg ctgaacaatt gaaagagaat   2220
ggagtgataa attattccgt actcgatcta acagccgaag agttggaggc aattaaacat   2280
caattgaatc cgaaagataa tgacgttgag ttgtgagtta ataaaaaatg gggcaaataa   2340
atcatcatgg aaaagtttgc tcctgaattc catggagaag acgcaaataa tagggcaaca   2400
aaattcttag agtcaatcaa gggtaagttt acaagtccaa aagatccaaa gaagaaagat   2460
agtataataa gcgtaaactc aattgatatc gaggtgacaa aggaatcacc tataacatct   2520
aatagtacaa taataaatcc cactaacgaa acagacgata ccgcaggcaa taaacctaat   2580
tatcaacgga aacccttagt gtcattcaaa gaagatccaa cacctagtga taatcccttt   2640
agtaaattgt ataaggaaac aatcgaaaca ttcgataata acgaagaaga atcatcatac   2700
tcatacgaag agataaacga tcagactaac gataatataa ccgctagact agatagaata   2760
gacgaaaaac tatctgaaat actaggtatg ttacacacac tagtagtcgc atctgccgga   2820
cctacaagtg ctagagatgg gataagggat gcaatggtag ggttaaggga agaaatgata   2880
gagaaaatta gaaccgaagc attaatgact aacgatagac tcgaagcaat ggctagactt   2940
agaaacgaag aatccgaaaa gatggcaaaa gatacatctg acgaagtgtc acttaatcct   3000
actagcgaaa aattgaataa tctattagag ggaaacgata gtgataacga tctatcactc   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggatcaaca   3300
```

-continued

```
tatacagctg cagtccaata taacgtactc gaaaaagacg acgatcccgc tagcctaaca   3360
atatgggtcc caatgtttca atctagtatg cccgctgatc tattaatcaa agaactagct   3420
aacgttaaca tactagtcaa acaaattagt acacctaagg gaccctcact tagagtgatg   3480
attaatagta gatccgcagt cctagcacaa atgcctagta agtttacaat atgtgctaac   3540
gtaagcttag acgaacgatc aaaactagca tacgatgtga caacaccatg cgaaatcaaa   3600
gcatgttcat tgacatgtct taaatcaaag aatatgctaa caacagtcaa agatctaaca   3660
atgaaaacac ttaatcccac acacgatata atcgcactat gcgaattcga aaatatagtg   3720
actagtaaga aagtgataat ccctacatac cttagatcaa tatccgttag aaataaggat   3780
ctgaatacac tcgaaaatat aacaacaacc gaattcaaaa acgctataac taacgctaag   3840
ataatccctt actccggact attgttagtg ataaccgtaa ccgataataa gggagcattc   3900
aaatacataa aaccccaatc ccaatttata gtcgatttag gcgcatactt agaaaaagaa   3960
tcaatctatt acgttacaac taattggaaa cataccgcta ctagattcgc aatcaaacct   4020
atggaagatt aaccttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg gggcaaataa tcattggagg aaatccaact aatcacaata   4260
tctgttaaca tagacaagtc cacacaccat acagaatcaa ccaatggaaa atacatccat   4320
aacaatagaa ttctctagca aattttggcc ttactttaca ctaatacaca tgataactac   4380
aatcatatcc ctattaatca taatctcaat tatgatcgca atccttaaca aactatgtga   4440
gtataacgta ttccataaca aaacattcga attgccaaga gctcgagtga atacctgata   4500
aagtagttaa ttaaaaatag tcataacaat gaactaggat atcaagacta acaataacat   4560
tggggcaaat gcaaacatgt ccaaaaacaa ggaccaacgc accgctaaga cattagaaag   4620
gacctgggac actctcaatc atttattatt catatcatcg tgcttatata agttaaatct   4680
taaatctgta gcacaaatca cattatccat tctggcaatg ataatctcaa cttcacttat   4740
aattgcagcc atcatattca tagcctcggc aaaccacaaa gtcacaccaa caactgcaat   4800
catacaagat gcaacaagcc agatcaagaa cacaacccca acatacctca cccagaatcc   4860
tcagcttgga atcagtccct ctaatccgtc tgaaattaca tcacaaatca ccaccatact   4920
agcttcaaca acaccaggag tcaagtcaac cctgcaatcc acaacagtca agaccaaaaa   4980
cacaacaaca actcaaacac aacccagcaa gcccaccaca aaacaacgcc aaaacaaacc   5040
accaagcaaa cccaataatg attttcactt tgaagtgttc aactttgtac cctgcagcat   5100
atgcagcaac aatccaacct gctgggctat ctgcaaaaga ataccaaaca aaaaaccagg   5160
aaagaaaacc actaccaagc ccacaaaaaa accaaccctc aagacaacca aaaaagatcc   5220
caaacctcaa accactaaat caaaggaagt acccaccacc aagcccacag aagagccaac   5280
catcaacacc accaaaacaa acatcataac tacactactc acctccaaca ccacaggaaa   5340
tccagaactc acaagtcaaa tggaaacctt ccactcaact tcctccgaag gcaatccaag   5400
cccttctcaa gtctctacaa catccgagta cccatcacaa ccttcatctc cacccaacac   5460
accacgccag tagttactta aaaacatatt atcacaaaag gccttgacca acttaaacag   5520
aatcaaaata aactctgggg caaataacaa tggagttgct aatcctcaaa gcaaatgcaa   5580
ttaccacaat cctcactgca gtcacatttt gttttgcttc tggtcaaaac atcactgaag   5640
aattttatca atcaacatgc agtgcagtta gcaaaggcta tcttagtgct ctgagaactg   5700
```

-continued gttggtatac cagtgttata actatagaat taagtaatat caagaaaaat aagtgtaatg 5760
gaacagatgc taaggtaaaa ttgataaaac aagaattaga taaatataaa aatgctgtaa 5820
cagaattgca gttgctcatg caaagcacac aagcaacaaa caatcgagcc agaagagaac 5880
taccaaggtt tatgaattat acactcaaca atgccaaaaa aaccaatgta acattaagca 5940
agaaaaggaa aagaagattt cttggttttt tgttaggtgt tggatctgca atcgccagtg 6000
gcgttgctgt atctaaggtc ctgcacctag aaggggaagt gaacaagatc aaaagtgctc 6060
tactatccac aaacaaggct gtagtcagct tatcaaatgg agttagtgtt ttaaccagca 6120
aagtgttaga cctcaaaaac tatatagata aacaattgtt acctattgtg aacaagcaaa 6180
gctgcagcat atcaaatata gaaactgtga tagagttcca acaaaagaac aacagactac 6240
tagagattac cagggaattt agtgttaatg caggcgtaac tacacctgta agcacttaca 6300
tgttaactaa tagtgaatta ttgtcattaa tcaatgatat gcctataaca aatgatcaga 6360
aaaagttaat gtccaacaat gttcaaatag ttagacagca aagttactct atcatgtcca 6420
taataaaaga ggaagtctta gcatatgtag tacaattacc actatatggt gttatagata 6480
caccctgttg gaaactacac acatcccctc tatgtacaac caacacaaaa gaagggtcca 6540
acatctgttt aacaagaact gacagaggat ggtactgtga caatgcagga tcagtatctt 6600
tcttcccaca agctgaaaca tgtaaagttc aatcaaatcg agtattttgt gacacaatga 6660
acagtttaac attaccaagt gaagtaaatc tctgcaatgt tgacatattc aaccccaaat 6720
atgattgtaa aattatgact tcaaaaacag atgtaagcag ctccgttatc acatctctag 6780
gagccattgt gtcatgctat ggcaaaacta aatgtacagc atccaataaa aatcgtggaa 6840
tcataaagac attttctaac gggtgcgatt atgtatcaaa taaaggggtg gacactgtgt 6900
ctgtaggtaa cacattatat tatgtaaata agcaagaagg taaaagtctc tatgtaaaag 6960
gtgaaccaat aataaatttc tatgacccat tagtattccc ctctgatgaa tttgatgcat 7020
caatatctca agtcaacgag aagattaacc agagcctagc atttattcgt aaatccgatg 7080
aattattaca taatgtaaat gctggtaaat ccaccacaaa tatcatgata actactataa 7140
ttatagtgat tatagtaata ttgttatcat taattgctgt tggactgctc ttatactgta 7200
aggccagaag cacaccagtc acactaagca aagatcaact gagtggtata aataatattg 7260
catttagtaa ctaaataaaa atagcaccta atcatgttct tacaatggtt tactatctgc 7320
tcatagacaa cccatctgtc attggatttt cttaaaatct gaacttcatc gaaactctca 7380
tctataaacc atctcactta cactatttaa gtagattcct agtttatagt tatataaaac 7440
acaattgcat gccagattaa cttaccatct gtaaaaatga aaactggggc aaatatgtca 7500
cgaaggaatc cttgcaaatt tgaaattcga ggtcattgct taaatggtaa gaggtgtcat 7560
tttagtcata attattttga atggccaccc catgcactgc ttgtaagaca aaactttatg 7620
ttaaacagaa tacttaagtc tatggataaa agtatagata ccttatcaga aataagtgga 7680
gctgcagagt tggacagaac agaagagtat gctcttggtg tagttggagt gctagagagt 7740
tatataggat caataaacaa tataactaaa caatcagcat gtgttgccat gagcaaactc 7800
ctcactgaac tcaatagtga tgatatcaaa aagctgaggg acaatgaaga gctaaattca 7860
cccaagataa gagtgtacaa tactgtcata tcatatattg aaagcaacag gaaaaacaat 7920
aaacaaacta tccatctgtt aaaaagattg ccagcagacg tattgaagaa aaccatcaaa 7980
aacacattgg atatccataa gagcataacc atcaacaacc caaaagaatc aactgttagt 8040

-continued

```
gatacaaatg accatgccaa aaataatgat actacctgac aaatatcctt gtagtataac   8100
ttccatacta ataacaagta gatgtagagt tactatgtat aatcaaaaga acacactata   8160
tttcaatcaa aacaacccaa ataaccatat gtactcaccg aatcaaacat tcaatgaaat   8220
ccattggacc tctcaagaat tgattgacac aattcaaaat tttctacaac atctaggtat   8280
tattgaggat atatatacaa tatatatatt agtgtcataa cactcaattc taacactcac   8340
cacatcgtta cattattaat tcaaacaatt caagttgtgg gacaaaatgg atcccattat   8400
taatggaaat tctgctaatg tttatctaac cgatagttat ttaaaaggtg ttatctcttt   8460
ctcagagtgt aatgctttag gaagttacat attcaatggt ccttatctca aaaatgatta   8520
taccaactta attagtagac aaaatccatt aatagaacac atgaatctaa agaaactaaa   8580
tataacacag tccttaatat ctaagtatca taaaggtgaa ataaaattag aagaacctac   8640
ttattttcag tcattactta tgacatacaa gagtatgacc tcgtcagaac agattgctac   8700
cactaattta cttaaaaaga taataagaag agctatagaa ataagtgatg tcaaagtcta   8760
tgctatattg aataaactag ggcttaaaga aaaggacaag attaaatcca acaatggaca   8820
agatgaagac aactcagtta ttacgaccat aatcaaagat gatatacttt cagctgttaa   8880
agataatcaa tctcatctta aagcagacaa aaatcactct acaaaacaaa aagacacaat   8940
caaaacaaca ctcttgaaga aattgatgtg ttcaatgcaa catcctccat catggttaat   9000
acattggttt aacttataca caaaattaaa caacatatta acacagtatc gatcaaatga   9060
ggtaaaaaac catgggttta cattgataga taatcaaact cttagtggat ttcaatttat   9120
tttgaaccaa tatggttgta tagtttatca taaggaactc aaaagaatta ctgtgacaac   9180
ctataatcaa ttcttgacat ggaaagatat tagccttagt agattaaatg tttgtttaat   9240
tacatggatt agtaactgct tgaacacatt aaataaaagc ttaggcttaa gatgcggatt   9300
caataatgtt atcttgacac aactattcct ttatggagat tgtatactaa agctatttca   9360
caatgagggg ttctacataa taaaagaggt agagggattt attatgtctc taattttaaa   9420
tataacagaa gaagatcaat tcagaaaacg attttataat agtatgctca acaacatcac   9480
agatgctgct aataaagctc agaaaaatct gctatcaaga gtatgtcata cattattaga   9540
taagacagtg tccgataata taataaatgg cagatggata attctattaa gtaagttcct   9600
taaattaatt aagcttgcag gtgacaataa ccttaacaat ctgagtgaac tatatttttt   9660
gttcagaata tttggacacc caatggtaga tgaaagacaa gccatggatg ctgttaaaat   9720
taattgcaat gagaccaaat tttacttgtt aagcagtctg agtatgttaa gaggtgcctt   9780
tatatataga attataaaag ggtttgtaaa taattacaac agatggccta ctttaagaaa   9840
tgctattgtt ttacccttaa gatggttaac ttactataaa ctaaacactt atccttcttt   9900
gttggaactt acagaaagag atttgattgt gttatcagga ctacgtttct atcgtgagtt   9960
tcggttgcct aaaaaagtgg atcttgaaat gattataaat gataaagcta tatcacctcc  10020
taaaaatttg atatggacta gtttccctag aaattacatg ccatcacaca tacaaaacta  10080
tatagaacat gaaaaattaa aattttccga gagtgataaa tcaagaagag tattagagta  10140
ttatttaaga gataacaaat tcaatgaatg tgatttatac aactgtgtag ttaatcaaag  10200
ttatctcaac aaccctaatc atgtggtatc attgacaggc aaagaaagag aactcagtgt  10260
aggtagaatg tttgcaatgc aaccgggaat gttcagacag gttcaaatat tggcagagaa  10320
aatgatagct gaaaacattt tacaattctt tcctgaaagt cttacaagat atggtgatct  10380
agaactacaa aaaatattag aactgaaagc aggaataagt aacaaatcaa atcgctacaa  10440
```

-continued

```
tgataattac aacaattaca ttagtaagtg ctctatcatc acagatctca gcaaattcaa  10500
tcaagcattt cgatatgaaa cgtcatgtat ttgtagtgat gtgctggatg aactgcatgg  10560
tgtacaatct ctattttcct ggttacattt aactattcct catgtcacaa taatatgcac  10620
atataggcat gcaccccccct atataggaga tcatattgta gatcttaaca atgtagatga  10680
acaaagtgga ttatatagat atcacatggg tggcatcgaa gggtggtgtc aaaaactatg  10740
gaccatagaa gctatatcac tattggatct aatatctctc aaagggaaat tctcaattac  10800
tgctttaatt aatggtgaca atcaatcaat agatataagc aaaccaatca gactcatgga  10860
aggtcaaact catgctcaag cagattattt gctagcatta aatagcctta aattactgta  10920
taaagagtat gcaggcatag gccacaaatt aaaaggaact gagacttata tatcacgaga  10980
tatgcaattt atgagtaaaa caattcaaca taacggtgta tattacccag ctagtataaa  11040
gaaagtccta agagtgggac cgtggataaa cactatactt gatgatttca aagtgagtct  11100
agaatctata ggtagtttga cacaagaatt agaatataga ggtgaaagtc tattatgcag  11160
tttaatattt agaaatgtat ggttatataa tcagattgct ctacaattaa aaaatcatgc  11220
attatgtaac aataaactat atttggacat attaaaggtt ctgaaacact taaaaacctt  11280
ttttaatctt gataatattg atacagcatt aacattgtat atgaatttac ccatgttatt  11340
tggtggtggt gatcccaact tgttatatcg aagtttctat agaagaactc ctgacttcct  11400
cacagaggct atagttcact ctgtgttcat acttagttat tatacaaacc atgacttaaa  11460
agataaactt caagatctgt cagatgatag attgaataag ttcttaacat gcataatcac  11520
gtttgacaaa aaccctaatg ctgaattcgt aacattgatg agagatcctc aagctttagg  11580
gtctgagaga caagctaaaa ttactagcga aatcaataga ctggcagtta cagaggtttt  11640
gagtacagct ccaaacaaaa tattctccaa aagtgcacaa cattatacta ctacagagat  11700
agatctaaat gatattatgc aaaatataga acctacatat cctcatgggc taagagttgt  11760
ttatgaaagt ttacccttttt ataaagcaga gaaaatagta aatcttatat caggtacaaa  11820
atctataact aacatactgg aaaaaacttc tgccatagac ttaacagata ttgatagagc  11880
cactgagatg atgaggaaaa acataacttt gcttataagg atacttccat tggattgtaa  11940
cagagataaa agagagatat tgagtatgga aaacctaagt attactgaat taagcaaata  12000
tgttagggaa agatcttggt ctttatccaa tatagttggt gttacatcac ccagtatcat  12060
gtatacaatg gacatcaaat atactacaag cactatatct agtggcataa ttatagagaa  12120
atataatgtt aacagtttaa cacgtggtga gagaggaccc actaaaccat gggttggttc  12180
atctacacaa gagaaaaaaa caatgccagt ttataataga caagtcttaa ccaaaaaaca  12240
gagagatcaa atagatctat tagcaaaatt ggattgggtg tatgcatcta tagataacaa  12300
ggatgaattc atggaagaac tcagcatagg aacccttggg ttaacatatg aaaaggccaa  12360
gaaattattt ccacaatatt taagtgtcaa ttatttgcat cgccttacag tcagtagtag  12420
accatgtgaa ttccctgcat caataccagc ttatagaaca acaaattatc actttgacac  12480
tagccctatt aatcgcatat taacagaaaa gtatggtgat gaagatattg acatagtatt  12540
ccaaaactgt ataagctttg gccttagttt aatgtcagta gtagaacaat ttactaatgt  12600
atgtcctaac agaattattc tcatacctaa gcttaatgag atacatttga tgaaacctcc  12660
catattcaca ggtgatgttg atattcacaa gttaaaacaa gtgatacaaa aacagcatat  12720
gtttttacca gacaaaataa gtttgactca atatgtggaa ttattcttaa gtaataaaac  12780
```

-continued

```
actcaaatct ggatctcatg ttaattctaa tttaatattg gcacataaaa tatctgacta  12840
ttttcataat acttacattt taagtactaa tttagctgga cattggattc tgattataca  12900
acttatgaaa gattctaaag gtatttttga aaaagattgg ggagagggat atataactga  12960
tcatatgttt attaatttga aagttttctt caatgcttat aagacctatc tcttgtgttt  13020
tcataaaggt tatggcaaag caaagctgga gtgtgatatg aacacttcag atcttctatg  13080
tgtattggaa ttaatagaca gtagttattg gaagtctatg tctaaggtat ttttagaaca  13140
aaaagttatc aaatacattc ttagccaaga tgcaagttta catagagtaa aaggatgtca  13200
tagcttcaaa ttatggtttc ttaaacgtct taatgtagca gaattcacag tttgcccttg  13260
ggttgttaac atagattatc atccaacaca tatgaaagca atattaactt atatagatct  13320
tgttagaatg ggattgataa atatagatag aatacacatt aaaaataaac acaaattcaa  13380
tgatgaattt tatacttcta atctcttcta cattaattat aacttctcag ataatactca  13440
tctattaact aaacatataa ggattgctaa ttctgaatta gaaaataatt acaacaaatt  13500
atatcatcct acaccagaaa ccctagagaa tatactagcc aatccgatta aaagtaatga  13560
caaaaagaca ctgaatgact attgtatagg taaaaatgtt gactcaataa tgttaccatt  13620
gttatctaat aagaagctta ttaaatcgtc tgcaatgatt agaaccaatt acagcaaaca  13680
agatttgtat aatttattcc ctatggttgt gattgataga attatagatc attcaggcaa  13740
tacagccaaa tccaaccaac tttacactac tacttcccac caaatatcct tagtgcacaa  13800
tagcacatca ctttactgca tgcttccttg gcatcatatt aatagattca attttgtatt  13860
tagttctaca ggttgtaaaa ttagtataga gtatatttta aaagatctta aaattaaaga  13920
tcccaattgt atagcattca taggtgaagg agcagggaat ttattattgc gtacagtagt  13980
ggaacttcat cctgacataa gatatattta cagaagtctg aaagattgca atgatcatag  14040
tttacctatt gagtttttaa ggctgtacaa tggacatatc aacattgatt atggtgaaaa  14100
tttgaccatt cctgctacag atgcaaccaa caacattcat tggtcttatt tacatataaa  14160
gtttgctgaa cctatcagtc tttttgtctg tgatgccgaa ttgtctgtaa cagtcaactg  14220
gagtaaaatt ataatagaat ggagcaagca tgtaagaaag tgcaagtact gttcctcagt  14280
taataaatgt atgttaatag taaaatatca tgctcaagat gatattgatt tcaaattaga  14340
caatataact atattaaaaa cttatgtatg cttaggcagt aagttaaagg gatcggaggt  14400
ttacttagtc cttacaatag gtcctgcgaa tatattccca gtatttaatg tagtacaaaa  14460
tgctaaattg atactatcaa gaaccaaaaa tttcatcatg cctaagaaag ctgataaaga  14520
gtctattgat gcaaatatta aaagtttgat accctttctt tgttacccta taacaaaaaa  14580
aggaattaat actgcattgt caaaactaaa gagtgttgtt agtggagata tactatcata  14640
ttctatagct ggacgtaatg aagttttcag caataaactt ataaatcata agcatatgaa  14700
catcttaaaa tggttcaatc atgttttaaa tttcagatca acagaactaa actataacca  14760
tttatatatg gtagaatcta catatcctta cctaagtgaa ttgttaaaca gcttgacaac  14820
caatgaactt aaaaaactga ttaaaatcac aggtagtctg ttatacaact ttcataatga  14880
ataatgaata aagatcttat aataaaaatt cccatagcta tacactaaca ctgtattcaa  14940
ttatagttat taaaaattaa aaatcatata atttttaaa taacttttag tgaactaatc  15000
ctaaagttat cattttaatc ttggaggaat aaatttaaac cctaatctaa ttggtttata  15060
tgtgtattaa ctaaattacg agatattagt ttttgacact ttttttctcg t           15111
```

<210> SEQ ID NO 3
<211> LENGTH: 15111
<212> TYPE: DNA
<213> ORGANISM: Human respiratory syncytial virus

<400> SEQUENCE: 3
acgggaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360
atatatggga aatgatggaa ttaacacatt gctctcaacc taatggtcta ctagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactaacacc attagttaat ataaaactta acagaagaca aaaatggggc 600
aaataaatca attcagccaa cccaaccatg gacacaaccc acaatgataa tacaccacaa 660
agactgatga tcacagacat gagaccgttg tcacttgaga ccataataac atcactaacc 720
agagacatca taacacacaa atttatatac ttgataaatc atgaatgcat agtgagaaaa 780
cttgatgaaa gacaggccac atttacattc ctggtcaact atgaaatgaa actattacac 840
aaagtaggaa gcactaaata taaaaaatat actgaataca acacaaaata tggcactttc 900
cctatgccaa tattcatcaa tcatgatggg ttcttagaat gcattggcat taagcctaca 960
aagcatactc ccataatata caagtatgat ctcaatccat aaatttcaac acaatattca 1020
cacaatctaa aacaacaact ctatgcataa ctatactcca tagtccagat ggagcctgaa 1080
aattatagta atttaaaact taaggagaga tataagatag aagatggggc aaatacaacc 1140
atggctctta gcaaagtcaa gttgaatgat acactcaaca aagatcaact tctgtcatcc 1200
agcaaataca ccatccaacg gagcacagga gatagtattg atactcctaa ttatgatgtg 1260
cagaaacaca tcaataagtt atgtggcatg ttattaatca cagaagatgc taatcataaa 1320
ttcactgggt taataggtat gttatatgcg atgtctaggt taggaagaga agacaccata 1380
aaaatactca gagatgcggg atatcatgta aaagcaaatg gagtagatgt aacaacacat 1440
cgtcaagaca ttaatggaaa agaaatgaaa tttgaagtgt taacattggc aagcttaaca 1500
actgaaattc aaatcaacat tgagatagaa tctagaaaat cctacaaaaa aatgctaaaa 1560
gaaatgggag aggtagctcc agaatacagg catgactctc ctgattgtgg gatgataata 1620
ttatgtatag cagcattagt aataactaaa ttagcagcag gggacagatc tggtcttaca 1680
gccgtgatta ggagagctaa taatgtccta aaaaatgaaa tgaaacgtta caaaggctta 1740
ctacccaagg acatagccaa cagcttctat gaagtgtttg aaaaacatcc ccactttata 1800
gatgtttttg ttcattttgg tatagcacaa tcttctacca gaggtggcag tagagttgaa 1860
gggatttttg caggattgtt tatgaatgcc tatggtgcag ggcaagtgat gttacggtgg 1920
ggagtcttag caaaatcggt taaaaatatt atgttaggac atgctagtgt gcaagcagaa 1980
atggaacaag ttgttgaggt ttatgaatat gcccaaaaat tgggtggtga agcaggattc 2040
taccatatat tgaacaaccc aaaagcatca ttattatctt tgactcaatt tcctcacttc 2100
tccagtgtag tattaggcaa tgctgctggc ctaggcataa tgggagagta cagaggtaca 2160
ccgaggaatc aagatctata tgatgcagca aaggcatatg ctgaacaact caaagaaaat 2220
ggtgtgatta actacagtgt actagacttg acagcagaag aactagaggc tatcaaacat 2280
cagcttaatc caaaagataa tgatgtagag ctttgagtta ataaaaaatg gggcaaataa 2340
atcatcatgg aaaagtttgc tcctgaattc catggagaag atgcaaacaa cagggctact 2400
aaattcctag aatcaataaa gggcaaattc acatcaccca aagatcccaa gaaaaaagat 2460
agtatcatat ctgtcaactc aatagatata gaagtaacca aagaaagccc tataacatca 2520
aattcaacta ttatcaaccc aacaaatgag acagatgata ctgcagggaa caagcccaat 2580
tatcaaagaa aacctctagt aagtttcaaa gaagacccta caccaagtga taatcccttt 2640
tctaaactat acaaagaaac catagaaaca tttgataaca atgaagaaga atccagctat 2700
tcatacgaag aaataaatga tcagacaaac gataatataa cagcaagatt agataggatt 2760
gatgaaaaat taagtgaaat actaggaatg cttcacacat tagtagtggc aagtgcagga 2820
cctacatctg ctcgggatgg tataagagat gccatggttg gtttaagaga agaaatgata 2880
gaaaaaatca gaactgaagc attaatgacc aatgacagat tagaagctat ggcaagactc 2940
aggaatgagg aaagtgaaaa gatggcaaaa gacacatcag atgaagtgtc tctcaatcca 3000
acatcagaga aattgaacaa cctattggaa gggaatgata gtgacaatga tctatcactt 3060
gaagatttct gattagttac caatcttcac atcaacacac aataccaaca gaagaccaac 3120
aaactaacca acccaatcat ccaaccaaac atccatccgc caatcagcca aacagccaac 3180
aaaacaacca gccaatccaa aactaaccac ccggaaaaaa tctataatat agttacaaaa 3240
aaaggaaagg gtggggcaaa tatggaaaca tacgtgaaca agcttcacga aggctccaca 3300
tacacagctg ctgttcaata caatgtctta gaaaaagacg atgaccctgc atcacttaca 3360
atatgggtgc ccatgttcca atcatctatg ccagcagatt tacttataaa agaactagct 3420
aatgtcaaca tactagtgaa acaaatatcc acacccaagg gaccttcact aagagtcatg 3480
ataaactcaa gaagtgcagt gctagcacaa atgcccagca aatttaccat atgcgctaat 3540
gtgtccttgg atgaaagaag caaactagca tatgatgtaa ccacaccctg tgaaatcaag 3600
gcatgtagtc taacatgcct aaaatcaaaa aatatgttga ctacagttaa agatctcact 3660
atgaagacac tcaaccctac acatgatatt attgctttat gtgaatttga aaacatagta 3720
acatcaaaaa aagtcataat accaacatac ctaagatcca tcagtgtcag aaataaagat 3780
ctgaacacac ttgaaaatat aacaaccact gaattcaaaa atgctatcac aaatgcaaaa 3840
atcatccctt actcaggatt actattagtc atcacagtga ctgacaacaa aggagcattc 3900
aaatacataa agccacaaag tcaattcata gtagatcttg gagcttacct agaaaaagaa 3960
agtatatatt atgttaccac aaattggaag cacacagcta cacgatttgc aatcaaaccc 4020
atggaagatt aaccttttc ctctacatca gtgtgttaat tcatacaaac tttctaccta 4080
cattcttcac ttcaccatca caatcacaaa cactctgtgg ttcaaccaat caaacaaaac 4140
ttatctgaag tcccagatca tcccaagtca ttgtttatca gatctagtac tcaaataagt 4200
taataaaaaa tatacacatg gggcaaataa tcattggagg aaatccaact aatcacaata 4260
tctgttaaca tagacaagtc cacacaccat acagaatcaa ccaatggaaa atacatccat 4320
aacaatagaa ttctcaagca aattctggcc ttactttaca ctaatacaca tgatcacaac 4380
aataatctct ttgctaatca taatctccat catgattgca atactaaaca aactttgtga 4440
atataacgta ttccataaca aaacctttga gttaccaaga gctcgagtta atacttgata 4500
aagtagttaa ttaaaaatag tcataacaat gaactaggat atcaagacta acaataacat 4560

```
tggggcaaat gcaaacatgt ccaaaaacaa ggaccaacgc accgctaaaa cactcgaaag   4620
gacatgggat acccttaatc acctattatt cataagctca tgcttatata aattgaacct   4680
taaatccgtc gcacagataa ccctatcaat actcgcaatg ataatctcaa caagcttaat   4740
catagccgca ataatcttta tcgctagcgc taaccataag gtaaccccaa caaccgcaat   4800
tatacaggac gcaacatccc aaatcaaaaa cacaacccca acatacttaa cccaaaaccc   4860
acaactcgga atctcaccct ctaacccatc cgaaattacc tcacagatta caacgatact   4920
cgcaagtaca acccccggag tcaaatcgac actccaatcg acaaccgtaa agactaagaa   4980
tacaacaaca acccaaaccc aacctagtaa gcctacaact aagcaacgcc aaaacaaacc   5040
tccctctaaa ccgaataacg attttcactt cgaagtgttc aatttcgtac catgctcaat   5100
ttgctctaat aacccaacat gctgggccat atgcaaacgc atcccaaaca agaaacccgg   5160
aaagaaaaca accactaagc caacaaagaa accaaccctt aagacaacca agaaagatcc   5220
aaaaccccaa acaactaagt ctaaagaggt cccaacaact aagccaaccg aagagccaac   5280
aatcaataca actaagacta atataatcac aaccttactg acatctaaca caaccggaaa   5340
tcccgaactg acatcccaaa tggaaacctt tcactcaacc tctagcgaag gcaatccctc   5400
accatcccaa gtctcaacca ctagcgaata cccatcccaa cctagctcac ctcccaatac   5460
ccctagacag tagttactta aaaacatatt atcacaaaag gccttgacca acttaaacag   5520
aatcaaaata aactctgggg caaataacaa tggagttgct aatcctcaaa gcaaatgcaa   5580
tcacaacaat actaacagcc gttacatttt gtttcgctag cggacaaaac ataaccgaag   5640
agttttatca atctacatgt tccgccgtaa gtaaggggta tctatccgca cttagaaccg   5700
gatggtatac tagcgtaata acaatcgaac tatctaatat aaagaagaat aagtgtaacg   5760
gtacagacgc taaggttaaa ttgattaaac aggaactcga taagtataaa aacgccgtaa   5820
ccgaattgca attgttaatg caatctacac aagctactaa taatagggct agacgtgaat   5880
tgcctagatt tatgaattat acacttaata acgctaagaa aactaacgtt acactatcta   5940
agaaacgaaa acgtagattc ttagggtttt tactcggagt cggttccgca atcgctagcg   6000
gagtcgccgt aagtaaagtg ttacacctcg aaggcgaagt gaataagata aaatccgcac   6060
tattatcaac taataaggca gtcgttagcc tatctaacgg agtcagcgta ttgacatcta   6120
aagtgttaga cttaaagaat tatatagata agcaattgtt accaatcgtt aataaacaat   6180
catgttcaat atccaatatc gaaaccgtaa tcgaatttca acagaagaat aatagattac   6240
tcgaaattac tagagaattt agcgtaaacg ctggcgtaac aacacccgta agtacatata   6300
tgttaactaa ttccgaactg ttaagcttaa ttaacgatat gccaattact aacgatcaga   6360
agaaattgat gtctaataac gtacaaatcg ttagacagca atcatattca attatgtcaa   6420
ttataaaaga agaggtactc gcatacgtag tgcaattacc cctatatggc gtaatagata   6480
caccatgttg gaaattgcat acaagtccac tatgtacaac taatacaaaa gagggatcta   6540
atatatgctt aactagaacc gatagggggt ggtattgcga taacgcaggt agcgtaagtt   6600
tctttccaca agccgaaaca tgtaaagtgc aatctaatag agtgttttgc gatacaatga   6660
atagcttaac actacctagc gaagtcaatc tatgtaacgt cgatatattc aatcctaaat   6720
atgattgcaa aattatgact agtaagactg acgtaagtag tagcgtaatt actagtctcg   6780
gtgcaatagt gtcatgttat ggtaagacta agtgtaccgc tagcaataag aatagggga    6840
taataaaaac atttagtaac ggttgcgatt acgttagtaa taagggagtc gataccgtaa   6900
```

gcgtaggtaa tacactatat tatgttaata aacaggaagg taagtcatta tacgttaaag 6960
gcgaacctat aattaatttt tacgatccat tagtgtttcc atccgacgaa ttcgacgcta 7020
gtataagtca ggtaaacgaa aagattaacc aatcactcgc attcatacga aaatccgacg 7080
aactgttaca caacgttaac gcaggtaaga gtacaactaa cataatgata acaacaatta 7140
taatcgttat aatcgttata ctgttaagct taatcgcagt cggattactg ttatattgta 7200
aagctagatc aacacccgta acactatcta aagaccaatt atccggtata aataatatcg 7260
cattctcaaa ctaaataaaa atagcaccta atcatgttct tacaatggtt tactatctgc 7320
tcatagacaa cccatctgtc attggatttt cttaaaatct gaacttcatc gaaactctca 7380
tctataaacc atctcactta cactatttaa gtagattcct agtttatagt tatataaaac 7440
acaattgcat gccagattaa cttaccatct gtaaaaatga aaactggggc aaatatgtca 7500
cgaaggaatc cttgcaaatt tgaaattcga ggtcattgct taaatggtaa gaggtgtcat 7560
tttagtcata attattttga atggccaccc catgcactgc ttgtaagaca aaactttatg 7620
ttaaacagaa tacttaagtc tatggataaa agtatagata ccttatcaga aataagtgga 7680
gctgcagagt tggacagaac agaagagtat gctcttggtg tagttggagt gctagagagt 7740
tatataggat caataaacaa tataactaaa caatcagcat gtgttgccat gagcaaactc 7800
ctcactgaac tcaatagtga tgatatcaaa aagctgaggg acaatgaaga gctaaattca 7860
cccaagataa gagtgtacaa tactgtcata tcatatattg aaagcaacag gaaaaacaat 7920
aaacaaacta tccatctgtt aaaaagattg ccagcagacg tattgaagaa aaccatcaaa 7980
aacacattgg atatccataa gagcataacc atcaacaacc caaaagaatc aactgttagt 8040
gatacaaatg accatgccaa aaataatgat actacctgac aaatatcctt gtagtataac 8100
ttccatacta ataacaagta gatgtagagt tactatgtat aatcaaaaga acacactata 8160
tttcaatcaa aacaacccaa ataaccatat gtactcaccg aatcaaacat tcaatgaaat 8220
ccattggacc tctcaagaat tgattgacac aattcaaaat tttctacaac atctaggtat 8280
tattgaggat atatatacaa tatatatatt agtgtcataa cactcaattc taacactcac 8340
cacatcgtta cattattaat tcaaacaatt caagttgtgg gacaaaatgg atcccattat 8400
taatggaaat tctgctaatg tttatctaac cgatagttat ttaaaaggtg ttatctcttt 8460
ctcagagtgt aatgctttag gaagttacat attcaatggt ccttatctca aaaatgatta 8520
taccaactta attagtagac aaaatccatt aatagaacac atgaatctaa agaaactaaa 8580
tataacacag tccttaatat ctaagtatca taaaggtgaa ataaaattag aagaacctac 8640
ttattttcag tcattactta tgacatacaa gagtatgacc tcgtcagaac agattgctac 8700
cactaattta cttaaaaaga taataagaag agctatagaa ataagtgatg tcaaagtcta 8760
tgctatattg aataaactag ggcttaaaga aaaggacaag attaaatcca acaatggaca 8820
agatgaagac aactcagtta ttacgaccat aatcaaagat gatatacttt cagctgttaa 8880
agataatcaa tctcatctta aagcagacaa aaatcactct acaaaaacaa aagacacaat 8940
caaaacaaca ctcttgaaga aattgatgtg ttcaatgcaa catcctccat catggttaat 9000
acattggttt aacttataca caaaattaaa caacatatta acacagtatc gatcaaatga 9060
ggtaaaaaac catgggttta cattgataga taatcaaact cttagtggat ttcaatttat 9120
tttgaaccaa tatggttgta tagtttatca taaggaactc aaaagaatta ctgtgacaac 9180
ctataatcaa ttcttgacat ggaaagatat tagccttagt agattaaatg tttgtttaat 9240
tacatggatt agtaactgct tgaacacatt aaataaaagc ttaggcttaa gatgcggatt 9300

-continued

```
caataatgtt atcttgacac aactattcct ttatggagat tgtatactaa agctatttca   9360
caatgagggg ttctacataa taaaagaggt agagggattt attatgtctc taattttaaa   9420
tataacagaa gaagatcaat tcagaaaacg attttataat agtatgctca acaacatcac   9480
agatgctgct aataaagctc agaaaaatct gctatcaaga gtatgtcata cattattaga   9540
taagacagtg tccgataata taataaatgg cagatggata attctattaa gtaagttcct   9600
taaattaatt aagcttgcag gtgacaataa ccttaacaat ctgagtgaac tatatttttt   9660
gttcagaata tttggacacc caatggtaga tgaaagacaa gccatggatg ctgttaaaat   9720
taattgcaat gagaccaaat tttacttgtt aagcagtctg agtatgttaa gaggtgcctt   9780
tatatataga attataaaag ggtttgtaaa taattacaac agatggccta ctttaagaaa   9840
tgctattgtt ttacccttaa gatggttaac ttactataaa ctaaacactt atccttcttt   9900
gttggaactt acagaaagag atttgattgt gttatcagga ctacgtttct atcgtgagtt   9960
tcggttgcct aaaaaagtgg atcttgaaat gattataaat gataaagcta tatcacctcc  10020
taaaaatttg atatggacta gtttccctag aaattacatg ccatcacaca tacaaaacta  10080
tatagaacat gaaaaattaa aattttccga gagtgataaa tcaagaagag tattagagta  10140
ttatttaaga gataacaaat tcaatgaatg tgatttatac aactgtgtag ttaatcaaag  10200
ttatctcaac aaccctaatc atgtggtatc attgacaggc aaagaaagag aactcagtgt  10260
aggtagaatg tttgcaatgc aaccgggaat gttcagacag gttcaaatat tggcagagaa  10320
aatgatagct gaaaacattt tacaattctt tcctgaaagt cttacaagat atggtgatct  10380
agaactacaa aaaatattag aactgaaagc aggaataagt aacaaatcaa atcgctacaa  10440
tgataattac aacaattaca ttagtaagtg ctctatcatc acagatctca gcaaattcaa  10500
tcaagcattt cgatatgaaa cgtcatgtat ttgtagtgat gtgctggatg aactgcatgg  10560
tgtacaatct ctattttcct ggttacattt aactattcct catgtcacaa taatatgcac  10620
atataggcat gcaccccct atataggaga tcatattgta gatcttaaca atgtagatga  10680
acaaagtgga ttatatagat atcacatggg tggcatcgaa gggtggtgtc aaaaactatg  10740
gaccatagaa gctatatcac tattggatct aatatctctc aaagggaaat tctcaattac  10800
tgctttaatt aatggtgaca atcaatcaat agatataagc aaaccaatca gactcatgga  10860
aggtcaaact catgctcaag cagattattt gctagcatta aatagcctta aattactgta  10920
taaagagtat gcaggcatag gccacaaatt aaaaggaact gagacttata tatcacgaga  10980
tatgcaattt atgagtaaaa caattcaaca taacggtgta tattacccag ctagtataaa  11040
gaaagtccta agagtgggac cgtggataaa cactatactt gatgatttca aagtgagtct  11100
agaatctata ggtagtttga cacaagaatt agaatataga ggtgaaagtc tattatgcag  11160
tttaatattt agaaatgtat ggttatataa tcagattgct ctacaattaa aaaatcatgc  11220
attatgtaac aataaactat atttggacat attaaaggtt ctgaaacact taaaaacctt  11280
ttttaatctt gataatattg atacagcatt aacattgtat atgaatttac ccatgttatt  11340
tggtggtggt gatcccaact tgttatatcg aagtttctat agaagaactc ctgacttcct  11400
cacagaggct atagttcact ctgtgttcat acttagttat tatacaaacc atgacttaaa  11460
agataaactt caagatctgt cagatgatag attgaataag ttcttaacat gcataatcac  11520
gtttgacaaa aaccctaatg ctgaattcgt aacattgatg agagatcctc aagctttagg  11580
gtctgagaga caagctaaaa ttactagcga aatcaataga ctggcagtta cagaggtttt  11640
```

-continued

```
gagtacagct ccaaacaaaa tattctccaa aagtgcacaa cattatacta ctacagagat  11700
agatctaaat gatattatgc aaaatataga acctacatat cctcatgggc taagagttgt  11760
ttatgaaagt ttaccctttt ataaagcaga gaaaatagta aatcttatat caggtacaaa  11820
atctataact aacatactgg aaaaaacttc tgccatagac ttaacagata ttgatagagc  11880
cactgagatg atgaggaaaa acataacttt gcttataagg atacttccat tggattgtaa  11940
cagagataaa agagagatat tgagtatgga aaacctaagt attactgaat taagcaaata  12000
tgttagggaa agatcttggt ctttatccaa tatagttggt gttacatcac ccagtatcat  12060
gtatacaatg gacatcaaat atactacaag cactatatct agtggcataa ttatagagaa  12120
atataatgtt aacagtttaa cacgtggtga gagaggaccc actaaaccat gggttggttc  12180
atctacacaa gagaaaaaaa caatgccagt ttataataga caagtcttaa ccaaaaaaca  12240
gagagatcaa atagatctat tagcaaaatt ggattgggtg tatgcatcta tagataacaa  12300
ggatgaattc atggaagaac tcagcatagg aacccttggg ttaacatatg aaaaggccaa  12360
gaaattattt ccacaatatt taagtgtcaa ttatttgcat cgccttacag tcagtagtag  12420
accatgtgaa ttccctgcat caataccagc ttatagaaca acaaattatc actttgacac  12480
tagccctatt aatcgcatat taacagaaaa gtatggtgat gaagatattg acatagtatt  12540
ccaaaactgt ataagctttg gccttagttt aatgtcagta gtagaacaat ttactaatgt  12600
atgtcctaac agaattattc tcatacctaa gcttaatgag atacatttga tgaaacctcc  12660
catattcaca ggtgatgttg atattcacaa gttaaaacaa gtgatacaaa aacagcatat  12720
gtttttacca gacaaaataa gtttgactca atatgtggaa ttattcttaa gtaataaaac  12780
actcaaatct ggatctcatg ttaattctaa tttaatattg gcacataaaa tatctgacta  12840
ttttcataat acttacattt taagtactaa tttagctgga cattggattc tgattataca  12900
acttatgaaa gattctaaag gtatttttga aaaagattgg ggagagggat atataactga  12960
tcatatgttt attaatttga aagttttctt caatgcttat aagacctatc tcttgtgttt  13020
tcataaaggt tatggcaaag caaagctgga gtgtgatatg aacacttcag atcttctatg  13080
tgtattggaa ttaatagaca gtagttattg gaagtctatg tctaaggtat ttttagaaca  13140
aaaagttatc aaatacattc ttagccaaga tgcaagttta catagagtaa aaggatgtca  13200
tagcttcaaa ttatggtttc ttaaacgtct taatgtagca gaattcacag tttgcccttg  13260
ggttgttaac atagattatc atccaacaca tatgaaagca atattaactt atatagatct  13320
tgttagaatg ggattgataa atatagatag aatacacatt aaaaataaac acaaattcaa  13380
tgatgaattt tatacttcta atctcttcta cattaattat aacttctcag ataatactca  13440
tctattaact aaacatataa ggattgctaa ttctgaatta gaaaataatt acaacaaatt  13500
atatcatcct acaccagaaa ccctagagaa tatactagcc aatccgatta aaagtaatga  13560
caaaaagaca ctgaatgact attgtatagg taaaaatgtt gactcaataa tgttaccatt  13620
gttatctaat aagaagctta ttaaatcgtc tgcaatgatt agaaccaatt acagcaaaca  13680
agatttgtat aatttattcc ctatggttgt gattgataga attatagatc attcaggcaa  13740
tacagccaaa tccaaccaac tttacactac tacttcccac caaatatcct tagtgcacaa  13800
tagcacatca ctttactgca tgcttccttg gcatcatatt aatagattca attttgtatt  13860
tagttctaca ggttgtaaaa ttagtataga gtatatttta aaagatctta aaattaaaga  13920
tcccaattgt atagcattca taggtgaagg agcagggaat ttattattgc gtacagtagt  13980
ggaacttcat cctgacataa gatatattta cagaagtctg aaagattgca atgatcatag  14040
```

```
tttacctatt gagtttttaa ggctgtacaa tggacatatc aacattgatt atggtgaaaa  14100
tttgaccatt cctgctacag atgcaaccaa caacattcat tggtcttatt tacatataaa  14160
gtttgctgaa cctatcagtc tttttgtctg tgatgccgaa ttgtctgtaa cagtcaactg  14220
gagtaaaatt ataatagaat ggagcaagca tgtaagaaag tgcaagtact gttcctcagt  14280
taataaatgt atgttaatag taaaatatca tgctcaagat gatattgatt tcaaattaga  14340
caatataact atattaaaaa cttatgtatg cttaggcagt aagttaaagg gatcggaggt  14400
ttacttagtc cttacaatag gtcctgcgaa tatattccca gtatttaatg tagtacaaaa  14460
tgctaaattg atactatcaa gaaccaaaaa tttcatcatg cctaagaaag ctgataaaga  14520
gtctattgat gcaaatatta aaagtttgat accctttctt tgttacccta taacaaaaaa  14580
aggaattaat actgcattgt caaaactaaa gagtgttgtt agtggagata tactatcata  14640
ttctatagct ggacgtaatg aagttttcag caataaactt ataaatcata agcatatgaa  14700
catcttaaaa tggttcaatc atgttttaaa tttcagatca acagaactaa actataacca  14760
tttatatatg gtagaatcta catatcctta cctaagtgaa ttgttaaaca gcttgacaac  14820
caatgaactt aaaaaactga ttaaaatcac aggtagtctg ttatacaact ttcataatga  14880
ataatgaata aagatcttat aataaaaatt cccatagcta tacactaaca ctgtattcaa  14940
ttatagttat taaaaattaa aaatcatata atttttttaaa taacttttag tgaactaatc  15000
ctaaagttat cattttaatc ttggaggaat aaatttaaac cctaatctaa ttggtttata  15060
tgtgtattaa ctaaattacg agatattagt ttttgacact ttttttctcg t           15111
```

<210> SEQ ID NO 4
<211> LENGTH: 15111
<212> TYPE: DNA
<213> ORGANISM: Human respiratory syncytial virus

<400> SEQUENCE: 4

```
acgggaaaaa atgcgtacaa caaacttgca taaaccaaaa aaatggggca aataagaatt     60
tgataagtac cacttaaatt taactccctt ggttagagat gggcagcaat tcattgagta    120
tgataaaagt tagattacaa aatttgtttg acaatgatga agtagcattg ttaaaaataa    180
catgctatac tgataaatta atacatttaa ctaatgcttt ggctaaggca gtgatacata    240
caatcaaatt gaatggcatt gtgtttgtgc atgttattac aagtagtgat atttgcccta    300
ataataatat tgtagtaaaa tccaatttca caacaatgcc agtactacaa aatggaggtt    360
atatatggga aatgatggaa ttaacacatt gctctcaacc taatggtcta ctagatgaca    420
attgtgaaat taaattctcc aaaaaactaa gtgattcaac aatgaccaat tatatgaatc    480
aattatctga attacttgga tttgatctta atccataaat tataattaat atcaactagc    540
aaatcaatgt cactaacacc attagttaat ataaaactta acagaagaca aaaatggggc    600
aaataaatca attcagccaa cccaaccatg gacacaaccc acaatgataa tacaccacaa    660
agactgatga tcacagacat gagaccgttg tcacttgaga ccataataac atcactaacc    720
agagacatca taacacacaa atttatatac ttgataaatc atgaatgcat agtgagaaaa    780
cttgatgaaa gacaggccac atttacattc ctggtcaact atgaaatgaa actattacac    840
aaagtaggaa gcactaaata taaaaaatat actgaataca acacaaaata tggcactttc    900
cctatgccaa tattcatcaa tcatgatggg ttcttagaat gcattggcat taagcctaca    960
aagcatactc ccataatata caagtatgat ctcaatccat aaatttcaac acaatattca   1020
```

-continued

```
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acactcaaca aagatcaact tctgtcatcc   1200
agcaaataca ccatccaacg gagcacagga gatagtattg atactcctaa ttatgatgtg   1260
cagaaacaca tcaataagtt atgtggcatg ttattaatca cagaagatgc taatcataaa   1320
ttcactgggt taataggtat gttatatgcg atgtctaggt taggaagaga agacaccata   1380
aaaatactca gagatgcggg atatcatgta aaagcaaatg gagtagatgt aacaacacat   1440
cgtcaagaca ttaatggaaa agaaatgaaa tttgaagtgt taacattggc aagcttaaca   1500
actgaaattc aaatcaacat tgagatagaa tctagaaaat cctacaaaaa aatgctaaaa   1560
gaaatgggag aggtagctcc agaatacagg catgactctc ctgattgtgg gatgataata   1620
ttatgtatag cagcattagt aataactaaa ttagcagcag gggacagatc tggtcttaca   1680
gccgtgatta ggagagctaa taatgtccta aaaaatgaaa tgaaacgtta caaaggctta   1740
ctacccaagg acatagccaa cagcttctat gaagtgtttg aaaaacatcc ccactttata   1800
gatgttttttg ttcattttgg tatagcacaa tcttctacca gaggtggcag tagagttgaa   1860
gggatttttg caggattgtt tatgaatgcc tatggtgcag ggcaagtgat gttacggtgg   1920
ggagtcttag caaaatcggt taaaaatatt atgttaggac atgctagtgt gcaagcagaa   1980
atggaacaag ttgttgaggt ttatgaatat gcccaaaaat tgggtggtga agcaggattc   2040
taccatatat tgaacaaccc aaaagcatca ttattatctt tgactcaatt tcctcacttc   2100
tccagtgtag tattaggcaa tgctgctggc ctaggcataa tgggagagta cagaggtaca   2160
ccgaggaatc aagatctata tgatgcagca aaggcatatg ctgaacaact caaagaaaat   2220
ggtgtgatta actacagtgt actagacttg acagcagaag aactagaggc tatcaaacat   2280
cagcttaatc caaaagataa tgatgtagag ctttgagtta ataaaaaatg gggcaaataa   2340
atcatcatgg aaaagtttgc tcctgaattc catggagaag atgcaaacaa cagggctact   2400
aaattcctag aatcaataaa gggcaaattc acatcaccca aagatcccaa gaaaaaagat   2460
agtatcatat ctgtcaactc aatagatata gaagtaacca aagaaagccc tataacatca   2520
aattcaacta ttatcaaccc aacaaatgag acagatgata ctgcagggaa caagcccaat   2580
tatcaaagaa aacctctagt aagtttcaaa gaagacccta caccaagtga taatcccttt   2640
tctaaactat acaaagaaac catagaaaca tttgataaca atgaagaaga atccagctat   2700
tcatacgaag aaataaatga tcagacaaac gataatataa cagcaagatt agataggatt   2760
gatgaaaaat taagtgaaat actaggaatg cttcacacat tagtagtggc aagtgcagga   2820
cctacatctg ctcgggatgg tataagagat gccatggttg gtttaagaga agaaatgata   2880
gaaaaaatca gaactgaagc attaatgacc aatgacagat tagaagctat ggcaagactc   2940
aggaatgagg aaagtgaaaa gatggcaaaa gacacatcag atgaagtgtc tctcaatcca   3000
acatcagaga aattgaacaa cctattggaa gggaatgata gtgacaatga tctatcactt   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggctccaca   3300
tacacagctg ctgttcaata caatgtctta gaaaaagacg atgaccctgc atcacttaca   3360
atatgggtgc ccatgttcca atcatctatg ccagcagatt tacttataaa agaactagct   3420
```

```
aatgtcaaca tactagtgaa acaaatatcc acacccaagg gaccttcact aagagtcatg   3480
ataaactcaa gaagtgcagt gctagcacaa atgcccagca aatttaccat atgcgctaat   3540
gtgtccttgg atgaaagaag caaactagca tatgatgtaa ccacaccctg tgaaatcaag   3600
gcatgtagtc taacatgcct aaaatcaaaa aatatgttga ctacagttaa agatctcact   3660
atgaagacac tcaaccctac acatgatatt attgctttat gtgaatttga aaacatagta   3720
acatcaaaaa aagtcataat accaacatac ctaagatcca tcagtgtcag aaataaagat   3780
ctgaacacac ttgaaaatat aacaaccact gaattcaaaa atgctatcac aaatgcaaaa   3840
atcatccctt actcaggatt actattagtc atcacagtga ctgacaacaa aggagcattc   3900
aaatacataa agccacaaag tcaattcata gtagatcttg gagcttacct agaaaaagaa   3960
agtatatatt atgttaccac aaattggaag cacacagcta cacgatttgc aatcaaaccc   4020
atggaagatt aacctttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg gggcaaataa tcattggagg aaatccaact aatcacaata   4260
tctgttaaca tagacaagtc cacacaccat acagaatcaa ccaatggaaa atacatccat   4320
aacaatagaa ttctcaagca aattctggcc ttactttaca ctaatacaca tgatcacaac   4380
aataatctct ttgctaatca taatctccat catgattgca atactaaaca aactttgtga   4440
atataacgta ttccataaca aaacctttga gttaccaaga gctcgagtta atacttgata   4500
aagtagttaa ttaaaaatag tcataacaat gaactaggat atcaagacta acaataacat   4560
tggggcaaat gcaaacatgt ccaaaaacaa ggaccaacgc accgctaaga cattagaaag   4620
gacctgggac actctcaatc atttattatt catatcatcg tgcttatata agttaaatct   4680
taaatctgta gcacaaatca cattatccat tctggcaatg ataatctcaa cttcacttat   4740
aattgcagcc atcatattca tagcctcggc aaaccacaaa gtcacaccaa caactgcaat   4800
catacaagat gcaacaagcc agatcaagaa cacaacccca acatacctca cccagaatcc   4860
tcagcttgga atcagtccct ctaatccgtc tgaaattaca tcacaaatca ccaccatact   4920
agcttcaaca acaccaggag tcaagtcaac cctgcaatcc acaacagtca agaccaaaaa   4980
cacaacaaca actcaaacac aacccagcaa gcccaccaca aaacaacgcc aaaacaaacc   5040
accaagcaaa cccaataatg attttcactt tgaagtgttc aactttgtac cctgcagcat   5100
atgcagcaac aatccaacct gctgggctat ctgcaaaaga ataccaaaca aaaaaccagg   5160
aaagaaaacc actaccaagc ccacaaaaaa accaaccctc aagacaacca aaaaagatcc   5220
caaacctcaa accactaaat caaaggaagt acccaccacc aagcccacag aagagccaac   5280
catcaacacc accaaaacaa acatcataac tacactactc acctccaaca ccacaggaaa   5340
tccagaactc acaagtcaaa tggaaacctt ccactcaact tcctccgaag gcaatccaag   5400
cccttctcaa gtctctacaa catccgagta cccatcacaa ccttcatctc cacccaacac   5460
accacgccag tagttactta aaaacatatt atcacaaaag gccttgacca acttaaacag   5520
aatcaaaata aactctgggg caaataacaa tggagttgct aatcctcaaa gcaaatgcaa   5580
ttaccacaat cctcactgca gtcacatttt gttttgcttc tggtcaaaac atcactgaag   5640
aattttatca atcaacatgc agtgcagtta gcaaaggcta tcttagtgct ctgagaactg   5700
gttggtatac cagtgttata actatagaat taagtaatat caagaaaaat aagtgtaatg   5760
```

-continued

```
gaacagatgc taaggtaaaa ttgataaaac aagaattaga taaatataaa aatgctgtaa   5820
cagaattgca gttgctcatg caaagcacac aagcaacaaa caatcgagcc agaagagaac   5880
taccaaggtt tatgaattat acactcaaca atgccaaaaa aaccaatgta acattaagca   5940
agaaaaggaa aagaagattt cttggttttt tgttaggtgt tggatctgca atcgccagtg   6000
gcgttgctgt atctaaggtc ctgcacctag aaggggaagt gaacaagatc aaaagtgctc   6060
tactatccac aaacaaggct gtagtcagct tatcaaatgg agttagtgtt ttaaccagca   6120
aagtgttaga cctcaaaaac tatatagata aacaattgtt acctattgtg aacaagcaaa   6180
gctgcagcat atcaaatata gaaactgtga tagagttcca acaaaagaac aacagactac   6240
tagagattac cagggaattt agtgttaatg caggcgtaac tacacctgta agcacttaca   6300
tgttaactaa tagtgaatta ttgtcattaa tcaatgatat gcctataaca aatgatcaga   6360
aaaagttaat gtccaacaat gttcaaatag ttagacagca aagttactct atcatgtcca   6420
taataaaaga ggaagtctta gcatatgtag tacaattacc actatatggt gttatagata   6480
caccctgttg gaaactacac acatcccctc tatgtacaac caacacaaaa gaagggtcca   6540
acatctgttt aacaagaact gacagaggat ggtactgtga caatgcagga tcagtatctt   6600
tcttcccaca agctgaaaca tgtaaagttc aatcaaatcg agtattttgt gacacaatga   6660
acagtttaac attaccaagt gaagtaaatc tctgcaatgt tgacatattc aaccccaaat   6720
atgattgtaa aattatgact tcaaaaacag atgtaagcag ctccgttatc acatctctag   6780
gagccattgt gtcatgctat ggcaaaacta aatgtacagc atccaataaa aatcgtggaa   6840
tcataaagac attttctaac gggtgcgatt atgtatcaaa taaaggggtg gacactgtgt   6900
ctgtaggtaa cacattatat tatgtaaata agcaagaagg taaaagtctc tatgtaaaag   6960
gtgaaccaat aataaatttc tatgacccat tagtattccc ctctgatgaa tttgatgcat   7020
caatatctca agtcaacgag aagattaacc agagcctagc atttattcgt aaatccgatg   7080
aattattaca taatgtaaat gctggtaaat ccaccacaaa tatcatgata actactataa   7140
ttatagtgat tatagtaata ttgttatcat taattgctgt tggactgctc ttatactgta   7200
aggccagaag cacaccagtc acactaagca aagatcaact gagtggtata aataatattg   7260
catttagtaa ctaaataaaa atagcaccta atcatgttct tacaatggtt tactatctgc   7320
tcatagacaa cccatctgtc attggatttt cttaaaatct gaacttcatc gaaactctca   7380
tctataaacc atctcactta cactatttaa gtagattcct agtttatagt tatataaaac   7440
acaattgcat gccagattaa cttaccatct gtaaaaatga aaactggggc aaatatgtca   7500
cgaaggaatc cttgcaaatt tgaaattcga ggtcattgct taaatggtaa gaggtgtcat   7560
tttagtcata attattttga atggccaccc catgcactgc ttgtaagaca aaactttatg   7620
ttaaacagaa tacttaagtc tatggataaa agtatagata ccttatcaga aataagtgga   7680
gctgcagagt tggacagaac agaagagtat gctcttggtg tagttggagt gctagagagt   7740
tatataggat caataaacaa tataactaaa caatcagcat gtgttgccat gagcaaactc   7800
ctcactgaac tcaatagtga tgatatcaaa aagctgaggg acaatgaaga gctaaattca   7860
cccaagataa gagtgtacaa tactgtcata tcatatattg aaagcaacag gaaaaacaat   7920
aaacaaacta tccatctgtt aaaaagattg ccagcagacg tattgaagaa aaccatcaaa   7980
aacacattgg atatccataa gagcataacc atcaacaacc caaaagaatc aactgttagt   8040
gatacaaatg accatgccaa aaataatgat actacctgac aaatatcctt gtagtataac   8100
ttccatacta ataacaagta gatgtagagt tactatgtat aatcaaaaga acacactata   8160
```

-continued

```
tttcaatcaa aacaacccaa ataaccatat gtactcaccg aatcaaacat tcaatgaaat   8220
ccattggacc tctcaagaat tgattgacac aattcaaaat tttctacaac atctaggtat   8280
tattgaggat atatatacaa tatatatatt agtgtcataa cactcaattc taacactcac   8340
cacatcgtta cattattaat tcaaacaatt caagttgtgg gacaaaatgg atcccattat   8400
taatggaaat tctgctaacg tatacttaac cgatagttat ttaaaaggcg taatcagttt   8460
tagcgaatgt aacgcattag ggtcatatat ctttaacggt ccatatctta aaaacgatta   8520
tactaatcta atcagtagac agaatccgtt aatcgaacat atgaatctta agaaactgaa   8580
tatcacacaa tctttgatca gtaagtatca taaaggcgaa atcaaactcg aagaacctac   8640
atattttcaa tcactattaa tgacatataa gtctatgaca tctagcgaac agatcgctac   8700
tactaatctg ttgaagaaaa ttattagacg agctatagag atatctgacg ttaaggtata   8760
cgctatactg aataaattgg ggttaaaaga gaaagataag ataaaatcta ataacggtca   8820
agacgaagat aatagtgtaa ttactacaat tattaaagac gatatactat ccgcagtgaa   8880
ggataatcaa tcacatctta aagccgataa aaatcatagt actaaacaaa aagatacaat   8940
taaaactaca ttgttaaaga aattgatgtg ttctatgcaa catccaccta gttggttaat   9000
acattggttt aacttataca ctaagttgaa caatatactt acacaatatc gatcaaacga   9060
agtgaaaaat cacggtttta cattgataga taatcaaaca ttaagcggat ttcaattcat   9120
acttaaccaa tacggatgta tagtgtatca taaagaattg aaacgtataa ccgttacaac   9180
atataatcaa ttcttaacat ggaaagatat aagtctatct agattgaacg tatgcttaat   9240
tacatggatt tcgaattgtc ttaatacact taataaatca ttagggttaa gatgcggatt   9300
taataacgtt atacttacac aattgttctt atacggagat tgtatactta agttgttcca   9360
taacgaaggg ttttatataa taaaagaggt tgagggattt ataatgtcat tgatactgaa   9420
tattaccgaa gaggatcaat ttagaaaaag attctataat agtatgttaa acaatataac   9480
tgacgcagct aataaagcgc agaagaatct gttatctaga gtatgtcata cattgttaga   9540
caaaacagtg agcgataata ttataaacgg tagatggatt atactgttat ctaaattctt   9600
aaaattgatt aagttggcag gtgacaataa ccttaataac ttaagcgaat tgtatttctt   9660
attcagaata ttcggacatc ctatggttga cgaacgacaa gctatggacg cagtgaagat   9720
taattgtaac gaaactaaat tctatctatt atctagtcta tctatgctta gaggcgcatt   9780
catatataga attataaaag ggttcgttaa taattataat agatggccta cacttagaaa   9840
cgctatagtg ttaccactta gatggttaac atattataaa ttgaatacat atcctagttt   9900
actcgaatta accgaacgcg atctgatagt gttaagcgga cttagattct atagagagtt   9960
tagattgcct aagaaagtcg atctcgaaat gataattaac gataaggcaa ttagtccacc  10020
taaaaactta atatggacaa gcttccctag aaattatatg cctagtcata tacaaaatta  10080
tatcgaacac gaaaaattga aatttagcga atccgataag tctagaagag tgttagagta  10140
ttacttacgc gataataaat ttaacgaatg cgatctatat aattgcgtag tgaaccaatc  10200
atatcttaat aatcctaatc acgtagtgag tcttacaggt aaggaaagag agttgagcgt  10260
aggtagaatg ttcgctatgc aacccggtat gtttagacaa gtgcaaatac tcgcagaaaa  10320
gatgatagcc gaaaatatac tgcaattctt tcccgaatca ttgactagat acggagattt  10380
agaattgcaa aagatactcg aattgaaagc aggtatatct aataagtcta atagatataa  10440
cgataattat aataattata tatctaagtg tagtattatt accgatctat ctaaattcaa  10500
```

-continued

```
tcaggcattt agatacgaaa ctagttgtat atgctcagac gtattagacg aattacacgg  10560
agtgcaatct ttgtttagtt ggttacattt aactatacct cacgttacaa ttatatgtac  10620
atatagacac gcaccaccat atataggcga tcatatagtc gatctgaata acgtagacga  10680
acaatccgga ttgtatagat atcacatggg tggcatagag ggatggtgtc aaaaattgtg  10740
gactatagag gcaattagtc tgttagatct aattagtctt aagggtaagt tttcgattac  10800
cgcattgatt aacggtgata atcaatcaat tgatatatct aaaccgatac ggttaatgga  10860
gggacaaaca cacgctcaag ccgattactt actcgcactt aattcactta aactgttata  10920
caaagagtac gcaggtatag ggcataaact taagggtaca gagacatata taagtaggga  10980
tatgcaattt atgagtaaga ctatacaaca taacggagtg tattatcccg ctagtataaa  11040
gaaagtgctt agagtcggac cttggattaa tactatatta gacgatttta aggttagtct  11100
cgaatcaatc ggatcattga cacaagagtt ggagtataga ggcgaatctc tattatgctc  11160
attgattttt agaaacgtat ggttatacaa tcagattgca ttgcaattga aaaatcacgc  11220
actatgtaat aataagttgt acttagacat acttaaagtg ttaaaacatc ttaaaacatt  11280
ctttaatctc gataatatag ataccgcatt aacattgtat atgaatctac ctatgttatt  11340
cggaggggga gatcctaatc tattgtatag atcattctat agacgtacac ctgatttctt  11400
aaccgaagct atagtgcata gcgtattcat actatcatat tatactaatc acgatcttaa  11460
agataagttg caggatctat ctgacgatag attgaataaa ttcttaacat gtattataac  11520
attcgataaa aatcctaacg ctgaattcgt tacacttatg agagatccac aagcattagg  11580
ttcagagaga caggctaaaa ttactagcga aattaataga ttagccgtta ccgaagtgtt  11640
aagtaccgca cctaataaga tattctctaa atccgctcaa cattatacaa caaccgaaat  11700
agatcttaac gatattatgc aaaatatcga acctacatat cctcacggat tacgcgtagt  11760
ttacgaatca ttaccattct ataaagccga aaagatcgtt aacttaatta gcggtacaaa  11820
atcaattact aatatactcg aaaagactag cgcaattgat ttaaccgata tagatagagc  11880
taccgaaatg atgcgtaaaa atataacatt actgatacgt atactaccat tagattgtaa  11940
tagggataaa agagagatac tatctatgga gaatctatca attacagaat tgtcaaaata  12000
cgttagggaa cgatcatggt cactatctaa tatcgtaggc gtaactagtc ctagtattat  12060
gtatactatg gatattaagt atacaactag tacaattagt agcggtataa taatcgaaaa  12120
atataacgtt aatagtctaa cacgtggtga aaggggacct acaaaacctt gggtcggatc  12180
tagtacacaa gagaagaaaa ctatgcccgt atataataga caggtattga ctaagaaaca  12240
acgagatcaa atagatctat tagctaaact cgattgggta tacgctagta tagataataa  12300
agacgaattt atggaagagt tgtcaatcgg tacattaggg ttaacatacg aaaaagctaa  12360
gaaattgttc ccacaatatc tatcagtgaa ttatctacat agattgacag tgagtagtag  12420
accatgcgaa tttcccgcta gtatacccgc atatagaact actaattatc atttcgatac  12480
tagtccaatt aatagaatat taaccgaaaa atacggagac gaagatatag atatcgtatt  12540
ccaaaattgt attagtttcg gattgagtct tatgtccgta gtcgaacaat ttactaacgt  12600
atgtcctaat aggattatac tgatacctaa attgaacgaa atacatctta tgaaacctcc  12660
tatttttaca ggcgatgtcg atatacacaa attgaaacag gttatacaaa aacaacatat  12720
gttcttaccc gataagatat cgttaacgca atacgttgag ttgttcttat caaataaaac  12780
acttaaatca ggtagtcacg ttaatagtaa tctgatactc gcacataaaa ttagcgatta  12840
ctttcataat acatatatat tgagtactaa cttagccgga cattggatac tgattataca  12900
```

```
attgatgaaa gatagtaagg gtatattcga aaaagattgg ggtgagggat atataaccga  12960
tcatatgttt ataaacctta aggtcttctt taacgcatat aaaacttatc tattatgttt  13020
tcataaggga tacggtaagg ctaaactcga atgcgatatg aatacatccg atctattatg  13080
cgtactcgaa ttaattgata gtagctattg gaaatctatg agtaaggtat tcttagagca  13140
aaaggtgatc aagtatatac tatctcaaga cgctagtttg catagggtta agggatgtca  13200
tagttttaaa ttatggtttc ttaaaagatt gaacgtagcc gaatttacag tatgtccttg  13260
ggtcgttaac atagattatc atcctacaca tatgaaagct atacttacat atatagatct  13320
agtgagaatg ggattgatta acatagatag aatacatata aagaataaac ataaatttaa  13380
cgacgaattc tatactagta atctattcta tataaattat aatttttccg ataatacaca  13440
tctattaact aaacatatac gtatagctaa tagcgaactc gaaaataatt ataataaatt  13500
gtatcatcct acacccgaaa cattagagaa tatactcgct aatccgatta aatctaacga  13560
taagaaaaca cttaacgatt attgtatagg taaaaacgtt gattcaatta tgttaccatt  13620
actatcaaat aagaaattga ttaaatctag cgctatgatt agaactaatt atagtaaaca  13680
ggatctatat aacttattcc ctatggtcgt aattgataga attatagatc attccggtaa  13740
taccgctaaa tctaatcaat tgtatacaac tactagtcat caaatatcat tagtgcataa  13800
tagtactagt ctatattgta tgttaccatg gcatcatatt aatagattca atttcgtttt  13860
tagtagtaca gggtgtaaaa ttagtataga gtatatactt aaagatctta aaattaaaga  13920
tcctaattgt attgcattca taggcgaagg cgcaggtaat ctgttactta gaacagtagt  13980
cgaattgcat cccgatatta gatatatata tagatcactt aaagattgta acgatcatag  14040
tctaccaatc gaattcctta gattgtataa cggtcatata aacatagatt acggcgaaaa  14100
cttaacgata cccgctactg acgctactaa taatatacat tggtcatact tacatattaa  14160
attcgcagaa cctataagtc tattcgtatg cgacgcagaa ttatccgtta cagtgaattg  14220
gtctaaaatt attatcgaat ggtctaaaca cgttagaaaa tgcaaatatt gttctagcgt  14280
taataagtgt atgttaatcg ttaagtatca cgctcaagac gatatagatt ttaaattaga  14340
taatataact atacttaaaa catacgtatg cttaggtagt aagcttaagg gtagcgaagt  14400
atacttagtg ttaacgatag gtccagctaa tatttttccc gtttttaacg tagtgcaaaa  14460
cgctaaattg attctatcta gaactaaaaa ttttataatg cctaagaaag ctgataaaga  14520
gtcaattgac gctaatataa aatcattgat accattctta tgttatccta taactaagaa  14580
agggattaat accgcactat ctaaacttaa atccgtagtg agcggagata tactatctta  14640
tagtatagcc ggtagaaacg aagtttttag taataaattg attaatcata aacatatgaa  14700
tatacttaaa tggtttaatc acgtacttaa ttttagatca accgaattga attataatca  14760
tctatatatg gtcgaatcta catatccata cttatccgaa ctgttaaact cattgactac  14820
taacgaattg aagaaattga ttaaaattac aggtagtctg ttatacaatt ttcataacga  14880
ataatgaata aagatcttat aataaaaatt cccatagcta tacactaaca ctgtattcaa  14940
ttatagttat taaaaattaa aaatcatata attttttaaa taacttttag tgaactaatc  15000
ctaaagttat cattttaatc ttggaggaat aaatttaaac cctaatctaa ttggtttata  15060
tgtgtattaa ctaaattacg agatattagt ttttgacact ttttttctcg t           15111
```

<210> SEQ ID NO 5
<211> LENGTH: 15111
<212> TYPE: DNA

-continued

<213> ORGANISM: Human respiratory syncytial virus

<400> SEQUENCE: 5

```
acgggaaaaa atgcgtacaa caaacttgca taaaccaaaa aaatggggca aataagaatt     60
tgataagtac cacttaaatt taactccctt ggttagagat gggcagcaat tcattgagta    120
tgataaaagt cagattgcaa aatctattcg ataatgacga agtggcacta ttaaaaatta    180
catgttatac cgataaattg atacatctaa ctaatgcatt agctaaagct gtaatacata    240
caattaaact taatggaata gtgtttgtac atgtaattac atctagtgat atatgcccta    300
ataataatat cgtagtcaag tctaatttta caacaatgcc agtgttacaa aatggcggat    360
atatttggga aatgatggaa ttgacacatt gctcacaacc taatggtcta ttagacgata    420
attgcgaaat taaatttagt aagaaattat ccgatagtac aatgactaat tatatgaatc    480
aattatccga attgttaggt ttcgatctta atccataaat tataattaat atcaactagc    540
aaatcaatgt cactaacacc attagttaat ataaaactta acagaagaca aaaatggggc    600
aaataaatca attcagccaa cccaaccatg gacacaaccc acaatgataa tacaccacaa    660
agactgatga ttaccgatat gagaccgttg tcacttgaga caattataac tagcctaact    720
agagatataa taacacataa atttatatat ctgattaatc acgaatgcat cgtgaggaaa    780
ttggacgaaa gacaggccac atttacattc ttagtcaatt acgaaatgaa actattgcat    840
aaggtaggct caactaagta taagaaatat accgaatata acactaaata cggaacattc    900
ccaatgccta tattcataaa tcacgacggg tttctcgaat gcataggcat aaaacctaca    960
aaacatacac ccataatcta taaatacgat cttaacccat aaatttcaac acaatattca   1020
cacaatctaa aacaacaact ctatgcataa ctatactcca tagtccagat ggagcctgaa   1080
aattatagta atttaaaact taaggagaga tataagatag aagatggggc aaatacaacc   1140
atggctctta gcaaagtcaa gttgaatgat acattgaata aagatcaatt actatctagc   1200
tcgaaatata ctatccaacg gtctacaggc gattcaatag atacacctaa ttacgatgtg   1260
caaaaacata ttaataaatt gtgtggtatg ttattgatta ccgaagacgc aaatcataaa   1320
tttacagggt taatcggtat gttatacgct atgtctagat taggtaggga agatacaatt   1380
aaaatactta gagacgcagg atatcacgtt aaagctaacg gagtagacgt aactacacat   1440
agacaggata ttaacggtaa ggaaatgaaa ttcgaagtgt taacactcgc tagcttaact   1500
accgaaatac aaattaatat cgaaatcgaa tcacgtaaat cttataagaa aatgcttaaa   1560
gaaatgggcg aagtcgcacc cgaatataga cacgatagtc ccgattgtgg tatgattata   1620
ctatgtatag ccgcattagt gataactaag ttggccgcag gcgatagatc cggattaacc   1680
gcagtgatac gtagagcgaa taacgtactt aaaaacgaaa tgaaacggta taagggtcta   1740
ttaccaaaag atatagcgaa tagtttttac gaagtattcg aaaaacatcc acattttata   1800
gacgtttttg tgcatttcgg aatcgcacaa tctagtacta gaggaggatc tagggttgag   1860
ggtatattcg caggattgtt tatgaacgca tacggagcag gtcaagtcat gcttagatgg   1920
ggagtactcg caaaatccgt taaaaatatt atgttaggac acgctagcgt acaagccgaa   1980
atggaacaag tcgttgaggt atacgaatac gcacaaaaat taggtggaga agcaggattt   2040
tatcatatac tgaataatcc taaagctagt ctattaagct taacacaatt tccacatttt   2100
tctagcgtag tgttaggtaa cgcagctggc ctaggcataa tgggcgaata taggggtaca   2160
cctagaaatc aggatctata tgacgcagct aaagcatacg ctgaacaatt gaaagagaat   2220
ggagtgataa attattccgt actcgatcta acagccgaag agttggaggc aattaaacat   2280
```

-continued

```
caattgaatc cgaaagataa tgacgttgag ttgtgagtta ataaaaaatg gggcaaataa   2340
atcatcatgg aaaagtttgc tcctgaattc catggagaag acgcaaataa tagggcaaca   2400
aaattcttag agtcaatcaa gggtaagttt acaagtccaa aagatccaaa gaagaaagat   2460
agtataataa gcgtaaactc aattgatatc gaggtgacaa aggaatcacc tataacatct   2520
aatagtacaa taataaatcc cactaacgaa acagacgata ccgcaggcaa taaacctaat   2580
tatcaacgga aaccccttagt gtcattcaaa gaagatccaa cacctagtga taatcccttt   2640
agtaaattgt ataaggaaac aatcgaaaca ttcgataata acgaagaaga atcatcatac   2700
tcatacgaag agataaacga tcagactaac gataaatataa ccgctagact agatagaata   2760
gacgaaaaac tatctgaaat actaggtatg ttacacacac tagtagtcgc atctgccgga   2820
cctacaagtg ctagagatgg gataagggat gcaatggtag ggttaaggga agaaatgata   2880
gagaaaatta gaaccgaagc attaatgact aacgatagac tcgaagcaat ggctagactt   2940
agaaacgaag aatccgaaaa gatggcaaaa gatacatctg acgaagtgtc acttaatcct   3000
actagcgaaa aattgaataa tctattagag ggaaacgata gtgataacga tctatcactc   3060
gaagatttct gattagttac caatcttcac atcaacacac aataccaaca gaagaccaac   3120
aaactaacca acccaatcat ccaaccaaac atccatccgc caatcagcca aacagccaac   3180
aaaacaacca gccaatccaa aactaaccac ccggaaaaaa tctataatat agttacaaaa   3240
aaaggaaagg gtggggcaaa tatggaaaca tacgtgaaca agcttcacga aggatcaaca   3300
tatacagctg cagtccaata taacgtactc gaaaaagacg acgatcccgc tagcctaaca   3360
atatgggtcc caatgtttca atctagtatg cccgctgatc tattaatcaa agaactagct   3420
aacgttaaca tactagtcaa acaaattagt acacctaagg gaccctcact tagagtgatg   3480
attaatagta gatccgcagt cctagcacaa atgcctagta agtttacaat atgtgctaac   3540
gtaagcttag acgaacgatc aaaactagca tacgatgtga caacaccatg cgaaatcaaa   3600
gcatgttcat tgacatgtct taaatcaaag aatatgctaa caacagtcaa agatctaaca   3660
atgaaaacac ttaatcccac acacgatata atcgcactat gcgaattcga aaatatagtg   3720
actagtaaga aagtgataat ccctacatac cttagatcaa tatccgttag aaataaggat   3780
ctgaatacac tcgaaaatat aacaacaacc gaattcaaaa acgctataac taacgctaag   3840
ataatccctt actccggact attgttagtg ataaccgtaa ccgataataa gggagcattc   3900
aaatacataa aaccccaatc ccaatttata gtcgatttag gcgcatactt agaaaaagaa   3960
tcaatctatt acgttacaac taattggaaa cataccgcta ctagattcgc aatcaaacct   4020
atggaagatt aacctttttc ctctacatca gtgtgttaat tcatacaaac tttctaccta   4080
cattcttcac ttcaccatca caatcacaaa cactctgtgg ttcaaccaat caaacaaaac   4140
ttatctgaag tcccagatca tcccaagtca ttgtttatca gatctagtac tcaaataagt   4200
taataaaaaa tatacacatg gggcaaataa tcattggagg aaatccaact aatcacaata   4260
tctgttaaca tagacaagtc cacacaccat acagaatcaa ccaatggaaa atacatccat   4320
aacaatagaa ttctctagca aattttggcc ttactttaca ctaatacaca tgataactac   4380
aatcatatcc ctattaatca taatctcaat tatgatcgca atccttaaca aactatgtga   4440
gtataacgta ttccataaca aaacattcga attgccaaga gctcgagtga atacctgata   4500
aagtagttaa ttaaaaatag tcataacaat gaactaggat atcaagacta acaataacat   4560
tggggcaaat gcaaacatgt ccaaaaacaa ggaccaacgc accgctaaaa cactcgaaag   4620
```

```
gacatgggat acccttaatc acctattatt cataagctca tgcttatata aattgaacct   4680
taaatccgtc gcacagataa ccctatcaat actcgcaatg ataatctcaa caagcttaat   4740
catagccgca ataatcttta tcgctagcgc taaccataag gtaaccccaa caaccgcaat   4800
tatacaggac gcaacatccc aaatcaaaaa cacaacccca acatacttaa cccaaaaccc   4860
acaactcgga atctcaccct ctaacccatc cgaaattacc tcacagatta caacgatact   4920
cgcaagtaca acccccggag tcaaatcgac actccaatcg acaaccgtaa agactaagaa   4980
tacaacaaca acccaaaccc aacctagtaa gcctacaact aagcaacgcc aaaacaaacc   5040
tccctctaaa ccgaataacg attttcactt cgaagtgttc aatttcgtac catgctcaat   5100
ttgctctaat aacccaacat gctgggccat atgcaaacgc atcccaaaca agaaacccgg   5160
aaagaaaaca accactaagc caacaaagaa accaaccctt aagacaacca agaaagatcc   5220
aaaaccccaa acaactaagt ctaaagaggt cccaacaact aagccaaccg aagagccaac   5280
aatcaataca actaagacta atataatcac aaccttactg acatctaaca caaccggaaa   5340
tcccgaactg acatcccaaa tggaaacctt tcactcaacc tctagcgaag gcaatccctc   5400
accatcccaa gtctcaacca ctagcgaata cccatcccaa cctagctcac ctcccaatac   5460
ccctagacag tagttactta aaaacatatt atcacaaaag gccttgacca acttaaacag   5520
aatcaaaata aactctgggg caaataacaa tggagttgct aatcctcaaa gcaaatgcaa   5580
tcacaacaat actaacagcc gttacatttt gtttcgctag cggacaaaac ataaccgaag   5640
agttttatca atctacatgt tccgccgtaa gtaaggggta tctatccgca cttagaaccg   5700
gatggtatac tagcgtaata acaatcgaac tatctaatat aaagaagaat aagtgtaacg   5760
gtacagacgc taaggttaaa ttgattaaac aggaactcga taagtataaa aacgccgtaa   5820
ccgaattgca attgttaatg caatctacac aagctactaa taatagggct agacgtgaat   5880
tgcctagatt tatgaattat acacttaata acgctaagaa aactaacgtt acactatcta   5940
agaaacgaaa acgtagattc ttagggtttt tactcggagt cggttccgca atcgctagcg   6000
gagtcgccgt aagtaaagtg ttacacctcg aaggcgaagt gaataagata aaatccgcac   6060
tattatcaac taataaggca gtcgttagcc tatctaacgg agtcagcgta ttgacatcta   6120
aagtgttaga cttaaagaat tatatagata agcaattgtt accaatcgtt aataaacaat   6180
catgttcaat atccaatatc gaaaccgtaa tcgaatttca acagaagaat aatagattac   6240
tcgaaattac tagagaattt agcgtaaacg ctggcgtaac aacacccgta agtacatata   6300
tgttaactaa ttccgaactg ttaagcttaa ttaacgatat gccaattact aacgatcaga   6360
agaaattgat gtctaataac gtacaaatcg ttagacagca atcatattca attatgtcaa   6420
ttataaaaga agaggtactc gcatacgtag tgcaattacc cctatatggc gtaatagata   6480
caccatgttg gaaattgcat acaagtccac tatgtacaac taatacaaaa gagggatcta   6540
atatatgctt aactagaacc gatagggggt ggtattgcga taacgcaggt agcgtaagtt   6600
tctttccaca agccgaaaca tgtaaagtgc aatctaatag agtgttttgc gatacaatga   6660
atagcttaac actacctagc gaagtcaatc tatgtaacgt cgatatattc aatcctaaat   6720
atgattgcaa aattatgact agtaagactg acgtaagtag tagcgtaatt actagtctcg   6780
gtgcaatagt gtcatgttat ggtaagacta agtgtaccgc tagcaataag aatagggga    6840
taataaaaac atttagtaac ggttgcgatt acgttagtaa taagggagtc gataccgtaa   6900
gcgtaggtaa tacactatat tatgttaata aacaggaagg taagtcatta tacgttaaag   6960
gcgaacctat aattaatttt tacgatccat tagtgtttcc atccgacgaa ttcgacgcta   7020
```

```
gtataagtca ggtaaacgaa aagattaacc aatcactcgc attcatacga aaatccgacg   7080
aactgttaca caacgttaac gcaggtaaga gtacaactaa cataatgata acaacaatta   7140
taatcgttat aatcgttata ctgttaagct taatcgcagt cggattactg ttatattgta   7200
aagctagatc aacacccgta acactatcta aagaccaatt atccggtata aataatatcg   7260
cattctcaaa ctaaataaaa atagcaccta atcatgttct tacaatggtt tactatctgc   7320
tcatagacaa cccatctgtc attggatttt cttaaaatct gaacttcatc gaaactctca   7380
tctataaacc atctcactta cactatttaa gtagattcct agtttatagt tatataaaac   7440
acaattgcat gccagattaa cttaccatct gtaaaaatga aaactggggc aaatatgtca   7500
cgaaggaatc cttgcaaatt tgaaattcga ggtcattgct taaatggtaa gaggtgtcat   7560
tttagtcata attattttga atggccaccc catgcactgc ttgtaagaca aaactttatg   7620
ttaaacagaa tacttaagtc tatggataaa agtatagata ccttatcaga aataagtgga   7680
gctgcagagt tggacagaac agaagagtat gctcttggtg tagttggagt gctagagagt   7740
tatataggat caataaacaa tataactaaa caatcagcat gtgttgccat gagcaaactc   7800
ctcactgaac tcaatagtga tgatatcaaa aagctgaggg acaatgaaga gctaaattca   7860
cccaagataa gagtgtacaa tactgtcata tcatatattg aaagcaacag gaaaaacaat   7920
aaacaaacta tccatctgtt aaaaagattg ccagcagacg tattgaagaa aaccatcaaa   7980
aacacattgg atatccataa gagcataacc atcaacaacc caaaagaatc aactgttagt   8040
gatacaaatg accatgccaa aaataatgat actacctgac aaatatcctt gtagtataac   8100
ttccatacta ataacaagta gatgtagagt tactatgtat aatcaaaaga acacactata   8160
tttcaatcaa aacaacccaa ataaccatat gtactcaccg aatcaaacat tcaatgaaat   8220
ccattggacc tctcaagaat tgattgacac aattcaaaat tttctacaac atctaggtat   8280
tattgaggat atatatacaa tatatatatt agtgtcataa cactcaattc taacactcac   8340
cacatcgtta cattattaat tcaaacaatt caagttgtgg gacaaaatgg atcccattat   8400
taatggaaat tctgctaacg tatacttaac cgatagttat ttaaaaggcg taatcagttt   8460
tagcgaatgt aacgcattag ggtcatatat ctttaacggt ccatatctta aaaacgatta   8520
tactaatcta atcagtagac agaatccgtt aatcgaacat atgaatctta agaaactgaa   8580
tatcacacaa tctttgatca gtaagtatca taaaggcgaa atcaaactcg aagaacctac   8640
atattttcaa tcactattaa tgacatataa gtctatgaca tctagcgaac agatcgctac   8700
tactaatctg ttgaagaaaa ttattagacg agctatagag atatctgacg ttaaggtata   8760
cgctatactg aataaattgg ggttaaaaga gaaagataag ataaaatcta ataacggtca   8820
agacgaagat aatagtgtaa ttactacaat tattaaagac gatatactat ccgcagtgaa   8880
ggataatcaa tcacatctta aagccgataa aaatcatagt actaaacaaa aagatacaat   8940
taaaactaca ttgttaaaga aattgatgtg ttctatgcaa catccaccta gttggttaat   9000
acattggttt aacttataca ctaagttgaa caatatactt acacaatatc gatcaaacga   9060
agtgaaaaat cacggtttta cattgataga taatcaaaca ttaagcggat ttcaattcat   9120
acttaaccaa tacggatgta tagtgtatca taaagaattg aaacgtataa ccgttacaac   9180
atataatcaa ttcttaacat ggaaagatat aagtctatct agattgaacg tatgcttaat   9240
tacatggatt tcgaattgtc ttaatacact taataaatca ttagggttaa gatgcggatt   9300
taataacgtt atacttacac aattgttctt atacggagat tgtatactta agttgttcca   9360
```

-continued

```
taacgaaggg ttttatataa taaaagaggt tgagggattt ataatgtcat tgatactgaa   9420
tattaccgaa gaggatcaat ttagaaaaag attctataat agtatgttaa acaatataac   9480
tgacgcagct aataaagcgc agaagaatct gttatctaga gtatgtcata cattgttaga   9540
caaaacagtg agcgataata ttataaacgg tagatggatt atactgttat ctaaattctt   9600
aaaattgatt aagttggcag gtgacaataa ccttaataac ttaagcgaat tgtatttctt   9660
attcagaata ttcggacatc ctatggttga cgaacgacaa gctatggacg cagtgaagat   9720
taattgtaac gaaactaaat tctatctatt atctagtcta tctatgctta gaggcgcatt   9780
catatataga attataaaag ggttcgttaa taattataat agatggccta cacttagaaa   9840
cgctatagtg ttaccactta gatggttaac atattataaa ttgaatacat atcctagttt   9900
actcgaatta accgaacgcg atctgatagt gttaagcgga cttagattct atagagagtt   9960
tagattgcct aagaaagtcg atctcgaaat gataattaac gataaggcaa ttagtccacc  10020
taaaaactta atatggacaa gcttccctag aaattatatg cctagtcata tacaaaatta  10080
tatcgaacac gaaaaattga aatttagcga atccgataag tctagaagag tgttagagta  10140
ttacttacgc gataataaat ttaacgaatg cgatctatat aattgcgtag tgaaccaatc  10200
atatcttaat aatcctaatc acgtagtgag tcttacaggt aaggaaagag agttgagcgt  10260
aggtagaatg ttcgctatgc aacccggtat gtttagacaa gtgcaaatac tcgcagaaaa  10320
gatgatagcc gaaaatatac tgcaattctt tcccgaatca ttgactagat acggagattt  10380
agaattgcaa aagatactcg aattgaaagc aggtatatct aataagtcta atagatataa  10440
cgataattat aataattata tatctaagtg tagtattatt accgatctat ctaaattcaa  10500
tcaggcattt agatacgaaa ctagttgtat atgctcagac gtattagacg aattacacgg  10560
agtgcaatct ttgtttagtt ggttacattt aactatacct cacgttacaa ttatatgtac  10620
atatagacac gcaccaccat atataggcga tcatatagtc gatctgaata acgtagacga  10680
acaatccgga ttgtatagat atcacatggg tggcatagag ggatggtgtc aaaaattgtg  10740
gactatagag gcaattagtc tgttagatct aattagtctt aagggtaagt tttcgattac  10800
cgcattgatt aacggtgata atcaatcaat tgatatatct aaaccgatac ggttaatgga  10860
gggacaaaca cacgctcaag ccgattactt actcgcactt aattcactta aactgttata  10920
caaagagtac gcaggtatag ggcataaact taagggtaca gagacatata taagtaggga  10980
tatgcaattt atgagtaaga ctatacaaca taacggagtg tattatcccg ctagtataaa  11040
gaaagtgctt agagtcggac cttggattaa tactatatta gacgatttta aggttagtct  11100
cgaatcaatc ggatcattga cacaagagtt ggagtataga ggcgaatctc tattatgctc  11160
attgattttt agaaacgtat ggttatacaa tcagattgca ttgcaattga aaaatcacgc  11220
actatgtaat aataagttgt acttagacat acttaaagtg ttaaaacatc ttaaaacatt  11280
ctttaatctc gataatatag ataccgcatt aacattgtat atgaatctac ctatgttatt  11340
cggagggggga gatcctaatc tattgtatag atcattctat agacgtacac ctgatttctt  11400
aaccgaagct atagtgcata gcgtattcat actatcatat tatactaatc acgatcttaa  11460
agataagttg caggatctat ctgacgatag attgaataaa ttcttaacat gtattataac  11520
attcgataaa aatcctaacg ctgaattcgt tacacttatg agagatccac aagcattagg  11580
ttcagagaga caggctaaaa ttactagcga aattaataga ttagccgtta ccgaagtgtt  11640
aagtaccgca cctaataaga tattctctaa atccgctcaa cattatacaa caaccgaaat  11700
agatcttaac gatattatgc aaaatatcga acctacatat cctcacggat tacgcgtagt  11760
```

-continued

```
ttacgaatca ttaccattct ataaagccga aaagatcgtt aacttaatta gcggtacaaa  11820
atcaattact aatatactcg aaaagactag cgcaattgat ttaaccgata tagatagagc  11880
taccgaaatg atgcgtaaaa atataacatt actgatacgt atactaccat tagattgtaa  11940
tagggataaa agagagatac tatctatgga gaatctatca attacagaat tgtcaaaata  12000
cgttagggaa cgatcatggt cactatctaa tatcgtaggc gtaactagtc ctagtattat  12060
gtatactatg gatattaagt atacaactag tacaattagt agcggtataa taatcgaaaa  12120
atataacgtt aatagtctaa cacgtggtga aaggggacct acaaaacctt gggtcggatc  12180
tagtacacaa gagaagaaaa ctatgcccgt atataataga caggtattga ctaagaaaca  12240
acgagatcaa atagatctat tagctaaact cgattgggta tacgctagta tagataataa  12300
agacgaattt atggaagagt tgtcaatcgg tacattaggg ttaacatacg aaaaagctaa  12360
gaaattgttc ccacaatatc tatcagtgaa ttatctacat agattgacag tgagtagtag  12420
accatgcgaa tttcccgcta gtatacccgc atatagaact actaattatc atttcgatac  12480
tagtccaatt aatagaatat taaccgaaaa atacggagac gaagatatag atatcgtatt  12540
ccaaaattgt attagtttcg gattgagtct tatgtccgta gtcgaacaat ttactaacgt  12600
atgtcctaat aggattatac tgatacctaa attgaacgaa atacatctta tgaaacctcc  12660
tatttttaca ggcgatgtcg atatacacaa attgaaacag gttatacaaa aacaacatat  12720
gttcttaccc gataagatat cgttaacgca atacgttgag ttgttcttat caaataaaac  12780
acttaaatca ggtagtcacg ttaatagtaa tctgatactc gcacataaaa ttagcgatta  12840
ctttcataat acatatatat tgagtactaa cttagccgga cattggatac tgattataca  12900
attgatgaaa gatagtaagg gtatattcga aaaagattgg ggtgagggat atataaccga  12960
tcatatgttt ataaacctta aggtcttctt taacgcatat aaaacttatc tattatgttt  13020
tcataaggga tacggtaagg ctaaactcga atgcgatatg aatacatccg atctattatg  13080
cgtactcgaa ttaattgata gtagctattg gaaatctatg agtaaggtat tcttagagca  13140
aaaggtgatc aagtatatac tatctcaaga cgctagtttg catagggtta agggatgtca  13200
tagttttaaa ttatggtttc ttaaaagatt gaacgtagcc gaatttacag tatgtccttg  13260
ggtcgttaac atagattatc atcctacaca tatgaaagct atacttacat atatagatct  13320
agtgagaatg ggattgatta acatagatag aatacatata aagaataaac ataaatttaa  13380
cgacgaattc tatactagta atctattcta tataaattat aatttttccg ataatacaca  13440
tctattaact aaacatatac gtatagctaa tagcgaactc gaaaataatt ataataaatt  13500
gtatcatcct acacccgaaa cattagagaa tatactcgct aatccgatta aatctaacga  13560
taagaaaaca cttaacgatt attgtatagg taaaaacgtt gattcaatta tgttaccatt  13620
actatcaaat aagaaattga ttaaatctag cgctatgatt agaactaatt atagtaaaca  13680
ggatctatat aacttattcc ctatggtcgt aattgataga attatagatc attccggtaa  13740
taccgctaaa tctaatcaat tgtatacaac tactagtcat caaatatcat tagtgcataa  13800
tagtactagt ctatattgta tgttaccatg gcatcatatt aatagattca atttcgtttt  13860
tagtagtaca gggtgtaaaa ttagtataga gtatatactt aaagatctta aaattaaaga  13920
tcctaattgt attgcattca taggcgaagg cgcaggtaat ctgttactta gaacagtagt  13980
cgaattgcat cccgatatta gatatatata tagatcactt aaagattgta acgatcatag  14040
tctaccaatc gaattcctta gattgtataa cggtcatata aacatagatt acggcgaaaa  14100
```

-continued

```
cttaacgata cccgctactg acgctactaa taatatacat tggtcatact tacatattaa  14160

attcgcagaa cctataagtc tattcgtatg cgacgcagaa ttatccgtta cagtgaattg  14220

gtctaaaatt attatcgaat ggtctaaaca cgttagaaaa tgcaaatatt gttctagcgt  14280

taataagtgt atgttaatcg ttaagtatca cgctcaagac gatatagatt ttaaattaga  14340

taatataact atacttaaaa catacgtatg cttaggtagt aagcttaagg gtagcgaagt  14400

atacttagtg ttaacgatag gtccagctaa tatttttccc gtttttaacg tagtgcaaaa  14460

cgctaaattg attctatcta gaactaaaaa ttttataatg cctaagaaag ctgataaaga  14520

gtcaattgac gctaatataa aatcattgat accattctta tgttatccta taactaagaa  14580

agggattaat accgcactat ctaaacttaa atccgtagtg agcggagata tactatctta  14640

tagtatagcc ggtagaaacg aagtttttag taataaattg attaatcata aacatatgaa  14700

tatacttaaa tggtttaatc acgtacttaa ttttagatca accgaattga attataatca  14760

tctatatatg gtcgaatcta catatccata cttatccgaa ctgttaaact cattgactac  14820

taacgaattg aagaaattga ttaaaattac aggtagtctg ttatacaatt ttcataacga  14880

ataatgaata aagatcttat aataaaaatt cccatagcta tacactaaca ctgtattcaa  14940

ttatagttat taaaaattaa aaatcatata atttttaaa taacttttag tgaactaatc  15000

ctaaagttat cattttaatc ttggaggaat aaatttaaac cctaatctaa ttggtttata  15060

tgtgtattaa ctaaattacg agatattagt ttttgacact ttttttctcg t           15111
```

ATTENUATION OF HUMAN RESPIRATORY SYNCYTIAL VIRUS BY GENOME SCALE CODON-PAIR DEOPTIMIZATION

CROSS REFERENCE TO RELATED APPLICATIONS

This application is a divisional application of U.S. patent application Ser. No. 14/766,620. filed Aug. 7, 2015, which is a national stage application under 35 U.S.C. 371 and claims the benefit of PCT Application No. PCT/US2014/015274 having an international filing date of Feb. 7, 2014, which designated the United States, which PCT application claims priority to U.S. Provisional Application Ser. No. 61/794,155, filed Mar. 15, 2013 and U.S. Provisional Application Ser. No. 61/762,768, filed Feb. 8, 2013. All these applications are incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Feb. 6, 2014, is named NIHB-2629_SL.txt and is 99,152 bytes in size.

TECHNICAL FIELD

The subject matter disclosed herein relates to paramyxoviruses, in particular, respiratory syncytial virus and attenuated, mutant strains thereof.

BACKGROUND

Human respiratory syncytial virus (RSV) infects nearly everyone worldwide early in life and is responsible for considerable mortality and morbidity. In the United States alone, RSV is responsible for 75,000-125,000 hospitalizations yearly, and worldwide conservative estimates conclude that RSV is responsible for 64 million pediatric infections and 160,000 pediatric deaths. Another unusual feature of RSV is that severe infection in infancy can be followed by years of airway dysfunction, including a predisposition to airway reactivity. RSV infection exacerbates asthma and may be involved in initiating asthma.

RSV is a member of the Paramyxoviridae family and, as such, is an enveloped virus that replicates in the cytoplasm and matures by budding through the host cell plasma membrane. The genome of RSV is a single, negative-sense strand of RNA of 15.2 kilobases that is transcribed by the viral polymerase into 10 mRNAs by a sequential stop-start mechanism that initiates at a single viral promoter at the 3' end of the genome. Each mRNA encodes a single major protein, with the exception of the M2 mRNA, which has two overlapping open reading frames that encode two separate proteins. The 11 RSV proteins are: the RNA-binding nucleocapsid protein (N), the phosphoprotein (P), the large polymerase protein (L), the attachment glycoprotein (G), the fusion protein (F), the small hydrophobic (SH) surface glycoprotein, the internal matrix protein (M), the two non-structural proteins NS1 and NS2, and the M2-1 and M2-2 proteins encoded by the M2 mRNA. The RSV gene order is: 3'-NS1-NS2-N-P-M-SH-G-F-M2-L. Each gene is flanked by short transcription signals called the gene-start (GS) signal, present on the upstream end of the gene and involved in initiating transcription of the respective gene, and the gene-end (GE) signal, present at the downstream end of the gene and involved in directing synthesis of a polyA tail followed by release of the mRNA.

Vaccines and new antiviral drugs are in pre-clinical and clinical development; however, no vaccines for RSV are commercially available yet. The goal of the present study was to design and generate new vaccine candidates for RSV by using the recently described synthetic attenuated virus engineering (SAVE) technique. (Coleman, et al., Science 320:1784-1787 (2008)). This technique is used to recode a genome in which the wild type (wt) amino acid sequence is unmodified, but synonymous codons are rearranged to create a suboptimal arrangement of pairs of codons that deviates from the natural frequency of occurrence of certain codon pairs. For pathogens, the attenuation resulting from this rearrangement of codons can be 'titrated' by adjusting the extent of codon-pair deoptimization (CPD). Recombinant pathogens that were attenuated by this approach encode proteins with wt aa sequences. Thus, these pathogens are likely to induce a cellular and humoral immunity against the same epitopes as the wt pathogen.

SUMMARY

Described herein are RSV polynucleotide sequences that make use of multiple codons that are containing silent nucleotide substitutions engineered in multiple locations in the genome, wherein the substitutions introduce a numerous synonymous codons into the genome. This substitution of synonymous codons alters various parameters, including codon bias, codon pair bias, density of deoptimized codons and deoptimized codon pairs, RNA secondary structure, CpG dinucleotide content, C+G content, translation frameshift sites, translation pause sites, the presence or absence of tissue specific microRNA recognition sequences, or any combination thereof, in the genome. Because of the large number of defects involved, the attenuated virus of the invention provides a means of producing stably attenuated, live vaccines against RSV.

BRIEF DESCRIPTION OF THE DRAWINGS

FIG. 7 shows an alignment of the genome sequences for wt RSV (SEQ ID NO: 1), RSV Min A (SEQ ID NO: 2), RSV Min B (SEQ ID NO: 3), RSV Min L (SEQ ID NO: 4), and RSV FLC (SEQ ID NO: 5).

DETAILED DESCRIPTION OF ILLUSTRATIVE EMBODIMENTS

Figure 1:
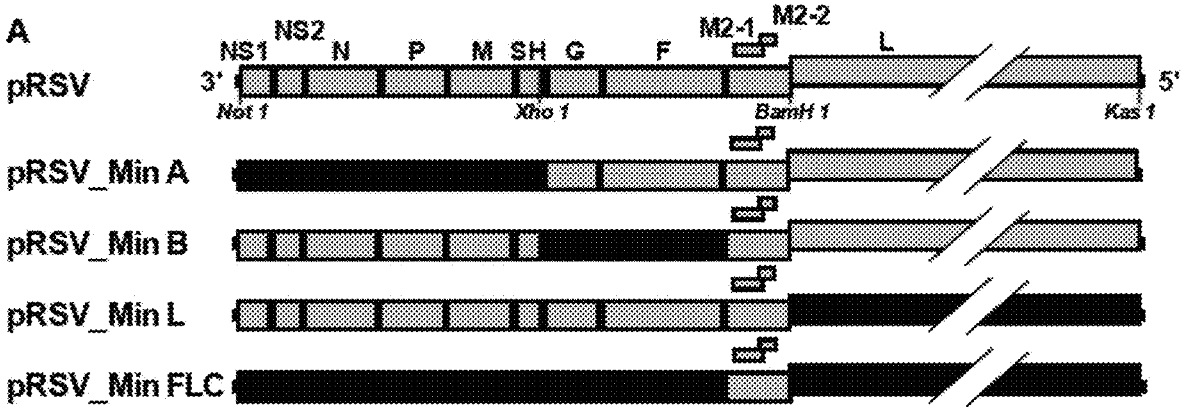
FIG. 1. Generation of synthetic codon-pair deoptimized rRSVs and characterization of their growth on Vero cells. (A) Four chimeric synthetic codon-pair deoptimized (CPD) rRSVs were generated based on the wt RSV backbone (Genbank Accession number M74568). Min A contained CPD ORFs of NS1, NS2, N, P, M and SH. Min B contained CPD ORFs of G and F. Min L contained a CPD ORF of polymerase protein L. Min FLC, all coding regions except M2, were codon pair deoptimized. CPD and wt coding sequences are represented by a black or grey shading boxes, respectively. (B) Multi-cycle growth kinetics of wt and codon-pair deoptimized rRSVs on Vero cells at 32 and 37° C. (C) Plaque size phenotype on Vero cells at 32° C. of rRSV and CPD rRSVs. (D) Specific infectivity of CPD rRSVs relative to rRSV was evaluated using strand-specific qRT-PCRs (Bessaud, M., et al., 2008. J Virol Methods 153:182-189). Viral RNAs derived from $4\times10^6$ pfu of rRSV, Min A, Min L or Min FLC were extracted using a viral RNA extraction kit (Qiagen). Four microliters of the 60 μl RNA extraction were used in an RT reaction using superscript III reverse transcriptase and tagged primer containing an RSV-specific 3'-tail complementary to the RSV genomic RNA, and an unrelated 5'-tag sequence. Then, 10% of each cDNA reaction (corresponding to $2.7\times10^4$ pfu) was used in the genome-specific qPCR described above. Results of the quantification of genomic RNA are expressed as fold difference compared to rRSV.
Figure 1:
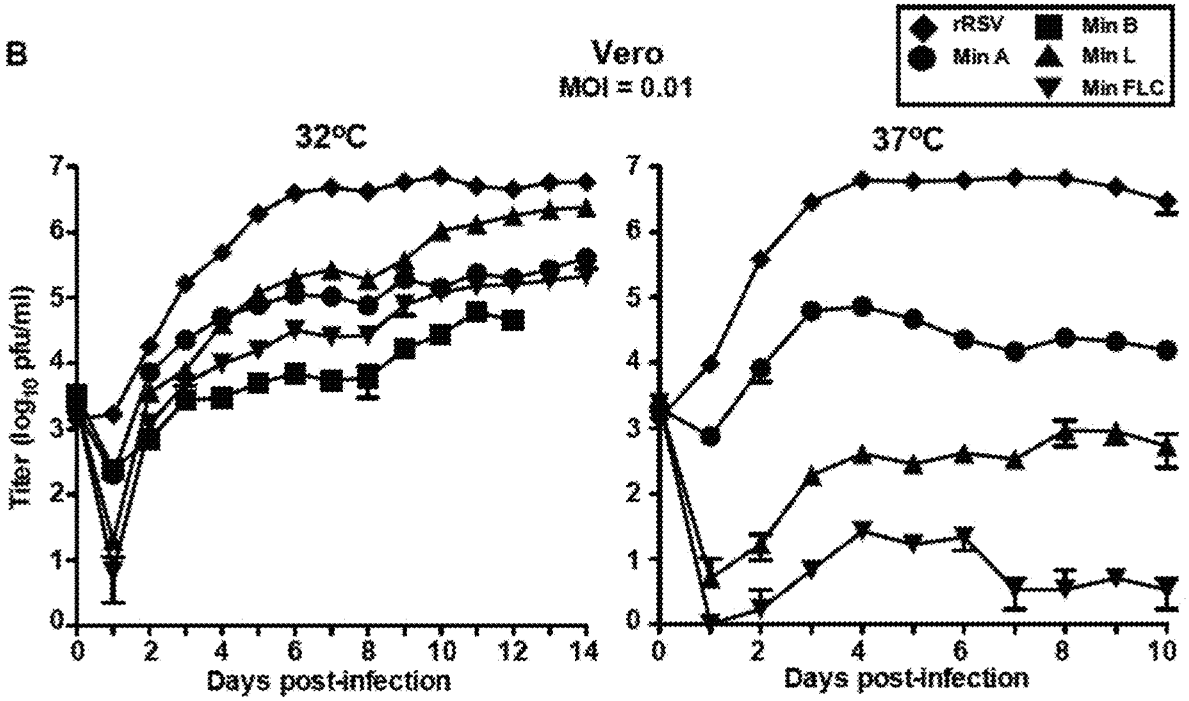
Figure 1:
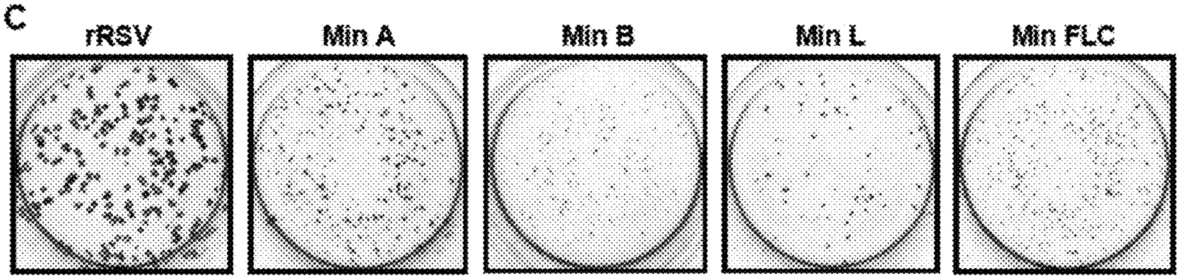
Figure 1:
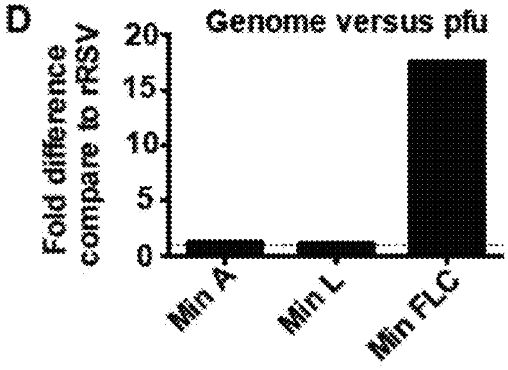

Provided herein are recombinant RSVs suitable for vaccine use in humans. Attenuated RSVs described herein are produced by introducing codon changes in the viral genome that are not optimally processed by the host cell. The majority of these mutations will not cause a change in the resulting amino acid of proteins encoded by the viral genome, thus allowing for the production of viruses that have the same antigenic features of wild-type viruses. It should be understood, however, that widespread noncoding changes to the codons of the viral genome may result in a selective pressure that gives rise to one or more amino acid mutations in the viruses described herein. Additionally, the described viruses may be combined with known attenuating mutations of RSV, of related viruses to yield an attenuated virus.

As used herein, the term "temperature sensitive" refers to the property of reduced replication compared to wild-type virus at temperatures at which the wild-type virus normally replicates. For example, wild-type RSV replicates efficiently within the range of 32° C. to 40° C., whereas a temperature-sensitive mutant would be restricted in replication at the higher temperatures within this range, but could be propagated efficiently at 32° C., which is called the "permissive temperature." These viruses can be made using recombinant methods useful in identifying attenuated RSV strains. Once identified, the attenuating mutations can be introduced into biologically-derived strains, used to further attenuate or stabilize existing attenuated RSV strains, or attenuated RSV strains may be designed de novo.

The term "wild-type" as used herein refers to a viral phenotype that is consistent with efficient replication in a suitable permissive human host, and that may induce disease in a susceptible human host (for example, an RSV-naïve infant). The prototype A2 strain, represented by Genbank accession number M74568 but not strictly limited to that sequence, is considered to be an example of a wild-type strain. Derivative viruses that contain mutations that are presumed to not significantly reduce replication or disease in vivo also have the "wild-type" phenotype. In contrast, viral derivatives that exhibit reductions in replication of approximately 10-fold, 100-fold, or more in vivo may be considered to be "restricted". Generally, restricted replication in vivo in a susceptible host is associated with reduced disease, or "attenuation." Thus, infection of a susceptible host with an "attenuated" virus results in reduced disease in that host, as compared to a wild-type strain.

The term "parent" used in the context of a virus, protein, or polynucleotide denotes the virus, protein, or polynucleotide from which another virus is derived. The derived virus may be made by recombinant means, or by culturing the parent virus under conditions that give rise to a mutation, and thus a different virus. The term may refer to viral genomes and protein encoding sequences from which new sequences, which may be more or less attenuated, are derived. Parent viruses and sequences are usually wild type or naturally occurring prototypes or isolates of variants for which it is desired to obtain a more highly attenuated virus. However, parent viruses also include mutants specifically created or selected in the laboratory on the basis of real or perceived desirable properties. Accordingly, parent viruses that are candidates for attenuation include mutants of wild type or naturally occurring viruses that have deletions, insertions, amino acid substitutions and the like, and also include mutants which have codon substitutions.

The term "gene" or "gene sequence" refers to a polynucleotide sequence that encodes a protein and includes only the open reading frame portion of such a polynucleotide sequence.

RSV Protein Sequences Encoded by Codon Deoptimized Polynucleotides

Described herein are RSV polynucleotide sequences that make use of multiple codons that are containing silent nucleotide substitutions engineered in multiple locations in the genome, wherein the substitutions introduce a numerous synonymous codons into the genome. This substitution of synonymous codons alters various parameters, including codon bias, codon pair bias, density of deoptimized codons and deoptimized codon pairs, RNA secondary structure, CpG dinucleotide content, C+G content, translation frameshift sites, translation pause sites, the presence or absence of tissue specific microRNA recognition sequences, or any combination thereof, in the genome. Because of the large number of defects involved, the attenuated virus of the invention provides a means of producing stably attenuated, live vaccines against RSV.

In one embodiment, an attenuated virus is provided which comprises a nucleic acid sequence encoding a viral protein or a portion thereof that is identical to the corresponding sequence of a parent virus, wherein the nucleotide sequence of the attenuated virus contains the codons of a parent sequence from which it is derived, and wherein the nucleotide sequence is less than 90% identical to the nucleotide sequence of the parent virus. In another embodiment, the nucleotide sequence is less than 80% identical to the sequence of the parent virus. In another embodiment, the nucleotide sequence is less than 70% identical to the sequence of the parent virus. The substituted nucleotide sequence which provides for attenuation is at least 100 nucleotides in length, or at least 250 nucleotides in length, or at least 500 nucleotides in length, or at least 1000 nucleotides in length. The codon pair bias of the attenuated sequence is less than the codon pair bias of the parent virus, and is reduced by at least about 0.05, or at least about 0.1, or at least about 0.2.

Described herein are codon pair deoptimized recombinant polynucleotides encoding a respiratory syncytial virus (RSV) amino acid sequence of a parent RSV, where the nucleotide sequence differs from the corresponding nucleotide sequence of the parent virus, resulting in a nucleotide identity of about 77% to about 93%. In some embodiments the amino acid sequence of the parent RSV may have an existing attenuating mutation, such that the resulting recombinant polynucleotide will encode the attenuating mutation to be encoded. The recombinant polynucleotides described herein, can encode any one of the RSV proteins NS1, NS2, N, P, M, SH, G, F, or L, or a combination of these proteins.

The recombinant polynucleotides described herein can encode the RSV NS1 protein. In one embodiment the nucleotide sequence encoding the RSV NS1 protein is from about 75% to about 95% identical to the corresponding nucleotide sequence of a parent virus. In one embodiment the nucleotide sequence encoding the RSV NS1 protein is from about 80% to about 90% identical to the corresponding nucleotide sequence of a parent virus. In one embodiment the nucleotide sequence encoding the RSV NS1 protein is about 87% identical to the corresponding nucleotide sequence of a parent virus. In one embodiment the nucleotide sequence encoding the RSV NS1 protein is from about 75% to about 95% identical to nucleotides 99 to 518 of SEQ ID NO: 5. In one embodiment the nucleotide sequence encoding the RSV NS1 protein is from about 80% to about 90% identical to nucleotides 99 to 518 of SEQ ID NO: 5. In one embodiment the nucleotide sequence encoding the RSV NS1 protein is about 87% identical to nucleotides 99 to 518 of SEQ ID NO: 5. In one embodiment the recombinant polynucleotide has the sequence of nucleotides 99 to 518 of SEQ ID NO: 5. In some embodiments the parent virus is an RSV subgroup A virus. In some embodiments the parent virus is an RSV subgroup B virus.

The recombinant polynucleotides described herein can encode the RSV NS2 protein. In one embodiment the nucleotide sequence encoding the RSV NS2 protein is from about 75% to about 95% identical to the corresponding nucleotide sequence of a parent virus. In one embodiment the nucleotide sequence encoding the RSV NS2 protein is from about 80% to about 90% identical to the corresponding nucleotide sequence of a parent virus. In one embodiment the nucleotide sequence encoding the RSV NS2 protein is about 88% identical to the corresponding nucleotide sequence of a parent virus. In one embodiment the nucleotide sequence encoding the RSV NS2 protein is from about 75% to about 95% identical to nucleotides 628 to 1002 of SEQ ID NO: 5. In one embodiment the nucleotide sequence encoding the RSV NS2 protein is from about 80% to about 90% identical to nucleotides 628 to 1002 of SEQ ID NO: 5. In one embodiment the nucleotide sequence encoding the RSV NS2 protein is about 88% identical to nucleotides 628 to 1002 of SEQ ID NO: 5. In one embodiment the recombinant polynucleotide has the sequence of nucleotides 628 to 1002 of SEQ ID NO: 5. In some embodiments the parent virus is an RSV subgroup A virus. In some embodiments the parent virus is an RSV subgroup B virus.

The recombinant polynucleotides described herein can encode the RSV N protein. In one embodiment the nucleotide sequence encoding the RSV N protein is from about 70% to about 90% identical to the corresponding nucleotide sequence of a parent virus. In one embodiment the nucleotide sequence encoding the RSV N protein is from about 75% to about 85% identical to the corresponding nucleotide sequence of a parent virus. In one embodiment the nucleotide sequence encoding the RSV N protein is about 80% identical to the corresponding nucleotide sequence of a parent virus. In one embodiment the nucleotide sequence encoding the RSV N protein is from about 70% to about 90% identical to nucleotides 1141 to 2316 of SEQ ID NO: 5. In one embodiment the nucleotide sequence encoding the RSV N protein is from about 75% to about 85% identical to nucleotides 1141 to 2316 of SEQ ID NO: 5. In one embodiment the nucleotide sequence encoding the RSV N protein is about 80% identical to nucleotides 1141 to 2316 of SEQ ID NO: 5. In one embodiment the recombinant polynucleotide has the sequence of nucleotides 1141 to 2316 of SEQ ID NO: 5. In some embodiments the parent virus is an RSV subgroup A virus. In some embodiments the parent virus is an RSV subgroup B virus.

The recombinant polynucleotides described herein can encode the RSV P protein. In one embodiment the nucleotide sequence encoding the RSV P protein is from about 75% to about 95% identical to the corresponding nucleotide sequence of a parent virus. In one embodiment the nucleotide sequence encoding the RSV P protein is from about 80% to about 90% identical to the corresponding nucleotide sequence of a parent virus. In one embodiment the nucleotide sequence encoding the RSV P protein is about 84% identical to the corresponding nucleotide sequence of a parent virus. In one embodiment the nucleotide sequence encoding the RSV P protein is from about 75% to about 95% identical to nucleotides 2347 to 3072 of SEQ ID NO: 5. In one embodiment the nucleotide sequence encoding the RSVP protein is from about 80% to about 90% identical to nucleotides 2347 to 3072 of SEQ ID NO: 5. In one embodiment the nucleotide sequence encoding the RSV P protein is about 84% identical to nucleotides 2347 to 3072 of SEQ ID NO: 5. In one embodiment the recombinant polynucleotide has the sequence of nucleotides 2347 to 3072 of SEQ ID NO: 5. In some embodiments the parent virus is an RSV subgroup A virus. In some embodiments the parent virus is an RSV subgroup B virus.

The recombinant polynucleotides described herein can encode the RSV M protein. In one embodiment the nucleotide sequence encoding the RSV M protein is from about 75% to about 95% identical to the corresponding nucleotide sequence of a parent virus. In one embodiment the nucleotide sequence encoding the RSV M protein is from about 80% to about 90% identical to the corresponding nucleotide sequence of a parent virus. In one embodiment the nucleotide sequence encoding the RSV M protein is about 83% identical to the corresponding nucleotide sequence of a parent virus. In one embodiment the nucleotide sequence encoding the RSV M protein is from about 75% to about 95% identical to nucleotides 3262 to 4032 of SEQ ID NO: 5. In one embodiment the nucleotide sequence encoding the RSV M protein is from about 80% to about 90% identical to nucleotides 3262 to 4032 of SEQ ID NO: 5. In one embodiment the nucleotide sequence encoding the RSV M protein is about 83% identical to nucleotides 3262 to 4032 of SEQ ID NO: 5. In one embodiment the recombinant polynucleotide has the sequence of nucleotides 3262 to 4032 of SEQ ID NO: 5. In some embodiments the parent virus is an RSV subgroup A virus. In some embodiments the parent virus is an RSV subgroup B virus.

The recombinant polynucleotides described herein can encode the RSV SH protein. In one embodiment the nucleotide sequence encoding the RSV SH protein is from about 85% to about 95% identical to the corresponding nucleotide sequence of a parent virus. In one embodiment the nucleotide sequence encoding the RSV SH protein is about 92% identical to the corresponding nucleotide sequence of a parent virus. In one embodiment the nucleotide sequence encoding the RSV SH protein is from about 85% to about 95% identical to nucleotides 4304 to 4498 of SEQ ID NO: 5. In one embodiment the nucleotide sequence encoding the RSV SH protein is about 92% identical to nucleotides 4304 to 4498 of SEQ ID NO: 5. In one embodiment the recombinant polynucleotide has the sequence of nucleotides 4304 to 4498 of SEQ ID NO: 5. In some embodiments the parent virus is an RSV subgroup A virus. In some embodiments the parent virus is an RSV subgroup B virus.

The recombinant polynucleotides described herein can encode the RSV G protein. In one embodiment the nucleotide sequence encoding the RSV G protein is from about 70% to about 90% identical to the corresponding nucleotide sequence of a parent virus. In one embodiment the nucleotide sequence encoding the RSV G protein is from about 75% to about 85% identical to the corresponding nucleotide sequence of a parent virus. In one embodiment the nucleotide sequence encoding the RSV G protein is about 78% identical to the corresponding nucleotide sequence of a parent virus. In one embodiment the nucleotide sequence encoding the RSV G protein is from about 70% to about 90% identical to nucleotides 4577 to 5473 of SEQ ID NO: 5. In one embodiment the nucleotide sequence encoding the RSV G protein is from about 75% to about 85% identical to nucleotides 4577 to 5473 of SEQ ID NO: 5. In one embodiment the nucleotide sequence encoding the RSV G protein is about 78% identical to nucleotides 4577 to 5473 of SEQ ID NO: 5. In one embodiment the recombinant polynucleotide has the sequence of nucleotides 4577 to 5473 of SEQ ID NO: 5. In some embodiments the parent virus is an RSV subgroup A virus. In some embodiments the parent virus is an RSV subgroup B virus.

The recombinant polynucleotides described herein can encode the RSV F protein. In one embodiment the nucleotide sequence encoding the RSV F protein is from about 70% to about 90% identical to the corresponding nucleotide sequence of a parent virus. In one embodiment the nucleotide sequence encoding the RSV F protein is from about 75% to about 85% identical to the corresponding nucleotide sequence of a parent virus. In one embodiment the nucleotide sequence encoding the RSV F protein is about 77% identical to the corresponding nucleotide sequence of a parent virus. In one embodiment the nucleotide sequence encoding the RSV F protein is from about 70% to about 90% identical to nucleotides 5550 to 7274 of SEQ ID NO: 5. In one embodiment the nucleotide sequence encoding the RSV F protein is from about 75% to about 85% identical to nucleotides 5550 to 7274 of SEQ ID NO: 5. In one embodiment the nucleotide sequence encoding the RSV F protein is about 77% identical to nucleotides 5550 to 7274 of SEQ ID NO: 5. In one embodiment the recombinant polynucleotide has the sequence of nucleotides 5550 to 7274 of SEQ ID NO: 5. In some embodiments the parent virus is an RSV subgroup A virus. In some embodiments the parent virus is an RSV subgroup B virus.

The recombinant polynucleotides described herein can encode the RSV L protein. In one embodiment the nucleotide sequence encoding the RSV L protein is from about 70% to about 90% identical to the corresponding nucleotide sequence of a parent virus. In one embodiment the nucleotide sequence encoding the RSV L protein is from about 75% to about 85% identical to the corresponding nucleotide sequence of a parent virus. In one embodiment the nucleotide sequence encoding the RSV L protein is about 79% identical to the corresponding nucleotide sequence of a parent virus. In one embodiment the nucleotide sequence encoding the RSV L protein is from about 70% to about 90% identical to nucleotides 8387 to 14884 of SEQ ID NO: 5. In one embodiment the nucleotide sequence encoding the RSV L protein is from about 75% to about 85% identical to nucleotides 8387 to 14884 of SEQ ID NO: 5. In one embodiment the nucleotide sequence encoding the RSV L protein is about 79% identical to nucleotides 8387 to 14884 of SEQ ID NO: 5. In one embodiment the recombinant polynucleotide has the sequence of nucleotides 8387 to 14884 of SEQ ID NO: 5. In some embodiments the parent virus is an RSV subgroup A virus. In some embodiments the parent virus is an RSV subgroup B virus.

The described deoptimized RSV polynucleotide sequences described herein can be used in combination with one another to form polynucleotides with two or more deoptimized gene sequences. In some embodiments the described polynucleotide may include any two codon deoptimized recombinant polynucleotides encoding RSV proteins selected from: NS1, NS2, N, P, M, SH, G, F, and L. In some embodiments the described polynucleotide may include any three codon deoptimized recombinant polynucleotides encoding RSV proteins selected from: NS1, NS2, N, P, M, SH, G, F, and L. In some embodiments the described polynucleotide may include any four codon deoptimized recombinant polynucleotides encoding RSV proteins selected from: NS1, NS2, N, P, M, SH, G, F, and L. In some embodiments the described polynucleotide may include any five codon deoptimized recombinant polynucleotides encoding RSV proteins selected from: NS1, NS2, N, P, M, SH, G, F, and L. In some embodiments the described polynucleotide may include any six codon deoptimized recombinant polynucleotides encoding RSV proteins selected from: NS1, NS2, N, P, M, SH, G, F, and L. In some embodiments the described polynucleotide may include any seven codon deoptimized recombinant polynucleotides encoding RSV proteins selected from: NS1, NS2, N, P, M, SH, G, F, and L. In some embodiments the described polynucleotide may include any eight codon deoptimized recombinant polynucleotides encoding RSV proteins selected from: NS1, NS2, N, P, M, SH, G, F, and L. In some embodiments the described polynucleotide may include nine codon deoptimized recombinant polynucleotides encoding RSV proteins: NS1, NS2, N, P, M, SH, G, F, and L. In some embodiments these described polynucleotides can be an RSV genome or antigenome having one or more codon deoptimized RSV gene sequences. The viruses RSV Min A, RSV Min B, RSV Min L, and RSV Min FLC have genome sequences representative of such virus constructs; however, other such viruses and viral genomes or antigenomes could be produced using the polynucleotide sequences provided herein.

The codon deoptimized sequences provided herein can also incorporate mutations to the amino acid sequence that are either derived from the parent gene sequence, are known to exist for the gene or protein encoded by the gene, or occur in the deoptimized gene de novo during the lifecycle of a virus having the deoptimized gene. In some embodiments the mutation can be a coding mutation, giving rise to a different amino acid residue in a given protein. In other embodiments, the mutation may occur in a gene having an unmodified, or parental sequence. For example, in one embodiment the mutation may occur in the codon encoding amino acid residue 136 of the N protein. In one embodiment the mutation in the codon encoding amino acid residue 136 of the N protein may cause an amino acid other than lysine to be encoded at position 136 of the N protein. In one embodiment the mutation in the codon encoding amino acid residue 136 of the N protein that causes an amino acid other than lysine to be encoded at position 136 of the N protein may occur in a virus having a codon deoptimized L protein, such as RSV Min L. In one embodiment the amino acid other than lysine encoded at position 136 of the N protein may be arginine. In one embodiment the mutation may occur in the codon encoding amino acid residue 114 of the P protein. In one embodiment the mutation in the codon encoding amino acid residue 114 of the P protein may cause an amino acid other than glutamic acid to be encoded at position 114 of the P protein. In one embodiment the mutation in the codon encoding amino acid residue 114 of the P protein that causes an amino acid other than glutamic acid to be encoded at position 114 of the P protein may occur in a virus having a codon deoptimized L protein, such as RSV Min L. In one embodiment the amino acid other than glutamic acid encoded at position 114 of the P protein may be valine. In one embodiment the mutation may occur in the codon encoding amino acid residue 88 of the M2-1 protein. In one embodiment the mutation in the codon encoding amino acid residue 88 of the M2-1 protein may cause an amino acid other than asparagine to be encoded at position 88 of the M2-1 protein. In one embodiment the mutation in the codon encoding amino acid residue 88 of the M2-1 protein that causes an amino acid other than asparagine to be encoded at position 88 of the M2-1 protein may occur in a virus having a codon deoptimized L protein, such as RSV Min L. In one embodiment the amino acid other than asparagine encoded at position 88 of the M2-1 protein may be lysine. In one embodiment the mutation may occur in the codon encoding amino acid residue 73 of the M2-1 protein. In one embodiment the mutation in the codon encoding amino acid residue 73 of the M2-1 protein may cause an amino acid other than alanine to be encoded at position 73 of the M2-1 protein. In one embodiment the mutation in the codon encoding amino acid residue 73 of the M2-1 protein that causes an amino acid other than alanine to be encoded at position 73 of the M2-1 protein may occur in a virus having a codon deoptimized L protein, such as RSV Min L. In one embodiment the amino acid other than alanine encoded at position 73 of the M2-1 protein may be serine.

Methods of Producing Recombinant RSV

The ability to produce infectious RSV from cDNA permits the introduction of specific engineered changes, including site specific attenuating mutations, gene deletion, gene start sequence deletion or modification, and a broad spectrum of other recombinant changes, into the genome of a recombinant virus to produce an attenuated virus and, in some embodiments, effective RSV vaccine strains. Such engineered changes may, or may not, be based on biological mutations identified in other virus strains.

Described herein are infectious RSVs produced by recombinant methods, e.g., from cDNA. In one embodiment, infectious RSV is produced by the intracellular coexpression of a cDNA that encodes the RSV genomic RNA, together with those viral proteins necessary to generate a transcribing, replicating nucleocapsid, such as one or more sequences that encode major nucleocapsid (N) protein, nucleocapsid phosphoprotein (P), large (L) polymerase protein, and a transcriptional elongation factor M2-1 protein. Plasmids encoding other RSV, such as nonstructural protein 1 (NS1), nonstructural protein 2 (NS2), matrix protein (M), small hydrophobic protein (SH), glycoprotein (G), fusion protein (F), and protein M2-2, may also be included with these essential proteins. Accordingly, also described herein are isolated polynucleotides that encode the described mutated viruses, make up the described genomes or antigenomes, express the described genomes or antigenomes, or encode various proteins useful for making recombinant RSV in vitro. These polynucleotides can be included within or expressed by vectors in order to produce a recombinant RSV. Accordingly, cells transfected with the isolated polynucleotides or vectors are also within the scope of the invention and are exemplified herein. In addition, a number of methods relating to the described RSVs are also disclosed. For example, methods of producing the recombinant RSVs described herein are disclosed; as are methods producing an immune response to a viral protein in an animal, mammal or human.

The invention permits incorporation of biologically derived mutations, along with a broad range of other desired changes, into recombinant RSV vaccine strains. For example, the capability of producing virus from cDNA allows for incorporation of mutations occurring in attenuated RSV vaccine candidates to be introduced, individually or in various selected combinations, into a full-length cDNA clone, and the phenotypes of rescued recombinant viruses containing the introduced mutations to be readily determined. In exemplary embodiments, amino acid changes identified in attenuated, biologically-derived viruses, for example in a cold-passaged RSV (cpRSV), or in a further attenuated strain derived therefrom, such as a temperature-sensitive derivative of cpRSV (cptsRSV), are incorporated within recombinant RSV clones. These changes from a wild-type or biologically derived mutant RSV sequence specify desired characteristics in the resultant clones, e.g., an attenuated or further attenuated phenotype compared to a wild-type or incompletely attenuated parental RSV phenotype. In this regard, disclosed herein are novel RSV mutations that can be combined, either individually or in combination with one another, with preexisting attenuated RSV strains to produce viruses having desired characteristics, such as increased attenuation or enhanced genetic (and thereby phenotypic) stability in vitro and in vivo.

In addition to single and multiple point mutations and site-specific mutations, changes to recombinant RSV disclosed herein include deletions, insertions, substitutions or rearrangements of whole genes or gene segments. These mutations can affect small numbers of bases (e.g., from 15-30 bases, up to 35-50 bases or more), or large blocks of nucleotides (e.g., 50-100, 100-300, 300-500, 500-1,000 bases) depending upon the nature of the change (i.e., a small number of bases may be changed to insert or ablate an immunogenic epitope or change a small gene segment or delete one or more codons for purposes of attenuation, whereas large block(s) of bases are involved when genes or large gene segments are added, substituted, deleted or rearranged. These alterations will be understood by those of skill in the art based on prior work done with either RSV or related viruses. Viruses having block mutations of this sort can also be combined with the novel RSV mutations described herein, either individually or in combination with one another, to produce viruses having desired characteristics, such as increased attenuation or enhanced genetic (and thereby phenotypic) stability in vitro and in vivo.

In additional aspects, the invention provides for supplementation of mutations adopted from biologically derived RSV, e.g., cp and is mutations, many of which occur in the L gene, with additional types of mutations involving the same or different genes or RNA signals in a recombinant RSV clone. RSV encodes ten mRNAs and eleven proteins. Three of these are transmembrane surface proteins, namely the attachment G protein, fusion F protein involved in penetration, and small hydrophobic SH protein. While specific functions may be assigned to single proteins, it is recognized that these assignments are provisional and descriptive. G and F are the major viral neutralization and protective antigens. Four additional proteins are associated with the viral nucleocapsid, namely the RNA binding protein N, the phosphoprotein P, the large polymerase protein L, and the transcription elongation factor M2-1. The matrix M protein is part of the inner virion and probably mediates association between the nucleocapsid and the envelope. Finally, there are two nonstructural proteins, NS1 and NS2, of unknown function. These proteins can be selectively altered in terms of its expression level, or can be added, deleted, substituted or rearranged, in whole or in part, alone or in combination with other desired modifications, in a recombinant RSV to obtain novel infectious RSV clones. In addition, the RNA genome contains cis-acting signals, including but not limited to the leader and trailer regions as well as the transcription gene-start (GS) and gene-end (GE) signals that border each gene. These signals help control encapsidation, transcription, and replication, and may have other roles as well. These signals can be selectively altered to obtain novel RSV clones.

The invention also provides methods for producing an infectious RSV from one or more isolated polynucleotides, e.g., one or more cDNAs. According to the present invention cDNA encoding a RSV genome or antigenome is constructed for intracellular or in vitro coexpression with the necessary viral proteins to form infectious RSV. By "RSV antigenome" is meant an isolated positive-sense polynucleotide molecule which serves as the template for the synthesis of progeny RSV genome. Preferably a cDNA is constructed which is a positive-sense version of the RSV genome, corresponding to the replicative intermediate RNA, or antigenome, so as to minimize the possibility of hybridizing with positive-sense transcripts of the complementing sequences that encode proteins necessary to generate a transcribing, replicating nucleocapsid, i.e., sequences that encode N, P, L and M2-1 protein.

A native RSV genome typically comprises a negative-sense polynucleotide molecule which, through complementary viral mRNAs, encodes eleven species of viral proteins, i.e., the nonstructural proteins NS1 and NS2, N, P, matrix (M), small hydrophobic (SH), glycoprotein (G), fusion (F), M2-1, M2-2, and L, substantially as described in Mink et al., Virology 185: 615-624 (1991), Stec et al., Virology 183:

273-287 (1991), and Connors et al., Virol. 208:478-484 (1995). For purposes of the present invention the genome or antigenome of the recombinant RSV of the invention need only contain those genes or portions thereof necessary to render the viral or subviral particles encoded thereby infectious. Further, the genes or portions thereof may be provided by more than one polynucleotide molecule, i.e., a gene may be provided by complementation or the like from a separate nucleotide molecule.

By recombinant RSV is meant a RSV or RSV-like viral or subviral particle derived directly or indirectly from a recombinant expression system or propagated from virus or subviral particles produced therefrom. The recombinant expression system will employ a recombinant expression vector which comprises an operably linked transcriptional unit comprising an assembly of at least a genetic element or elements having a regulatory role in RSV gene expression, for example, a promoter, a structural or coding sequence which is transcribed into RSV RNA, and appropriate transcription initiation and termination sequences.

To produce infectious RSV from cDNA-expressed genome or antigenome, the genome or antigenome is coexpressed with those RSV proteins necessary to (i) produce a nucleocapsid capable of RNA replication, and (ii) render progeny nucleocapsids competent for both RNA replication and transcription. Transcription by the genome nucleocapsid provides the other RSV proteins and initiates a productive infection. Additional RSV proteins needed for a productive infection can also be supplied by coexpression.

Alternative means to construct cDNA encoding the genome or antigenome include by reverse transcription-PCR using improved PCR conditions (e.g., as described in Cheng et al., Proc. Natl. Acad. Sci. USA 91:5695-5699 (1994); Samal et al., J. Virol 70:5075-5082 (1996)) to reduce the number of subunit cDNA components to as few as one or two pieces. In other embodiments, different promoters can be used (e.g., T3, SP6) or different ribozymes (e.g., that of hepatitis delta virus). Different DNA vectors (e.g., cosmids) can be used for propagation to better accommodate the large size genome or antigenome.

The N, P, L and M2-1 proteins are encoded by one or more expression vectors which can be the same or separate from that which encodes the genome or antigenome, and various combinations thereof. Additional proteins may be included as desired, encoded by its own vector or by a vector encoding a N, P, L, or M2-1 protein or the complete genome or antigenome. Expression of the genome or antigenome and proteins from transfected plasmids can be achieved, for example, by each cDNA being under the control of a promoter for T7 RNA polymerase, which in turn is supplied by infection, transfection or transduction with an expression system for the T7 RNA polymerase, e.g., a vaccinia virus MVA strain recombinant which expresses the T7 RNA polymerase (Wyatt et al., Virology, 210:202-205 (1995)). The viral proteins, and/or T7 RNA polymerase, can also be provided from transformed mammalian cells, or by transfection of preformed mRNA or protein.

To produce recombinant viruses having a codon deoptimized genome with the protein sequences described herein, one may use plasmids encoding an RSV genome having one or more gene sequences replaced with the corresponding codon deoptimized sequence provided herein. For example, the RSV genomes encoded by any one of SEQ ID NO: 2, SEQ ID NO: 3, SEQ ID NO: 4, and SEQ ID NO: 5 may be used in this manner. The constructs pRSV_Min A, pRSV_Min B, pRSV_Min L, pRSV_Min FLC, pRSV_Min L_N, pRSV_Min L_p, pRSV_Min L_M21, pRSV_Min L_NP, pRSV_Min L_NM21, pRSV_Min L_PM21, or pRSV_Min L_NPM21 provide examples in this regard.

Alternatively, synthesis of antigenome or genome can be done in vitro (cell-free) in a combined transcription-translation reaction, followed by transfection into cells. Or, antigenome or genome RNA can be synthesized in vitro and transfected into cells expressing RSV proteins.

Uses of RSV Codon Deoptimized RSV Genes and Viruses

To select candidate vaccine viruses from the host of recombinant RSV strains capable of being produced using the codon deoptimized polynucleotide sequences provided herein, the criteria of viability, efficient replication in vitro, attenuation in vivo, immunogenicity, and phenotypic stability are determined according to well-known methods. Viruses which will be most desired in vaccines of the invention must maintain viability, must replicate sufficiently in vitro well under permissive conditions to make vaccine manufacture possible, must have a stable attenuation phenotype, must exhibit replication in an immunized host (albeit at lower levels), and must effectively elicit production of an immune response in a vaccine sufficient to confer protection against serious disease caused by subsequent infection from wild-type virus. Clearly, the heretofore known and reported RSV mutants do not meet all of these criteria. Indeed, contrary to expectations based on the results reported for known attenuated RSV, viruses of the invention are not only viable and more attenuated then previous mutants, but are more stable genetically in vivo than those previously studied mutants.

To propagate a RSV virus for vaccine use and other purposes, a number of cell lines which allow for RSV growth may be used. RSV grows in a variety of human and animal cells. Preferred cell lines for propagating attenuated RSV for vaccine use include DBS-FRhL-2, MRC-5, and Vero cells. Highest virus yields are usually achieved with epithelial cell lines such as Vero cells. Cells are typically inoculated with virus at a multiplicity of infection ranging from about 0.001 to 1.0, or more, and are cultivated under conditions permissive for replication of the virus, e.g., at about 30-37° C. and for about 3-10 days, or as long as necessary for virus to reach an adequate titer. Temperature-sensitive viruses often are grown using 32° C. as the "permissive temperature." Virus is removed from cell culture and separated from cellular components, typically by well-known clarification procedures, e.g., centrifugation, and may be further purified as desired using procedures well known to those skilled in the art.

RSV which has been attenuated as described herein can be tested in various well known and generally accepted in vitro and in vivo models to confirm adequate attenuation, resistance to phenotypic reversion, and immunogenicity for vaccine use. In in vitro assays, the modified virus, which can be a multiply attenuated, biologically derived or recombinant RSV, is tested for temperature sensitivity of virus replication or "ts phenotype," and for the small plaque phenotype. Modified viruses are further tested in animal models of RSV infection. A variety of animal models (e.g., murine, cotton rat, and primate) have been described and are known to those skilled in the art.

In accordance with the foregoing description and based on the Examples below, the invention also provides isolated, infectious RSV compositions for vaccine use. The attenuated virus which is a component of a vaccine is in an isolated and typically purified form. By isolated is meant to refer to RSV which is in other than a native environment of a wild-type virus, such as the nasopharynx of an infected individual. More generally, isolated is meant to include the attenuated virus as a component of a cell culture or other artificial medium. For example, attenuated RSV of the invention may be produced by an infected cell culture, separated from the cell culture and added to a stabilizer which contains other non-naturally occurring RSVs.

RSV vaccines of the invention contain as an active ingredient an immunogenically effective amount of RSV produced as described herein. Biologically derived or recombinant RSV can be used directly in vaccine formulations. The biologically derived or recombinantly modified virus may be introduced into a host with a physiologically acceptable carrier and/or adjuvant. Useful carriers are well known in the art, and include, e.g., water, buffered water, 0.4% saline, 0.3% glycine, hyaluronic acid and the like. The resulting aqueous solutions may be packaged for use as is, or lyophilized, the lyophilized preparation being combined with a sterile solution prior to administration, as mentioned above. The compositions may contain pharmaceutically acceptable auxiliary substances as required to approximate physiological conditions, which include, but are not limited to, pH adjusting and buffering agents, tonicity adjusting agents, wetting agents and the like, for example, sodium acetate, sodium lactate, sodium chloride, potassium chloride, calcium chloride, sucrose, magnesium sulfate, phosphate buffers, HEPES (4-(2-hydroxyethyl)-1-piperazineethanesulfonic acid) buffer, sorbitan monolaurate, and triethanolamine oleate. Acceptable adjuvants include incomplete Freund's adjuvant, aluminum phosphate, aluminum hydroxide, or alum, which are materials well known in the art. Preferred adjuvants also include Stimulon™ QS-21 (Aquila Biopharmaceuticals, Inc., Worchester, Mass.), MPL™ (3-0-deacylated monophosphoryl lipid A; RIBI ImmunoChem Research, Inc., Hamilton, Mont.), and interleukin-12 (Genetics Institute, Cambridge, Mass.).

Upon immunization with a RSV vaccine composition as described herein, via injection, aerosol, droplet, oral, topical or other route, the immune system of the host responds to the vaccine by producing antibodies specific for RSV virus proteins, e.g., F and G glycoproteins. As a result of the vaccination the host becomes at least partially or completely immune to RSV infection, or resistant to developing moderate or severe RSV disease, particularly of the lower respiratory tract.

The host to which the vaccine is administered can be any mammal susceptible to infection by RSV or a closely related virus and capable of generating a protective immune response to antigens of the vaccinizing strain. Thus, suitable hosts include humans, non-human primates, bovine, equine, swine, ovine, caprine, lagamorph, rodents, such as mice or cotton rats, etc. Accordingly, the invention provides methods for creating vaccines for a variety of human and veterinary uses.

The vaccine compositions containing the attenuated RSV of the invention are administered to a subject susceptible to or otherwise at risk of RSV infection in an "immunogenically effective dose" which is sufficient to induce or enhance the individual's immune response capabilities against RSV. An RSV vaccine composition may be administered to a subject via injection, aerosol delivery, nasal spray, nasal droplets, oral inoculation, or topical application. In the case of human subjects, the attenuated virus of the invention is administered according to well established human RSV vaccine protocols (Karron et al JID 191:1093-104, 2005). Briefly, adults or children are inoculated intranasally via droplet with an immunogenically effective dose of RSV vaccine, typically in a volume of 0.5 ml of a physiologically acceptable diluent or carrier. This has the advantage of simplicity and safety compared to parenteral immunization with a non-replicating vaccine. It also provides direct stimulation of local respiratory tract immunity, which plays a major role in resistance to RSV. Further, this mode of vaccination effectively bypasses the immunosuppressive effects of RSV-specific maternally-derived serum antibodies, which typically are found in the very young. Also, while the parenteral administration of RSV antigens can sometimes be associated with immunopathologic complications, this has never been observed with a live virus.

In all subjects, the precise amount of RSV vaccine administered and the timing and repetition of administration will be determined by various factors, including the patient's state of health and weight, the mode of administration, the nature of the formulation, etc. Dosages will generally range from about $10^3$ to about $10^6$ plaque forming units ("PFU") or more of virus per patient, more commonly from about $10^4$ to $10^5$ PFU virus per patient. In one embodiment, about $10^5$ to $10^6$ PFU per patient could be administered during infancy, such as between 1 and 6 months of age, and one or more additional booster doses could be given 2-6 months or more later. In another embodiment, young infants could be given a dose of about $10^5$ to $10^6$ PFU per patient at approximately 2, 4, and 6 months of age, which is the recommended time of administration of a number of of other childhood vaccines. In yet another embodiment, an additional booster dose could be administered at approximately 10-15 months of age. In any event, the vaccine formulations should provide a quantity of attenuated RSV of the invention sufficient to effectively stimulate or induce an anti-RSV immune response (an "effective amount"). The resulting immune response can be characterized by a variety of methods. These include taking samples of nasal washes or sera for analysis of RSV-specific antibodies, which can be detected by tests including, but not limited to, complement fixation, plaque neutralization, enzyme-linked immunosorbent assay, luciferase-immunoprecipitation assay, and flow cytometry. In addition, immune responses can be detected by assay of cytokines in nasal washes or sera, ELISPOT of immune cells from either source, quantitative RT-PCR or microarray analysis of nasal wash or serum samples, and restimulation of immune cells from nasal washes or serum by re-exposure to viral antigen in vitro and analysis for the production or display of cytokines, surface markers, or other immune correlates measures by flow cytometry or for cytotoxic activity against indicator target cells displaying RSV antigens. In this regard, individuals are also monitored for signs and symptoms of upper respiratory illness. As with administration to chimpanzees, the attenuated virus of the vaccine grows in the nasopharynx of vaccines at levels approximately 10-fold or more lower than wild-type virus, or approximately 10-fold or more lower when compared to levels of incompletely attenuated RSV.

In some embodiments, neonates and infants are given multiple doses of RSV vaccine to elicit sufficient levels of immunity. Administration may begin within the first month of life, and at intervals throughout childhood, such as at two months, four months, six months, one year and two years, as necessary to maintain sufficient levels of protection against natural RSV infection. In other embodiments, adults who are particularly susceptible to repeated or serious RSV infection, such as, for example, health care workers, day care workers, family members of young children, the elderly, individuals with compromised cardiopulmonary function, are given multiple doses of RSV vaccine to establish and/or maintain protective immune responses. Levels of induced immunity can be monitored by measuring amounts of neutralizing secretory and serum antibodies, and dosages adjusted or vaccinations repeated as necessary to maintain desired levels of protection. Further, different vaccine viruses may be indicated for administration to different recipient groups. For example, an engineered RSV strain expressing a cytokine or an additional protein rich in T cell epitopes may be particularly advantageous for adults rather than for infants. Vaccines produced in accordance with the present invention can be combined with viruses of the other subgroup or strains of RSV to achieve protection against multiple RSV subgroups or strains, or selected gene segments encoding, e.g., protective epitopes of these strains can be engineered into one RSV clone as described herein. In such embodiments, the different viruses can be in admixture and administered simultaneously or present in separate preparations and administered separately. For example, as the F glycoproteins of the two RSV subgroups differ by only about 11% in amino acid sequence, this similarity is the basis for a cross-protective immune response as observed in animals immunized with RSV or F antigen and challenged with a heterologous strain. Thus, immunization with one strain may protect against different strains of the same or different subgroup.

The vaccines of the invention elicit production of an immune response that may be protective against, or reduce the magnitude of serious lower respiratory tract disease, such as pneumonia and bronchiolitis when the individual is subsequently infected with wild-type RSV. While the naturally circulating virus is still capable of causing infection, particularly in the upper respiratory tract, there is a very greatly reduced possibility of rhinitis as a result of the vaccination and possible boosting of resistance by subsequent infection by wild-type virus. Following vaccination, there may be detectable levels of host engendered serum and, in some instances, secretory antibodies which are capable of neutralizing homologous (of the same subgroup) wild-type virus in vitro and in vivo. In many instances the host antibodies will also neutralize wild-type virus of a different, non-vaccine subgroup.

The level of attenuation of vaccine virus may be determined by, for example, quantifying the amount of virus present in the respiratory tract of an immunized host and comparing the amount to that produced by wild-type RSV or other attenuated RSVs which have been evaluated as candidate vaccine strains. For example, the attenuated virus of the invention will have a greater degree of restriction of replication in the upper respiratory tract of a highly susceptible host, such as a chimpanzee, compared to the levels of replication of wild-type virus, e.g., 10- to 1000-fold less. In order to further reduce the development of rhinorrhea, which is associated with the replication of virus in the upper respiratory tract, an ideal vaccine candidate virus should exhibit a restricted level of replication in both the upper and lower respiratory tract. However, the attenuated viruses of the invention must be sufficiently infectious and immunogenic in humans to confer protection in vaccinated individuals. Methods for determining levels of RSV in the nasopharynx of an infected host are well known in the literature. Specimens are obtained by aspiration or washing out of nasopharyngeal secretions and virus quantified in tissue culture or other by laboratory procedure. See, for example, Belshe et al., J. Med. Virology 1:157-162 (1977), Friedewald et al., J. Amer. Med. Assoc. 204:690-694 (1968); Gharpure et al., J. Virol. 3:414-421 (1969); and Wright et al., Arch. Ges. Virusforsch. 41:238-247 (1973). The virus can conveniently be measured in the nasopharynx of host animals, such as chimpanzees.

The following examples are provided by way of illustration, not limitation.

Example 1: Design and Production of CPD RSVs

The sequences of all RSV open reading frames, except those encoding the M2-1 and M2-2 proteins, were codon pair deoptimized using previously described computational algorithms (Coleman et al., Science 320: 1784-1787 (2008); Coleman et al., J Infect Dis 203:1264-1273 (2011)). Briefly. recombinant virus was recoded to use codon pairs that are underrepresented relative to the human genome. Constructs with underrepresented codon pairs were synthesized. sequenced and used to produce recombinant viruses. To preserve putative cis-acting signals and secondary structures present at the 5' end of mRNAs, the original wt RSV nucleotide sequence was maintained for the first ten codons of each open reading frame. Runs of more than six identical nucleotides and RSV gene-end like or gene start like sequences were removed from the computer-generated CPD sequences by manual editing. The G/C content and the percentage of A, G, T, and C nucleotides, and of AT and GC dinucleotides, was similar between WT and CPD sequences. Percent nucleotide identity and number of nucleotide differences between WT and CPD RSV open reading frames are indicated in table 1. All nucleotide changes were silent on the amino acid level.

TABLE 1

Percent nucleotide identity and number of mutations between WT and CPD RSV open reading frames (ORF).

| ORF | % identity | Number of mutations |
|---|---|---|
| NS1 | 87.8 | 65 |
| NS2 | 88.1 | 60 |
| N | 80.0 | 241 |
| P | 84.4 | 143 |
| M | 83.0 | 163 |
| SH | 92.3 | 23 |
| G | 78.7 | 197 |
| F | 77.8 | 422 |
| L | 79.1 | 1378 |

Recombinant (r)RSVs were constructed using a reverse genetic system based on strain A2 (Collins et al., Proc Natl Acad Sci USA 92:11563-11567 (1995)). Recombinant viruses were constructed using the antigenome cDNA D46/6120, a derivative of the rA2 cDNA plasmid with a deletion of a 112-nt fragment of the downstream non-coding region of the SH gene. This cDNA exhibits improved stability during growth in *E. coli*. The changes in the SH noncoding region do not affect the efficiency of virus replication in vitro or in mice. Although the D46/6120 cDNA contains this deletion, for simplicity the numbering of sequence positions herein is based on the complete sequence of biologically derived strain A2 (Genbank accession number M74568) (SEQ ID NO: 1).

Four full-length cDNAs were generated, based on the D46/6120 backbone. These four cDNAs were named pRSV_Min A (SEQ ID NO: 2), pRSV_Min B (SEQ ID NO: 3), pRSV_Min L (SEQ ID NO: 4) and pRSV_Min FLC (SEQ ID NO: 5) (FIG. 1A). pRSV_Min A contains the CPD ORFs of NS1, NS2, N, P, M and SH. To construct pRSV_Min A, a 4508 base pair (bp) NotI-XhoI fragment of synthetic RSV cDNA with these six CPD ORFs was transferred into the similarly cleaved D46/6120 cDNA.

pRSV_Min B contains the CPD G and F coding sequences that were transferred by cloning a 3907 bp XhoI-BamHI cDNA fragment with synthetic CPD ORFs into the similarly cleaved D46/6120 cDNA. pRSV_Min L contains a 6750 bp BamHI-KasI fragment with the CPD coding sequence of the L ORF that was transferred into the similarly cleaved D46/6120 cDNA. pRSV_Min FLC (FLC for full length clone) contained the entire RSV coding genes CPD. This full-length plasmid was generated by successively transferring all three synthetized CPD fragments (NotI-XhoI, XhoI-BamHI and BamHI-KasI) into the D46/6120 cDNA. After the generation of endo-free DNA preparations (Qiagen, Valencia, Calif.), the sequence of wt and of all four CPD plasmids were confirmed by sequence analysis of the RSV antigenome sequences contained in the cDNA plasmids.

To generate recombinant viruses from a wt RSV genome or the CPD RSV cDNA genomes (pRSV_Min A, pRSV_Min B, pRSV_Min L and pRSV_Min FLC) BSR T7/5 cells (a variant of baby hamster kidney 21 (BHK-21) cells constitutively expressing T7 RNA polymerase) were grown to 95% confluency in 6 well plates. Before transfection, cells were washed twice with GMEM containing 3% FBS, 1 mM l-glutamine, and 2% MEM amino acids prior to the addition of 2 ml of media per well. Cells were transfected using Lipofectamine 2000 and a plasmid mixture containing 5 μg of full-length plasmid (FIG. 1A), 2 μg each of pTM1-N (encoding the wt RSV N protein) and pTM1-P (encoding the wt RSV N protein), and 1 μg each of pTM1-M2-1 (encoding the wt RSV N protein) and pTM1-L (encoding the wt RSV N protein). After overnight incubation at 37° C., transfected cells were harvested by scraping into media, added to subconfluent monolayers of Vero cells, and incubated at 32° C. The rescued viruses rRSV, rRSV_Min A (Min A), rRSV_Min B (Min B), rRSV_Min L (Min L) and rRSV_Min FLC (Min FLC) were harvested between 11 and 14 days post-transfection.

Following rescue, virus stocks were generated by scraping infected cells into media, followed by vortexing for 30 sec, clarification of the supernatant by centrifugation, and addition of 10×SPG (2.18 M sucrose, 0.038 M KH2PO4, 0.072 M K2HPO4, 0.06 M l-glutamine at pH 7.1) to a final concentration of 1×. Virus aliquots were snap frozen and stored at −80° C. Virus titers were determined by plaque assay on Vero cells under 0.8% methylcellulose overlay. After a 10 to 12-day incubation at 32° C., plates were fixed with 80% cold methanol, and plaques were visualized by immunostaining with a cocktail of three RSV specific monoclonal antibodies. Titers were expressed as plaque forming unit (pfu) per ml. Viral RNA was isolated from all virus stocks, and sequence analysis of the viral genomes was performed using overlapping PCR fragments, confirming that the genomic sequences of the recombinant viruses were correct. The only sequences that were not directly confirmed for each genome were the positions of the outer-most primers, namely nt 1-29 and 1562-15089.

Example 2: Kinetics of CPD rRSV Replication In Vitro

To assess the characteristics of the CPD RSVs multi-cycle and single cycle replication experiments were performed in Vero cells. In multi-cycle replication experiments, confluent monolayer cultures of Vero cells in 6-well plates were infected in triplicate at a multiplicity of infection (MOI) of 0.01 and incubated at 32 or 37° C. Viruses were harvested daily from day 1 to 14 (with the exception of Min B, the low stock titer of which only allowed to have time points from day 1 to 12 at 32° C.) by scraping infected cells into media followed by vortexing for 30 sec, clarification of the supernatant by centrifugation. Virus aliquots were snap frozen and stored at −80° C. until titration as described above. After all inoculations, the MOIs were confirmed by back-titration of the inoculum on Vero cells at 32° C.

At 32° C., the growth of all CPD viruses was delayed compared to rRSV; rRSV reached its maximum titer of $10^7$ pfu/ml on day 7, whereas Min A, Min L and Min FLC reached maximum titer on day 14. The maximum titer of Min L was only three fold lower than that of rRSV. Min A and Min FLC were slightly more restricted in growth, as their maximum titers were around 15 and 30-fold lower than rRSV, respectively. Surprisingly, Min B was the most restricted for replication, as its maximum titer on day 12 was around 100 fold lower than that of rRSV. At 37° C., rRSV replicated faster than at 32° C., but it reached similar peak titers (about $10^7$ pfu/ml on day 4). At 37° C., the CPD viruses also reached their maximum titers earlier [at day 4 (Min A, Min FLC) or day 8 (Min L)]. Min A reached about the same maximum titers at 32° C. and at 37° C. (about $10^5$ pfu/ml). Surprisingly, despite the same amino acid sequence of all viruses, growth restriction at 37° C. was even greater than at 32° C. for Min L and Min FLC, which exhibited an about 100,000 and 1,000,000 fold restriction in growth compared to rRSV, respectively.

A plaque results from several cycles of virus replication, such that any differences in replication rates may be correlated to plaque size. Compared to rRSV, which induced large plaques on Vero cells at 32° C., Min A and Min L induced small plaques, and Min B and Min FLC induced microplaques (FIG. 1C).

Example 3: Large-Extent Codon Pair Deoptimization Affects the Specific Infectivity of RSV Experiments were conducted to assess the infectivity of the CPD viruses compared to rRSV using a strand-specific qRT-PCR designed to quantify viral genomic RNA (FIG. 1D). Viral RNA from virus stocks grown at 32° C. was purified using cell-free virus stocks with known titers. Genomic RNA corresponding to $2.7\times10^4$ pfu of rRSV, Min A, Min L, and Min FLC virus stocks was quantified in Taqman® assays. In a typical experiment, Min A and Min L exhibited the same abundance of genomic RNA copies per $2.7\times10^4$ plaque forming units as rRSV. However, the same amount of $2.7\times10^4$ plaque forming units of the Min FLC virus stock contained 17.5 fold more genomic RNA than rRSV, Min A or Min L. This suggests that full length codon pair deoptimization of RSV greatly reduces its specific infectivity.

Example 4: Temperature Sensitivity of CPD RSV

Studies were conducted to determine the shut off temperature (TsH) of the CPD viruses on Vero and Hep2 cells (Table 2). The $T_{SH}$ is defined as the lowest restrictive temperature at which there is a reduction in virus titer compared to the permissive temperature 32° C. that is 100-fold or greater.

As expected, rRSV was not sensitive to temperature on both Vero and Hep2 cells. Confirming the results obtained from the multi-cycle replication experiment, replication of Min A was also not sensitive to temperature, as its $T_{SH}$ was 40° C. on both Vero and Hep2 cells. Min B had a $T_{SH}$ of 38° C. and 39° C. on Vero and Hep2 cells, respectively. Min L was more sensitive to temperature, with a $T_{SH}$ of 37° C. and 38° C. on Vero and Hep2 cells, respectively. Finally, Min FLC was the most temperature sensitive virus, with a $T_{SH}$ of 35° C. and 36° C. on Vero and Hep2 cells, respectively.

TABLE 2

Temperature sensitivity of the codon-pair deoptimized RSVs on Hep2 and Vero cells. Virus titer (in $\log_{10}$ PFU per ml) at indicated temperature (° C.) [a]

| Virus | Cell line | 32 | 35 | 36 | 37 | 38 | 39 | 40 | $T_{SH}$ [b] |
|---|---|---|---|---|---|---|---|---|---|
| Min A | Vero | 7.2 | 6.6 | 6.2 | 6.1 | 5.7 | 5.4 | 4.4 | **40** |
| Min B | | 4.2 | 3.1 | 3.2 | 2.8 | 2.0 | 1.7 | <1 | **38** |
| Min L | | 7.5 | 7.1 | 6.5 | 5.2 | 4.2 | <1 | <1 | **37** |
| Min FLC | | 6.7 | 4.5 | 3.4 | <1 | <1 | <1 | <1 | **35** |
| WT | | 8.4 | 8.3 | 8.3 | 8.0 | 8.1 | 8.1 | 8.1 | >40 |
| Min A | HEp-2 | 7.1 | 6.7 | 6.6 | 6.4 | 6.3 | 5.6 | 4.8 | **40** |
| Min B | | 4.0 | 4.0 | 4.0 | 4.0 | 3.7 | 2.0 | <1 | **39** |
| Min L | | 7.6 | 7.1 | 6.7 | 6.1 | 4.5 | 3.2 | 2.3 | **38** |
| Min FLC | | 6.5 | 5.0 | 4.0 | 2.0 | <1 | <1 | < | **36** |
| WT | | 8.3 | 8.1 | 8.3 | 8.3 | 8.1 | 8.3 | 8.1 | >40 |

[a] The ts phenotype for each virus was evaluated by plaque assay on Vero and HEp-2 cells at the indicated temperatures. For viruses with a ts phenotype, the shut-off temperatures are marked (underlined). See footnote b for definition of shut-off temperature.

[b] Shut off temperature ($T_{SH}$) is defined as the lowest restrictive temperature at which the reduction compared to 32° C. is 100-fold or greater than that observed for wt RSV at the two temperatures. The ts phenotype is defined as having a $T_{SH}$ of 40° C. or less (bold).

Example 5: Reduced Transcription of CPD rRSVs In Vitro

To investigate at which step(s) the growth restriction of the CPD viruses occurred, experiments were conducted to assess the viral mRNA/antigenome and genome synthesis, protein, and virus particle production in Vero cells in a single step replication experiment from 4 to 24 hours post-infection (hpi) at 32 and 37° C. Total RNA was used to quantify positive sense (antigenomic and mRNA) and negative sense (genomic) RSV RNA by strand specific Taqman® assays. Protein lysates were used to analyze viral protein synthesis by Western blot.

Figure 2:
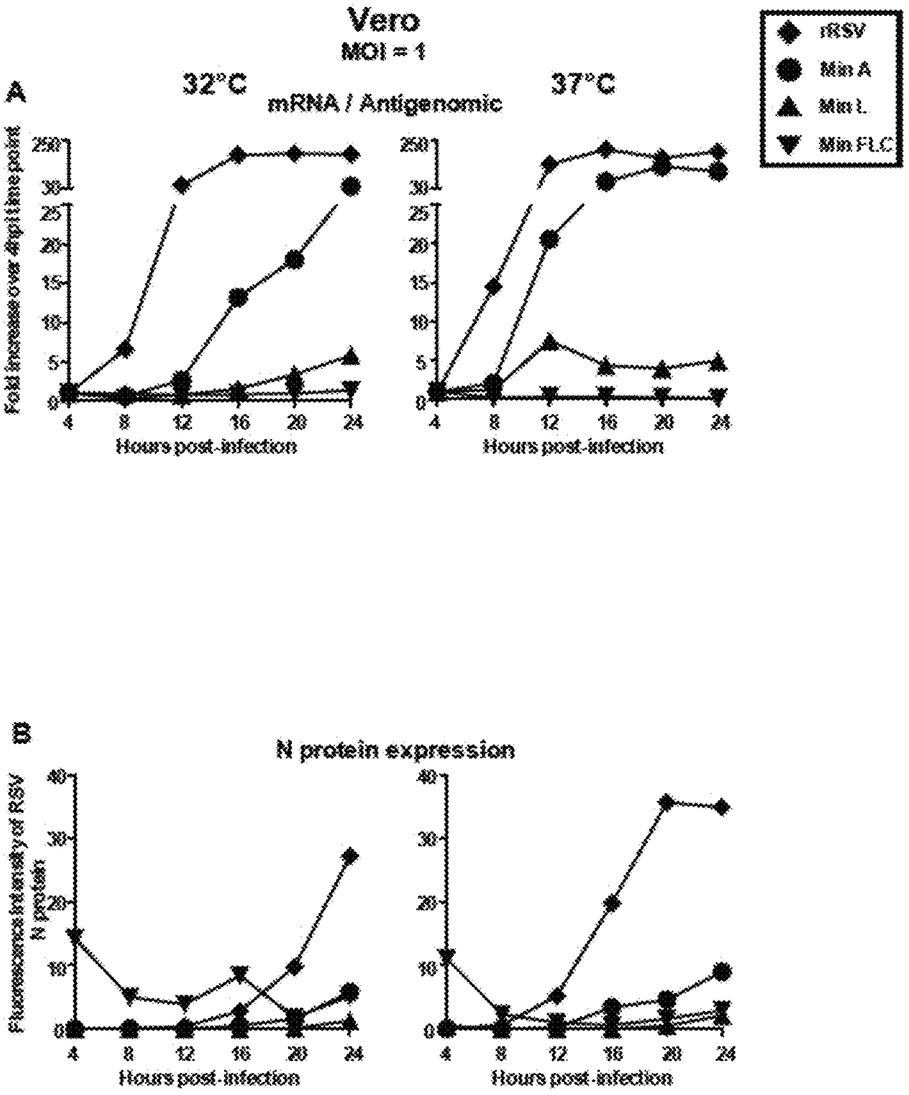
FIG. 2: Single cycle replication of CPD rRSVs compared to rRSV in Vero cells. Duplicate wells of confluent monolayer cultures of Vero cells in 6-well plates were mock-infected or infected at an MOI of 1 with rRSV, Min A, Min L and Min FLC and incubated at 32 or 37° C. Cultures were washed once after 2 h adsorption. Every four hours (from 4 to 24 h pi), viruses from one well were harvested and snap frozen for virus titration. Cells from a replica well were harvested for analysis of RNA and protein synthesis. Cell-associated RNA was used to specifically target and quantify (A) the virus antigenomic/mRNAs or (D) the RSV genomic RNA by a strand specific qPCR (Bessaud, M., et al., 2008. J Virol Methods 153:182-189). qPCR results were analyzed using the comparative threshold cycle (ΔCt) method, normalized to 18S rRNA and then for each virus expressed as fold increase over the 4 hour time point. (B, C) Ten micrograms of cell lysates were separated on NuPAGE 4-12% Bis-Tris SDS-PAGE gels and proteins were transferred to PVDF-F membranes. The membranes were blocked with Odyssey® blocking buffer and incubated with rabbit RSV-specific pAb and mouse α-tubulin used as a loading control. After washing, membranes were incubated with secondary antibodies goat anti-rabbit IgG IRDye 800 and goat anti-mouse IgG IRDye 680. Membrane strips were scanned on the Odyssey® Infrared Imaging System, background was corrected and fluorescence intensity of the N protein was evaluated using Odyssey® software, version 3.0 (Li-Cor). The 20 hour time point is shown in (D). (E) Virus titers from 4 to 24 hpi are expressed in $\log_{10}$ pfu/ml. Virus aliquots were titrated in duplicate at the permissive temperature of 32° C. For each time point, the mean value of the duplicate is shown.
Figure 2:
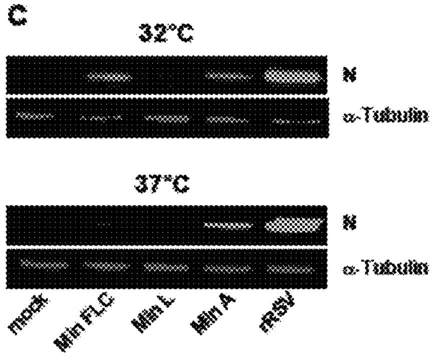
Figure 2:
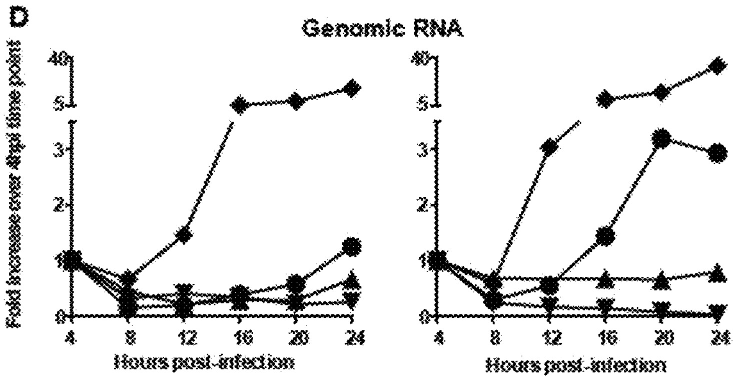
Figure 2:
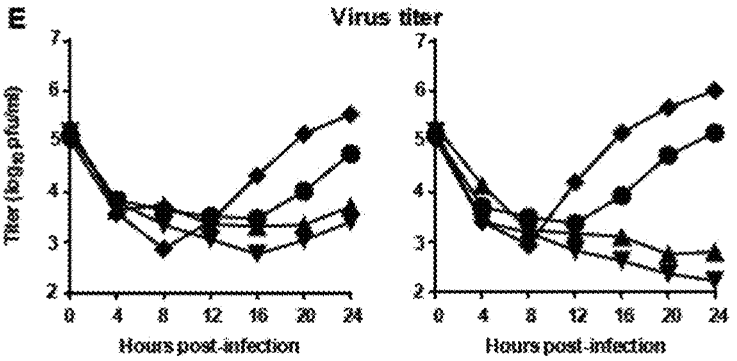

As shown in FIG. 2, rRSV exhibited strong transcription of viral genes as early as 8 hpi, and transcription was more efficient at 37° C. than at 32° C. (14 and 6 fold increase from 4 to 8 hpi at 37° C. and 32° C., respectively; FIG. 2A). Maximum gene transcription was reached at 16 hpi (188 and 196 fold increase of positive sense RNA at 32° C. or 37° C., respectively). Compared to rRSV, all CPD viruses exhibited reduced transcription. Min A gene transcription was delayed, and reduced compared to rRSV, at both 32° C. and 37° C. The first Min A transcripts were detected only at 12 hpi (3 and 21 fold increase of positive sense RNA from 4 to 12 hours at 32° C. and 37° C., respectively). Maximum Min A transcription was lower than that of rRSV at both 32° C. and 37° C. (a 41 fold increase of mRNA/antigenomic RNA from 4 to 24 hpi at 32° C., and a 129 fold increase at 20 hpi at 37° C.). Min L gene transcription was also reduced, as the first virus transcripts were detected only at 16 hpi at 32° C. at very modest levels (a 1.5 fold increase from 4 hpi to 16 hpi; maximum transcription at 24 hpi with only a 6 fold increase compared to 4 hpi). Transcription was not more efficient at 37° C., as an increase in positive-sense RNA was detectable starting at 16 hpi (a 4 fold increase compared to the 4 hour time point), with maximum transcription at 24 hpi (5 fold increase). Min FLC gene transcription was the least efficient, as a small increase of positive sense RNA was detected only 24 hpi at 32° C. (1.3 fold increase compared to 4 hpi), and was completely inefficient at 37° C., with no increase over time.

Reduced virus gene transcription in cells infected with the CDP viruses resulted in reduced protein synthesis. In rRSV infected cells, an increase in RSV N protein was detectable earlier (at 12 hpi and 16 hpi at 37° C. and 32° C., respectively) than in Min L and Min FLC infected cells; rRSV yielded higher levels of N protein expression than either of the three Min viruses at both 32 and 37° C. (FIGS. 2B and C).

The production of genomic RNA paralleled the production of virus particles, and as expected was delayed compared to virus gene transcription. rRSV genomic RNA and virus particles were detected as early as 12 hpi and increased until 24 hours pi. All CPD viruses exhibited delayed and reduced synthesis of genomic RNA and virus particle production. Indeed, at 32° C., an increase of Min A genomic RNA and the first virus particles were detected at 20 hpi. At 37° C., Min A genomic RNA was detected at 12 hpi and the first virus particles were present at 16 hpi. Min L genomic RNA and particle release were also strongly delayed compared to rRSV. At 32 and 37° C., the first genomic RNAs as well as the first virus particles were detected at 24 hpi. Finally, at 32° C. Min FLC genomic RNA and virus particles were detected at 24 hpi, whereas no genomic RNA synthesis and virus particle release were detected at 37° C.

Example 6: Replication of CPD rRSVs are Reduced in Balb/c Mice

Figure 3:
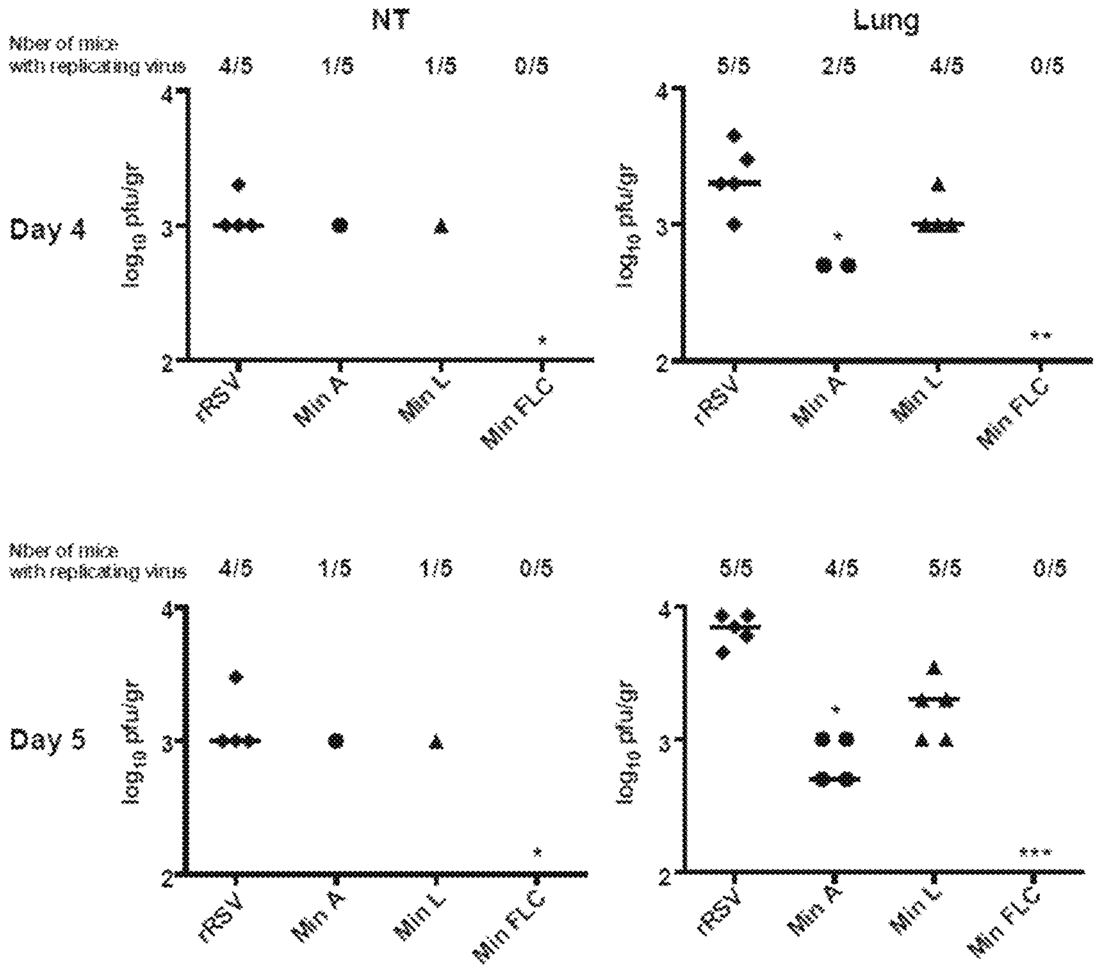
FIG. 3: Reduced replication of the CPD rRSVs in Balb/c mice. Six-week old Balb/c mice were inoculated intranasally in groups of ten with $4.5\times10^5$ pfu of rRSV, Min A, Min L or Min FLC. At day 4 and 5, five mice per group were sacrificed. Nasal turbinates (NT) and lung tissue were harvested and homogenized separately. Virus titers were determined in duplicate by plaque assay on Vero cells incubated at 32° C. and expressed as $\log_{10}$ pfu/gr. The median value is shown. Data sets were assessed for significance using non-parametric Kruskal-Wallis with Dunns post hoc test. Data were only considered significant at $p<0.05$ (*=$p<0.05$, =$p<0.01$ and *=$p<0.001$ compared to rRSV).

Replication of the CPD rRSVs compared to rRSV was evaluated in mice (FIG. 3). As expected, rRSV was detected in the nasal turbinates (NT) in 8 out of 10 mice on days 4 and 5 (median replication of $10^3$ pfu/g). Min A and Min L were only detected in the NT of a total of two out of 10 mice (one positive mouse on each day), whereas Min FLC was not detected in the NT of any mouse on any day ($p<0.05$ compared to rRSV). In the lungs, rRSV titer reached $10^3$ and $10^4$ pfu/g on days 4 and 5, respectively. Min A replication was significantly reduced compared to rRSV and was detected in only two mice on day 4. On day 5, 4 out of 5 mice exhibited virus replication. However, the titer was about 10-fold lower than that of rRSV ($p<0.05$). Min L replication was only slightly reduced as its titer was only two-fold lower than rRSV on day 4, and five-fold lower on day 5 ($p>0.05$). Finally, no Min FLC was detected in any mouse on day 4 or 5 ($p<0.01$ and $p<0.001$ at day 4 and 5, respectively), showing that this virus is strongly attenuated in mice. Taken together, these results show that Min A and Min FLC are attenuated in mice.

Example 7: Replication of CPD rRSVs are Reduced in African Green Monkeys

Figure 4:
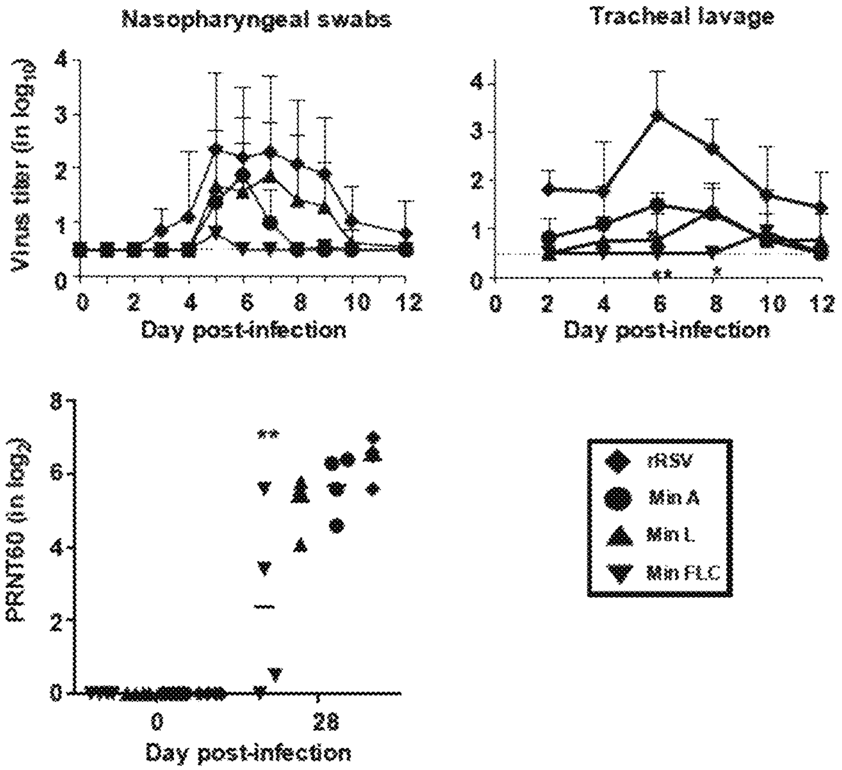
FIG. 4: Reduced replication of the CPD rRSVs in African Green Monkeys (AGM). AGM in groups of four were inoculated intranasally and intratracheally with $1\times10^6$ pfu of Min A, Min L, Min FLC or rRSV per AGM. Nasopharyngeal (NP) swabs were collected every day from 0 to 12 days post inoculation and tracheal lavage (TL) samples were collected every other day from day 0 to 12. Virus titers in NP and TL were determined in duplicate on Vero cells incubated at 32° C. as described above. Sera were collected at day 0 and 28 and the 60% plaque reduction neutralizing-antibody titers ($PRNT_{60}$) were determined in a plaque reduction neutralization assay on Vero cells using GFP-expressing rRSV. Data sets were assessed for significance using non-parametric Kruskal-Wallis with Dunns post hoc test. Data were only considered significant at $p<0.05$ (*=$p<0.05$, **=$p<0.01$ compared to rRSV).

Studies were conducted to evaluate the replication of the CPD rRSVs in non-human primates (Table 3, 4 and FIG. 4). African green monkeys (AGM) in groups of four were inoculated intranasally and intratracheally with $1\times10^6$ pfu of Min A, Min L, Min FLC or rRSV per AGM. Virus titers were evaluated from NP swabs and TL samples from 0 to 12 days.

While Min FLC did not replicate in the upper respiratory tract, virus shedding of Min A and Min L inoculated animals was slightly delayed and of shorter duration compared to rRSV inoculated animals. Peak titers of Min A and Min L were slightly lower than those of rRSV. In the lower respiratory tract, all CPD rRSV replicated poorly compared to rRSV (100 fold lower than rRSV; $p<0.05$). Despite strong restriction of replication of CPD rRSVs, Min A and Min L induced an efficient neutralizing antibody response (no significant difference between rRSV, Min A and Min L). However, as a consequence of inefficient replication, Min FLC was the only virus inducing a poor antibody response ($p<0.05$ compared to wt rRSV).

TABLE 3

Viral titers of nasal wash samples from nonhuman primates inoculated with Min A, Min L, Min FLC or WT [a].

| Virus | Animal ID | NW virus titer ($log_{10}$ PFU/mL) on indicated days[b] 1 | 2 | 3 | 4 | 5 | 6 | 7 | 8 | 9 | 10 | 12 | Duration of Shedding[c] | Peak virus titer | Sum of daily titers [d] |
|---|---|---|---|---|---|---|---|---|---|---|---|---|---|---|---|
| Min A | 7197 | — | — | — | — | — | 1.2 | 1.7 | — | — | — | — | 2 | 1.7 | 2.9 |
| | 7289 | — | — | — | — | 2.0 | 1.7 | — | — | — | — | — | 2 | 2.0 | 3.7 |
| | 7502 | — | — | — | — | — | 2.6 | 1.3 | — | — | — | — | 2 | 2.6 | 3.9 |
| | 7737 | — | — | — | 1.7 | 2.5 | 2.0 | — | — | — | — | — | 3 | 2.5 | 6.2 |
| | Mean: | | | | | | | | | | | | 2.3 | 2.2 | 4.2 |
| Min L | 7739 | — | — | — | — | 1.2 | — | 2.6 | 1.4 | 1.0 | — | 0.7 | 7 | 2.6 | 7.9 |
| | 7280 | — | — | — | — | 2.2 | 2.0 | 1.5 | 0.7 | — | — | — | 4 | 2.2 | 6.4 |
| | 7821 | — | — | — | — | — | — | 0.7 | — | 1.3 | 1.0 | — | 4 | 1.3 | 3.5 |
| | 7740 | — | — | — | — | 2.8 | 3.3 | 2.7 | 3.1 | 2.4 | — | — | 5 | 3.3 | 14.3 |
| | Mean: | | | | | | | | | | | | 5.0 | 2.4 | 8.0 |
| Min FLC | 7444 | — | — | — | — | — | — | — | — | — | — | — | 0 | <0.5 | — |
| | 7431 | — | — | — | — | 1.7 | — | — | — | 0.7 | — | — | 5 | 1.7 | 3.9 |
| | 7798 | — | — | — | — | — | — | — | — | — | — | — | 0 | <0.5 | — |
| | 7632 | — | — | — | — | — | — | — | — | — | — | — | 0 | <0.5 | — |
| | Mean: | | | | | | | | | | | | 1.3 | 0.4 | 1.0 |
| WT | 7489 | — | — | 1.2 | 2.9 | 3.3 | 3.5 | 2.0 | 3.3 | 3.0 | 1.8 | — | 8 | 3.5 | 21.0 |
| | 7538 | — | — | 1.2 | — | 2.0 | 2.8 | 3.0 | 2.5 | 2.2 | — | — | 7 | 3.0 | 14.2 |
| | 7370 | — | — | — | — | — | 2.0 | — | — | 1.9 | 1.3 | 1.7 | 6 | 2.0 | 7.9 |
| | 7667 | — | — | — | — | 3.6 | — | 3.7 | 2.0 | — | — | — | 4 | 3.7 | 9.8 |
| | Mean: | | | | | | | | | | | | 6.3 | 3.1 | 13.2 |

[a] Nonhuman primates were inoculated by the combined intranasal and intratracheal routes with $10^6$ PFU of the indicated virus in a 1 ml inoculum per site (total dose = $2 \times 10^6$ PFU per animal).

[b] Nasal wash was performed with 2 ml of Leibovitz L-15 medium with 1x SP used as stabilizator. Virus titrations were performed on Vero cells at 32° C. The lower limit of detection was 0.7 $log_{10}$ PFU/ml of nasal wash solution. Samples with no detectable virus are represented as "—". Peak titers for each animal are underlined.

[c] The period of days from the first to the last day on which virus was detected, including negative days (if any) in between.

[d] The sum of daily titers is used as an estimate for the magnitude of shedding (area under the curve). A value of 0.5 was used for samples with no detectable virus.

TABLE 4

Viral titers of bronchoalveolar and tracheal lavage samples from nonhuman primates inoculated with Min A, Min L, Min FLC or WT [a].

| Virus | Animal ID | Tracheal Lavage virus titer ($log_{10}$ PUF/ml) on indicated days[b] 2 | 4 | 6 | 8 | 10 | 12 | Duration of Shedding[c] | Peak virus titer | Sum of daily titers [d] |
|---|---|---|---|---|---|---|---|---|---|---|
| Min A | 7197 | 1.3 | — | 1.3 | 1.3 | — | — | 7 | 1.3 | 4.9 |
| | 7289 | 1.0 | 1.3 | 1.6 | — | 1.6 | — | 9 | 1.6 | 6.5 |
| | 7502 | — | 2.1 | 1.8 | 1.5 | — | — | 6 | 2.1 | 5.4 |
| | 7737 | — | — | 1.3 | 2.0 | — | — | 3 | 2.0 | 3.3 |
| | Mean: | | | | | | | 6.3 | 1.8 | 5.0 |
| Min L | 7739 | — | 1.5 | — | 2.0 | — | 1.6 | 9 | 2.0 | 7.1 |
| | 7280 | — | — | — | 1.0 | — | — | 1 | 1.0 | 1.0 |
| | 7821 | — | — | — | 1.0 | — | — | 1 | 1.0 | 1.0 |
| | 7740 | — | — | 1.6 | 1.5 | 1.6 | — | 5 | 1.6 | 4.7 |
| | Mean: | | | | | | | 4.0 | 1.4 | 3.5 |
| Min FLC | 7444 | — | — | — | — | — | — | 0 | <1.0 | — |
| | 7431 | — | — | — | — | — | — | 0 | <1.0 | — |
| | 7798 | — | — | — | — | 2.3 | — | 1 | 2.3 | 2.3 |
| | 7632 | — | — | — | — | — | — | 0 | <1.0 | — |
| | Mean: | | | | | | | 0.3 | 1.3 | 0.6 |

TABLE 4-continued

Viral titers of bronchoalveolar and tracheal lavage samples from nonhuman primates inoculated with Min A, Min L, Min FLC or WT [a].

| Virus | Animal ID | Tracheal Lavage virus titer ($log_{10}$ PUF/ml) on indicated days[b] 2 | 4 | 6 | 8 | 10 | 12 | Duration of Shedding[c] | Peak virus titer | Sum of daily titers [d] |
|---|---|---|---|---|---|---|---|---|---|---|
| WT | 7489 | 2.3 | — | 2.6 | 3.3 | 2.6 | 1.5 | 11 | 3.3 | 13.3 |
| | 7538 | 1.5 | 1.5 | 2.5 | 2.7 | 2.4 | 2.3 | 11 | 2.7 | 12.9 |
| | 7370 | 2.0 | 2.2 | 4.2 | 1.9 | 1.3 | 1.5 | 11 | 4.2 | 13.1 |
| | 7667 | 1.5 | 2.9 | 4.1 | 2.9 | — | — | 7 | 4.1 | 11.4 |
| | Mean: | | | | | | | 10.0 | 3.6 | 12.7 |

[a] Nonhuman primates were inoculated by the combined intranasal and intratracheal routes with $10^6$ PFU of the indicated virus in a 1 ml inoculum per site (total dose = $2 \times 10^6$ PFU per animal).

[b] On days 2, 4, 6, and 8, bronchoalveolar lavage was performed with 3 ml of PBS and mixed 1:1 with L15 medium with 2x SP. Virus titrations were performed on Vero cells at 32° C. The lower limit of detection was 1.0 $log_{10}$ PFU/mL of lavage solution. Samples with no detectable virus are represented as "—". Peak titers for each animal are underlined.

[c] The period of days from the first to the last day on which virus was detected, including negative days (if any) in between.

[d] The sum of daily titers is used as an estimate for the magnitude of shedding (area under the curve). A value of 1.0 was used for samples with no detectable virus.

Figure 5:
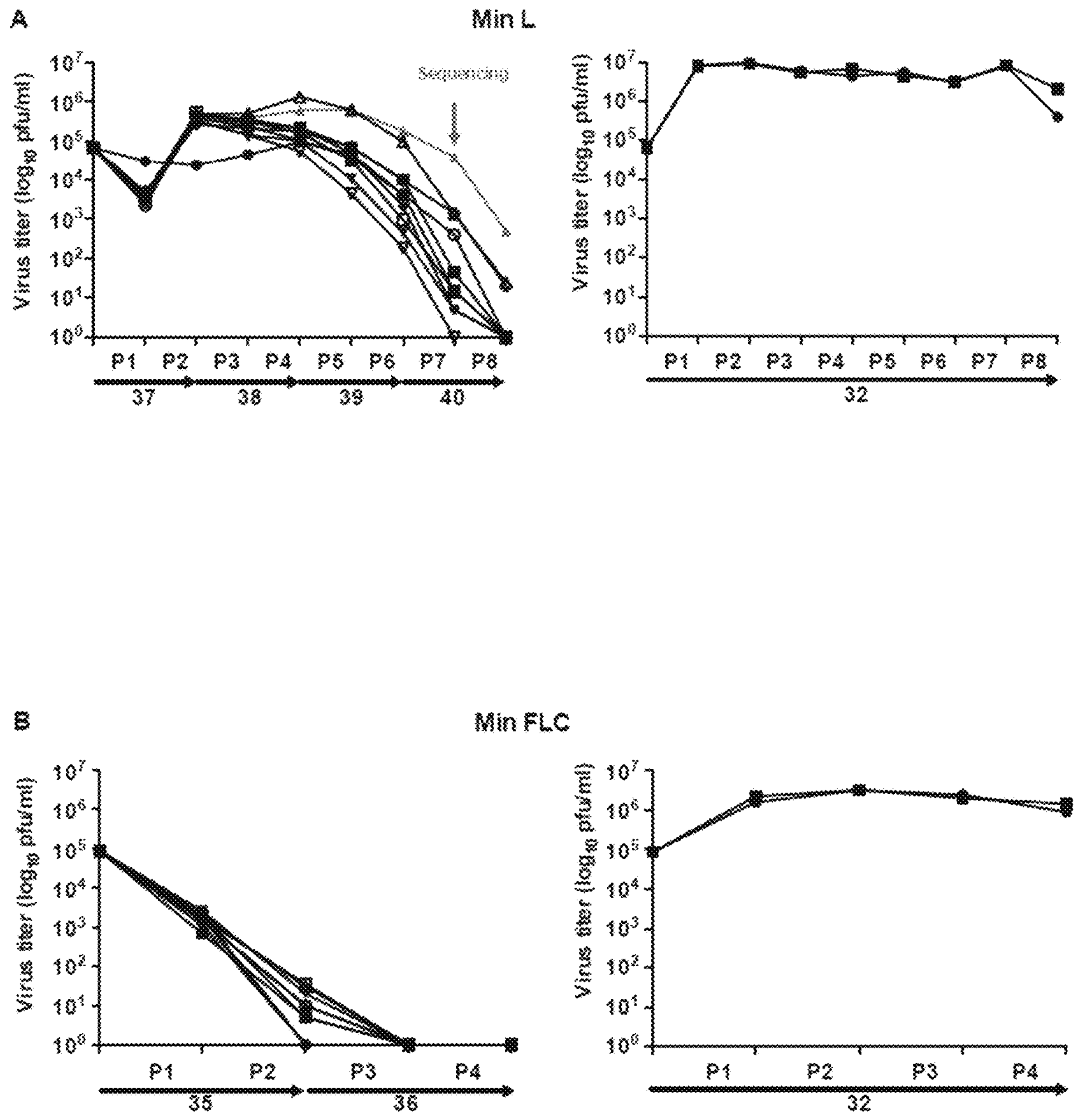
FIG. 5: Growth of Min L and Min FLC at increasing restrictive temperatures. Ten replicates cultures of Min L (A) and Min FLC (B) were grown serially at an increasing restrictive temperature starting at the shut off temperature (37 and 35° C. for Min L and Min FLC, respectively) with an input MOI of 0.1 pfu/cell until a maximum cytopathology was observed (between day 7 and 14). Two passages were performed for a given temperature before it was increased by 1° C. In parallel, as a control, duplicate samples of both viruses were grown on Vero cells in the same way but at 32° C. only (non-restrictive temperature). For each passage, 1 ml (out of 5 ml) of the supernatant was used to inoculate the next passage. For each passage, aliquots were frozen for titration and sequence analysis. Virus titer was determined in duplicate by plaque assay on Vero cells at the permissive temperature (32° C.). Passage number 0 represents the input virus. (C) The electropherograms show the nucleotide sequence of three mutations that were detected in N (aa 136), P (aa 114) and M2-1 (aa 88) of one replicate of Min L (gray filled triangle in (A)) which exhibited extensive syncytia at 39 and 40° C.
Figure 5:
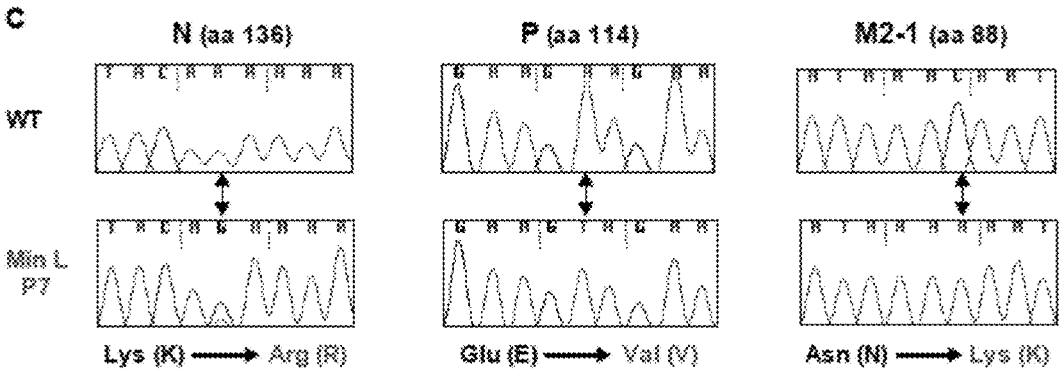

Example 8: Growth of Min L and Min FLC at Increasing Restrictive Temperatures Ten replicates cultures of Min L (FIG. 5A) and Min FLC (FIG. 5B) were grown serially at an increasing restrictive temperature starting at the shut off temperature (37 and 35° C. for Min L and Min FLC, respectively) with an input MOI of 0.1 pfu/cell until a maximum cytopathology was observed (between day 7 and 14). Two passages were performed for a given temperature before it was increased by 1° C. In parallel, as a control, duplicate samples of both viruses were grown on Vero cells in the same way but at 32° C. only (non-restrictive temperature). For each passage, 1 ml (out of 5 ml) of the supernatant was used to inoculate the next passage. For each passage, aliquots were frozen for titration and sequence analysis. Virus titer was determined in duplicate by plaque assay on Vero cells at the permissive temperature (32° C.). Sequence analysis revealed three mutations in a single Min L replicate (FIG. 5C). The N protein had a mutation in the codon encoding amino acid 136, resulting in a change in the encoded amino acid from lysine to arginine. The P protein had a mutation in the codon encoding amino acid 114, resulting in a change in the encoded amino acid from glutamic acid to valine. Also the M2-1 protein had a mutation in the codon encoding amino acid 88, resulting in a change in the encoded amino acid from asparagine to lysine. The Min L replicate with these mutations exhibited extensive syncytia at 39 and 40° C. (red filled triangle in (FIG. 5A)).

Figure 6:
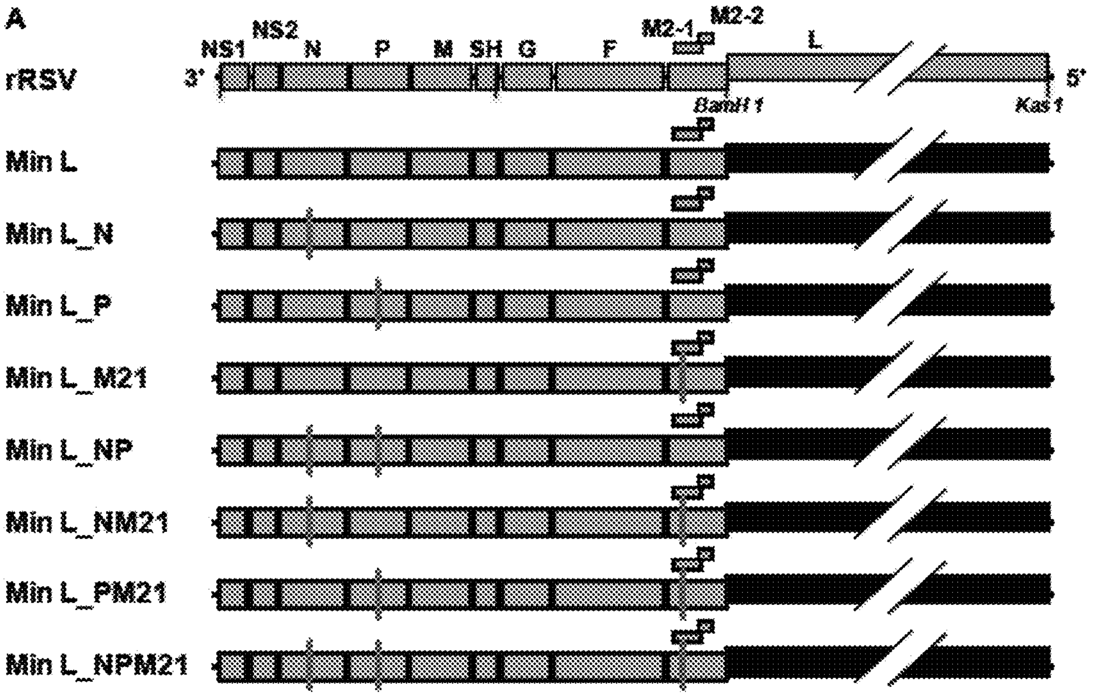
FIG. 6: Generation of synthetic codon-pair deoptimized rRSVs derived from Min L virus and characterization of their growth on Vero cells. (A) One chimeric synthetic codon-pair deoptimized (CPD) rRSV (Min L) was generated based on the wt RSV backbone (Genbank Accession number M74568). Min L contained a CPD ORF of polymerase protein L. CPD polymerase and wt coding sequences are represented by a black or grey shading boxes, respectively. Name of the genes as well as enzymatic restriction sites used for the generation of the chimeric synthetic cDNA are indicated. Mutations identified in N (aa 136), P (aa 114) and M2-1 (aa 88, cf FIG. 1) were introduced in all possible combinations. (B) Multi-cycle growth kinetics on Vero cells at 32 and 37° C. Confluent monolayer cultures of Vero cells in 6-well plates were infected in duplicate with rRSV, Min L or Min L containing the mutations of interest in all possible combinations at a multiplicity of infection (MOI) of 0.01 and incubated at 32 or 37° C. Viruses were harvested daily from day 1 to 14 by scraping infected cells into media followed by vortexing, clarification of the supernatant by centrifugation and freezing of virus aliquots. Each aliquot was titrated in duplicate at the permissive temperature of 32° C. For each time point, the mean value of the duplicate and standard deviation is shown. (C) Plaque size phenotype on Vero cells at 32° C. of rRSV and CPD rRSVs.
Figure 6:
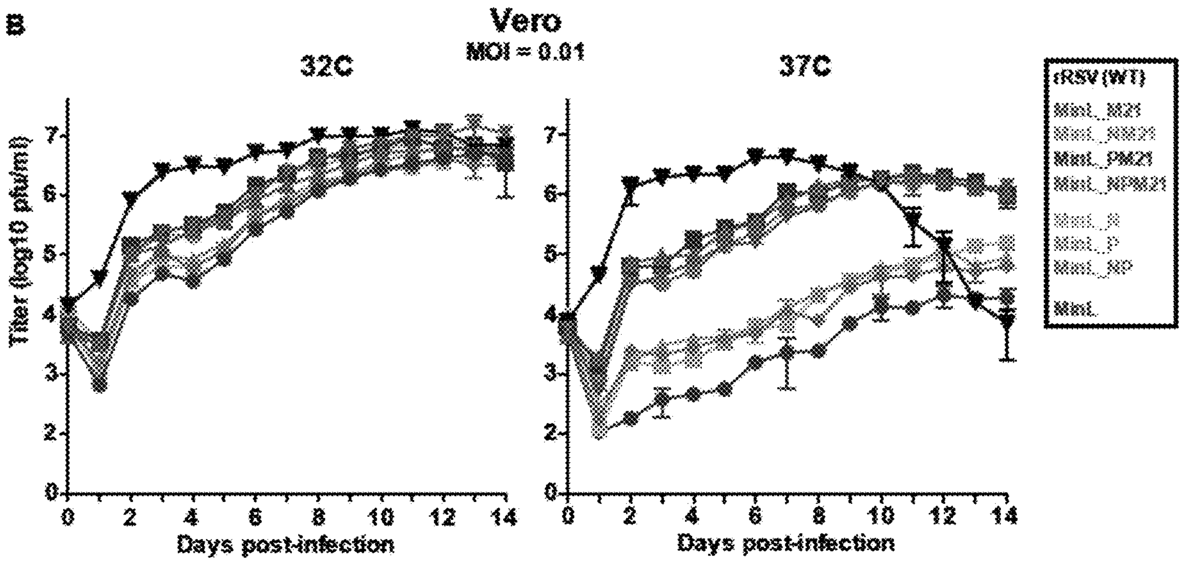
Figure 6:
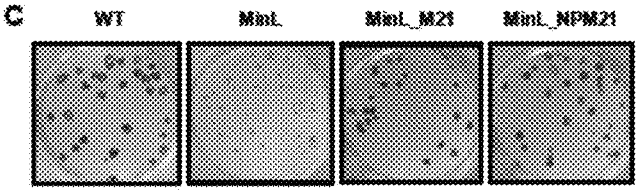

Example 9: Generation of Synthetic Codon-Pair Deoptimized rRSVs Derived from Min L Virus and Characterization of their Growth on Vero Cells To further assess the characteristics of viruses having the mutations identified in the Min L replicate described in Example 8, one chimeric synthetic codon-pair deoptimized (CPD) rRSV (Min L) was generated based on the wt RSV backbone (Genbank Accession number M74568) that contained a CPD ORF of polymerase protein L. Variant forms of this virus were also created with the mutations identified in N (aa 136), P (aa 114) and M2-1 (aa 88) introduced in all possible combinations (FIG. 6A). Multi-cycle growth kinetics were then determined. In brief, confluent monolayer cultures of Vero cells in 6-well plates were infected in duplicate with rRSV, Min L or Min L containing the mutations of interest in all possible combinations at a multiplicity of infection (MOI) of 0.01 and incubated at 32 or 37° C. Viruses were harvested daily from day 1 to 14 by scraping infected cells into media followed by vortexing, clarification of the supernatant by centrifugation and freezing of virus aliquots. Each aliquot was titrated in duplicate at the permissive temperature of 32° C. For each time point, the mean value of the duplicate and standard deviation is shown (FIG. 6B). Plaque size phenotype on Vero cells at 32° C. of rRSV and CPD rRSVs is shown in FIG. 6C. Results indicating the temperature sensitivity of the codon-pair deoptimized RSVs are provided in Table 5.

TABLE 5

Temperature sensitivity of the codon-pair deoptimized RSVs on Vero cells. Virus titer (in $log_{10}$ PFU per ml) at indicated temperature (° C.) [a]

| Virus | 32 | 35 | 36 | 37 | 38 | 39 | 40 | $T_{SH}$ [b] |
|---|---|---|---|---|---|---|---|---|
| Min L | 7.1 | 6.0 | 5.4 | **4.6** | 3.9 | <1 | <1 | **37** |
| Min L-N | 6.8 | 6.3 | 5.7 | 5.3 | **4.3** | 3.2 | <1 | **38** |
| Min L-P | 7.0 | 6.5 | 6.1 | 5.1 | **4.8** | 3.3 | <1 | **38** |
| Min L-M21 | 7.5 | 7.5 | 7.5 | 7.3 | 6.9 | **4.8** | <1 | **39** |
| Min L-NP | 6.8 | 6.7 | 6.3 | 5.8 | 4.9 | **3.8** | <1 | **39** |
| Min L-NM21 | 7.3 | 7.3 | 7.2 | 7.3 | 7.1 | 5.7 | **<1** | **40** |
| Min L-PM21 | 7.4 | 7.4 | 7.5 | 7.3 | 7.0 | 6.4 | **<1** | **40** |
| Min L-NPM21 | 7.2 | 7.1 | 7.2 | 7.1 | 6.9 | 6.7 | **3.2** | **40** |
| WT | 7.5 | 7.5 | 7.5 | 7.4 | 7.4 | 7.3 | 6.9 | **>40** |

[a] The ts phenotype for each virus was evaluated by plaque assay on Vero cells at the indicated temperatures. For viruses with a ts phenotype, the shut-off temperatures are marked (underlined). See footnote b for definition of shut-off temperature.

[b] Shut off temperature ($T_{SH}$) is defined as the lowest restrictive temperature at which the reduction compared to 32° C. is 100-fold or greater than that observed for wt RSV at the two temperatures. The ts phenotype is defined as having a $T_{SH}$ of 40° C. or less (bold).

What is claimed:

1. A recombinant polynucleotide comprising a recombinant nucleotide sequence encoding respiratory syncytial virus (RSV) proteins NS1, NS2, G, F, or L or a combination thereof, wherein the codon pair bias of each recombinant nucleotide sequence encoding the RSV protein is reduced by at least 0.05 compared to a wild type RSV subgroup A virus for a corresponding nucleotide sequence encoding the RSV protein, wherein a recombinant nucleotide sequence encoding RSV protein NS1 has about 75% to about 95% identity to the wild type RSV subgroup A virus for the corresponding nucleotide sequence encoding RSV protein NS1, wherein a recombinant nucleotide sequence encoding RSV protein NS2 has about 75% to about 95% identity to the wild type RSV subgroup A virus for the corresponding nucleotide sequence encoding RSV protein NS2, wherein a recombinant nucleotide sequence encoding RSV protein G has about 65% to about 85% identity to the wild type RSV subgroup A virus for the corresponding nucleotide sequence encoding RSV protein G, wherein a recombinant nucleotide sequence encoding RSV protein F has about 65% to about 85% identity to the wild type RSV subgroup A virus for the corresponding nucleotide sequence encoding RSV protein F, wherein a recombinant nucleotide sequence encoding RSV protein L has about 70% to about 90% identity to the wild type RSV subgroup A virus for the corresponding nucleotide sequence encoding RSV protein L, and wherein the recombinant nucleotide sequence encodes a RSV amino acid sequence that is the same as the corresponding wild type RSV subgroup A virus amino acid sequence, or a RSV amino acid sequence with up to four amino acid substitutions, additions or deletions compared to the corresponding wild type RSV subgroup A virus amino acid sequence.

2. A recombinant RSV genome or antigenome comprising the recombinant polynucleotide of claim 1, said recombinant RSV genome or antigenome comprising the genome encoded by pRSV_Min A, pRSV_Min B, pRSV_Min L, pRSV_Min FLC, pRSV_Min L_N, pRSV_Min L_p, pRSV_Min L_M21, pRSV_Min L_NP, pRSV_Min L_NM21, pRSV_Min L_PM21, or pRSV_Min L_NPM21.

3. A recombinant RSV genome or antigenome comprising the recombinant polynucleotide of claim 1, said recombinant RSV genome or antigenome further comprising a nucleotide change in one or more of the following:

a. a change in the codon encoding amino acid 136 of the N protein, b. a change in the codon encoding amino acid 114 of the P protein, or c. a change in the codon encoding amino acid 88 of the M2-1 protein.

4. The recombinant RSV genome or antigenome of claim 3, wherein any one of said nucleotide changes causes an amino acid other than:

a. lysine to be encoded at position 136 of the N protein, b. glutamic acid to be encoded at position 114 of the P protein, or c. asparagine to be encoded at position 88 of the M2-1 protein.

5. The recombinant RSV genome or antigenome of claim 4, wherein arginine is encoded at position 136 of the N protein, valine is encoded at position 114 of the P protein, and/or lysine is encoded at position 88 of the M2-1 protein.

6. A method of producing a recombinant RSV, comprising expressing the genome or antigenome of claim 2 in a cell.

7. A method of producing an immune response to a viral protein, comprising administering the recombinant RSV produced by the method of claim 6 to an animal.

8. The method of claim 7, wherein the RSV is administered via injection, aerosol delivery, nasal spray, nasal droplets, oral inoculation, or topical application.

9. The method of claim 7, wherein the animal is a mammal.

10. The method of claim 9, wherein the mammal is a human.

11. A recombinant RSV produced by the method of claim 6, wherein said virus is attenuated.

12. The recombinant RSV of claim 11, wherein the genome or antigenome is further modified to include a previously characterized RSV mutation or deletion.

13. A vaccine composition comprising the recombinant RSV produced by the method of claim 6.

14. The recombinant polynucleotide of claim 1, wherein the codon pair bias of the recombinant nucleotide encoding each RSV protein is reduced by at least 0.1 compared to the corresponding wild type RSV subgroup A virus nucleotide sequence encoding the RSV protein.

15. The recombinant polynucleotide of claim 1, wherein the codon pair bias of the recombinant nucleotide encoding each RSV protein is reduced by at least 0.2 compared to the corresponding wild type RSV subgroup A virus nucleotide sequence encoding the RSV protein.

16. The recombinant polynucleotide of claim 1, wherein the codon pair bias is calculated relative to the human genome.

17. A recombinant RSV genome or antigenome comprising the recombinant polynucleotide of claim 1.

* * * * *